US008907091B2

(12) United States Patent
Raeppel et al.

(10) Patent No.: US 8,907,091 B2
(45) Date of Patent: Dec. 9, 2014

(54) PROCESSES AND INTERMEDIATES FOR PREPARING FUSED HETEROCYCLIC KINASE INHIBITORS

(75) Inventors: Franck Raeppel, Montreal (CA); Ljubomir Isakovic, Beaconsfield (CA); Stephen William Claridge, Montreal (CA); Michael Mannion, Montreal (CA); Lijie Zhan, Montreal (CA); Marie-Claude Granger, LaPrairie (CA); Arkadii Vaisburg, Kirkland (CA); Miguel Nantel, Saint Jerome (CA)

(73) Assignee: Methylgene Inc., Montreal (CA)

( * ) Notice: Subject to any disclaimer, the term of this patent is extended or adjusted under 35 U.S.C. 154(b) by 1272 days.

(21) Appl. No.: 12/231,297

(22) Filed: Aug. 29, 2008

(65) Prior Publication Data

US 2009/0286984 A1   Nov. 19, 2009

Related U.S. Application Data

(60) Provisional application No. 60/968,672, filed on Aug. 29, 2007.

(51) Int. Cl.
*C07D 513/04* (2006.01)
*C07D 213/51* (2006.01)
*C07D 495/04* (2006.01)
*C07D 213/61* (2006.01)
*C07D 213/38* (2006.01)

(52) U.S. Cl.
CPC ............ *C07D 495/04* (2013.01); *C07D 213/51* (2013.01); *C07D 213/61* (2013.01); *C07D 213/38* (2013.01)
USPC ........................................................ 546/114

(58) Field of Classification Search
USPC ........................................................ 546/114
See application file for complete search history.

(56) References Cited

U.S. PATENT DOCUMENTS

| 6,214,344 | B1 | 4/2001 | Schwall | |
|---|---|---|---|---|
| 2006/0074056 | A1* | 4/2006 | Vaisburg et al. | 514/151 |
| 2006/0287343 | A1 | 12/2006 | Saavedra et al. | |
| 2007/0004675 | A1 | 1/2007 | Saavedra et al. | |
| 2007/0197537 | A1 | 8/2007 | Blake et al. | |

FOREIGN PATENT DOCUMENTS

| CA | 2571680 | 1/2006 |
|---|---|---|
| CA | 2603125 | 10/2006 |
| CA | 2605680 | 11/2006 |
| CA | 2611370 | 11/2006 |
| WO | WO2006/019264 | 2/2006 |
| WO | WO2006/050121 | 5/2006 |
| WO | WO2006/075160 | 7/2006 |
| WO | WO2007/054831 | 5/2007 |
| WO | WO2007/107005 | 9/2007 |
| WO | WO2008/063202 | 5/2008 |

OTHER PUBLICATIONS

Banker (Modern Pharmaceutics) Banker, G.S. et al, "Modern Pharmaceutics, 3ed.", Marcel Dekker, New York, 1996, pp. 451 and 596.*
Wolff (Medicinal Chemistry) summarizes the state of the prodrug art. Wolff, Manfred E. "Burger's Medicinal Chemistry, 5ed, Part I", John Wiley & Sons, 1995, pp. 975-977.*
West, Anthony R., Solid State Chemistry and its Applications, Wiley, New York, 1988, pp. 358 & 365.*
M.O.Lozinskii and P.S.Pel'kis "The Chemistry of Acyl and Sulphonyl Isocyanates, Isothiocyanates, and Isoselenocyanates" Russian Chemical Reviews, 37 (5), 1968 363-375.*
Aragoni et. al. "Reactions of pyridyl donors with halogens and interhalogens: an X-ray diffraction and FT-Raman investigation." Journal of Organometallic Chemistry 690 (2005) 1923-1934.*
Ulrich et. al. "Potential Antitrypanosomal Agents. 1,N2-Disubstituted 2-Amino-5-hydroxy-4-methylnaphtho[1,2-d]thiazolium Salts and Related Compounds" J. Med. Chem. 1982, 25, 654-657.*
Jia, Xueshun Synthesis of 1-aroyl-3-(4-benzosulfonamidopyrimidine)thiourea Youji Huaxue, 13(3), 250-2 1993 (abstract only).*
Li et. al. "Syntheses and biological activities of acyl thiourea containing triazolyl." Huazhong Shifan Daxue Xuebao Zirankexueban, 36(1), 55-57 2002 (abstract only).*
Mekuskiene, G et. al. "Synthesis of 1-(4-oxo-3,4-dihydro-2-quinazolinecarbonyl)-4-substituted thiosemicarbazides and their cyclization to 2-(4-substituted-5-thioxo-4,5-dihydro-1H-1,2,4-triazol-3-yl)-3,4-dihydro-4-quinazolinones." Chemija, 12(2), 172-174 2001 (abstract only).*
El-Badry et. al. "Pyridine and reduced pyridine analogues of cimetidine as histamine H2-receptor antagonists" European Journal of Organic Chemistry 1987, 22, 579-582.*
Saunders "The Chemistry of the Organic Isocyanates" Chemical Reviews 1948, 203-218.*
Stabile et al.; "Inhibition of Human Non-Small Cell Lung Tumors by a C-MET Antisense/U6 Expression Plasmid Strategy"; Gene Therapy, 11:325-335, 2004.

(Continued)

*Primary Examiner* — David K O Dell
(74) *Attorney, Agent, or Firm* — Wood, Phillips, Katz, Clark & Mortimer

(57) ABSTRACT

This invention relates to processes and intermediates for manufacturing fused heterocyclic-type kinase inhibitor compounds, such as thienopyridine-based compounds, and to processes and intermediates for preparing intermediates that are useful in the manufacture of fused heterocyclic-type kinase inhibitor compounds, such as thienopyridine-based compounds, particularly at an industrial level.

4 Claims, No Drawings

(56) References Cited

OTHER PUBLICATIONS

Jiang et al.; "Reduction of Stromal Fibroblast-Induced Mammary Tumor Growth, by Retroviral Ribozyme Transgenes to Hepatocyte Growth Factor/Scatter Factor and its Receptor, C-MET"; Clin. Cancer Res., 9:4274-4281, 2003.

Abdel-Magid et al.; "Reductive Amination of Aldehydes and Ketones with Sodium Triacetoxyborohydride. Studies on Direct and Indirect Reductive Amination Procedures"; J.Org. Chem., 61, 3849-3862, 1996.

Scott et al.; "Development of a Scalable Synthesis to VEGFR Inhibitor AG-28262"; Org. process Research & Development, 10, 296-303, 2006.

Ragan et al.; "Cross-Coupling Methods for the Large-Scale Preparation of an Imidazole-Thienopyridine: Synthesis of [2-(3-Methyl-3H-Imidazol-4-yl)-thieno[3,2-b]pyridin-7-yl]-(2-methyl-1H-indol-5-yl)-Amine"; Org. process Research & Development, 7, 676-683, 2003.

Zhang et al.; "Palladium-Catalyzed Selective Cross-Coupling Between 2-Bromopyridines and Aryl Bromides"; J. Org. Chem., 66, 1500-1502, 2001.

Klemm et al.; "Chemistry of Thienopyridines. XXXIII. Synthetic Routes to 5- and 7-Substituted Thieno[3,2-b]pyridines from the N-Oxide [1]"; J. Heterocyclic Chem., 22, 1249-1252, 1985.

Romero-Salguero et al.; "Synthesis of Multitopic Bidentate Ligands Based on Alternating Pyridine and Pyridazine Rings"; Tetrahedron Letters, 40, 859-862, 1999.

Claridge et al.; "Discovery of a Novel and Potent Series of Thieno[3,2-b] Pyridine-Based Inhibitors of c-Met and VEGFR2 tyrosine Kinases"; Bioorg. Med. Chem. Lett 18, 2793-2798, 2008.

\* cited by examiner

PROCESSES AND INTERMEDIATES FOR PREPARING FUSED HETEROCYCLIC KINASE INHIBITORS

RELATED APPLICATION

This application claims the benefit of U.S. Provisional Application Ser. No. 60/968,672, filed Aug. 29, 2007. The entire teachings of the above-referenced application is incorporated herein by reference.

BACKGROUND OF THE INVENTION

1. Field of the Invention

This invention relates to processes and intermediates for manufacturing fused heterocyclic-type compounds, such as thienopyridine-based kinase inhibitor compounds, and to processes and intermediates for preparing intermediates that are useful in the manufacture of fused heterocyclic-type compounds, such as thienopyridine-based kinase inhibitor compounds, particularly at an industrial level. Fused heterocyclic-type compounds have been found to be useful to inhibit protein tyrosine kinase activity. In particular, fused heterocyclic-type compounds, such as thienopyridine-based compounds, have been found useful to inhibit the protein tyrosine kinase activity of growth factor receptors, resulting in the inhibition of receptor signaling, for example, the inhibition of VEGF receptor signaling and HGF receptor signaling. Fused heterocyclic-type compounds have been found to be useful in the treatment of cancer by inhibiting protein tyrosine kinase activity. The pharmaceutical compositions that comprise these compounds are also useful in the treatment of diseases, other than cancer, which are associated with signal transduction pathways operating through growth factor and anti-angiogenesis receptors such as c-Met.

2. Summary of the Related Art

Tyrosine kinases may be classified as growth factor receptor (e.g. EGFR, PDGFR, FGFR and erbB2) or non-receptor (e.g. c-src and bcr-abl) kinases. The receptor type tyrosine kinases make up about 20 different subfamilies. The non-receptor type tyrosine kinases make up numerous subfamilies. These tyrosine kinases have diverse biological activity. Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Aberrant or inappropriate protein kinase activity can contribute to the rise of disease states associated with such aberrant kinase activity.

Angiogenesis is an important component of certain normal physiological processes such as embryogenesis and wound healing, but aberrant angiogenesis contributes to some pathological disorders and in particular to tumor growth. VEGF-A (vascular endothelial growth factor A) is a key factor promoting neovascularization (angiogenesis) of tumors. VEGF induces endothelial cell proliferation and migration by signaling through two high affinity receptors, the fms-like tyrosine kinase receptor, Flt-1, and the kinase insert domain-containing receptor, KDR. These signaling responses are critically dependent upon receptor dimerization and activation of intrinsic receptor tyrosine kinase (RTK) activity. The binding of VEGF as a disulfide-linked homodimer stimulates receptor dimerization and activation of the RTK domain. The kinase activity autophosphorylates cytoplasmic receptor tyrosine residues, which then serve as binding sites for molecules involved in the propagation of a signaling cascade.

Although multiple pathways are likely to be elucidated for both receptors, KDR signaling is most extensively studied, with a mitogenic response suggested to involve ERK-1 and ERK-2 mitogen-activated protein kinases.

Disruption of VEGF receptor signaling is a highly attractive therapeutic target in cancer, as angiogenesis is a prerequisite for all solid tumor growth, and that the mature endothelium remains relatively quiescent (with the exception of the female reproductive system and wound healing). A number of experimental approaches to inhibiting VEGF signaling have been examined, including use of neutralizing antibodies, receptor antagonists, soluble receptors, antisense constructs and dominant-negative strategies.

Despite the attractiveness of anti-angiogenic therapy by VEGF inhibition alone, several issues may limit this approach. VEGF expression levels can themselves be elevated by numerous diverse stimuli and perhaps most importantly, the hypoxic state of tumors resulting from VEGFr inhibition, can lead to the induction of factors that themselves promote tumor invasion and metastasis thus, potentially undermining the impact of VEGF inhibitors as cancer therapeutics.

The HGF (hepatocyte growth factor) and the HGF receptor, c-Met, are implicated in the ability of tumor cells to undermine the activity of VEGF inhibition. HGF derived from either stromal fibroblasts surrounding tumor cells or expressed from the tumor itself has been suggested to play a critical role in tumor angiogenesis, invasion and metastasis. For example, invasive growth of certain cancer cells is drastically enhanced by tumor-stromal interactions involving the HGF/c-Met (HGF receptor) pathway. HGF, which was originally identified as a potent mitogen for hepatocytes, is primarily secreted from stromal cells, and the secreted HGF can promote motility and invasion of various cancer cells that express c-Met in a paracrine manner. Binding of HGF to c-Met leads to receptor phosphorylation and activation of Ras/mitogen-activated protein kinase (MAPK) signaling pathway, thereby enhancing malignant behaviors of cancer cells. Moreover, stimulation of the HGF/c-Met pathway itself can lead to the induction of VEGF expression, itself contributing directly to angiogenic activity.

Biological agents, such as ribozymes, antibodies and antisense RNA targeting either HGF or Met have been shown to inhibit tumorogenesis (Stabile et al., (2004) Gene Therapy, 11: 325-335; Jiang et al., (2003) Clin. Cancer Res., 9: 4274-4281; and Genentech U.S. Pat. No. 6,214,344).

Thus, anti-tumor and/or anti-angiogenic strategies or approaches that target either or both VEGF/VEGFr signaling and HGF/c-Met signaling may circumvent the ability of tumor cells to overcome VEGF inhibition alone and may represent improved cancer therapeutics.

BRIEF SUMMARY OF THE INVENTION

This invention is directed to processes and intermediates for manufacturing fused heterocyclic-type compounds, such as thienopyridine-based kinase inhibitor compounds, and to processes and intermediates for preparing intermediates that are useful in the manufacture of fused heterocyclic-type compounds, such as thienopyridine-based kinase inhibitor compounds.

In one embodiment of the present invention, processes and intermediates are provided for preparing compounds having the formula (A):

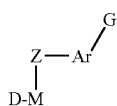

(A)

and N-oxides, hydrates, solvates, pharmaceutically acceptable salts, prodrugs and complexes thereof, and racemic and scalemic mixtures, diastereomers, tautomers and enantiomers thereof, wherein D, M, Z, Ar and G are as defined herein.

The foregoing merely summarizes certain aspects of the invention and is not intended to be limiting in nature. These aspects and other aspects and embodiments are described more fully below.

DETAILED DESCRIPTION

This invention relates to processes and intermediates for manufacturing fused heterocyclic-type compounds, such as thienopyridine-based kinase inhibitor compounds, and to processes and intermediates for preparing intermediates that are useful in the manufacture of fused heterocyclic-type compounds, such as thienopyridine-based kinase inhibitor compounds. Fused heterocyclic-type compounds have been found to be useful to inhibit protein tyrosine kinase activity. In particular, fused heterocyclic-type compounds, such as thienopyridine-based compounds, have been found useful to inhibit the protein tyrosine kinase activity of growth factor receptors, resulting in the inhibition of receptor signaling, for example, the inhibition of VEGF receptor signaling and HGF receptor signaling. Fused heterocyclic-type compounds have been found to be useful in the treatment of cancer by inhibiting protein tyrosine kinase activity. The pharmaceutical compositions that comprise these compounds are also useful in the treatment of diseases, other than cancer, which are associated with signal transduction pathways operating through growth factor and anti-angiogenesis receptors such as c-Met.

The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

For simplicity, reference to a "$C_n$-$C_m$" heterocyclyl or "$C_n$-$C_m$" heteroaryl means a heterocyclyl or heteroaryl having from "n" to "m" annular atoms, where "n" and "m" are integers. Thus, for example, a $C_5$-$C_6$-heterocyclyl is a 5- or 6-membered ring having at least one heteroatom, and includes pyrrolidinyl ($C_{5-}$) and piperazinyl and piperidinyl ($C_6$); $C_6$-heteroaryl includes, for example, pyridyl and pyrimidyl.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$ hydrocarbyl" includes a covalent bond, methyl, ethyl, ethenyl, ethynyl, propyl, propenyl, propynyl, and cyclopropyl.

The term "alkyl" is intended to mean a straight chain or branched aliphatic group having from 1 to 12 carbon atoms, alternatively 1-8 carbon atoms, and alternatively 1-6 carbon atoms. Other examples of alkyl groups have from 2 to 12 carbon atoms, alternatively 2-8 carbon atoms and alternatively 2-6 carbon atoms. Examples of alkyl groups include, without limitation, methyl, ethyl, propyl, isopropyl, butyl, isobutyl, sec-butyl, tert-butyl, pentyl, hexyl and the like. A "$C_0$" alkyl (as in "$C_0$-$C_3$alkyl") is a covalent bond.

The term "alkenyl" is intended to mean an unsaturated straight chain or branched aliphatic group with one or more carbon-carbon double bonds, having from 2 to 12 carbon atoms, alternatively 2-8 carbon atoms, and alternatively 2-6 carbon atoms. Examples of alkenyl groups include, without limitation, ethenyl, propenyl, butenyl, pentenyl, and hexenyl.

The term "alkynyl" is intended to mean an unsaturated straight chain or branched aliphatic group with one or more carbon-carbon triple bonds, having from 2 to 12 carbon atoms, alternatively 2-8 carbon atoms, and alternatively 2-6 carbon atoms. Examples of alkynyl groups include, without limitation, ethynyl, propynyl, butynyl, pentynyl, and hexynyl.

The terms "alkylene," "alkenylene," or "alkynylene" as used herein are intended to mean an alkyl, alkenyl, or alkynyl group, respectively, as defined hereinabove, that is positioned between and serves to connect two other chemical groups. Examples of alkylene groups include, without limitation, methylene, ethylene, propylene, and butylene. Examples of alkenylene groups include, without limitation, ethenylene, propenylene, and butenylene. Examples of alkynylene groups include, without limitation, ethynylene, propynylene, and butynylene.

The term "carbocycle" as employed herein is intended to mean a cycloalkyl or aryl moiety.

The term "cycloalkyl" is intended to mean a saturated or unsaturated mono-, bi-, tri- or poly-cyclic hydrocarbon group having about 3 to 15 carbons, alternatively having 3 to 12 carbons, alternatively 3 to 8 carbons, alternatively 3 to 6 carbons, and alternatively 5 or 6 carbons. In certain embodiments, the cycloalkyl group is fused to an aryl, heteroaryl or heterocyclic group. Examples of cycloalkyl groups include, without limitation, cyclopenten-2-enone, cyclopenten-2-enol, cyclohex-2-enone, cyclohex-2-enol, cyclopropyl, cyclobutyl, cyclobutenyl, cyclopentyl, cyclopentenyl, cyclohexyl, cyclohexenyl, cycloheptyl, cyclooctyl, etc.

The term "heteroalkyl" is intended to mean a saturated or unsaturated, straight chain or branched aliphatic group, wherein one or more carbon atoms in the group are independently replaced by a heteroatom selected from the group consisting of O, S, and N.

The term "aryl" is intended to mean a mono-, bi-, tri- or polycyclic aromatic moiety, for example a $C_6$-$C_{14}$aromatic moiety, for example comprising one to three aromatic rings. Alternatively, the aryl group is a $C_6$-$C_{10}$ aryl group, alternatively a $C_6$ aryl group. Examples of aryl groups include, without limitation, phenyl, naphthyl, anthracenyl, and fluorenyl.

The terms "aralkyl" or "arylalkyl" are intended to mean a group comprising an aryl group covalently linked to an alkyl group. If an aralkyl group is described as "optionally substituted", it is intended that either or both of the aryl and alkyl moieties may independently be optionally substituted or unsubstituted. Alternatively, the aralkyl group is $(C_1$-$C_6)$alk $(C_6$-$C_{10})$aryl, including, without limitation, benzyl, phenethyl, and naphthylmethyl. For simplicity, when written as "arylalkyl" this term, and terms related thereto, is intended to indicate the order of groups in a compound as "aryl-alkyl". Similarly, "alkyl-aryl" is intended to indicate the order of the groups in a compound as "alkyl-aryl".

The terms "heterocyclyl", "heterocyclic" or "heterocycle" are intended to mean a group which is a mono-, bi-, or polycyclic structure having from about 3 to about 14 atoms, wherein one or more atoms are independently selected from the group consisting of N, O, and S. The ring structure may be saturated, unsaturated or partially unsaturated. In certain embodiments, the heterocyclic group is non-aromatic, in which case the group is also known as a heterocycloalkyl. In a bicyclic or polycyclic structure, one or more rings may be aromatic; for example one ring of a bicyclic heterocycle or one or two rings of a tricyclic heterocycle may be aromatic, as in indan and 9,10-dihydro anthracene. Examples of heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain embodiments, the heterocyclic group is a heteroaryl group. As used herein, the term "heteroaryl" is intended to mean a mono-, bi-, tri- or polycyclic group having 5 to 14 ring atoms, alternatively 5, 6, 9, or 10 ring atoms; having 6, 10, or 14 pi electrons shared in a cyclic array; and having, in addition to carbon atoms, between one or more heteroatoms independently selected from the group consisting of N, O, and S. For example, a heteroaryl group may be pyrimidinyl, pyridinyl, benzimidazolyl, thienyl, benzothiazolyl, benzofuranyl and indolinyl. Examples of heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

The terms "arylene," "heteroarylene," or "heterocyclylene" are intended to mean an aryl, heteroaryl, or heterocyclyl group, respectively, as defined hereinabove, that is positioned between and serves to connect two other chemical groups.

Examples of heterocyclyls and heteroaryls include, but are not limited to, azepinyl, azetidinyl, acridinyl, azocinyl, benzidolyl, benzimidazolyl, benzofuranyl, benzofurazanyl, benzofuryl, benzothiofuranyl, benzothiophenyl, benzoxazolyl, benzothiazolyl, benzothienyl, benztriazolyl, benztetrazolyl, benzisoxazolyl, benzisothiazolyl, benzimidazolinyl, benzoxazolyl, benzoxadiazolyl, benzopyranyl, carbazolyl, 4aH-carbazolyl, carbolinyl, chromanyl, chromenyl, cinnolinyl, coumarinyl, decahydroquinolinyl, 1,3-dioxolane, 2H,6H-1,5,2-dithiazinyl, dihydrofuro[2,3-b]tetrahydrofuran, dihydroisoindolyl, dihydroquinazolinyl (such as 3,4-dihydro-4-oxo-quinazolinyl), furanyl, furopyridinyl (such as fuor[2,3-c]pyridinyl, furo[3,2-b]pyridinyl or furo[2,3-b]pyridinyl), furyl, furazanyl, hexahydrodiazepinyl, imidazolidinyl, imidazolinyl, imidazolyl, indazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolidinyl, isothiazolyl, isoxazolinyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, oxetanyl, 2-oxoazepinyl, 2-oxopiperazinyl, 2-oxopiperidinyl, 2-oxopyrrolodinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolopyridyl, 2H-pyrrolyl, pyrrolyl, quinazolinyl, quinolinyl, 4H-quinolizinyl, quinoxalinyl, quinuclidinyl, tetrahydro-1,1-dioxothienyl, tetrahydrofuranyl, tetrahydrofuryl, tetrahydroisoquinolinyl, tetrahydroquinolinyl, tetrahydropyranyl, tetrazolyl, thiazolidinyl, 6H-1,2,5-thiadiazinyl, thiadiazolyl (e.g., 1,2,3-thiadiazolyl, 1,2,4-thiadiazolyl, 1,2,5-thiadiazolyl, 1,3,4-thiadiazolyl), thiamorpholinyl, thiamorpholinyl sulfoxide, thiamorpholuiyl sulfone, thianthrenyl, thiazolyl, thienyl, thienothiazolyl, thienooxazolyl, thienoimidazolyl, thiophenyl, triazinyl, triazinylazepinyl, triazolyl (e.g., 1,2,3-triazolyl, 1,2,4-triazolyl, 1,2,5-triazolyl, 1,3,4-triazolyl), and xanthenyl.

The term "azolyl" as employed herein is intended to mean a five-membered saturated or unsaturated heterocyclic group containing two or more hetero-atoms, as ring atoms, selected from the group consisting of nitrogen, sulfur and oxygen, wherein at least one of the hetero-atoms is a nitrogen atom. Examples of azolyl groups include, but are not limited to, optionally substituted imidazolyl, oxazolyl, thiazolyl, pyrazolyl, isoxazolyl, isothiazolyl, 1,3,4-thiadiazolyl, 1,2,4-thiadiazolyl, 1,2,4-oxadiazolyl, and 1,3,4-oxadiazolyl.

As employed herein, and unless stated otherwise, when a moiety (e.g., alkyl, heteroalkyl, cycloalkyl, aryl, heteroaryl, heterocyclyl, etc.) is described as "optionally substituted" it is meant that the group optionally has from one to four, alternatively from one to three, alternatively one or two, independently selected non-hydrogen substituents. Suitable substituents include, without limitation, halo, hydroxy, oxo (e.g., an annular —CH— substituted with oxo is —C(O)—) nitro, halohydrocarbyl, hydrocarbyl, alkyl, cycloalkyl, heterocyclyl, aryl, heteroaryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Examples of substituents, which are themselves not further substituted (unless expressly stated otherwise) are:

(a) halo, cyano, oxo, carboxy, formyl, nitro, amino, amidino, guanidino, $C_1$-$C_5$alkyl or alkenyl or arylalkyl imino, carbamoyl, azido, carboxamido, mercapto, hydroxy, hydroxyalkyl, alkylaryl, arylalkyl, $C_1$-$C_8$alkyl, $C_1$-$C_8$alkenyl, $C_1$-$C_8$alkoxy, $C_1$-$C_8$alkyamino, $C_1$-$C_8$alkoxycarbonyl, aryloxycarbonyl, $C_2$-$C_8$acyl, $C_2$-$C_8$acylamino, $C_1$-$C_8$alkylthio, arylalkylthio, arylthio, $C_1$-$C_8$alkylsulfinyl, arylalkylsulfinyl, arylsulfinyl, $C_1$-$C_8$alkylsulfonyl, arylalkylsulfonyl, arylsulfonyl, $C_0$-$C_6$N-alkyl carbamoyl, $C_2$-$C_{15}$N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$heterocycle, $C_5$-$C_{15}$heteroaryl or any of these rings fused or spiro-fused to a cycloalkyl, heterocyclyl, or aryl, wherein each of the foregoing is further optionally substituted with one more moieties listed in (a), above; and (b) —$(CR^{32}R^{33})_s$—$NR^{30}R^{31}$, wherein
s is from 0 (in which case the nitrogen is directly bonded to the moiety that is substituted) to 6,
$R^{32}$ and $R^{33}$ are each independently hydrogen, halo, hydroxyl or $C_1$-$C_4$alkyl, and
$R^{30}$ and $R^{31}$ are each independently hydrogen, cyano, oxo, hydroxyl, $C_1$-$C_8$alkyl, $C_1$-$C_8$heteroalkyl, $C_1$-$C_8$alkenyl, carboxamido, $C_1$-$C_3$alkyl-carboxamido, carboxamido-$C_1$-$C_3$alkyl, amidino, $C_2$-$C_8$hydroxyalkyl, $C_1$-$C_3$alkylaryl, aryl-$C_1$-$C_3$alkyl, $C_1$-$C_3$alkylheteroaryl, heteroaryl-$C_1$-$C_3$alkyl, $C_1$-$C_3$alkylheterocyclyl, heterocyclyl-$C_1$-$C_3$alkyl $C_1$-$C_3$alkylcycloalkyl, cycloalkyl-$C_1$-$C_3$alkyl, $C_2$-$C_8$alkoxy, $C_2$-$C_8$alkoxy-$C_1$-$C_4$alkyl, $C_1$-$C_8$alkoxycarbonyl, aryloxycarbonyl, aryl-$C_1$-$C_3$alkoxycarbonyl, heteroaryloxycarbonyl, heteroaryl-$C_1$-$C_3$alkoxycarbonyl, $C_1$-$C_8$acyl, $C_0$-$C_8$alkyl-carbonyl, aryl-$C_0$-$C_8$alkyl-carbonyl, heteroaryl-$C_0$-$C_8$alkyl-carbonyl, cycloalkyl-$C_0$-$C_8$alkyl-carbonyl, $C_0$-$C_8$alkyl-NH-carbonyl, aryl-$C_0$-$C_8$alkyl-NH-carbonyl, heteroaryl-$C_0$-$C_8$alkyl-NH-carbonyl, cycloalkyl-$C_0$-$C_8$alkyl-NH-carbonyl, $C_0$-$C_8$alkyl-O-carbonyl, aryl-$C_0$-$C_8$alkyl-O-carbonyl, heteroaryl-$C_0$-$C_8$alkyl-O-carbonyl, cycloalkyl-$C_0$-$C_8$alkyl-O-carbonyl, $C_1$-$C_8$alkylsulfonyl, arylalkylsulfonyl, arylsulfonyl, heteroarylalkylsulfonyl, heteroarylsulfonyl, $C_1$-$C_8$alkyl-NH-sulfonyl, arylalkyl-NH-sulfonyl, aryl-NH-sulfonyl, heteroarylalkyl-NH-sulfonyl, heteroaryl-NH-sulfonyl aroyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, or protecting group, wherein each of the foregoing is further optionally substituted with one more moieties listed in (a), above; or
$R^{30}$ and $R^{31}$ taken together with the N to which they are attached form a heterocyclyl or heteroaryl, each of which is optionally substituted with from 1 to 3 substituents selected from the group consisting of (a) above, a protecting group, and ($X^{30}$—$Y^{31}$—), wherein said heterocyclyl may also be bridged (forming a bicyclic moiety with a methylene, ethylene or propylene bridge); wherein
$X^{30}$ is selected from the group consisting of $C_1$-$C_8$alkyl, $C_2$-$C_8$alkenyl-, $C_2$-$C_8$alkynyl-, —CO—$C_3$alkyl-$C_2$-$C_8$alkenyl-$C_0$-$C_3$alkyl, $C_0$-$C_3$alkyl-$C_2$-$C_8$alkynyl-$C_0$-$C_3$alkyl, $C_0$-$C_3$alkyl-O—CO—$C_3$alkyl-, HO—$C_0$-$C_3$alkyl-, $C_0$-$C_4$alkyl-N($R^{30}$)—$C_0$-$C_3$alkyl-, N($R^{30}$)($R^{31}$)—CO—$C_3$alkyl-, N($R^{30}$)($R^{31}$)—CO—$C_3$alkenyl-, N($R^{30}$)($R^{31}$)—$C_0$-$C_3$alkynyl-, (N($R^{30}$)($R^{31}$))$_2$—C═N—, CO—$C_3$alkyl-S(O)$_{0-2}$—$C_0$-$C_3$alkyl-, $CF_3$—CO—$C_3$alkyl-, $C_1$-$C_8$heteroalkyl, aryl, cycloalkyl, heterocyclyl, heteroaryl, aryl-$C_1$-$C_3$alkyl-, cycloalkyl-$C_1$-$C_3$alkyl-, heterocyclyl-$C_1$-$C_3$alkyl-, heteroaryl-$C_1$-$C_3$alkyl-, N($R^{31}$)($R^{31}$)-heterocyclyl-$C_1$-$C_3$alkyl-, wherein the aryl, cycloalkyl, heteroaryl and heterocycyl are optionally substituted with from 1 to 3 substituents from (a); and
$Y^{31}$ is selected from the group consisting of a direct bond, —O—, —N($R^{30}$)—, —C(O)—, —O—C(O)—, —C(O)—O—, —N($R^{30}$)—C(O)—, —C(O)—N($R^{30}$)—, —N($R^{30}$)—C(S)—, —C(S)—N($R^{30}$)—, —N($R^{30}$)—C(O)—N($R^{31}$)—, —N($R^{30}$)—C(N$R^{30}$)—N($R^{31}$)—, —N($R^{30}$)—C(NR$^3$)—, —C(N$R^{31}$)—N($R^{30}$)—, —N($R^{30}$)—C(S)—N($R^{31}$)—, —N($R^{30}$)—C(O)—O—, —O—C(O)—N($R^{31}$)—, —N($R^{30}$)—C(S)—O—, —O—C(S)—N($R^{31}$)—, —S(O)$_{0-2}$—, —SO$_2$N($R^{31}$)—, —N($R^{31}$)—SO$_2$— and —N($R^{30}$)—SO$_2$N($R^{31}$)—.

A moiety that is substituted is one in which one or more (for example one to four, alternatively from one to three and alternatively one or two), hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted n-octyls include 2,4-dimethyl-5-ethyl-octyl and 3-cyclopentyl-octyl. Included within this definition are methylenes (—CH$_2$—) substituted with oxygen to form carbonyl —CO—.

When there are two optional substituents bonded to adjacent atoms of a ring structure, such as for example a phenyl, thiophenyl, or pyridinyl, the substituents, together with the atoms to which they are bonded, optionally form a 5- or 6-membered cycloalkyl or heterocycle having 1, 2, or 3 annular heteroatoms.

In one embodiment, a hydrocarbyl, heteroalkyl, heterocyclic and/or aryl group is unsubstituted.

In another embodiment, a hydrocarbyl, heteroalkyl, heterocyclic and/or aryl group is substituted with from 1 to 3 independently selected substituents.

Examples of substituents on alkyl groups include, but are not limited to hydroxyl, halogen (e.g., a single halogen substituent or multiple halo substituents; in the latter case, groups such as $CF_3$ or an alkyl group bearing $Cl_3$), oxo, cyano, nitro, alkyl, cycloalkyl, alkenyl, cycloalkenyl, alkynyl, heterocycle, aryl, —$OR^a$, —$SR^a$, —$S(═O)R^e$, —$S(═O)_2R^e$, —$P(═O)_2R^e$, —$S(═O)_2OR^e$, $P(═O)_2OR^e$, $NR^bR^c$, —$NR^bS(═O)_2R^e$, —$NR^bP(═O)_2R^e$, —$S(═O)_2NR^bR^c$, —$P(═O)_2NR^bR^c$, —$C(═O)OR^e$, —$C(═O)R^a$, —$C(═O)NR^bR^c$, —$OC(═O)R^a$, —$OC(═O)NR^bR^c$, —$NR^bC(═O)OR^e$, —$NR^dC(═O)NR^bR^c$, —$NR^dS(═O)_2NR^bR^c$, —$NR^dP(═O)_2NR^bR^c$, —$NR^bC(═O)R^a$ or —$NR^bP(═O)_2R^e$, wherein $R^a$ is hydrogen, alkyl, cycloalkyl, alkenyl, cycloalkenyl, alkynyl, heterocycle or aryl; $R^b$, $R^c$ and $R^d$ are independently hydrogen, alkyl, cycloalkyl, heterocycle or aryl, or said $R^b$ and $R^c$ together with the N to which they are bonded optionally form a heterocycle; and $R^e$ is alkyl, cycloalkyl, alkenyl, cycloalkenyl, alkynyl, heterocycle or aryl. In the aforementioned exemplary substituents, groups such as alkyl, cycloalkyl, alkenyl, alkynyl, cycloalkenyl, heterocycle and aryl can themselves be optionally substituted.

Examples of substituents on alkenyl and alkenyl groups include, but are not limited to, alkyl or substituted alkyl, as well as those groups recited as examples of alkyl substituents.

Examples of substituents on cycloalkyl groups include, but are not limited to, nitro, cyano, alkyl or substituted alkyl, as well as those groups recited above as examples of alkyl substituents. Other examples of substituents include, but are not limited to, spiro-attached or fused cyclic substituents, for example spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on cycloalkenyl groups include, but are not limited to, nitro, cyano, alkyl or substituted alkyl, as well as those groups recited as examples of alkyl substituents. Other examples of substituents include, but are not limited to, spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents can themselves be optionally substituted.

Examples of substituents on aryl groups include, but are not limited to, nitro, cycloalkyl or substituted cycloalkyl, cycloalkenyl or substituted cycloalkenyl, cyano, alkyl or substituted alkyl, as well as those groups recited above as examples of alkyl substituents. Other examples of substituents include, but are not limited to, fused cyclic groups, especially fused cycloalkyl, fused cycloalkenyl, fused heterocycle, or fused aryl, where the aforementioned cycloalkyl, cylcoalkenyl, heterocycle and aryl substituents can themselves be optionally substituted. Still other examples of substituents on aryl groups (phenyl, as a non-limiting example) include, but are not limited to, haloalkyl and those groups recited as examples of alkyl substituents.

Examples of substituents on heterocylic groups include, but are not limited to, cycloalkyl, substituted cycloalkyl, cycloalkenyl, substituted cycloalkenyl, nitro, oxo (i.e., =O), cyano, alkyl, substituted alkyl, as well as those groups recited as examples of alkyl substituents. Other examples of substituents on heterocyclic groups include, but are not limited to, spiro-attached or fused cylic substituents at any available point or points of attachment, for example spiro-attached cycloalkyl, spiro-attached cycloalkenyl, spiro-attached heterocycle (excluding heteroaryl), fused cycloalkyl, fused cycloakenyl, fused heterocycle and fused aryl, where the aforementioned cycloalkyl, cycloalkenyl, heterocycle and aryl substituents can themselves be optionally substituted.

In certain embodiments, a heterocyclic group is substituted on carbon, nitrogen and/or sulfur at one or more positions. Examples of substituents on nitrogen include, but are not limited to alkyl, aryl, aralkyl, alkylcarbonyl, alkylsulfonyl, arylcarbonyl, arylsulfonyl, alkoxycarbonyl, or aralkoxycarbonyl. Examples of substituents on sulfur include, but are not limited to, oxo and $C_{1-6}$alkyl. In certain embodiments, nitrogen and sulfur heteroatoms may independently be optionally oxidized and nitrogen heteroatoms may independently be optionally quaternized.

In other embodiments, substituents on ring groups, such as aryl, heteroaryl, cycloalkyl and heterocyclyl, include halogen, alkoxy and alkyl.

In other embodiments, substituents on alkyl groups include halogen and hydroxy.

A "halohydrocarbyl" as employed herein is a hydrocarbyl moiety, in which from one to all hydrogens have been replaced with halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, dialkylamino (wherein the alkyl groups are independently selected) arylamino, and cyclic amino groups. The term "ureido" as employed herein refers to a substituted or unsubstituted urea moiety.

The term "radical" as used herein means a chemical moiety comprising one or more unpaired electrons.

Where optional substituents are chosen from "one or more" groups it is to be understood that this definition includes all substituents being chosen from one of the specified groups or the substituents being chosen from two or more of the specified groups.

In addition, substituents on cyclic moieties (i.e., cycloalkyl, heterocyclyl, aryl, heteroaryl) include 5- to 6-membered mono- and 9- to 14-membered bi-cyclic moieties fused to the parent cyclic moiety to form a bi- or tri-cyclic fused ring system. Substituents on cyclic moieties also include 5- to 6-membered mono- and 9- to 14-membered bi-cyclic moieties attached to the parent cyclic moiety by a covalent bond to form a bi- or tri-cyclic bi-ring system. For example, an optionally substituted phenyl includes, but is not limited to, the following:

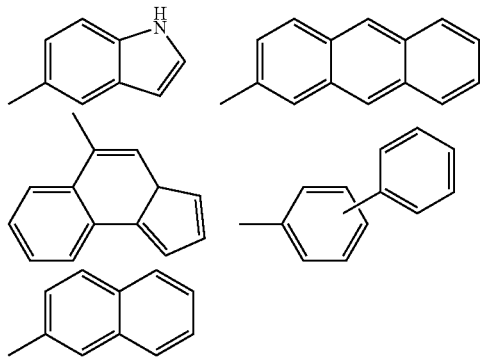

An "unsubstituted" moiety (e.g., unsubstituted cycloalkyl, unsubstituted heteroaryl, etc.) means a moiety as defined above that does not have any optional substituents.

A saturated or unsaturated three- to eight-membered carbocyclic ring is for example a four- to seven-membered, alternatively five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

A saturated or unsaturated three- to eight-membered heterocyclic ring contains at least one heteroatom selected from oxygen, nitrogen, and sulfur atoms. The saturated or unsaturated three- to eight-membered heterocyclic ring for example contains one or two heteroatoms with the remaining ring-constituting atoms being carbon atoms. The saturated or unsaturated three- to eight-membered heterocyclic ring is for example a saturated or unsaturated four- to seven-membered heterocyclic ring, alternatively a saturated or unsaturated five- or six-membered heterocyclic ring. Examples of saturated or unsaturated three- to eight-membered heterocyclic groups include thienyl, pyridyl, 1,2,3-triazolyl, imidazolyl, isoxazolyl, pyrazolyl, piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

A saturated or unsaturated carboxylic and heterocyclic group may condense with another saturated or heterocyclic group to form a bicyclic group, for example a saturated or unsaturated nine- to twelve-membered bicyclic carbocyclic or heterocyclic group. Bicyclic groups include naphthyl, quinolyl, 1,2,3,4-tetrahydroquinolyl, 1,4-benzoxanyl, indanyl, indolyl, and 1,2,3,4-tetrahydronaphthyl.

When a carbocyclic or heterocyclic group is substituted by two alkyl groups, the two alkyl groups may combine together to form an alkylene chain, for example a $C_{1-3}$ alkylene chain. Carbocyclic or heterocyclic groups having this crosslinked structure include bicyclo[2.2.2]octanyl and norbornanyl.

Throughout the specification, particular embodiments of one or more chemical substituents are identified. Also encompassed are combinations of particular embodiments. For example, the invention describes particular embodiments of D in the compounds and describes particular embodiments of group G. Thus, as an example, also contemplated as within the scope of the invention are compounds in which particular examples of D are as described and in which particular examples of group G are as described.

In one embodiment, the invention provides a process and intermediates for preparing a compound having the Formula (A)

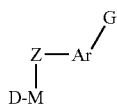

(A)

and N-oxides, hydrates, solvates, pharmaceutically acceptable salts, prodrugs and complexes thereof, and racemic and scalemic mixtures, diastereomers, tautomers and enantiomers thereof, wherein, D is selected from the group consisting of an aromatic, heteroaromatic, cycloalkyl or heterocyclic ring system, each of which is optionally substituted with 1 to 5 independently selected $R^{38}$;

M is an optionally substituted fused heterocyclic moiety;

Z is selected from the group consisting of covalent bond, —O—, —O—CH$_2$—, —CH$_2$—O—, —S(O)$_{0-2}$—, —CH$_2$—, —N(R$^5$)—, —N(R$^5$)—CH$_2$— and —CH$_2$—N(R$^5$)—;

Ar is a 5 to 7 membered cycloalkyl, aromatic, heterocyclic or heteroaromatic ring system, any of which is optionally substituted with 0 to 4 $R^2$ groups; and G is a group B-L-T, wherein B is selected from the group consisting of absent, —N(R$^3$)—, —N(SO$_2$R$^{13}$)—, —O—, —S(O)$_{0-2}$ and —C(=O)—;

L is selected from the group consisting of absent, —C(=S)N(R$^{13}$)—, —C(=NR$^{14}$)N(R$^{13}$)—, —SO$_2$N(R$^{13}$)—, —SO$_2$—, —C(=O)N(R$^{13}$)—, —N(R$^{13}$)—, —C(=O)C$_{1-2}$alkyl-N(R$^{13}$)—, —N(R$^{13}$)C$_{1-2}$alkyl-C(=O)—, —C(=O)C$_{0-1}$ alkyl-C(=O)N(R$^{13}$)—, —C$_{0-4}$alkylene, —C(=O)C$_{0-1}$alkyl-C(=O)OR$^3$—, —C(=NR$^{14}$)—C$_{0-1}$alkyl-C(=O)—, —C(=O)—, —C(=O)C$_{0-1}$alkyl-C(=O)— and an optionally substituted four to six-membered heterocyclyl containing between one and three annular heteroatoms including at least one nitrogen, wherein an alkyl group of the aforementioned L group is optionally substituted; and T is selected from the group consisting of —H, —R$^{13}$, —C$_{0-5}$alkyl, —C$_{0-5}$alkyl-Q, —O—C$_{0-5}$alkyl-Q, —C$_{0-5}$alkyl-O-Q, —N(R$^{13}$)—C$_{0-5}$alkyl-Q, —C$_{0-5}$alkyl-SO$_2$—C$_{0-5}$alkyl-Q, —C(=O)—C$_{0-5}$alkyl-Q, —C(=S)—C$_{0-5}$-alkyl-Q, —C(=NR$^{14}$)—C$_{0-5}$-alkyl-Q, —C$_{0-5}$alkyl-N(R$^{13}$)-Q, —C(=O)—N(R$^{13}$)—C$_{0-5}$alkyl-Q, —C(=S)—N(R$^{13}$)—C$_{0-5}$alkyl-Q, —C(=NR$^{14}$)—N(R$^{13}$)—C$_{0-5}$alkyl-Q, —(C$_{0-5}$alkyl-C(O))$_{0-1}$—C$_{0-5}$alkyl-Q wherein each C$_{0-5}$alkyl is optionally substituted;

or G is a group

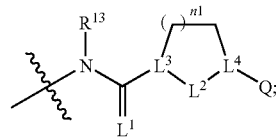

or G is selected from the group consisting of:

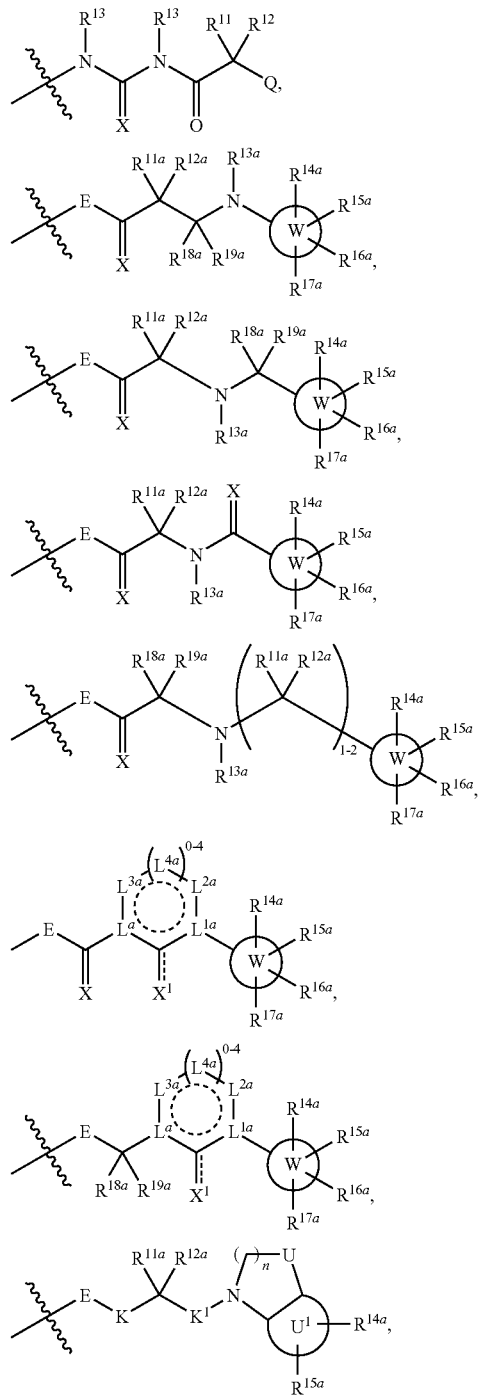

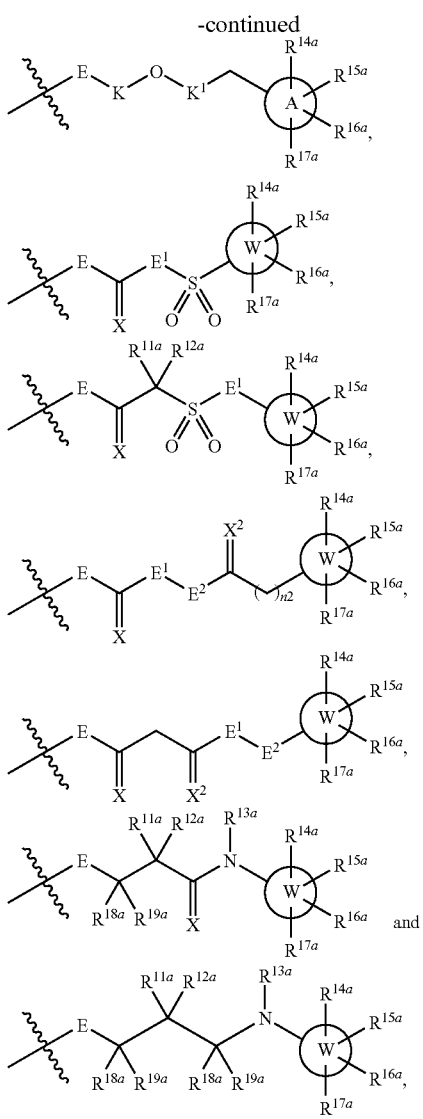

wherein
each $R^{38}$ is independently selected from halo, cyano, nitro, trifluoromethoxy, trifluoromethyl, azido, —C(O)$R^{40}$, —C(O)O$R^{40}$, —OC(O)$R^{40}$, —OC(O)O$R^{40}$, —N$R^{36}$C(O)$R^{39}$, —C(O)N$R^{36}R^{39}$, —N$R^{36}R^{39}$, —O$R^{37}$, —SO$_2$N$R^{36}R^{39}$, C$_1$-C$_6$ alkyl, (C$_3$-C$_{10}$)cycloalkyl, —(CH$_2$)$_j$O(CH$_2$)$_i$N$R^{36}R^{39}$, —(CH$_2$)$_n$O(CH$_2$)$_i$O$R^{37}$, —(CH$_2$)$_n$O$R^{37}$, —S(O)$_j$(C$_1$-C$_6$ alkyl), —(CH$_2$)$_n$(C$_6$-C$_{10}$ aryl), —(CH$_2$)$_n$(5-10 membered heterocyclyl), —C(O)(CH$_2$)$_n$(C$_6$-C$_{10}$ aryl), —(CH$_2$)$_n$O(CH$_2$)$_j$(C$_6$-C$_{10}$ aryl), —(CH$_2$)$_n$O(CH$_2$)$_i$(5-10 membered heterocyclyl), —C(O)(CH$_2$)$_n$(5-10 membered heterocyclyl), —(CH$_2$)$_n$N$R^{39}$(CH$_2$)$_i$N$R^{36}R^{39}$, —(CH$_2$)$_n$N$R^{39}$CH$_2$C(O)N$R^{36}R^{39}$, —(CH$_2$)$_n$N$R^{39}$(CH$_2$)$_i$N$R^{37}$C(O)$R^{40}$, —(CH$_2$)$_n$N$R^{39}$(CH$_2$)$_n$O (CH$_2$)$_i$O$R^{37}$, —(CH$_2$)$_n$N$R^{39}$(CH$_2$)$_i$S(O)$_j$(C$_1$-C$_6$ alkyl), —(CH$_2$)$_n$N$R^{39}$(CH$_2$)$_i$NHSO$_2$(C$_1$-C$_6$ alkyl), —(CH$_2$)$_n$N$R^{39}$(CH$_2$)$_i$SO$_2$NH(C$_1$-C$_6$ alkyl), —(CH$_2$)$_n$N$R^{39}$(CH$_2$)$_n$R$^{36}$, —SO$_2$(CH$_2$)$_n$(C$_6$-C$_{10}$ aryl), —SO$_2$(CH$_2$)$_n$(5-10 membered heterocyclyl), —(CH$_2$)$_n$N$R^{36}R^{39}$, —N$R^{37}$SO$_2$N$R^{36}R^{39}$, SO$_2R^{36}$, C$_2$-C$_6$alkenyl, C$_3$-C$_{10}$cycloalkyl and C$_1$-C$_6$alkylamino, wherein each j is an integer independently ranging from 0 to 4, n is an integer ranging from 0 to 6, i is an integer ranging from 2 to 6, the —(CH$_2$)$_i$—, —(CH$_2$)$_j$— and —(CH$_2$)$_n$— moieties of the foregoing $R^{38}$ groups optionally include a carbon-carbon double or triple bond where i, j, and n are an integer between 2 and 6, and the alkyl, aryl and heterocyclyl moieties of the foregoing $R^{38}$ groups are optionally substituted by one or more substituents independently selected from halo, cyano, nitro, trifluoromethyl, azido, —OH, —C(O)$R^{40}$, —C(O)O$R^{40}$, —OC(O)$R^{40}$, —OC(O)O$R^{40}$, —N$R^6$C(O)$R^{39}$, —C(O)N$R^{36}R^{39}$, —(CH$_2$)N$R^{36}R^{39}$, C$_1$-C$_6$alkyl, C$_3$-C$_{10}$cycloalkyl, —(CH$_2$)$_n$(C$_6$-C$_{10}$aryl), —(CH$_2$)$_n$(5-10 membered heterocyclyl), —(CH$_2$)$_n$—O—(CH$_2$)$_i$O$R^3$, and —(CH$_2$)$_n$O$R^{37}$;

$R^{36}$ is selected from the group consisting of H, —OH, C$_1$-C$_6$alkyl, C$_3$-C$_{10}$cycloalkyl, —(CH$_2$)$_n$(C$_6$-C$_{10}$aryl), —(CH$_2$)$_n$(5-10 membered heterocyclyl), —(CH$_2$)$_n$—O—(CH$_2$)$_i$O$R^{37}$, —(CH$_2$)$_n$CN(CH$_2$)$_n$O$R^{37}$, —(CH$_2$)$_n$CN (CH$_2$)$_n$R$^{37}$ and —(CH$_2$)$_n$A$^4R^{37}$, wherein each n is an integer independently ranging from 0 to 6, i is an integer ranging from 2 to 6, A$^4$ is selected from the group consisting of O, S, SO, SO$_2$, NH and N(optionally substituted C$_1$-C$_4$alkyl), and the alkyl, aryl and heterocyclyl moieties of the foregoing $R^{36}$ groups are optionally substituted by one or more substituents independently selected from —OH, halo, cyano, nitro, trifluoromethyl, azido, —C(O)$R^{40}$, —C(O)O$R^{40}$, —CO(O)$R^{40}$, —OC(O)O$R^{40}$, —N$R^{37}$C(O)$R^{41}$, —C(O)N$R^{37}R^{41}$, —N$R^{37}R^{41}$, —C$_1$-C$_6$alkyl, —(CH$_2$)$_n$(C$_6$-C$_{10}$aryl), —(CH$_2$)$_n$(5 to 10 membered heterocyclyl), —(CH$_2$)$_n$—O—(CH$_2$)$_i$O$R^{37}$, and —(CH$_2$)$_n$O$R^{37}$, with the proviso that when $R^{36}$ and $R^{39}$ are both attached to the same nitrogen, then $R^{36}$ and $R^{39}$ are not both bonded to the nitrogen directly through an oxygen;

each $R^{37}$ and $R^{41}$ is independently selected from H, —O—C$_1$-C$_6$alkyl, —O—C$_3$-C$_{10}$cycloalkyl, —O—(CH$_2$)$_n$(C$_6$-C$_{10}$aryl), —O—(CH$_2$)$_n$(5-10 membered heterocyclyl), optionally substituted C$_1$-C$_6$alkyl, optionally substituted C$_2$-C$_6$alkenyl, optionally substituted C$_2$-C$_6$alkynyl, optionally substituted C$_3$-C$_{10}$cycloalkyl, optionally substituted —O—(CH$_2$)$_n$A$^4$-C$_1$-C$_6$alkyl, optionally substituted —O—(CH$_2$)$_n$A$^4$-C$_2$-C$_6$alkenyl, optionally substituted —O—(CH$_2$)$_n$A$^4$-C$_2$-C$_6$alkynyl and optionally substituted —O—(CH$_2$)$_n$A$^4$-C$_3$-C$_{10}$cyclaoalkyl;

$R^{39}$ is selected from the group consisting of H, —OH, C$_1$-C$_6$alkyl, C$_3$-C$_{10}$cycloalkyl, —(CH$_2$)$_n$(C$_6$-C$_{10}$aryl), —(CH$_2$)$_n$(5-10 membered heterocyclyl), —(CH$_2$)$_n$O (CH$_2$)$_i$O$R^{37}$, —(CH$_2$)$_n$CN(CH$_2$)$_n$O$R^{37}$, —(CH$_2$)$_n$CN (CH$_2$)$_n$R$^{37}$, —(CH$_2$)$_n$O$R^{37}$, —NMe$_2$, —NHMe, —NEt$_2$, —SO$_2$—C$_1$-C$_6$alkyl, and a protecting group used to protect secondary amino groups, wherein n is an integer ranging from 0 to 6, and the alkyl, aryl and heterocyclyl moieties of the foregoing $R^{39}$ groups are optionally substituted by one or more substituents independently selected from —OH, halo, cyano, nitro, trifluoromethyl, azido, —C(O)$R^{40}$, —C(O)O$R^{40}$, —CO(O)$R^{40}$, —OC(O)O$R^{40}$, —N$R^{37}$C(O)$R^{41}$, —C(O)N$R^{37}R^{41}$, —N$R^{37}R^{41}$, —C$_1$-C$_6$alkyl, —(CH$_2$)$_n$(C$_6$-C$_{10}$aryl), —(CH$_2$)$_n$(5 to 10 membered heterocyclyl), —(CH$_2$)$_n$—O—(CH$_2$)$_i$O$R^{37}$, and —(CH$_2$)$_n$O$R^{37}$, with the proviso that when $R^{36}$ and $R^{39}$ are both attached to the same nitrogen, then $R^{36}$ and $R^{39}$ are not both bonded to the nitrogen directly through an oxygen;

$R^z$ is selected from the group consisting of H, C$_1$-C$_6$alkyl, C$_1$-C$_6$cycloalkyl, C$_1$-C$_6$heterocyclyl and aryl (for example benzyl and C$_5$-C$_6$heterocycle);

each $R^{40}$ is independently selected from H, C$_1$-C$_{10}$alkyl, —(CH$_2$)$_n$(C$_6$-C$_{10}$aryl), C$_3$-C$_{10}$cycloalkyl, and —(CH$_2$)$_n$(5-10 membered heterocyclyl), wherein n is an integer ranging from 0 to 6;

$R^5$ is selected from the group consisting of H, an optionally substituted (C$_1$-C$_5$)acyl and C$_1$-C$_6$alkyl-O—C(O), wherein C$_1$-C$_6$alkyl is optionally substituted;

$R^2$ at each occurrence is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, C(O)NR$^3$R$^3$, —N(R$^3$)SO$_2$R$^3$, —N(R$^3$)C(O)R$^3$, —N(R$^3$)CO$_2$R$^3$, —C(O)R$^3$, C$_1$-C$_4$alkoxy, C$_1$-C$_4$alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), C$_1$-C$_6$alkyl, C$_2$-C$_6$alkenyl, C$_2$-C$_6$alkynyl, —CH$_2$(CH$_2$)$_{0-4}$-T$^2$, wherein the aryl, heteroaryl, C$_1$-C$_6$alkyl, C$_2$-C$_6$alkenyl, and C$_2$-C$_6$alkynyl are optionally substituted;

T$^2$ is selected from the group consisting of —OH, —OMe, —OEt, —NH$_2$, —NHMe, —NMe$_2$, —NHEt and —NEt$_2$;

each R$^3$ is independently selected from the group consisting of —H and R$^4$;

R$^4$ is selected from the group consisting of a (C$_1$-C$_6$)alkyl, an aryl, a lower arylalkyl, a heterocyclyl and a lower heterocyclylalkyl, each of which is optionally substituted, or R$^3$ and R$^4$, taken together with a common nitrogen to which they are attached, form an optionally substituted five- to seven-membered heterocyclyl, the optionally substituted five- to seven-membered heterocyclyl optionally containing at least one additional annular heteroatom selected from the group consisting of N, O, S and P;

each R$^{13}$ is independently selected from the group consisting of —H, halogen, trihalomethyl, —CN, —NO$_2$, —NH$_2$, —OR$^3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, —C(O)SR$^3$, C$_1$-C$_4$alkoxy, C$_1$-C$_4$alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), —(CH$_2$)$_{0-5}$(cycloalkyl), C$_1$-C$_6$alkyl, C$_2$-C$_6$alkenyl, C$_2$-C$_6$alkynyl, —CH$_2$(CH$_2$)$_{0-4}$-T$^2$, an optionally substituted C$_{1-4}$alkylcarbonyl, and a saturated or unsaturated three- to seven-membered carboxyclic or heterocyclic group, wherein the aryl, heteroaryl, C$_1$-C$_6$alkyl, C$_2$-C$_6$alkenyl, and C$_2$-C$_6$alkynyl are optionally substituted; or two R$^{13}$, together with the atom or atoms to which they are attached, can combine to form a heteroalicyclic optionally substituted with between one and four of R$^{60}$, wherein the heteroalicyclic can have up to four annular heteroatoms, and the heteroalicyclic can have an aryl or heteroaryl fused thereto, in which case the aryl or heteroaryl is optionally substituted with an additional one to four of R$^{60}$;

R$^{14}$ is selected from the group —H, —NO$_2$, —NH$_2$, —N(R$^3$)R$^4$, —CN, —OR$^3$, an optionally substituted (C$_1$-C$_6$) alkyl, an optionally substituted heteroalicyclylalkyl, an optionally substituted aryl, an optionally substituted arylalkyl and an optionally substituted heteroalicyclic, R$^{60}$ is selected from the group consisting of —H, halogen, trihalomethyl, —CN, —NO$_2$, —NH$_2$, —OR$^3$, —NR$^3$R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted (C$_1$-C$_6$)alkyl, an optionally substituted aryl, an optionally substituted heteroarylalkyl and an optionally substituted arylalkyl; or two R$^{60}$, when attached to a non-aromatic carbon, can be oxo;

Q is a five- to ten-membered ring system, optionally substituted with between zero and four of R$^{20}$;

each R$^{20}$ is independently selected from the group consisting of —H, halogen, trihalomethyl, —O-trihalomethyl, oxo, —CN, —NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$—C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, C$_1$-C$_4$alkoxy, C$_1$-C$_4$alkylthio, —O(CH$_2$)$_{0-6}$aryl, —O(CH$_2$)$_{0-6}$heteroaryl, —(CH$_2$)$_{0-5}$(aryl), —(CH$_2$)$_{0-5}$(heteroaryl), C$_1$-C$_6$alkyl, C$_2$-C$_6$alkenyl, C$_2$-C$_6$alkynyl, —CH$_2$(CH$_2$)$_{0-4}$-T$^2$, an optionally substituted C$_{1-4}$alkylcarbonyl, C$_{1-4}$alkoxy, an amino optionally substituted by C$_{1-4}$alkyl optionally substituted by C$_{1-4}$alkoxy and a saturated or unsaturated three- to seven-membered carboxyclic or heterocyclic group and wherein the aryl, heteroaryl, C$_1$-C$_6$alkyl, C$_2$-C$_6$alkenyl, and C$_2$-C$_6$alkynyl are optionally substituted, wherein the aryl, heteroaryl, C$_1$-C$_6$alkyl, C$_2$-C$_6$alkenyl, and C$_2$-C$_6$alkynyl are optionally substituted;

L$^1$ is selected from the group consisting of O, S and N(R$^{14}$);
L$^2$ is selected from the group consisting of —C(O)—, —C(S)—, —C(NH)—, >C=N(C$_1$-C$_6$ alkyl) and —CH$_2$—;
L$^3$ is selected from the group consisting of —CH—, —C(C$_1$-C$_6$alkyl)- and N;
L$^4$ is selected from the group consisting of —CH— and N;
n1 is an integer from 0 to 5;

each X is independently selected from the group consisting of O, S, NH, N-alkyl, N—OH, N—O— alkyl and NCN;

R$^{11}$ and R$^{12}$ are independently selected from the group consisting of H, C$_1$-C$_6$alkyl, halo, cyano and nitro, wherein the alkyl is optionally substituted; or R$^{11}$ and R$^{12}$, taken together with the atom to which they are attached, form a C$_3$-C$_7$cycloalkyl;

E is selected from the group consisting of O, S, —CH$_2$—, —CH(C$_1$-C$_6$alkyl), —N(H)—, —N(C$_1$-C$_6$alkyl)-, —CH$_2$N (H)— and —N(H)CH$_2$—;

R$^{11a}$ and R$^{12a}$ are independently selected from the group consisting of H, halogen, —OH, unsubstituted —O—(C$_1$-C$_6$alkyl), substituted —O—(C$_1$-C$_6$alkyl), unsubstituted —O-(cycloalkyl), substituted —O-(cycloalkyl), unsubstituted —NH(C$_1$-C$_6$alkyl), substituted —NH(C$_1$-C$_6$alkyl), —NH$_2$, —SH, unsubstituted —S—(C$_1$-C$_6$alkyl), substituted —S—(C$_1$-C$_6$alkyl), unsubstituted C$_1$-C$_6$alkyl and substituted C$_1$-C$_6$alkyl; or R$^{11a}$ and R$^{12a}$ taken together with the atom to which they are attached form a C$_3$-C$_7$ ring system, wherein said ring system is optionally substituted;

each R$^{13a}$ is independently selected from the group consisting of H, C$_1$-C$_6$alkyl, substituted C$_1$-C$_6$alkyl, cycloalkyl, substituted cycloalkyl, OH, unsubstituted —O—(C$_1$-C$_6$alkyl), substituted —O—(C$_1$-C$_6$alkyl); or R$^{12a}$ and R$^{13a}$ taken together with the atoms to which they are attached optionally form a 4 to 8 membered cycloalkyl or heterocyclic ring system, which ring system is optionally substituted;

R$^{14a}$, R$^{15a}$, R$^{16a}$ and R$^{17a}$ are independently selected from the group consisting of —H, halogen, trihalomethyl, —O-trihalomethyl, —CN$_1$—NO$_2$, —NH$_2$, —OR$^3$, —OCF$_3$, —NR$^3$R$^4$, —S(O)$_{0-2}$R$^3$, —S(O)$_2$NR$^3$R$^3$, —C(O)OR$^3$, —C(O)NR$^3$R$^3$, —N(R$^3$)SO$_2$R$^3$, —N(R$^3$)C(O)R$^3$, —N(R$^3$)C(O)OR$^3$, —C(O)R$^3$, —C(O)SR$^3$, C$_1$-C$_4$alkoxy, C$_1$-C$_4$alkylthio, —O(CH$_2$)$_n$aryl, —O(CH$_2$) heteroaryl, —(CH$_2$)$_{0-5}$(aryl), —(CH$_2$)$_{0-5}$(heteroaryl), C$_1$-C$_6$alkyl, C$_2$-C$_6$alkenyl, C$_2$-C$_6$alkynyl, —CH$_2$(CH$_2$)$_{0-4}$-T 2, an optionally substituted C$_{1-4}$alkylcarbonyl, C$_{1-4}$alkoxy, an amino optionally substituted by C$_{1-4}$alkyl optionally substituted by C$_{1-4}$alkoxy and a saturated or unsaturated three- to seven-membered carboxyclic or heterocyclic group, wherein n is an integer ranging from 0 to 6, and the aryl, heteroaryl, C$_1$-C$_6$alkyl, C$_2$-C$_6$alkenyl, and C$_2$-C$_6$alkynyl are optionally substituted; or R$^{13a}$ and R$^{14a}$ taken together with the atoms to which they are attached optionally form a 4 to 8 membered cycloalkyl or heterocyclic ring system, which ring system is optionally substituted;

R$^{18a}$ and R$^{19a}$ are independently selected from the group consisting of H, OH, halogen, NO$_2$, unsubstituted —O—(C$_1$-C$_6$alkyl), substituted —O—(C$_1$-C$_6$alkyl), CH$_3$, CH$_2$F, CHF$_2$, $CF_3$, CN, $C_1$-$C_6$alkyl, substituted $C_1$-$C_6$alkyl, partially fluorinated $C_1$-$C_6$alkyl, per-fluorinated $C_1$-$C_6$alkyl, heteroalkyl, substituted heteroalkyl and —$SO_2$($C_1$-$C_6$alkyl); or $R^{18a}$ and $R^{19a}$ together with the atom to which they are attached form a 3 to 6 membered cycloalkyl or heterocycle, each of which is optionally substituted with 1 to 4 halo, for example F;

W is selected from the group consisting of H, alkyl, alkenyl, alkynyl, —$(CH_2)_{0-5}$(five- to ten-membered cycloalkyl), —$(CH_2)_{0-5}$(aryl), —$(CH_2)_{0-5}$(heterocylic) and —$(CH_2)_{0-5}$(heteroaryl), each of which is optionally substituted; and ⚏ is a single or double bond;

$X^1$ is selected from the group consisting of O, S, $CH_2$, N—CN, N—O-alkyl, NH and N($C_1$-$C_6$alkyl) when ⚏ is a double bond, or $X^1$ is selected from the group consisting of H, halogen, alkyl, alkenyl, alkynyl, CN, alkoxy, NH(alkyl) and alkyl-thio, when ⚏ is a single bond;

$L^a$ and $L^{1a}$ are independently selected from the group consisting of —CH—, —N—, —C(halogen)- and —C($C_1$-$C_6$alkyl)-;

$L^{2a}$ and $L^{3a}$ are independently selected from the group consisting of CH, $CH_2$, N, O and S;

$L^4a$ is selected from the group consisting of absent, CH, $CH_2$, N, O and S; and the group

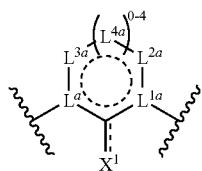

is aromatic or non-aromatic, provided that two O are not adjacent to each other;

K and $K^1$ are independently selected from the group consisting of —C(O)—, —C(S)—, —C(NH)—, —C(NCN)— and —C($R^{18a}R^{19a}$)—;

U is selected from the group consisting of O, S, $SO_2$, NH, and N($C_1$-$C_6$alkyl), wherein the $C_1$-$C_6$alkyl is optionally substituted with a substituent selected from the group consisting of —OH, -alkoxy, amino, NH($C_1$-$C_6$alkyl), N($C_1$-$C_6$alkyl)$_2$,

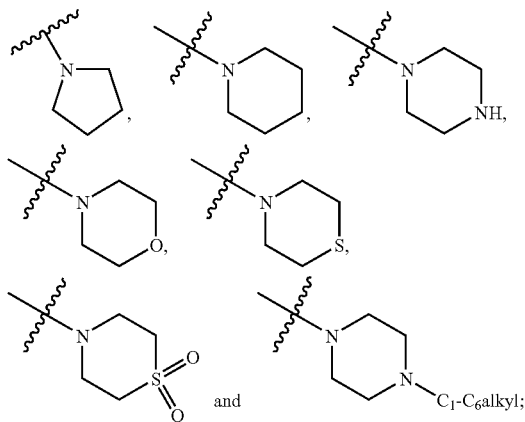

$U^1$ is a ring system selected from the group consisting of cycloalkyl, substituted cycloalkyl, heterocyclyl, substituted heterocyclyl, aryl, substituted aryl, heteroaryl and substituted heteroaryl;

$E^1$ is selected from the group consisting of —N(H)—, —N($C_1$-$C_6$alkyl)-, —$CH_2$N(H)— and —N(H)$CH_2$—;

$E^2$ is selected from the group consisting of —N(H)—, —N($C_1$-$C_6$alkyl)-, —$CH_2$N(H)— and —N(H)$CH_2$—;

$X^2$ is selected from the group consisting of O, S, NH, NOH, NOMe, NOEt and NCN; and $n^2$ is 0, 1, 2, 3 or 4;

the process comprising reacting a compound represented by the Formula (A-1)

wherein $RG^1$ is a reactive group (for example, selected from the group consisting of nitro, —$NH_2$, —NH—$C_1$-$C_4$alkyl-, —NH—$C_2$-$C_4$alkenyl, —NH—$C_2$-$C_4$alkynyl, —NH—$C_3$-$C_6$cycloalkyl, —OH, —SH, —NH—$NH_2$, —NHOH, —N(Me)OH, —N(Me)$NH_2$, —N(Me)—NHMe, —$CH_2NH_2$, and —$CH_2$NHMe);

with a compound represented by the Formula (A-2):

wherein $RG^2$ is a functional group reactive with —$RG^1$, and $RG^2$-$G^1$ is a precursor of group G, such that the reaction of —$RG^1$ with $RG^2$-$G^1$ forms -G; and if $R^{38}$ comprises a protecting group, removing the protecting group.

In an example of the compounds according to Formula (A) D is an aromatic or heteroaromatic ring system, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is substituted with one $R^{38}$ group.

in another example of the compounds according to Formula (A), D is a 5- or 6-membered aromatic or 5- or 6-membered heteroaromatic ring system, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is a 6-membered aromatic or 6-membered heteroaromatic ring system, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is a 6-membered aromatic ring system, optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is a 6-membered heteroaromatic ring system, optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is selected from the group consisting of

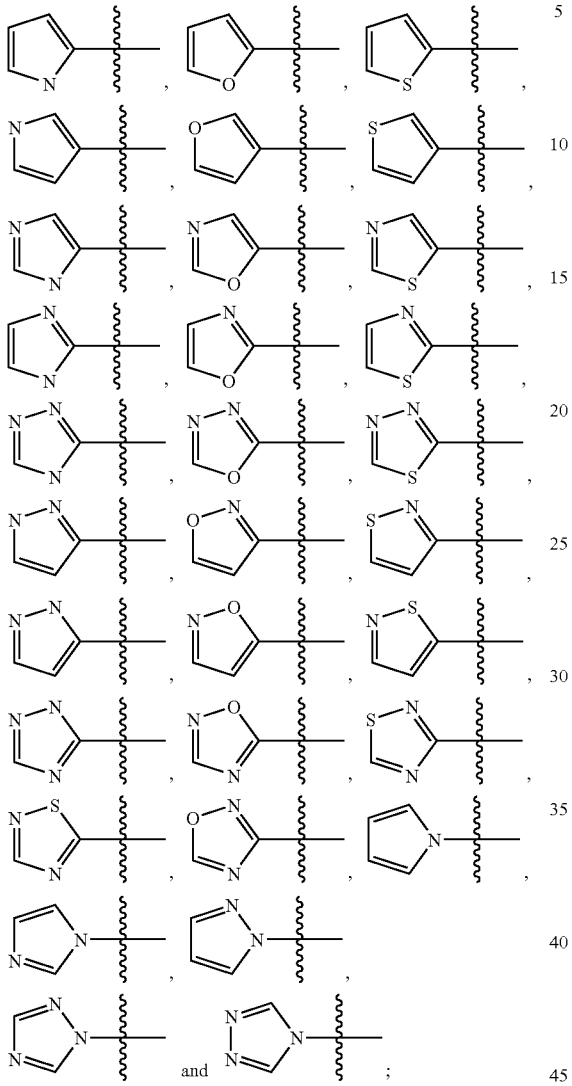

wherein the members of said group are optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is selected from the group consisting of

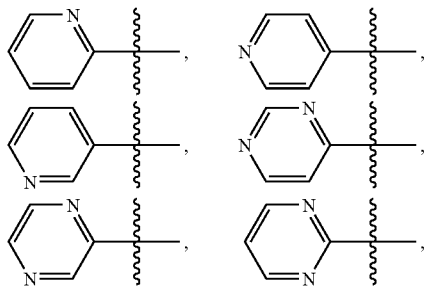

wherein the members of said group are optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is phenyl or pryidinyl, each of which is optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is phenyl, optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is pyridine, optionally substituted with 1 to 5 independently selected $R^{38}$ groups, alternatively 1 to 3 independently selected $R^{38}$ groups, and alternatively 1 or 2 independently selected $R^{38}$ groups.

In another example of the compounds according to Formula (A), D is phenyl, optionally substituted with one $R^{38}$.

In another example of the compounds according to Formula (A), D is pyridine, optionally substituted with one $R^{38}$.

In another example of the compounds according to Formula (A), D is phenyl, substituted with one $R^{38}$.

In another example of the compounds according to Formula (A), D is pyridine, substituted with one $R^{38}$.

In another example of the compounds according to Formula (A), each $R^{38}$ is independently selected from the group consisting of $-(CH_2)_jO(CH_2)_iNR^{36}R^{39}$, $-(CH_2)_nO(CH_2)_iOR^{37}$, $-(CH_2)_nOR^{37}$, $-(CH_2)_n-O-(CH_2)_j(C_6-C_{10}\ aryl)$, $-(CH_2)_nO(CH_2)_i(5\text{-}10\ \text{membered heterocyclyl})$, $-(CH_2)_jNR^{39}(CH_2)_iNR^{36}R^{39}$, $-(CH_2)_jNR^{39}CH_2C(O)NR^{36}R^{39}$, $-(CH_2)_jNR^{39}(CH_2)_iNR^{37}C(O)R^{40}$, $-(CH_2)_jNR^{39}(CH_2)_n-O-(CH_2)_iOR^{37}$, $-(CH_2)_jNR^{39}(CH_2)_iS(O)_j(C_1\text{-}C_6\ \text{alkyl})$, $-(CH_2)_jNR^{39}(CH_2)_iNHSO_2(C_1\text{-}C_6\ \text{alkyl})$, $-(CH_2)_jNR^{39}(CH_2)_iSO_2NH(C_1\text{-}C_6\ \text{alkyl})$, $-(CH_2)_jNR^{39}(CH_2)_nR^{36}$, $-(CH_2)_nNR^{36}R^{39}$ and $-NR^{37}SO_2NR^{36}R^{39}$, alternatively $-(CH_2)_jO$ $(CH_2)_nNR^{36}R^{39}$, $-(CH_2)_nO(CH_2)_iOR^{37}$, $-(CH_2)_jNR^{39}(CH_2)_jNR^{36}R^{39}$, $-(CH_2)_jNR^{39}CH_2C(O)NR^{36}R^{39}$, $-(CH_2)_jNR^{39}(CH_2)_iNR^{37}C(O)R^{40}$, $-(CH_2)_jNR^{39}(CH_2)_nO$ $(CH_2)_iOR^{37}$, $-(CH_2)_jNR^{39}(CH_2)_iS(O)_j(C_1-C_6 \text{ alkyl})$ and $-(CH_2)_jNR^{39}(CH_2)_nR^{36}$, and alternatively $-(CH_2)_jNR^{39}(CH_2)_nR^{36}$.

In another example of the compounds according to Formula (A), $R^{36}$ is selected from the group consisting of H, $-OH$, $C_1-C_6$ alkyl, $-(CH_2)_nO(CH_2)_iOR^{37}$, $-(CH_2)_nCN(CH_2)_nOR^{37}$, $-(CH_2)_nCN(CH_2)_nR^{37}$, and $-(CH_2)_nOR^{37}$, alternatively $-(CH_2)_nOR^{37}$, wherein each n is an integer independently ranging from 0 to 6 (alternatively 0 to 4, alternatively 0 to 2, alternatively 1 or 0, alternatively 0), and i is an integer ranging from 2 to 6.

In another example of the compounds according to Formula (A), each $R^{38}$ is independently $C_1-C_6$alkyl, $-(CH_2)_jNR^{39}(CH_2)_nR^{36}$ or $-(CH_2)_nNR^{36}R^{39}$.

In another example of the compounds according to Formula (A), each $R^{38}$ is independently $-(CH_2)_jNR^{39}(CH_2)_nR^{36}$, wherein j is 1 and n is 2.

In another example of the compounds according to Formula (A), $R^{39}$ is selected from the group consisting of H, $C_1-C_6$alkyl, $C_1-C_6$cycloalkyl, $-OMe$, $-C(O)-C_1-C_6$alkyl, $-C(O)-O-C_1-C_6$alkyl, $-SO_2-C_1-C_6$alkyl, and a protecting group used to protect secondary amino groups.

In another example of the compounds according to Formula (A), $R^{39}$ is a protecting group used to protect secondary amino groups, wherein said protecting group is selected from the group consisting of tert-butoxycarbonyl (Boc), benzyloxycarbonyl (Cbz), F-Moc, $-CH_2Ph$, $-COCF_3$, $-C(O)-R^z$ and $-C(O)O-R^z$.

In another example of the compounds according to Formula (A), $R^{39}$ is H or $C_1-C_6$alkyl, alternatively H.

In another example of the compounds according to Formula (A), $R^{39}$ is selected from the group consisting of

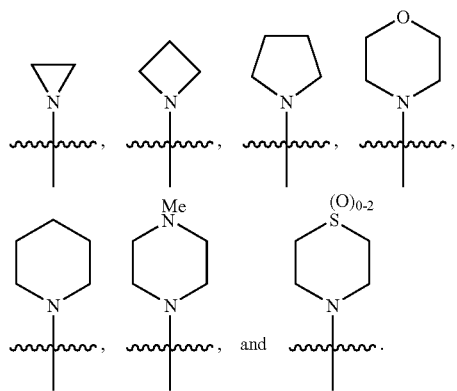

In another embodiment of the present invention, D is optionally substituted with one or two (alternatively one) $R^{38}$, wherein each said $R^{38}$ is independently selected from $C_1-C_6$alkyl, $-(CH_2)_jNR^{39}(CH_2)_nR^{36}$ or $-(CH_2)_nNR^{36}R^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, $-OH$, $C_1-C_6$alkyl, $C_3-C_{10}$cycloalkyl, $-C(O)-R^z$ and $-C(O)-O-R^z$, $-SO_2-C_1-C_6$alkyl, and a protecting group used to protect secondary amino groups (for example tert-butoxycarbonyl (Boc), benzylocycarbonyl (Cbz), F-Moc, $-CH_2Ph$, $-COCF_3$, $-C(O)-R^z$ or $-C(O)O-R^z$), (alternatively $R^{39}$ is H or $C_1-C_6$alkyl, alternatively H), and $R^{36}$ is selected from the group consisting of H, $-OH$, $C_1-C_6$ alkyl, $-(CH_2)_n-O-(CH_2)_iOR^{37}$, $-(CH_2)_nCN(CH_2)_nOR^{37}$, $-(CH_2)_nCN(CH_2)_nR^{37}$, and $-(CH_2)_nOR^{37}$, alternatively $-(CH_2)_nOR^{37}$, wherein each n is an independently selected integer ranging from 0 to 6 (alternatively 0 to 4, alternatively 0 to 2, alternatively 1 or 0, alternatively 0), $R^{37}$ is H, $C_1-C_6$alkyl or $C_3-C_{10}$cycloalkyl (alternatively H or $C_1-C_6$alkyl, alternatively $C_1-C_6$alkyl, alternatively $C_1-C_2$alkyl) and $R^z$ is selected from the group consisting of H, $C_1-C_6$alkyl, $C_1-C_6$cycloalkyl, $C_1-C_6$heterocyclyl and aryl (for example benzyl and $C_5-C_6$heterocycle).

In another example of the compounds according to Formula (A), D is phenyl or pryidinyl (for example pyridinyl), optionally substituted with one or two (for example one) $R^{38}$, wherein each said $R^{38}$ is independently selected from $C_1-C_6$alkyl, $-(CH_2)_jNR^{39}(CH_2)_nR^{36}$ or $-(CH_2)_nNR^{36}R^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, $-OH$, $C_1-C_6$alkyl, $C_3-C_{10}$cycloalkyl, $-C(O)-R^z$ and $-C(O)-O-R^z$, $-SO_2-C_1-C_6$alkyl, and a protecting group used to protect secondary amino groups (for example tert-butoxycarbonyl (Boc), benzylocycarbonyl (Cbz), F-Moc, $-CH_2Ph$, $-COCF_3$, $-C(O)-R^z$ or $-C(O)O-R^z$), (alternatively $R^{39}$ is H or $C_1-C_6$alkyl, alternatively H), and $R^{36}$ is selected from the group consisting of H, $-OH$, $C_1-C_6$ alkyl, $-(CH_2)_n-O-(CH_2)_iOR^{37}$, $-(CH_2)_nCN(CH_2)_nOR^{37}$, $-(CH_2)_nCN(CH_2)_nR^{37}$, and $-(CH_2)_nOR^{37}$, alternatively $-(CH_2)_nOR^{37}$, wherein each n is an independently selected integer ranging from 0 to 6 (alternatively 0 to 4, alternatively 0 to 2, alternatively 1 or 0, alternatively 0), $R^{37}$ is H, $C_1-C_6$alkyl or $C_3-C_{10}$cycloalkyl (alternatively H or $C_1-C_6$alkyl, alternatively $C_1-C_6$alkyl, alternatively $C_1-C_2$alkyl) and $R^z$ is selected from the group consisting of H, $C_1-C_6$alkyl, $C_1-C_6$cycloalkyl, $C_1-C_6$heterocyclyl and aryl (for example benzyl and $C_5-C_6$heterocycle).

In another example of the compounds according to Formula (A) $A^4$ is O.

In another example of the compounds according to Formula (A), M is a structure selected from the group consisting of

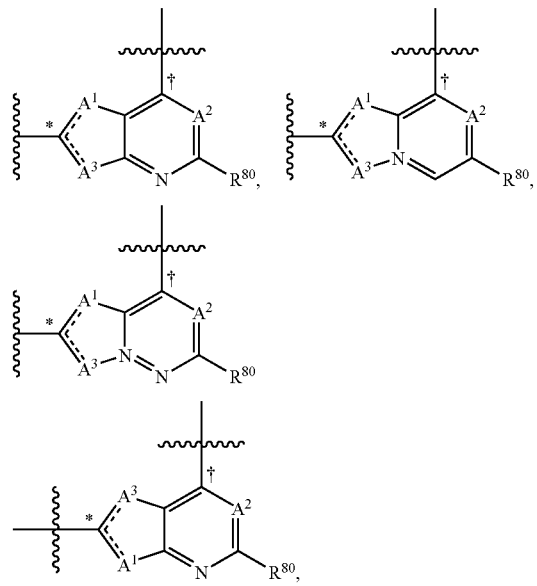

-continued

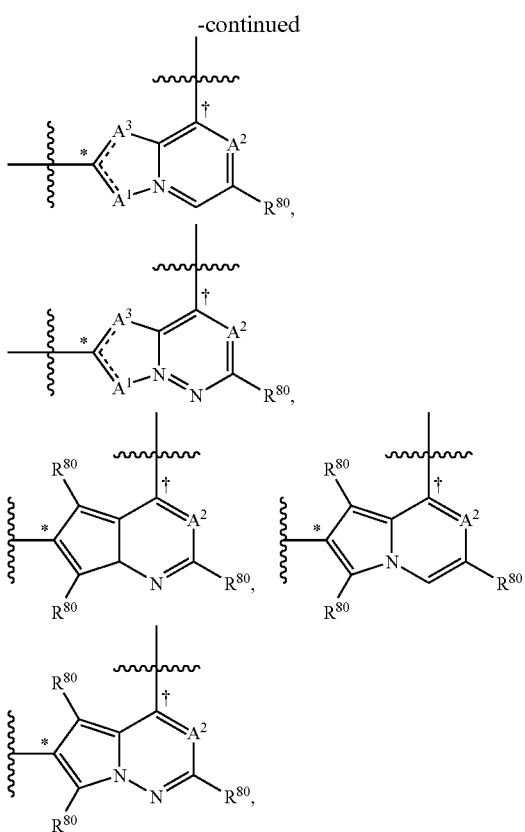

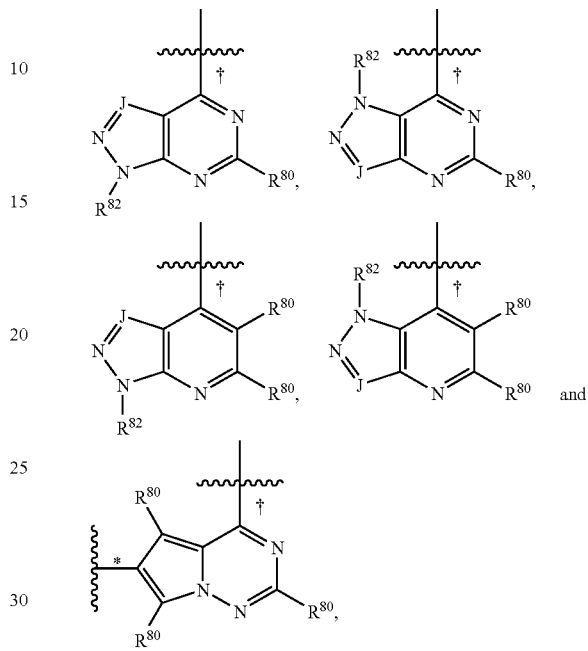

wherein
* represents the point of attachment to D;
† represents the point of attachment to Z;
$A^1$ is selected from the group consisting of —CH$_2$—, —O—, —S—, —N(H)—, —N(C$_1$-C$_6$ alkyl)-, —N—(Y-aryl)-, —N—OMe, —NCH$_2$OMe and N-Bn;
Y is a bond or —(C(R$^x$)(H))$_t$—, wherein t is an integer from 1 to 6; and
R$^x$ at each occurrence is independently selected from the group consisting of H and C$_1$-C$_6$ alkyl, wherein the C$_1$-C$_6$ alkyl is optionally substituted;
$A^2$ is selected from the group consisting of N and CR, wherein R is selected from the group consisting of —H, halogen, —CN, C$_1$-C$_6$ alkyl, C$_2$-C$_6$ alkenyl, C$_2$-C$_6$ alkynyl, —COOH and —C(O)Oalkyl, wherein the C$_1$-C$_6$ alkyl, C$_2$-C$_6$ alkenyl, C$_2$-C$_6$ alkynyl and —C(O)Oalkyl are optionally substituted;
$A^3$ is selected from the group consisting of CH, C-D and N, alternatively CH and N;
each R$^{80}$ is independently selected from the group consisting of H, halogen, NO$_2$, cyano, OR$^{83}$, N(R$^{83}$)$_2$, CO$_2$R$^{83}$, C(O)N(R$^3$)$_2$, SO$_2$R$^{83}$, SO$_2$N(R$^{83}$)$_2$, NR$^{83}$SO$_2$R$^{83}$, NR$^{83}$C(O) R$^{83}$, NR$^{83}$CO$_2$R$^{83}$, —CO(CH$_2$)$_l$R$^{83}$, —CONH(CH$_2$)$_n$R$^{83}$, alkylaminoalkyl, alkylaminoalkynyl, C$_1$-C$_6$alkyl, substituted C$_1$-C$_6$alkyl, C$_3$-C$_7$cycloalkyl, substituted C$_3$-C$_7$cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, and substituted heterocycloalkyl; and
each R$^{83}$ is independently selected from the group consisting of H, alkyl, substituted alkyl, cycloalkyl, substituted cycloalkyl, aryl, substituted aryl, arylalkyl, substituted arylalkyl, heteroaryl, substituted heteroaryl, heterocycloalkyl, and substituted heterocycloalkyl; or two R$^{83}$ taken together with the N atom to which they are attached form a heterocyclic ring.

In another example of the compounds according to Formula (A), M is a structure selected from the group consisting of wherein
J is CR$^{80}$ or N;
R$^{82}$ is selected from the group consisting of H, C$_1$-C$_6$alkyl or substituted C$_1$-C$_6$alkyl, —Y-(aryl), —Y-(heteroaryl), -alkoxy and —CH$_2$OMe;
wherein *, †, R$^{80}$ and Y are as defined above.

In another example of the compounds according to Formula (A), M is a structure selected from the group consisting of

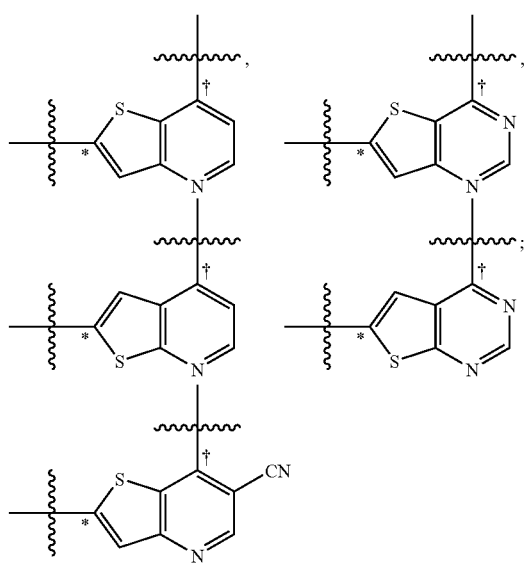

-continued

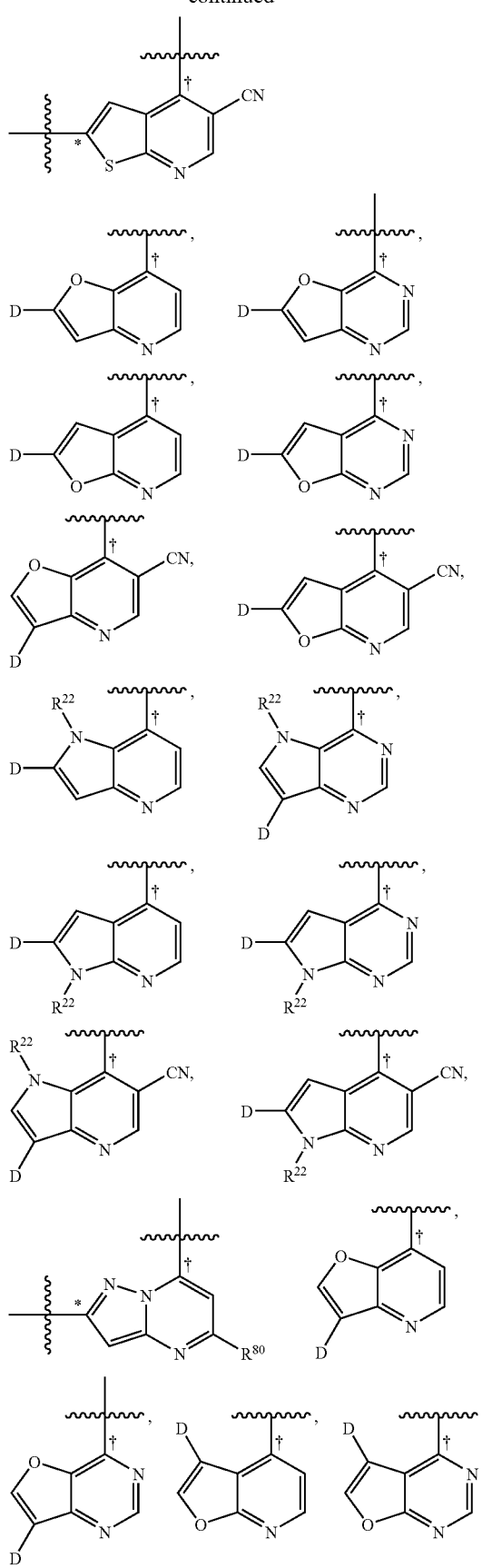

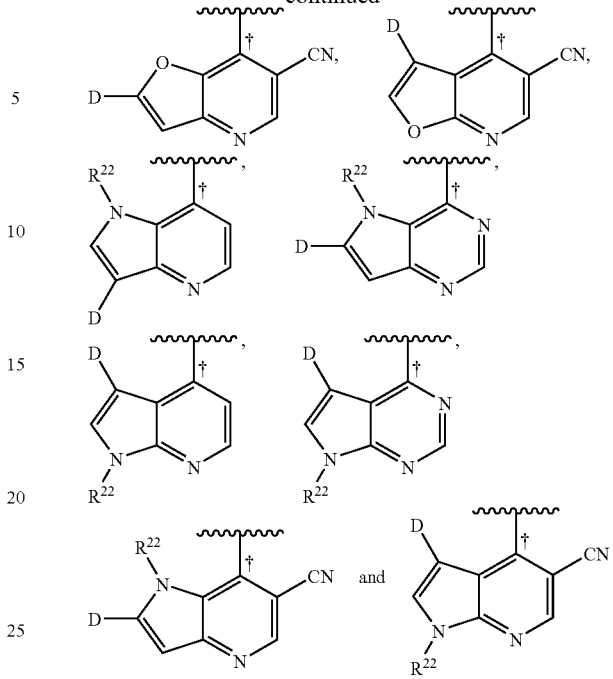

wherein
* and † are as defined above;
D is selected and as defined above; and
$R^{22}$ is selected from the group consisting of —H, —$C_1$-$C_6$alkyl, —Y-aryl, alkoxy, —$CH_2$—O-Me and —Bn.

In another example of the compounds according to Formula (A), M is

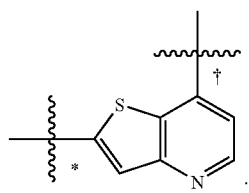 [SMILES: *c1cc2nccc(*)c2s1]

In another example of the compounds according to Formula (A), $A^1$ is S.

In another example of the compounds according to Formula (A), $A^2$ is —CH— or —C(CN)—.

In another example of the compounds according to Formula (A), $A^3$ is —C($R^q$)— or N, wherein $R^q$ is selected from the group consisting of H, halogen, $NO_2$, cyano, $OR^r$, $NR'R^r$, $CO_2R^r$, $C(O)NR'R^r$, $SO_2R^r$, $SO_2NR'R^r$, $NR'SO_2R^r$, $NR'C(O)R^r$, $NR'CO_2R^r$, —CO($CH_2$)$_{0-4}R^r$, —CONH($CH_2$)$_{0-4}R^r$, alkylaminoalkyl, alkylaminoalkynyl, $C_1$-$C_6$alkyl, substituted $C_1$-$C_6$alkyl, $C_3$-$C_7$cycloalkyl, substituted $C_3$-$C_7$cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl and substituted heterocycloalkyl; wherein each $R^r$ is independently selected from the group consisting of H, alkyl, substituted alkyl, cycloalkyl, substituted cycloalkyl, aryl, substituted aryl, arylalkyl, substituted arylalkyl, heteroaryl, substituted heteroaryl, heterocycloalkyl and substituted heterocycloalkyl.

In another example of the compounds according to Formula (A), Z is selected from the group consisting of —O—, —S— and —NR$^5$—, wherein R$^5$ is selected from the group consisting of H, an optionally substituted (C$_1$-C$_5$)acyl and C$_1$-C$_6$ alkyl-O—C(O), wherein C$_1$-C$_6$ alkyl is optionally substituted.

In another example of the compounds according to Formula (A), Z is —O—.

In another example of the compounds according to Formula (A), Ar is selected from the group consisting of phenyl, pyrazine, pyridazine, pryimidine and pyridine, wherein each of said phenyl, pyrazine, pyridazine, pryimidine and pyridine is optionally substituted with 0 to 4 R$^2$ groups.

In another example of the compounds according to Formula (A), Ar is phenyl, optionally substituted with 0 to 4 R$^2$ groups, alternatively with between zero and four halo.

In another example of the compounds according to Formula (A), G is selected from the group consisting of

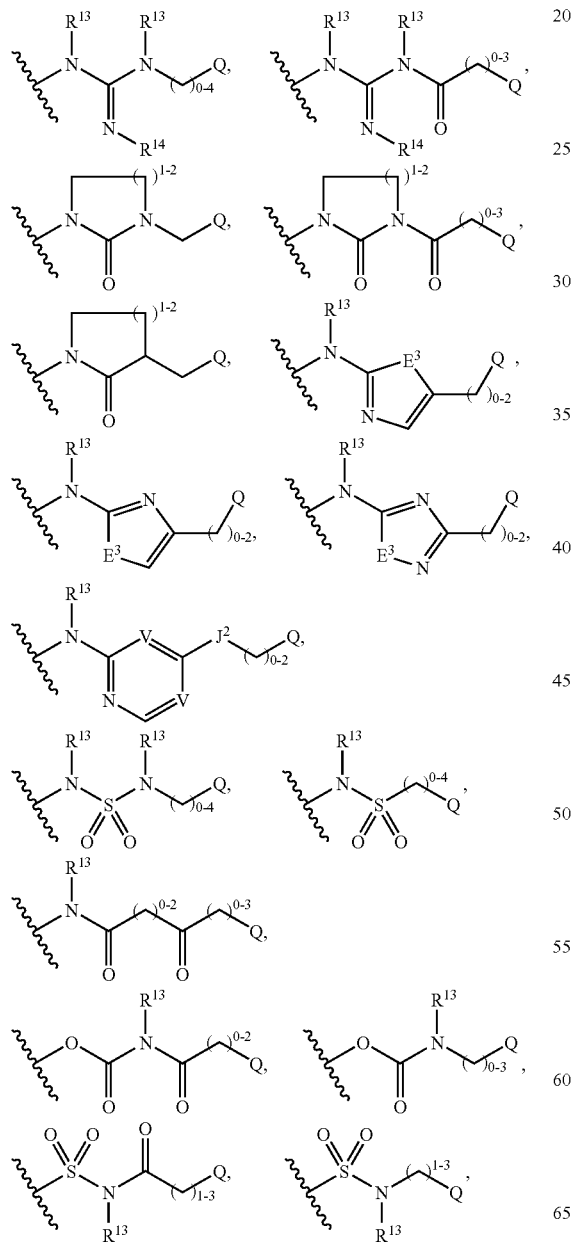

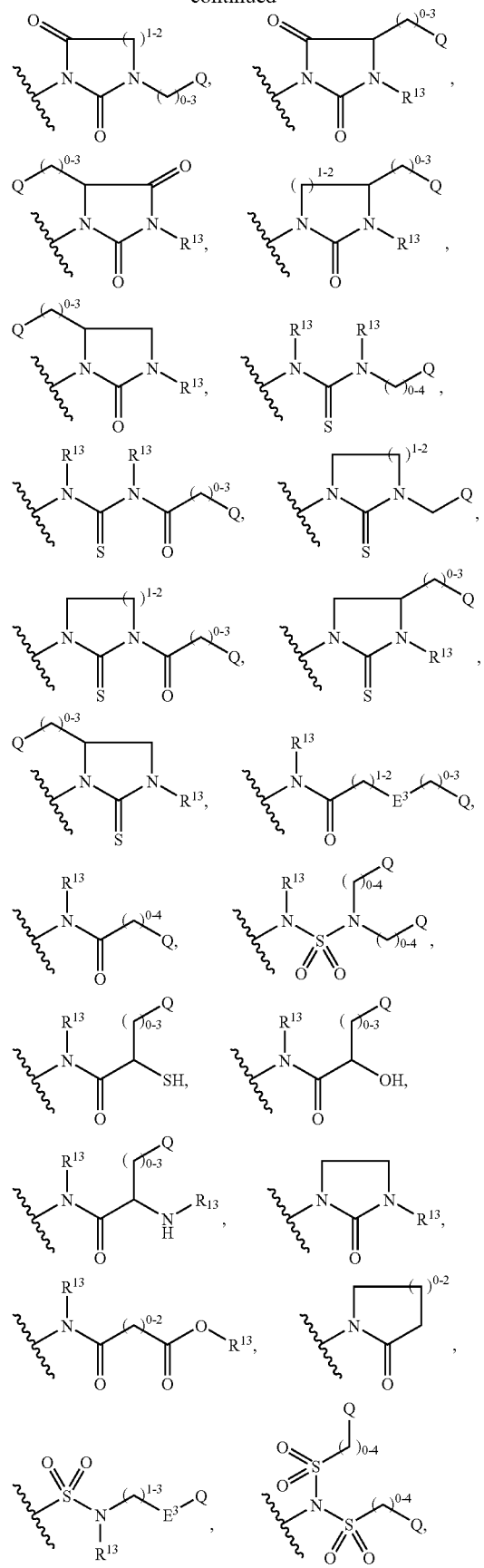

-continued

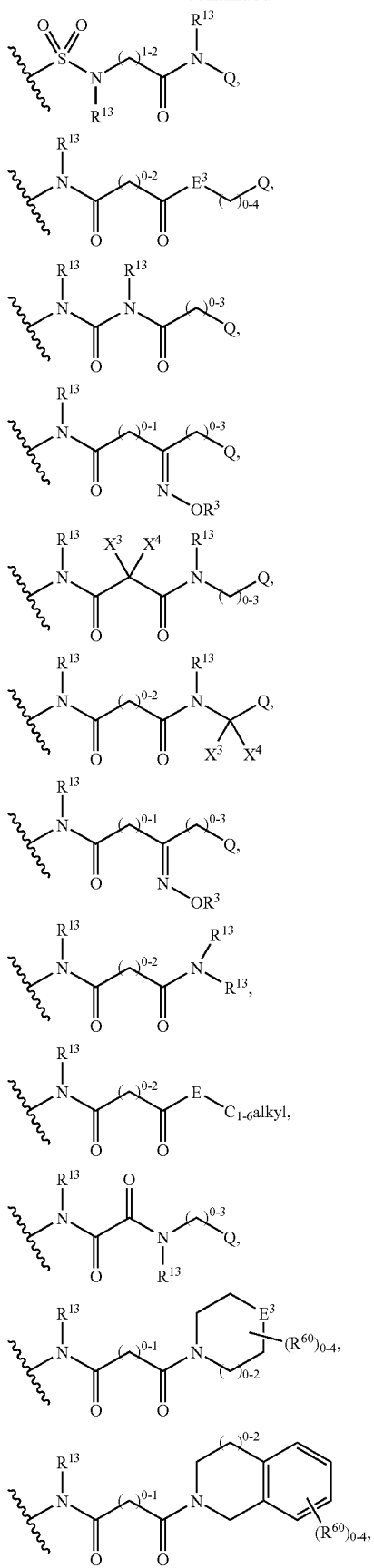

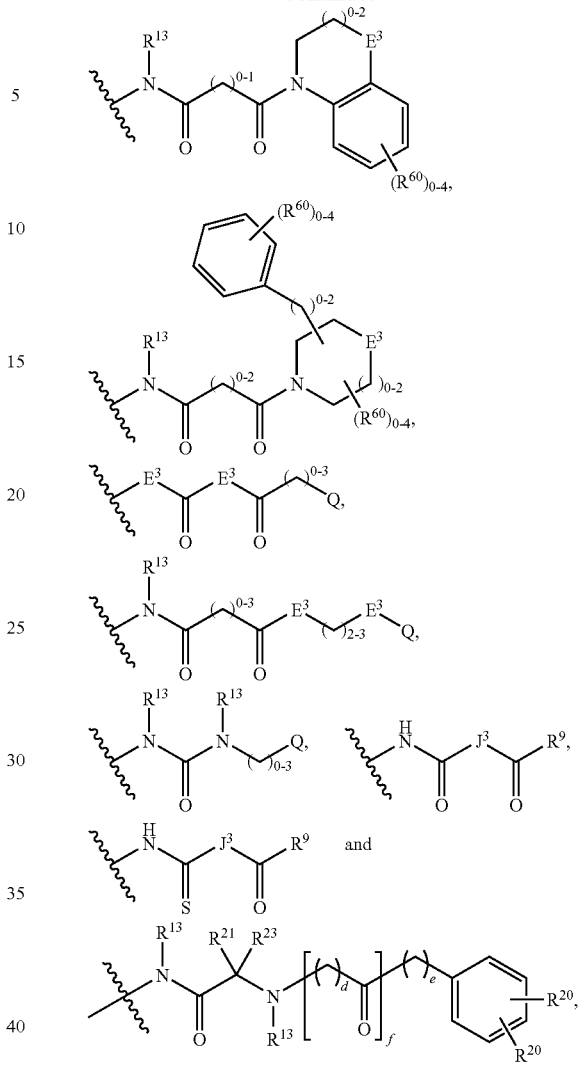

wherein $R^{13}$, $R^{14}$, Q, $R^{60}$ and $R^3$ are as defined above;

any methylene group is independently optionally substituted with $R^{25}$, wherein $R^{25}$ is selected from the group consisting of halogen, trihalomethyl, —CN, —$NO_2$, —$NH_2$, —$OR^3$—$NR^3$, $R^4$, —$S(O)_{0-2}R^3$—$SO_2NR^3R^3$, —$CO_2R^3$, —$C(O)NR^3R^3$, —$N(R^3)S_2R^3$, —$N(R^3)C(O)R^3$, $N(R^3)CO_2R^3$, —$C(O)R^3$, an optionally substituted aryl, an optionally substituted arylalkyl, an optionally substituted heteroarylalkyl, and an optionally substituted ($C_1$-$C_6$)alkyl, or two $R^{25}$, together with the carbon or carbons to which they are attached, can combine to form a three- to seven-membered alicyclic or heteroalicyclic, or two $R^{25}$, on a single carbon can be oxo;

$R^9$ is selected from the group consisting of a $C_{1-6}$ alkyl on which one or more hydrogen atoms are optionally substituted by —$R^{24}$, -$T^1$-$R^{15}$, or —$NR^{16}R^{17}$, a —$N(R^{18})(R^{19})$ moiety and a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_1$ alkylthio, a phenoxy, an acetyl, or a saturated or unsaturated five- or six-membered heterocyclyl ring wherein, when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, wherein $T^1$ is selected from the group consisting of —O—, —S— and —NH—;

$R^{24}$ represents a saturated or unsaturated three- to eight-membered carbocyclic or heterocyclic group;

$R^{15}$, $R^{16}$, and $R^{17}$, which may be the same or different, represent a $C_{1-6}$ alkyl or a saturated or unsaturated three- to eight-membered carbocyclic or heterocyclic group; wherein the three- to eight-membered carbocyclic or heterocyclic group represented by $R^{24}$, $R^{15}$, $R^{16}$, and $R^{17}$ is optionally substituted by a $C_{1-6}$ alkyl, a $C_{1-6}$ alkoxy, a halogen atom, nitro, a trifluoromethyl, a $C_{1-6}$ alkoxy carbonyl, a cyano, a cyano $C_{1-6}$ alkyl, a $C_{1-6}$ alkylthio, a phenoxy, an acetyl, or a saturated or unsaturated five- or six-membered heterocyclyl ring; and wherein when the three- to eight-membered carbocyclic or heterocyclic group is substituted by two $C_{1-6}$ alkyl groups, the two alkyl groups may combine together to form an alkylene chain; and wherein the three- to eight-membered carbocyclic or heterocyclic group may be a bicyclic group condensed with another saturated or unsaturated three- to eight-membered carbocyclic or heterocyclic group; and $R^{18}$ and $R^{19}$, which may be the same or different, represent (1) a hydrogen atom, (2) a $C_{1-6}$ alkyl which is optionally substituted by a $C_{1-6}$ alkoxy, a $C_{1-6}$ alkylthio, or a saturated or unsaturated three- to eight-membered carbocyclic or heterocyclic group in which the three- to eight-membered carbocyclic or heterocyclic group is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and wherein when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or (3) a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and in which, when the three to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group;

$X^3$ and $X^4$ are each independently selected from the group consisting of —H, halogen, cyano, nitro, $C_1$-$C_6$ alkyl, or $X^3$ and $X^4$ together with the atom to which they are attached form a $C_3$-$C_4$ cycloalkyl;

each $E^3$ is independently selected from the group consisting of —O—, —N($R^{13}$)—, —CH$_2$— and —S(O)$_{0-2}$;

$J^2$ is selected from the group consisting of —O—, —N($R^{13}$)—, —CH$_2$— and —C(=O)N($R^{13}$);

$J^3$ represents —C($R^{26}$)($R^{27}$)—, wherein $R^{26}$ and $R^{27}$ are independently selected from the group consisting of a hydrogen atom, a $C_{1-4}$ alkyl, a $C_{1-4}$ alkoxy and —N($R^{12b}$), wherein $R^{12b}$ is a hydrogen atom or a $C_{1-4}$ alkyl;

each V is independently selected from the group consisting of =N— and =C(H)—;

$R^{21}$ and $R^{23}$ are independently selected from the group consisting of H, halogen, —OH, unsubstituted —O—($C_1$-$C_6$alkyl), substituted —O—($C_1$-$C_6$alkyl), unsubstituted —O-(cycloalkyl), substituted —O-(cycloalkyl), unsubstituted —NH($C_1$-$C_6$alkyl), substituted —NH($C_1$-$C_6$alkyl), —NH$_2$, —SH, unsubstituted —S—($C_1$-$C_6$alkyl), substituted —S—($C_1$-$C_6$alkyl), unsubstituted $C_1$-$C_6$alkyl and substituted $C_1$-$C_6$alkyl; or $R^{21}$ and $R^{23}$ taken together with the atom to which they are attached form a $C_3$-$C_7$ ring system, wherein said ring system is optionally substituted;

d is 0, 1, 2 or 3;

e is 0, 1, 2 or 3; and f is 0 or 1.

In another example of the compounds according to Formula (A), G is selected from the group consisting of

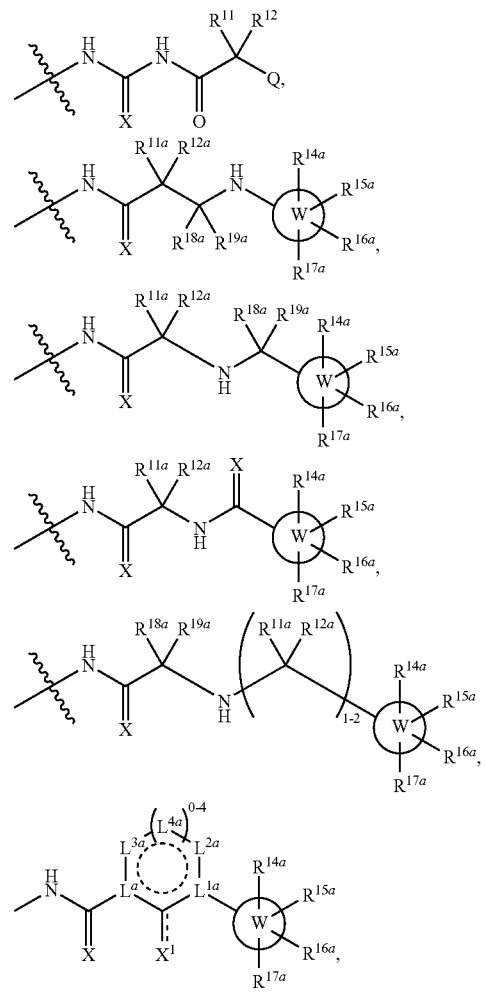

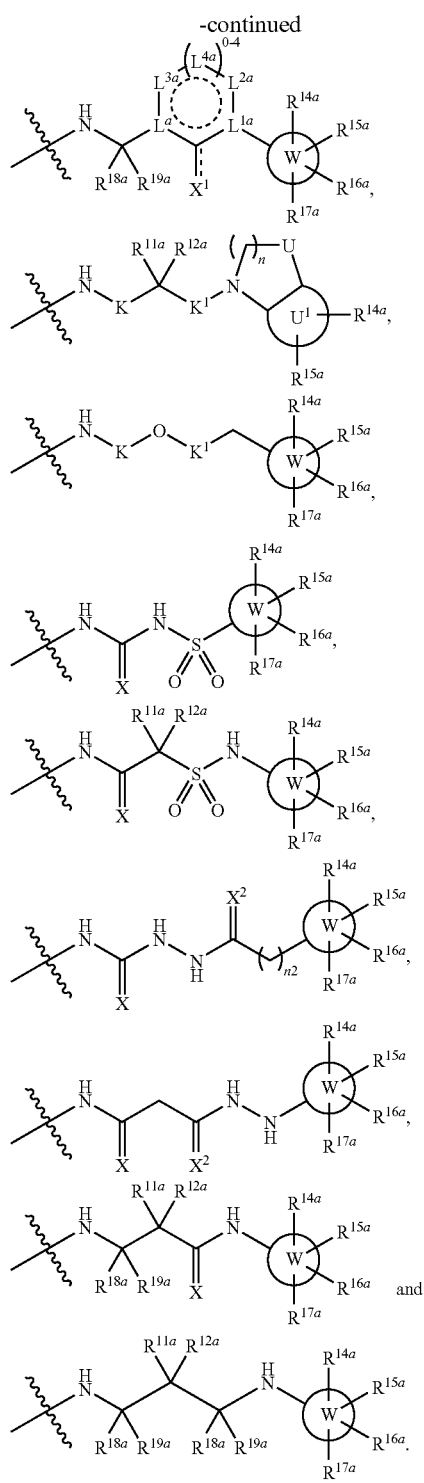
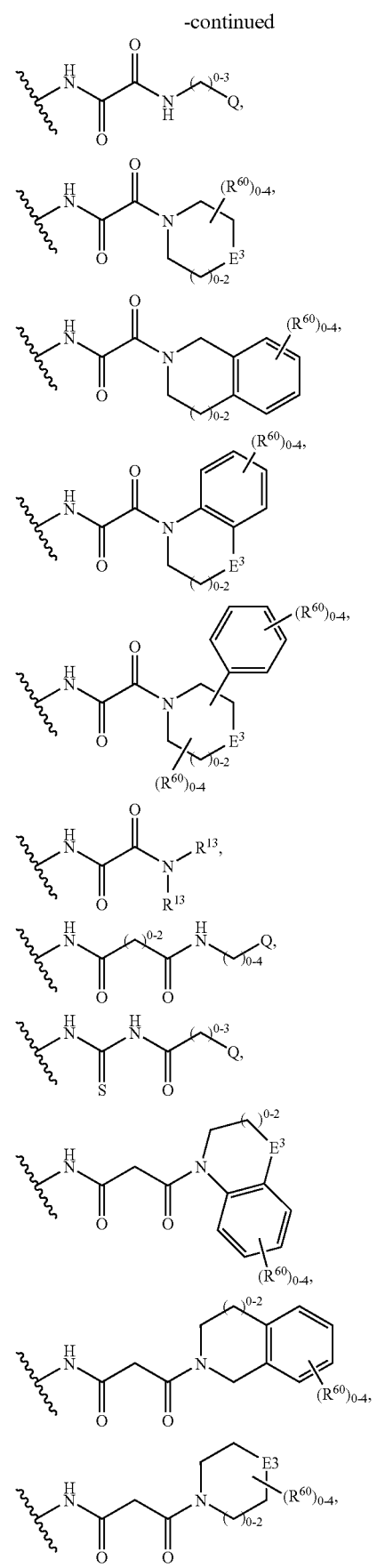
In another example of the compounds according to Formula (A), G is selected from the group consisting of
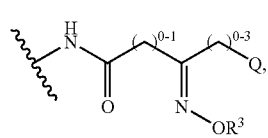

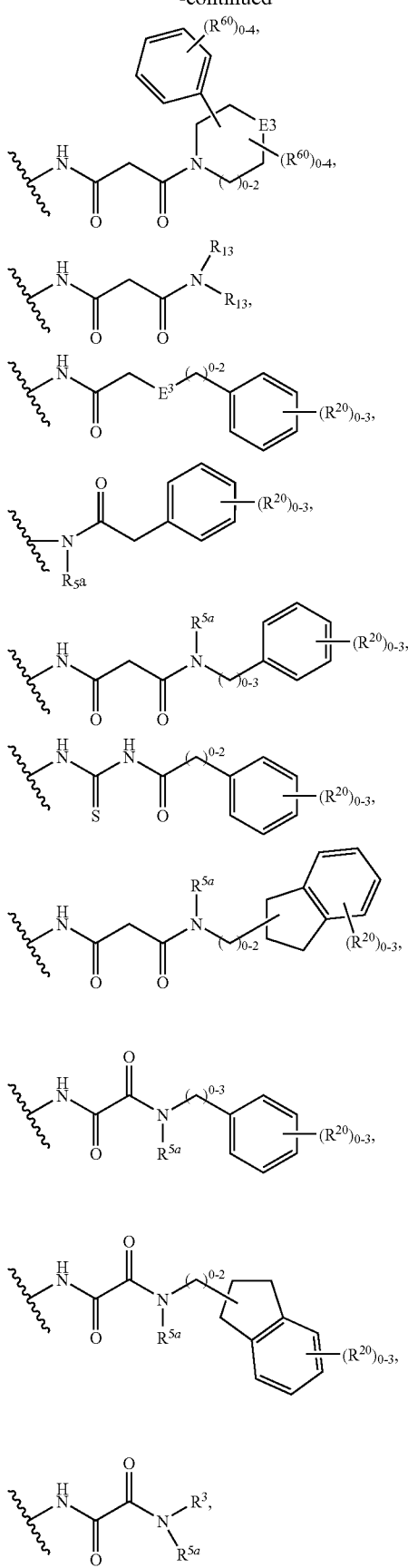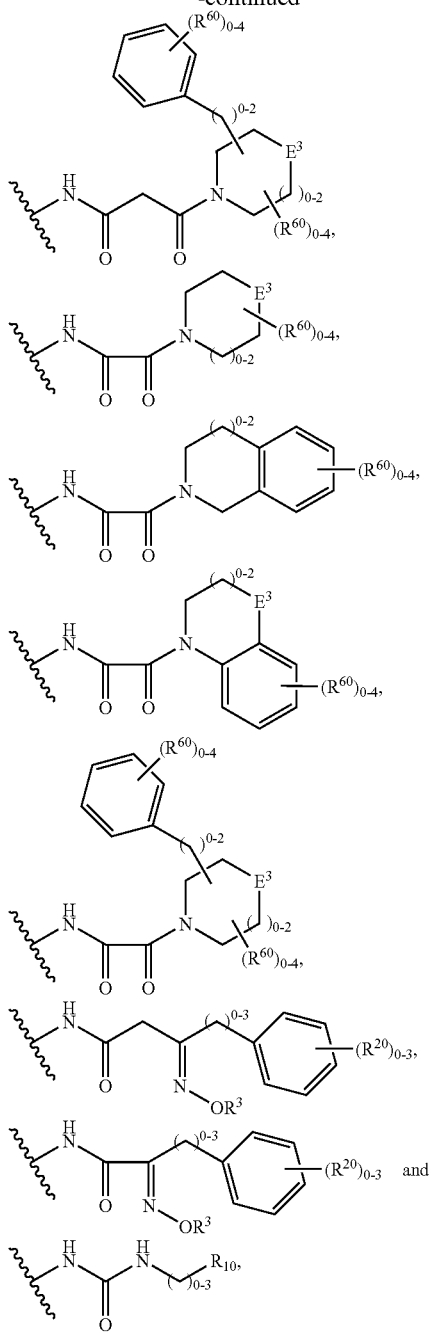

wherein each methylene in any of the above formulae, other than those in a depicted ring, is independently optionally substituted with $R^{25}$;

$R^{5a}$ is —H or an optionally substituted $(C_1-C_6)$alkyl;

$R^{10}$ is an azolyl, wherein one or more hydrogen atoms are optionally substituted by a moiety selected from the group consisting of a halogen, $C_{1-4}$ alkyl, $C_{1-4}$ alkoxy, $C_{1-4}$ alkylthio, trihalomethyl, nitro, amino optionally independently substituted by one or two of $C_{1-4}$ alkyl, a $C_{1-4}$ alkoxycarbonyl $C_{1-4}$ alkyl, a $C_{1-4}$ alkylcarbonyl and a $C_{3-5}$ cyclic alkyl.

In another example of the compounds according to Formula (A), a methylene group between two carbonyl groups is mono- or di-substituted with either an optionally substituted $(C_1-C_6)$alkyl or an optionally substituted spirocycle.

In another example of the compounds according to Formula (A), $R^{10}$ is selected from the group consisting of

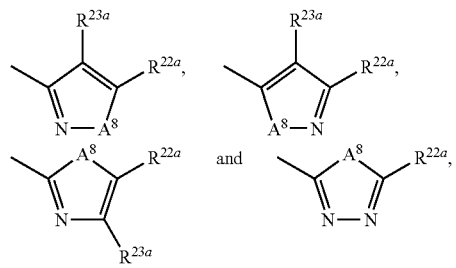

wherein $A^8$ is selected from the group consisting of —O—, —S— and —NH—; and $R^{22a}$ and $R^{23a}$ are independently selected from the group consisting of —H, halogen, $C_{1-4}$ alkyl, $C_{1-4}$ alkoxy, $C_{1-4}$ alkylthio, trihalomethyl, nitro, amino optionally independently substituted by one or two of $C_{1-4}$ alkyl, a $C_{1-4}$ alkoxycarbonyl $C_{1-4}$ alkyl, a $C_{1-4}$ alkylcarbonyl and a $C_{3-5}$ cyclic alkyl.

In another example of the compounds according to Formula (A) example of the compounds according to Formula (A), G is selected from the group consisting of

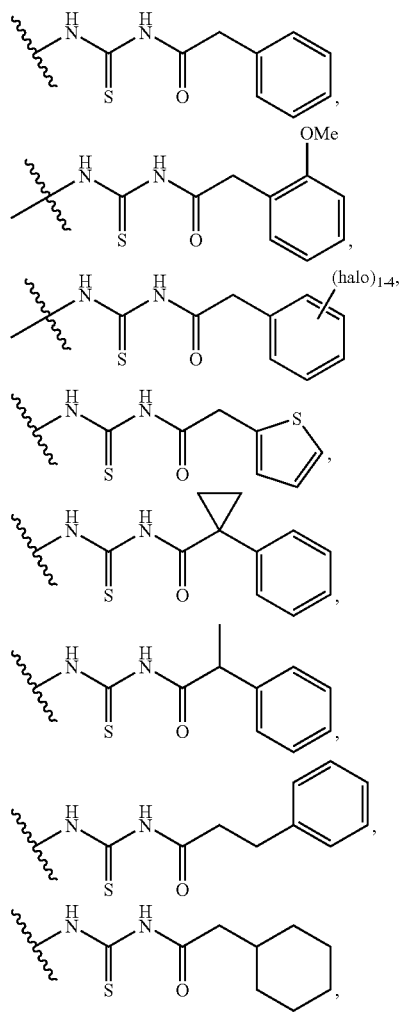

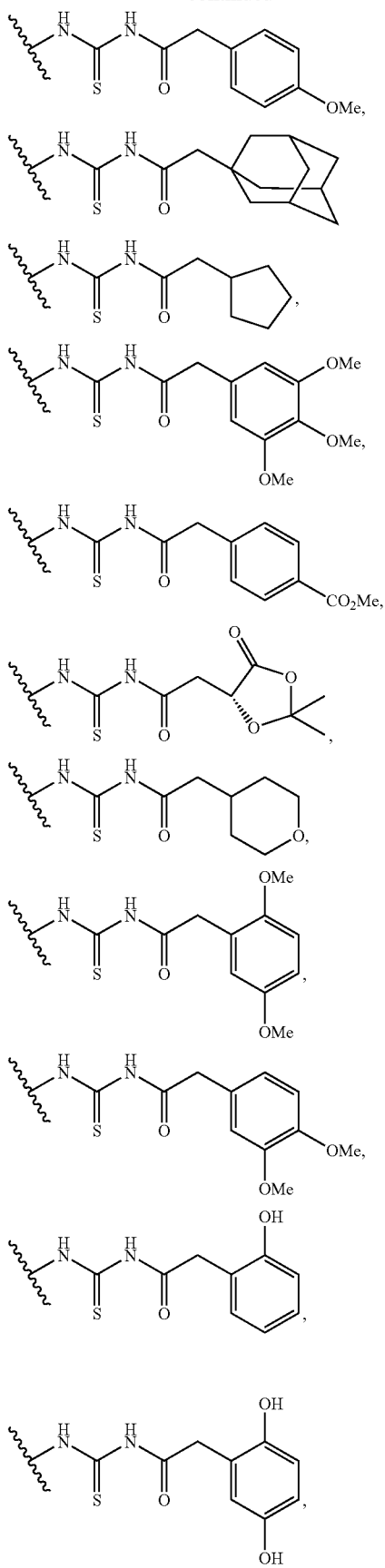

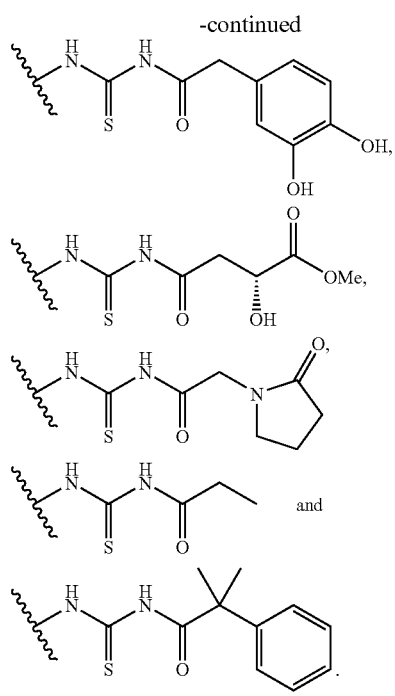
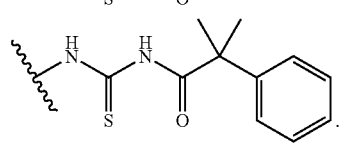 and
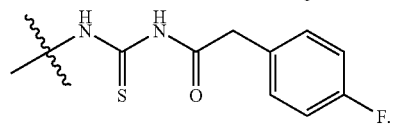
In another example of the compounds according to Formula (A), G is selected from the group consisting of
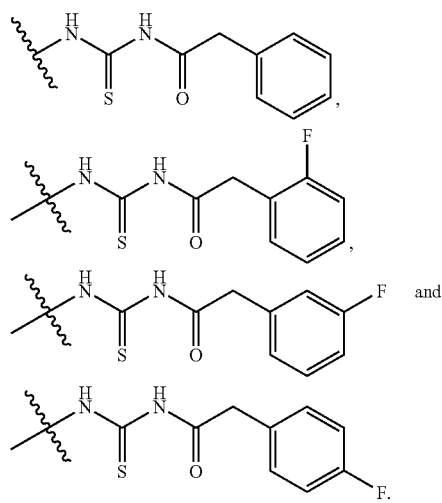 and
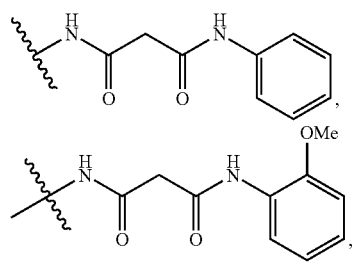
In another example of the compounds according to Formula (A), G is selected from the group consisting of
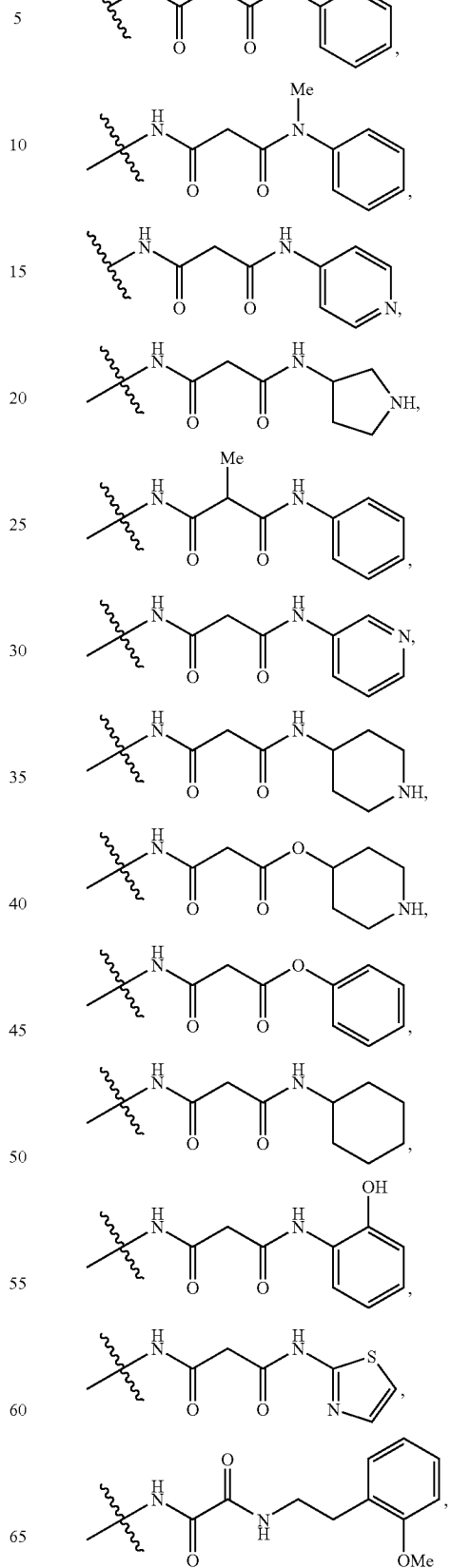

41
-continued
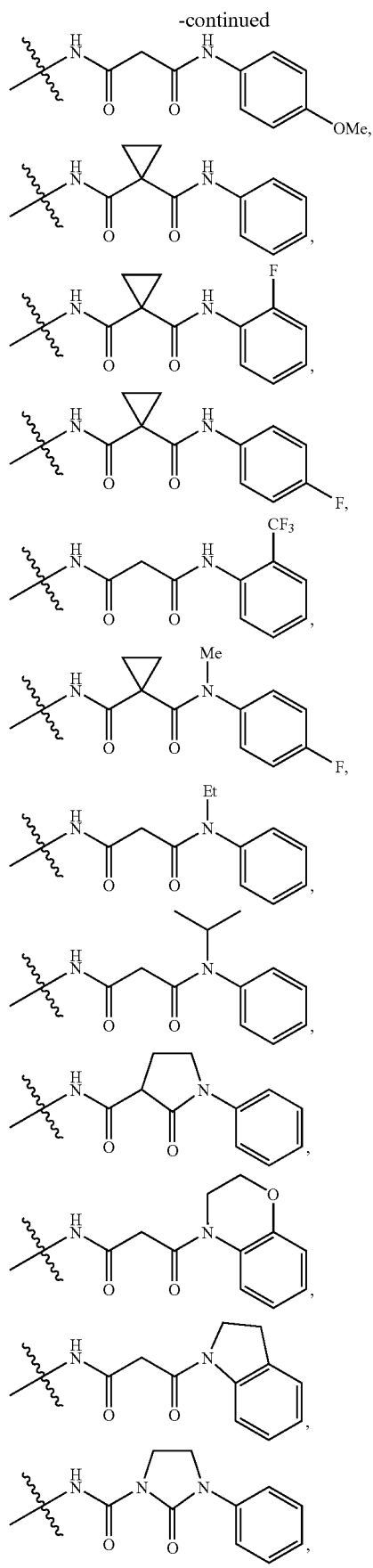
42
-continued
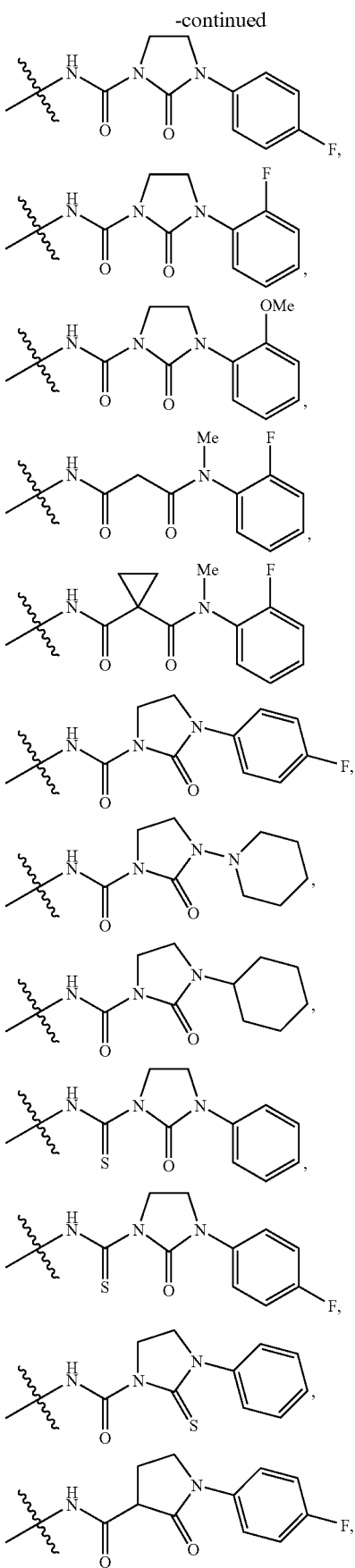

-continued
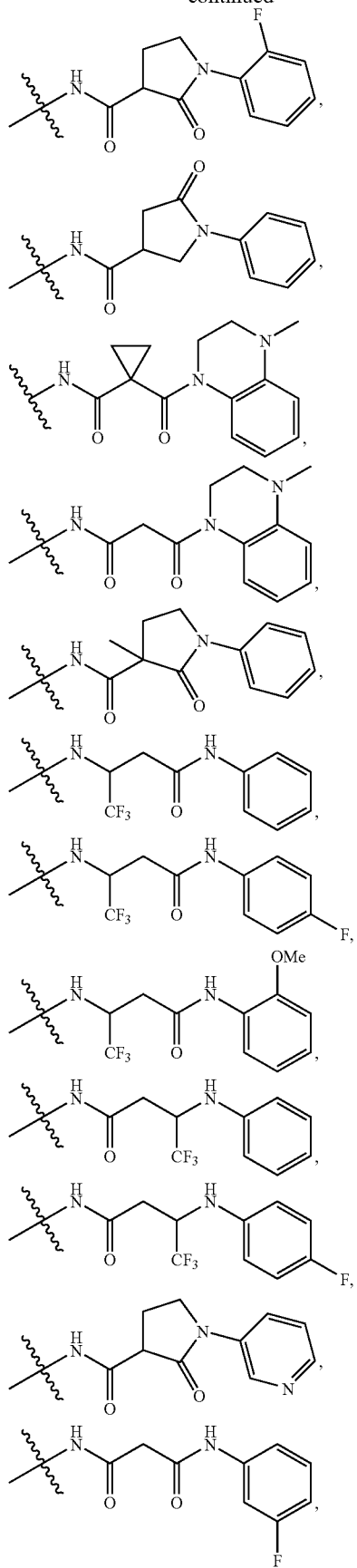
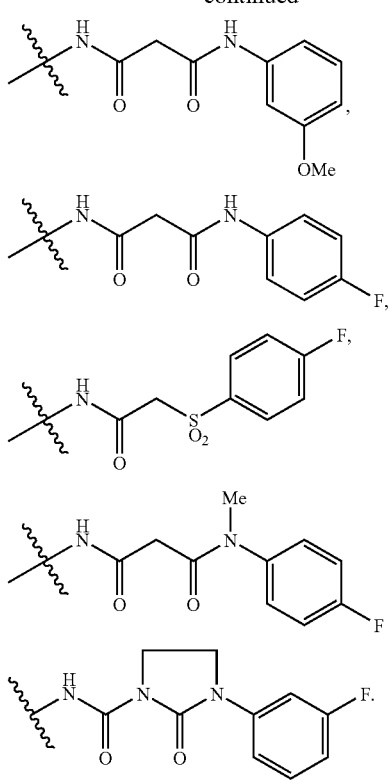
In another example of the compounds according to Formula (A), G is selected from the group consisting of
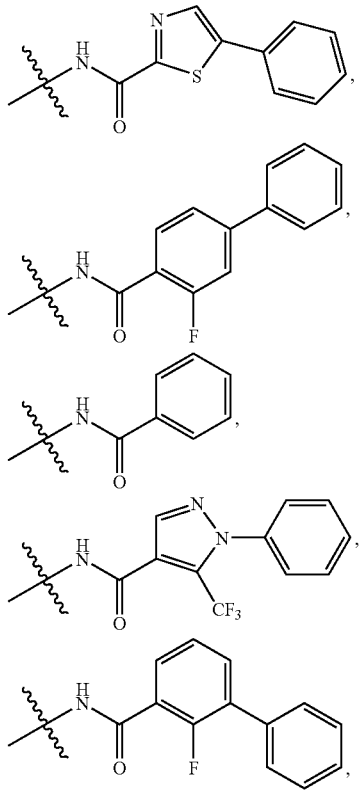

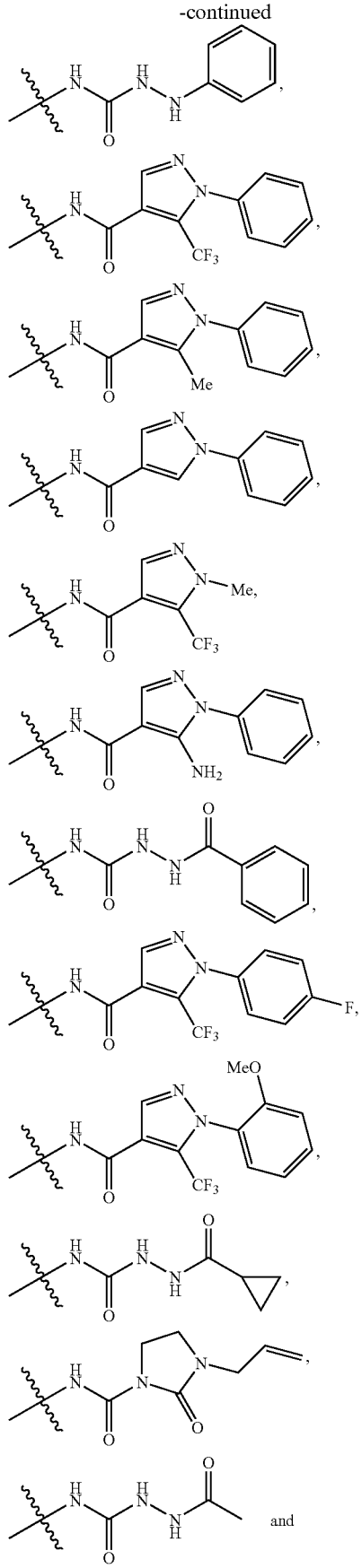
In another example of the compounds according to Formula (A), G is selected from the group consisting of -continued

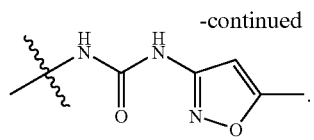

In another example of the compounds according to Formula (A), any of E, $E^1$, $E^2$ or $E^3$ are independently —NH—.

In another example of the compounds according to Formula (A), one of $R^{18a}$ and $R^{19a}$ is —$CF_3$ and the other is —H.

In another example of the compounds according to Formula (A), $R^{11}$ and $R^{12}$ are each —H.

In another example of the compounds according to Formula (A), X is S or O.

In another example of the compounds according to Formula (A), X is S.

In another example of the compounds according to Formula (A), $R^{13}$ is H.

In another example of the compounds according to Formula (A), $R^{11}$, $R^{12}$ and $R^{13}$ are each —H.

In another example of the compounds according to Formula (A), X is O, one of $R^{18a}$ and $R^{19a}$ is —$CF_3$ and the other is —H, and $R^{11}$, $R^{12}$ and $R^{13}$ are each —H.

In another example of the compounds according to Formula (A), W is selected from the group consisting of

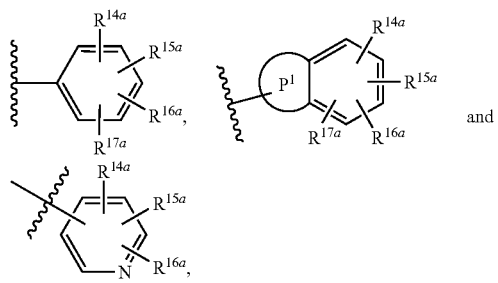

wherein $P^1$ is a five- to seven-membered ring, including the two shared carbon atoms of the aromatic ring to which $P^1$ is fused, and wherein $P^1$ optionally contains between one and three heteroatoms.

In another example of the compounds according to Formula (A), W is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted.

In another example of the compounds according to Formula (A), W is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted with one or more of $R^{14a}$, $R^{15a}$, $R^{16a}$ and $R^{17a}$.

In another example of the compounds according to Formula (A), W is phenyl, optionally substituted.

In another example of the compounds according to Formula (A), W is phenyl, optionally substituted with one or more of $R^{14a}$, $R^{15a}$, $R^{16a}$ and $R^{17a}$.

In another example of the compounds according to Formula (A), W is substituted by a halogen and either an alkenyl or alkynyl.

In another example of the compounds according to Formula (A), W is phenyl substituted by a halogen and either an alkenyl or alkynyl.

In another example of the compounds according to Formula (A), Q is selected from the group consisting of

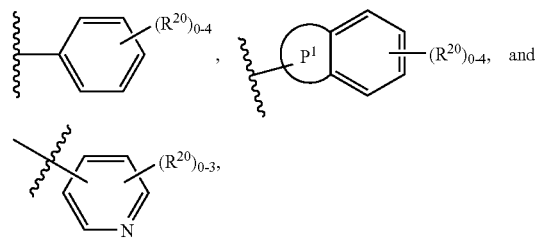

wherein $P^1$ is a five- to seven-membered ring, including the two shared carbon atoms of the aromatic ring to which $P^1$ is fused, and wherein $P^1$ optionally contains between one and three heteroatoms.

In another example of the compounds according to Formula (A), Q is selected from the group consisting of phenyl, napthyl, 1,2,3,4-tetrahydronaphthyl, indanyl, benzodioxanyl, benzofuranyl, phenazinyl, phenothiazinyl, phenoxazinyl, tetrahydroisoquinolyl, pyrrolyl, pyrazolyl, pyrazolidinyl, imidazolyl, imidazolinyl, imidazolidinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, thiazolyl, thiazolinyl, thiazolidinyl, isothiazolyl, isothiazolidinyl, indolyl, isoindolyl, indolinyl, isoindolinyl, octahydroindolyl, octahydroisoindolyl, quinolyl, isoquinolyl, benzimidazolyl, thiadiazolyl, benzopyranyl, benzothiazolyl, benzoxazolyl, furyl, thienyl, benzothieliyl, and oxadiazolyl; each optionally substituted with between one and four of $R^{20}$, wherein In another example of the compounds according to Formula (A), Q is phenyl, optionally substituted.

In another example of the compounds according to Formula (A), Q is phenyl, optionally substituted with one or more of $R^{20}$.

In another example of the compounds according to Formula (A), Q is substituted by a halogen and either an alkenyl or alkynyl.

In another example of the compounds according to Formula (A), Q is phenyl substituted by a halogen and either an alkenyl or alkynyl.

In another example of the compounds according to Formula (A), $R^{14a}$ and $R^{15a}$ are both H, $R^{16a}$ is $C_2$-$C_7$ alkenyl or $C_2$-$C_6$ alkynyl and $R^{17a}$ is halogen, for example fluorine.

In another example of the compounds according to Formula (A), $L^3$ and $L^4$ are independently —CH— or N.

In another example of the compounds according to Formula (A), $R^{39}$ is selected from the group consisting of H, $C_1$-$C_6$alkyl, $C_1$-$C_6$cycloalkyl, —OMe, —C(O)—$C_1$-$C_6$alkyl, —C(O)—O—$C_1$-$C_6$alkyl, —SO$_2$—$C_1$-$C_6$alkyl, and a protecting group used to protect secondary amino groups.

In another example of the compounds according to Formula (A), $R^{39}$ is a protecting group used to protect secondary amino groups, wherein said protecting group is selected from the group consisting of tert-butoxycarbonyl (Boc), benzyloxycarbonyl (Cbz), F-Moc, —CH$_2$Ph, —COCF$_3$, —C(O)—$R^z$ and —C(O)O—$R^z$.

In an alternate embodiment of the compounds according to Formula (A), D is -(aryl), -(heterocycle) or -(heteroaryl), each of which is optionally substituted with 1 to 5 independently selected $R^{38}$ groups, alternatively 1 to 3 independently selected $R^{38}$ groups, and alternatively 1 or 2 independently selected $R^{38}$ group;

M is

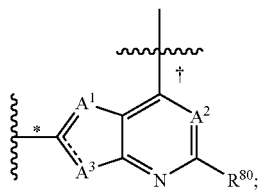

Z is —O—, —S—, —SO—, —SO$_2$—, —CH$_2$O—, —OCH$_2$—, —CH$_2$— or —N($R^5$)—, for example —O—;

Ar is aryl or heteroaryl, for example selected from the group consisting of phenyl, pyrazine, pyridazine, pryimidine and pyridine, for example phenyl, each of which is optionally substituted with 0 to 4 $R^2$ groups, alternatively with between zero and four halo; and G is

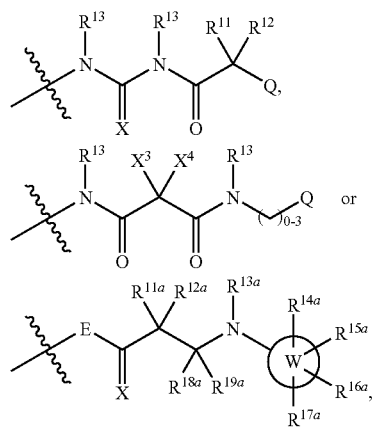

wherein Q is optionally substituted with from 0 to 4 (alternatively 0 to 2, alternatively 1) independently selected $R^{20}$, wherein said $R^{20}$ are for example halogen, trihalomethyl, alkoxy, optionally substituted $C_1$-$C_6$alkyl, optionally substituted $C_2$-$C_6$alkenyl or optionally substituted $C_2$-$C_6$alkynyl, for example halogen.

For example, in such embodiment, D is optionally substituted with one or two (alternatively one) $R^{38}$, wherein each said $R^{38}$ is independently $C_1$-$C_6$alkyl, —(CH$_2$)$_j$NR$^{39}$(CH$_2$)$_n$R$^{36}$ or —(CH$_2$)$_n$NR$^{36}$R$^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, —OH, $C_1$-$C_6$alkyl, $C_3$-$C_{10}$cycloalkyl, —C(O)—$R^z$ and —C(O)—O—$R^z$, —SO$_2$—$C_1$-$C_6$alkyl, and a protecting group used to protect secondary amino groups (for example tert-butoxycarbonyl (Boc), benzylocycarbonyl (Cbz), F-Moc, —CH$_2$Ph, —COCF$_3$, —C(O)—$R^z$ or —C(O)O—$R^z$), (alternatively $R^{39}$ is H or $C_1$-$C_6$alkyl, alternatively H), and $R^{36}$ is selected from the group consisting of H, —OH, $C_1$-$C_6$ alkyl, —(CH$_2$)$_n$—O—(CH$_2$)$_n$OR$^{37}$, —(CH$_2$)$_n$CN (CH$_2$)$_n$OR$^{37}$, —(CH$_2$)$_n$CN(CH$_2$)$_n$R$^{37}$, and —(CH$_2$)$_n$OR$^{37}$, alternatively —(CH$_2$)$_n$OR$^{37}$, wherein each n is an independently selected integer ranging from 0 to 6 (alternatively 0 to 4, alternatively 0 to 2, alternatively 1 or 0, alternatively 0), $R^{37}$ is H, $C_1$-$C_6$alkyl or $C_3$-$C_{10}$cycloalkyl (alternatively H or $C_1$-$C_6$alkyl, alternatively $C_1$-$C_6$alkyl, alternatively $C_1$-$C_2$alkyl) and $R^z$ is selected from the group consisting of H, $C_1$-$C_6$alkyl, $C_1$-$C_6$cycloalkyl, $C_1$-$C_6$heterocyclyl and aryl (for example benzyl and $C_5$-$C_6$heterocycle).

In an example of the compounds according to this alternate embodiment, D is phenyl or pyridinyl (for example pyridinyl), optionally substituted with one or two (alternatively one) $R^{38}$, wherein each said $R^{38}$ is independently selected from $C_1$-$C_6$alkyl, —(CH$_2$)$_j$NR$^{39}$(CH$_2$)$_n$R$^{36}$ or —(CH$_2$)$_n$NR$^{36}$R$^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, —OH, $C_1$-$C_6$alkyl, $C_3$-$C_{10}$cycloalkyl, —C(O)—$R^z$ and —C(O)—O—$R^z$, —SO$_2$—$C_1$-$C_6$alkyl, and a protecting group used to protect secondary amino groups (tert-butoxycarbonyl (Boc), benzylocycarbonyl (Cbz), F-Moc, —CH$_2$Ph, —COCF$_3$, —C(O)—$R^z$ or —C(O)O—$R^z$), (alternatively $R^{39}$ is H or $C_1$-$C_6$alkyl, alternatively H), and $R^{36}$ is selected from the group consisting of H, —OH, $C_1$-$C_6$ alkyl, —(CH$_2$)$_n$O (CH$_2$)OR$^{37}$, —(CH$_2$)$_n$CN(CH$_2$)$_n$OR$^{37}$—(CH$_2$)$_n$CN (CH$_2$)$_n$R$^{37}$, and —(CH$_2$)$_n$OR$^{37}$, alternatively —(CH$_2$)$_n$OR$^{37}$, wherein each n is an independently selected integer ranging from 0 to 6 (alternatively 0 to 4, alternatively 0 to 2, alternatively 1 or 0, alternatively 0), $R^{37}$ is H, $C_1$-$C_6$alkyl or $C_3$-$C_{10}$cycloalkyl (alternatively H or $C_1$-$C_6$alkyl, alternatively $C_1$-$C_6$alkyl, alternatively $C_1$-$C_2$alkyl) and $R^z$ is selected from the group consisting of H, $C_1$-$C_6$alkyl, $C_1$-$C_6$cycloalkyl, $C_1$-$C_6$heterocyclyl and aryl (for example benzyl and $C_5$-$C_6$heterocyclyl).

In another example of the compounds according to this alternate embodiment, $R^{39}$ is selected from the group consisting of H, $C_1$-$C_6$alkyl, $C_1$-$C_6$cycloalkyl, —OMe, —C(O)—$C_1$-$C_6$alkyl, —C(O)—O—$C_1$-$C_6$alkyl, —SO$_2$—$C_1$-$C_6$alkyl, and a protecting group used to protect secondary amino groups.

In another example of the compounds according to Formula (A), $R^{39}$ is a protecting group used to protect secondary amino groups, wherein said protecting group is selected from the group consisting of tert-butoxycarbonyl (Boc), benzyloxycarbonyl (Cbz), F-Moc, —CH$_2$Ph, —COCF$_3$, —C(O)—$R^z$ and —C(O)O—$R^z$.

In another alternate embodiment of the compounds according to Formula (A), D is -(aryl), -(heterocycle) or -(heteroaryl), each of which is optionally substituted with 1 to 5 independently selected $R^{38}$ groups, alternatively 1 to 3 independently selected $R^{38}$ groups, and alternatively 1 or 2 independently selected $R^{38}$ group;

M is

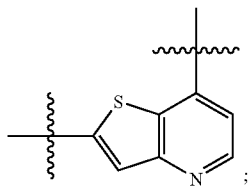 [SMILES: *c1cc2nccc(*)c2s1];

Z is —O—, —S—, —SO—, —SO₂—, —CH₂O—, —OCH₂—, —CH₂— or —N(R⁵)—, for example —O—;

Ar is aryl or heteroaryl, for example selected from the group consisting of phenyl, pyrazine, pyridazine, pyrimidine and pyridine, for example phenyl, each of which is optionally substituted with 0 to 4 R² groups, alternatively with between zero and four halo; and G is

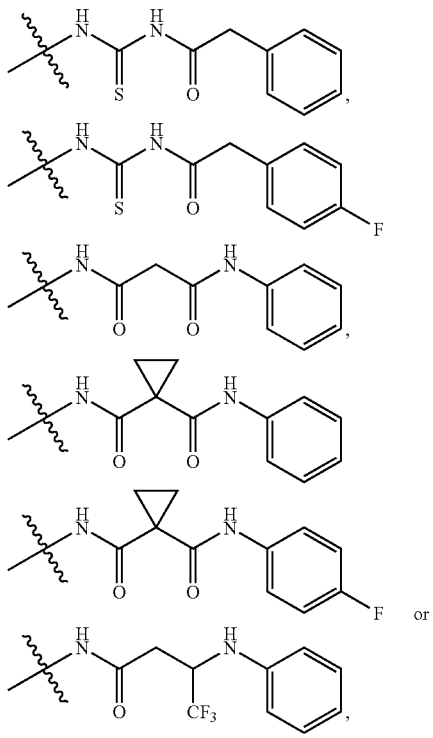

wherein said phenyl groups of G are optionally substituted with from 0 to 4 (alternatively 0 to 2, alternatively 1) independently selected R²⁰, wherein said R²⁰ are for example halogen, trihalomethyl, alkoxy, optionally substituted $C_1$-$C_6$alkyl, optionally substituted $C_2$-$C_6$alkenyl or optionally substituted $C_2$-$C_6$alkynyl, for example halogen.

In an example of the compounds according to this alternate embodiment, D is optionally substituted with one or two (alternatively one) R³⁸, wherein each said R³⁸ is independently selected from $C_1$-$C_6$alkyl, —(CH₂)ⱼNR³⁹(CH₂)ₙR³⁶ or —(CH₂)ₙNR³⁶R³⁹ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), R³⁹ is selected from the group consisting of H, —OH, $C_1$-$C_6$alkyl, $C_3$-$C_{10}$cycloalkyl, —C(O)—R$^z$ and —C(O)—O—R$^z$ (alternatively H or $C_1$-$C_6$alkyl, alternatively H), —SO₂—$C_1$-$C_6$alkyl, and a protecting group used to protect secondary amino groups (for example tert-butoxycarbonyl (Boc), benzylocycarbonyl (Cbz), F-Moc, —CH₂Ph, —COCF₃, —C(O)—R$^z$, —C(O)—R$^z$), and R³⁶ is selected from the group consisting of H, —OH, $C_1$-$C_6$ alkyl, —(CH₂)ₙ—O—(CH₂)₁₀R³⁷, —(CH₂)ₙCN(CH₂)ₙOR³⁷, —(CH₂)ₙCN(CH₂)ₙR³⁷, and —(CH₂)ₙOR³⁷, alternatively —(CH₂)ₙOR³⁷, wherein each n is an independently selected integer ranging from 0 to 6 (alternatively 0 to 4, alternatively 0 to 2, alternatively 1 or 0, alternatively 0), R³⁷ is H, $C_1$-$C_6$alkyl or $C_3$-$C_{10}$cycloalkyl (alternatively H or $C_1$-$C_6$alkyl, alternatively $C_1$-$C_6$alkyl, alternatively $C_1$-$C_2$alkyl) and R$^z$ is selected from the group consisting of H, $C_1$-$C_6$alkyl, $C_1$-$C_6$cycloalkyl, $C_1$-$C_6$heterocyclyl and aryl (for example benzyl and $C_5$-$C_6$heterocyclyl).

In another example of the compounds according to this alternate embodiment, D is phenyl or pyridinyl (for example pyridinyl), optionally substituted with one or two (alternatively one) R³⁸, wherein each said R³⁸ is independently selected from $C_1$-$C_6$alkyl, —(CH₂)ⱼNR³⁹(CH₂)ₙR³⁶ or —(CH₂)ₙNR³⁶R³⁹ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), R³⁹ is selected from the group consisting of H, —OH, $C_1$-$C_6$alkyl, $C_3$-$C_{10}$cycloalkyl, —C(O)—R$^z$ and —C(O)—O—R$^z$ (alternatively H or $C_1$-$C_6$alkyl, alternatively H), —SO₂—$C_1$-$C_6$alkyl, and a protecting group used to protect secondary amino groups (for example tert-butoxycarbonyl (Boc), benzylocycarbonyl (Cbz), F-Moc, —CH₂Ph, —COCF₃, —C(O)—R$^z$, —C(O)O—R$^z$), and R³⁶ is selected from the group consisting of H, —OH, $C_1$-$C_6$ alkyl, —(CH₂)ₙO(CH₂)ₜOR³⁷, —(CH₂)ₙCN(CH₂)ₙOR³⁷, —(CH₂)ₙCN(CH₂)ₙR³⁷, and —(CH₂)ₙOR³⁷, alternatively —(CH₂)ₙOR³⁷, wherein each n is an independently selected integer ranging from 0 to 6 (alternatively 0 to 4, alternatively 0 to 2, alternatively 1 or 0, alternatively 0), R³⁷ is H, $C_1$-$C_6$alkyl or $C_3$-$C_{10}$cycloalkyl (alternatively H or $C_1$-$C_6$alkyl, alternatively $C_1$-$C_6$alkyl, alternatively $C_1$-$C_2$alkyl) and R$^z$ is selected from the group consisting of H, $C_1$-$C_6$alkyl, $C_1$-$C_6$cycloalkyl, $C_1$-$C_6$heterocyclyl and aryl (for example benzyl and $C_5$-$C_6$heterocyclyl).

In another example of the compounds according to this alternate embodiment, R³⁹ is selected from the group consisting of H, $C_1$-$C_6$alkyl, $C_1$-$C_6$cycloalkyl, —OMe, —C(O)—$C_1$-$C_6$alkyl, —C(O)—O—$C_1$-$C_6$alkyl, —SO₂—$C_1$-$C_6$alkyl, and a protecting group used to protect secondary amino groups.

In another example of the compounds according to this alternate embodiment, R³⁹ is a protecting group used to protect secondary amino groups, wherein said protecting group is selected from the group consisting of tert-butoxycarbonyl (Boc), benzyloxycarbonyl (Cbz), F-Moc, —CH₂Ph, —COCF₃, —C(O)—Rz and —C(O)O—R$^z$.

In another example of the compounds according to this alternate embodiment, D is phenyl or pryidinyl, substituted with one R³⁸, wherein R³⁸ is —(CH₂)ⱼNR³⁹(CH₂)ₙR³⁶, wherein j is an integer from 0 to 4, n is an integer from 0 to 6, R³⁹ is H or $C_1$-$C_6$alkyl, and R³⁶ is —(CH₂)ₙOR³⁷, wherein n is an integer ranging from 0 to 6, and R³⁷ is H or $C_1$-$C_6$alkyl.

In another example of the compounds according to this alternate embodiment, RG² is SCN— or HO—.

In another example of the compounds according to this alternate embodiment, RG¹ is —NH₂.

In another embodiment of the present invention, a process and intermediates are provided for preparing compounds having Formula (D):

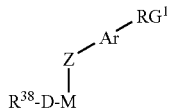
(D)

and N-oxides, hydrates, solvates, pharmaceutically acceptable salts, prodrugs and complexes thereof and racemic and scalemic mixtures, diastereomers, tautomers and enantiomers thereof,
wherein
$R^{38}$, D, M, Z and Ar are as defined above for any previous embodiment or alternative embodiment thereof or example thereof, and $RG^1$ is nitro, —$NH_2$, —NH—$C_1$-$C_4$alkyl-, —NH—$C_2$-$C_4$alkenyl, —NH—$C_2$-$C_4$alkynyl, —NH—$C_3$-$C_6$cycloalkyl, —OH, —SH, —NH—$NH_2$, —NHOH, —N(Me)OH, —N(Me)$NH_2$, —N(Me)-NHMe, —$CH_2NH_2$ or —$CH_2$NHMe;

the processes comprising
providing an intermediate group $R^{38}$-D-$LG^1$, wherein $R^{38}$ comprises zero or more protected reactive moieties therein, and wherein $LG^1$ is a leaving group;
reacting said intermediate group $R^{38}$-D-$LG^1$ or protected intermediate group $R^{38}$-D-$LG^1$ with

wherein $LG^2$ is a leaving group, * represents the point of attachment of group $R^{38}$-D-, and † represents the point of attachment of group Z, to form intermediate (D-1)

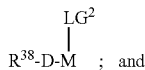
(D-1)

; and reacting (D-1) with intermediate (D-2) via moiety $Z^x$

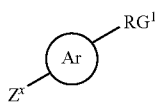
(D-2)

wherein
$Z^x$ is selected from the group consisting of H, —OH, —$CH_2$—OH, —SH, —N($R^5$)H, and —$CH_2$—N($R^5$)H, wherein $R^5$ is selected from the group consisting of H, $C_1$-$C_6$-alkyl, an optionally substituted ($C_1$-$C_5$)acyl and $C_1$-$C_6$ alkyl-O—C(O), wherein $C_1$-$C_6$ alkyl is optionally substituted.

In an example of the compounds according Formula (D), D is -(aryl) or -(heteroaryl);
Z is —O—, —S—, —SO—, —$SO_2$—, —$CH_2$O—, —$OCH_2$— or —N($R^5$)—; and
Ar is aryl or heteroaryl, each of which is optionally substituted with 0 to 4 $R^2$ groups.

In another example of the compounds according to Formula (D), D is optionally substituted phenyl or optionally substituted pyridinyl.

In another example of the compounds according to Formula (D), Z is O.

In another example of the compounds according to Formula (D), Ar is phenyl, pyrazine, pyridazine, pyrimidine or pyridine, each of which is optionally substituted.

In another example of the compounds according to Formula (D), Ar is optionally substituted phenyl.

In another example of the compounds according to Formula (D), M is

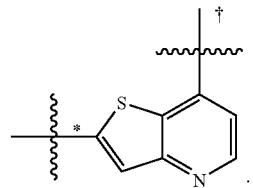 [SMILES: *c1cc2nccc(*)c2s1]

In another example of the compounds according to Formula (D), $R^{38}$ is $C_1$-$C_6$alkyl, —$(CH_2)_j$$NR^{39}$$(CH_2)_n$$R^{36}$ or —$(CH_2)_n$$NR^{36}R^{39}$, wherein j is an integer from 0 to 4, n is an integer from 0 to 6, $R^{39}$ is selected from the group consisting of H, —OH, $C_1$-$C_6$alkyl, $C_3$-$C_{10}$cycloalkyl, —C(O)—$R^z$, —C(O)—O—$R^z$, —$SO_2$—$C_1$-$C_6$alkyl, and a protecting group used to protect secondary amino groups (for example tert-butoxycarbonyl (Boc), benzylocycarbonyl (Cbz), F-Moc, —$CH_2$Ph, —$COCF_3$, —C(O)—$R^z$ or —C(O)O—$R^z$), (alternatively $R^{39}$ is H or $C_1$-$C_6$alkyl, alternatively H), and $R^{36}$ is selected from the group consisting of H, —OH, $C_1$-$C_6$ alkyl, —$(CH_2)_n$—O—$(CH_2)_i$$OR^{37}$, —$(CH_2)_n$CN $(CH_2)_n$$OR^{37}$, —$(CH_2)_n$CN$(CH_2)_n$$R^{37}$, and —$(CH_2)_n$$OR^{37}$, wherein each n is an independently selected integer ranging from 0 to 6, i is an integer from 2 to 6, $R^{37}$ is H, $C_1$-$C_6$alkyl or $C_3$-$C_{10}$cycloalkyl and $R^z$ is selected from the group consisting of H, $C_1$-$C_6$alkyl, $C_1$-$C_6$cycloalkyl, $C_1$-$C_6$heterocyclyl and aryl.

In another example of the compounds according to Formula (D), D is phenyl or pyridinyl, and $R^{38}$ is $C_1$-$C_6$alkyl, —$(CH_2)_j$$NR^{39}$$(CH_2)_n$$R^{36}$ or —$(CH_2)_n$$NR^{36}R^{39}$, wherein j is an integer from 0 to 4, n is an integer from 0 to 6, $R^{39}$ is selected from the group consisting of H, —OH, $C_1$-$C_6$alkyl, $C_3$-$C_{10}$cycloalkyl, —C(O)—$R^z$, —C(O)—O—$R^z$, —$SO_2$—$C_1$-$C_6$alkyl and a protecting group used to protect secondary amino groups (for example tert-butoxycarbonyl (Boc), benzylocycarbonyl (Cbz), F-Moc, —$CH_2$Ph, —$COCF_3$, —C(O)—$R^z$ or —C(O)O—$R^z$), (alternatively $R^{39}$ is H or $C_1$-$C_6$alkyl, alternatively H), and $R^{36}$ is selected from the group consisting of H, —OH, $C_1$-$C_6$ alkyl, —$(CH_2)_n$O $(CH_2)_i$$OR^{37}$, —$(CH_2)_n$CN$(CH_2)_n$$OR^{37}$, —$(CH_2)_n$CN $(CH_2)_n$$R^{37}$, and —$(CH_2)_n$$OR^{37}$, wherein each n is an independently selected integer ranging from 0 to 6, i is an integer from 2 to 6, $R^{37}$ is H, $C_1$-$C_6$alkyl or $C_3$-$C_{10}$cycloalkyl and $R^z$ is selected from the group consisting of H, $C_1$-$C_6$alkyl, $C_1$-$C_6$cycloalkyl, $C_1$-$C_6$heterocyclyl and aryl.

In another example of the compounds according to Formula (D), $LG^1$ and $LG^2$ are independently selected from the group consisting of halo, alkoxy, triflate, mesylate, tosylate, acetate, trifluoroacetate, $SO_2$Me, nosylate, p-nitrophenolate and the like.

In another example of the compounds according to Formula (D), $RG^1$ is nitro, and said nitro is subsequently reduced to amino.

In another example of the compounds according to Formula (D):

$R^{38}$ is as defined above, or alternatively is —$(CH_2)_nNR^{39}(CH_2)_mA^4R^{37}$;

D is -(aryl), -(heterocyclyl) or -(heteroaryl), for example phenyl or pyridinyl (for example pyridinyl);

M is an optionally substituted fused heterocyclic moiety, for example selected from the group consisting of

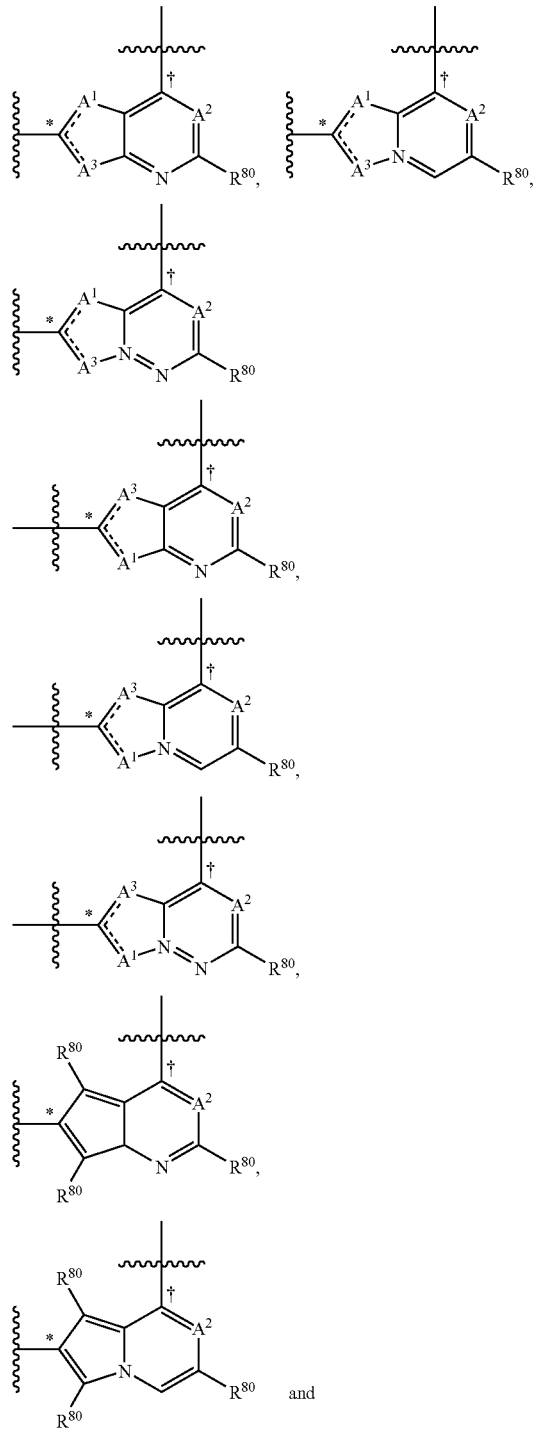

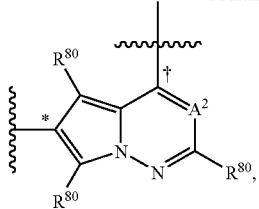

for example

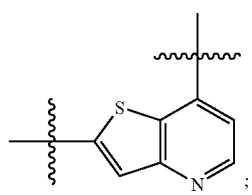 [SMILES: *c1cc2nccc(*)c2s1]

Z is —O—, —S—, —SO—, —SO$_2$—, —CH$_2$O—, —OCH$_2$—, —CH$_2$— or —N(R$^5$)—, for example —O—;

Ar is aryl or heteroaryl, for example selected from the group consisting of phenyl, pyrazine, pyridazine, pryimidine and pyridine, for example phenyl, each of which is optionally substituted with 0 to 4 $R^2$ groups, for example with between zero and four halo; and $RG^1$ is nitro, —NH$_2$, —NH—C$_1$-C$_4$alkyl-, —NH—C$_2$-C$_4$alkenyl, —NH—C$_2$-C$_4$alkynyl, —NH—C$_3$-C$_6$cycloalkyl, —OH, —SH, —NH—NH$_2$, —NHOH, —N(Me)OH, —N(Me)NH$_2$, —N(Me)-NHMe, —CH$_2$NH$_2$ or —CH$_2$NHMe.

In another example of the compounds according to Formula (D), $R^{38}$ is C$_1$-C$_6$alkyl, —(CH$_2$)$_j$NR$^{39}$(CH$_2$)$_n$R$^{36}$ or —(CH$_2$)$_n$NR$^{36}$R$^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, —OH, C$_1$-C$_6$alkyl, C$_3$-C$_{10}$cycloalkyl, —C(O)—R$^z$, —C(O)—O—R$^z$ and —SO$_2$—C$_1$-C$_6$alkyl, and a protecting group used to protect secondary amino groups (tert-butoxycarbonyl (Boc), benzylocycarbonyl (Cbz), F-Moc, —CH$_2$Ph, —COCF$_3$, —C(O)—R$^z$ or —C(O)O—R$^z$), (alternatively $R^{39}$ is H or C$_1$-C$_6$alkyl, alternatively H), and $R^{36}$ is selected from the group consisting of H, —OH, C$_1$-C$_6$ alkyl, —(CH$_2$)$_n$O (CH$_2$)$_n$OR$^{37}$, —(CH$_2$)$_n$CN(CH$_2$)$_n$OR$^{37}$, —(CH$_2$)$_n$CN (CH$_2$)$_n$R$^{37}$, and —(CH$_2$)$_n$OR$^{37}$, alternatively —(CH$_2$)$_n$OR$^{37}$, wherein each n is an independently selected integer ranging from 0 to 6 (alternatively 0 to 4, alternatively 0 to 2, alternatively 1 or 0, alternatively 0), $R^{37}$ is H, C$_1$-C$_6$alkyl or C$_3$-C$_{10}$cycloalkyl (alternatively H or C$_1$-C$_6$alkyl, alternatively C$_1$-C$_6$alkyl, alternatively C$_1$-C$_2$alkyl) and R$^z$ is selected from the group consisting of H, C$_1$-C$_6$alkyl, C$_1$-C$_6$cycloalkyl, C$_1$-C$_6$heterocyclyl and aryl (for example benzyl and C$_5$-C$_6$heterocyclyl).

In another example of the compounds according to Formula (D), D is phenyl or pyridinyl (for example pyridinyl), $R^{38}$ is C$_1$-C$_6$alkyl, —(CH$_2$)$_j$NR$^{39}$(CH$_2$)$_n$R$^{36}$ or —(CH$_2$)$_n$NR$^{36}$R$^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, —OH, C$_1$-C$_6$alkyl, C$_3$-C$_{10}$cycloalkyl, —C(O)—R$^z$, —C(O)—O—R$^z$, —SO$_2$—C$_1$-C$_6$alkyl, and a protecting group used to protect secondary amino groups (for example tert-butoxycarbonyl (Boc), benzylocycarbonyl (Cbz), F-Moc, —CH$_2$Ph, —COCF$_3$, —C(O)—R$^z$ or —C(O)O—R$^z$), (alternatively R$^{39}$ is H or C$_1$-C$_6$alkyl, alternatively H), and R$^{36}$ is selected from the group consisting of H, —OH, C$_1$-C$_6$ alkyl, —(CH$_2$)$_n$O(CH$_2$)$_j$OR$^{37}$, —(CH$_2$)$_n$CN(CH$_2$)$_n$OR$^{37}$, —(CH$_2$)$_n$CN(CH$_2$)$_n$R$^{37}$, and —(CH$_2$)$_n$OR$^{37}$, alternatively —(CH$_2$)$_n$OR$^{37}$, wherein each n is an independently selected integer ranging from 0 to 6 (alternatively 0 to 4, alternatively 0 to 2, alternatively 1 or 0, alternatively 0), R$^{37}$ is H, C$_1$-C$_6$alkyl or C$_3$-C$_{10}$cycloalkyl (alternatively H or C$_1$-C$_6$alkyl, alternatively C$_1$-C$_6$alkyl, alternatively C$_1$-C$_2$alkyl) and R$^z$ is selected from the group consisting of H, C$_1$-C$_6$alkyl, C$_1$-C$_6$cycloalkyl, C$_1$-C$_6$heterocyclyl and aryl (for example benzyl and C$_5$-C$_6$heterocyclyl).

In another example of the compounds according to Formula (D), R$^{39}$ is selected from the group consisting of H, C$_1$-C$_6$alkyl, C$_1$-C$_6$cycloalkyl, —OMe, —C(O)—C$_1$-C$_6$alkyl, —C(O)—O—C$_1$-C$_6$alkyl, —SO$_2$—C$_1$-C$_6$alkyl, and a protecting group used to protect secondary amino groups.

In another example of the compounds according to Formula (D), R$^{39}$ is a protecting group used to protect secondary amino groups, wherein said protecting group is selected from the group consisting of tert-butoxycarbonyl (Boc), benzyloxycarbonyl (Cbz), F-Moc, —CH$_2$Ph, —COCF$_3$, —C(O)—R$^z$ and —C(O)O—R$^z$.

According to another embodiment of the present invention, the invention provides a process for preparing an intermediate compound R$^{38}$-D-LG$^1$, wherein R$^{38}$ comprises zero or protected reactive moieties therein, and LG$^1$ is a leaving group, the process comprising (a) reacting a compound

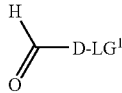

with a pre-R$^{38}$ group, and wherein the reaction of the aldehyde moiety of D with the pre-R$^{38}$ group gives the compound R$^{38}$-D-LG$^1$; and (b) protecting a reactive moiety of R$^{38}$.

In an example of this embodiment for preparing an intermediate compound R$^{38}$-D-LG$^1$, R$^{38}$ is —(CH$_2$)$_n$NR$^{39}$(CH$_2$)$_m$A$^4$R$^{37}$.

In another example of the embodiment for preparing an intermediate compound R$^{38}$-D-LG$^1$, a pre-R$^{38}$ compound is an amino derivative of R$^{38}$.

In another example of the embodiment for preparing an intermediate compound R$^{38}$-D-LG$^1$, the amine precursor of —(CH$_2$)$_n$NR$^{39}$(CH$_2$)$_m$A$^4$R$^{37}$ is H$_2$N(R$^{39}$)(CH$_2$)$_m$A$^4$R$^{37}$.

In another example of the embodiment for preparing an intermediate compound R$^{38}$-D-LG$^1$, D is -(aryl)-, -(heterocycle)- or -(heteroaryl)-, for example phenyl or pyridinyl, each of which is optionally substituted.

In another example of the embodiment for preparing an intermediate compound R$^{38}$-D-LG$^1$, R$^{38}$ is C$_1$-C$_6$alkyl, —(CH$_2$)$_j$NR$^{39}$(CH$_2$)$_n$R$^{36}$ or —(CH$_2$)$_n$NR$^{36}$R$^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), R$^{39}$ is selected from the group consisting of H, —OH, C$_1$-C$_6$alkyl, C$_3$-C$_{10}$cycloalkyl, —C(O)—R$^z$ and —C(O)—O—R$^z$, —SO$_2$—C$_1$-C$_6$alkyl, and a protecting group used to protect secondary amino groups (for example tert-butoxycarbonyl (Boc), benzylocycarbonyl (Cbz), F-Moc, —CH$_2$Ph, —COCF$_3$, —C(O)—R$^z$ or —C(O)O—R$^z$), (alternatively R$^{39}$ is H or C$_1$-C$_6$alkyl, alternatively H), and R$^{36}$ is selected from the group consisting of H, —OH, C$_1$-C$_6$ alkyl, —(CH$_2$)$_n$O(CH$_2$)$_j$OR$^{37}$, —(CH$_2$)$_n$CN(CH$_2$)$_n$OR$^{37}$, —(CH$_2$)$_n$CN(CH$_2$)$_n$R$^{37}$, and —(CH$_2$)$_n$OR$^{37}$, alternatively —(CH$_2$)$_n$OR$^{37}$, wherein each n is an independently selected integer ranging from 0 to 6 (alternatively 0 to 4, alternatively 0 to 2, alternatively 1 or 0, alternatively 0), R$^{37}$ is H, C$_1$-C$_6$alkyl or C$_3$-C$_{10}$cycloalkyl (alternatively H or C$_1$-C$_6$alkyl, alternatively C$_1$-C$_6$alkyl, alternatively C$_1$-C$_2$alkyl) and R$^z$ is selected from the group consisting of H, C$_1$-C$_6$alkyl, C$_1$-C$_6$cycloalkyl, C$_1$-C$_6$heterocyclyl and aryl (for example benzyl and C$_5$-C$_6$heterocyclyl).

In another example of the embodiment for preparing an intermediate compound R$^{38}$-D-LG$^1$, D is phenyl or pryidinyl (for example pyridinyl), R$^{38}$ is C$_1$-C$_6$alkyl, —(CH$_2$)$_j$NR$^{39}$(CH$_2$)$_n$R$^{36}$ or —(CH$_2$)$_n$NR$^{36}$R$^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), R$^{39}$ is selected from the group consisting of H, —OH, C$_1$-C$_6$alkyl, C$_3$-C$_{10}$cycloalkyl, —C(O)—R$^z$ and —C(O)—O—R$^z$, —SO$_2$—C$_1$-C$_6$alkyl, and a protecting group used to protect secondary amino groups (for example tert-butoxycarbonyl (Boc), benzylocycarbonyl (Cbz), F-Moc, —CH$_2$Ph, —COCF$_3$, —C(O)—R$^z$ or —C(O)O—R$^z$), (alternatively R$^{39}$ is H or C$_1$-C$_6$alkyl, alternatively H), and R$^{36}$ is selected from the group consisting of H, —OH, C$_1$-C$_6$ alkyl, —(CH$_2$)$_n$O(CH$_2$)$_j$OR$^{37}$, —(CH$_2$)$_n$CN(CH$_2$)$_n$OR$^{37}$, —(CH$_2$)$_n$CN(CH$_2$)$_n$R$^{37}$, and —(CH$_2$)$_n$OR$^{37}$, alternatively —(CH$_2$)$_n$OR$^{37}$, wherein each n is an independently selected integer ranging from 0 to 6 (alternatively 0 to 4, alternatively 0 to 2, alternatively 1 or 0, alternatively 0), R$^{37}$ is H, C$_1$-C$_6$alkyl or C$_3$-C$_{10}$cycloalkyl (alternatively H or C$_1$-C$_6$alkyl, alternatively C$_1$-C$_6$alkyl, alternatively C$_1$-C$_2$alkyl) and R$^z$ is selected from the group consisting of H, C$_1$-C$_6$alkyl, C$_1$-C$_6$cycloalkyl, C$_1$-C$_6$heterocyclyl and aryl (for example benzyl and C$_5$-C$_6$heterocyclyl).

In an alternate embodiment of the process and intermediates for preparing compounds having the Formula (D):

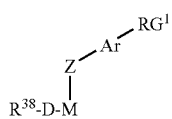

(D)

and N-oxides, hydrates, solvates, pharmaceutically acceptable salts, prodrugs and complexes thereof and racemic and scalemic mixtures, diastereomers, tautomers and enantiomers thereof, wherein R$^{38}$, D, M, Z and Ar are as defined above, wherein R$^{38}$ comprises zero or more reactive moieties therein, and RG$^1$ is a reactive group selected from the group consisting of nitro, —NH$_2$, —NH—C$_1$-C$_4$alkyl-, —NH—C$_2$-C$_4$alkenyl, —NH—C$_2$-C$_4$alkynyl, —NH—C$_3$-C$_6$cycloalkyl, —OH, —SH, —NH—NH$_2$, —NHOH, —N(Me)OH, —N(Me)NH$_2$, —N(Me)-NHMe, —CH$_2$NH$_2$ and —CH$_2$NHMe;

the process comprises:
reacting an intermediate

wherein LG² is a leaving group, * represents the point of attachment of group R³⁸-D-, and † represents the point of attachment of group Z with intermediate (D-2)

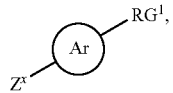 (D-2)

wherein Ar is optionally substituted with 0 to 4 R²,
to form intermediate (D-5)

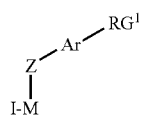 (D-5)

wherein $Z^x$ is selected from the group consisting of —OH, —CH₂—OH, —SH, —N(R⁵)H, and —CH₂—N(R⁵)H, wherein R⁵ is selected from the group consisting of H, $C_1$-$C_6$ alkyl, an optionally substituted ($C_1$-$C_5$)acyl and $C_1$-$C_6$ alkyl-O—C(O), wherein $C_1$-$C_6$ alkyl is optionally substituted;

reacting intermediate (D-5) with intermediate (D-6)

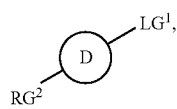 (D-6)

wherein LG¹ is a leaving group, and RG² is a reactive group for constructing R³⁸, to form intermediate (D-7)

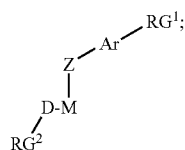 (D-7)

reacting the RG² moiety of intermediate (D-7) with a pre-R³⁸ compound, wherein the reaction of RG² with the pre-R³⁸ compound gives the substituent R³⁸; and if present, protecting a reactive moiety of R³⁸.

In an example of this alternate embodiment of the process and intermediates for preparing compounds having the Formula (D), RG² is —CHO or —CH₂Hal; pre-R³⁸ is NH₂(CH₂)ₘA⁴R³⁷ and R³⁸ is —(CH₂)ₙNH(CH₂)ₘA⁴R³⁷.

In another embodiment of the processes and intermediates for preparing compounds having the Formula (D), R³⁸ is —(CH₂)ₙNR³⁹(CH₂)ₘA⁴R³⁷;

D is -(aryl) or -(heteroaryl);

RG² is —CHO;

M is selected from the group consisting of

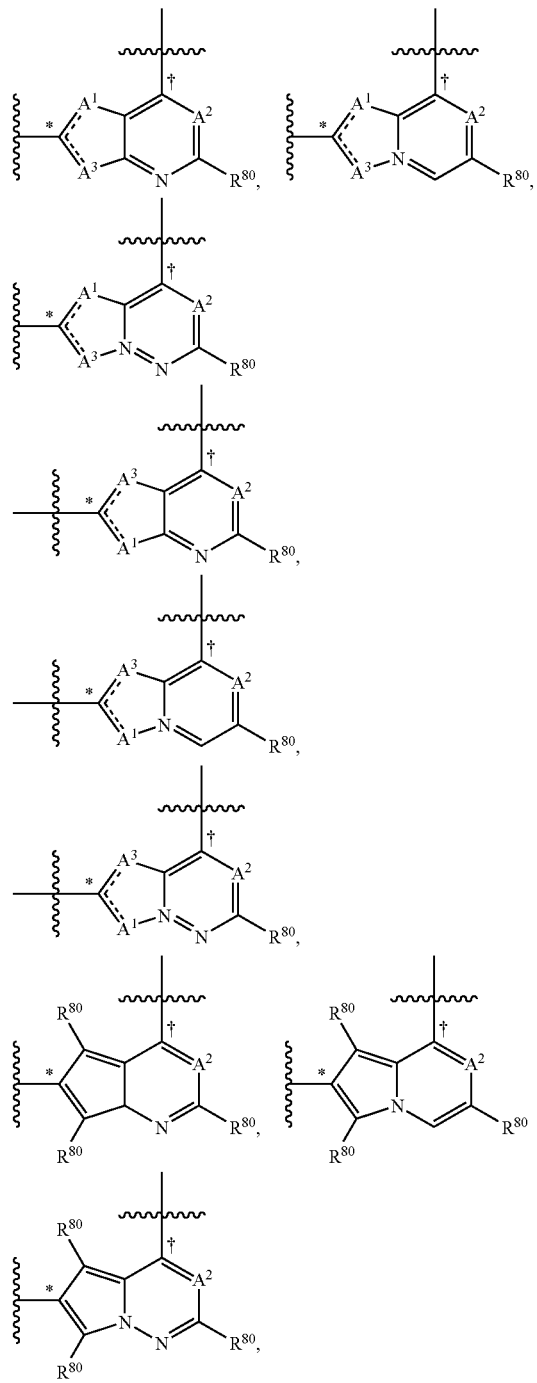

wherein * represents the point of attachment to group D and † represents the point of attachment of the group Z;

Z is —O—;

Ar is aryl or heteroaryl, each of which is optionally substituted with 0 to 4 R² groups; and RG¹ is nitro, —NH₂, —NH—$C_1$-$C_4$alkyl-, —NH—$C_2$-$C_4$alkenyl, —NH—$C_2$-$C_4$alkynyl, —NH—$C_3$-$C_6$cycloalkyl, —NH—NH₂, —NHOH, —N(Me)OH, —N(Me)NH₂, —N(Me)-NHMe, —CH₂NH₂ or —CH₂NHMe.

In another example of this alternate embodiment of the process and intermediates for preparing compounds having Formula (D), M is

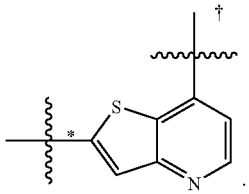 [SMILES: *c1cc2nccc(*)c2s1]

In another example of this alternate embodiment of the process and intermediates for preparing compounds having Formula (D), RG$^1$ is nitro, and said nitro is subsequently reduced to amino.

In another embodiment of the present invention there is provided, a process and intermediates for preparing a compound having the formula (E):

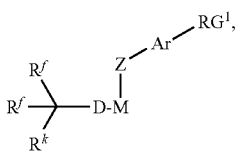
(E)

and N-oxides, hydrates, solvates, pharmaceutically acceptable salts, prodrugs and complexes thereof and racemic and scalemic mixtures, diastereomers, tautomers and enantiomers thereof,
wherein
D, M, Z and Ar are as defined above,
RG$^1$ is nitro, —NH$_2$, —NH—C$_1$-C$_4$alkyl-, —NH—C$_2$-C$_4$alkenyl, —NH—C$_2$-C$_4$alkynyl, —NH—C$_3$-C$_6$cycloalkyl, —OH, —SH, —NH—NH$_2$, —NHOH, —N(Me)OH, —N(Me)NH$_2$, —N(Me)-NHMe, —CH$_2$NH$_2$ or —CH$_2$NHMe;
R$^k$ is selected from the group consisting of H, C$_1$-C$_4$alkyl, C$_3$-C$_6$cycloalkyl, C$_2$-C$_4$ alkenyl and C$_2$-C$_4$ alkynyl;
each R$^f$ is independently —O—C$_1$-C$_7$alkyl, or both R$^f$ taken together with the atom to which there are attached may form a cyclic acetal (a 5 to 8 member ring system), or a carbonyl group;
the process comprising
reacting an intermediate compound of Formula (E-1)

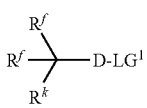
(E-1)

wherein
LG$^1$ is a leaving group,
with

wherein LG$^2$ is a leaving group, * represents the point of attachment of group R$^{38}$-D-, and † represents the point of attachment of group Z, to form intermediate compound (E-2)

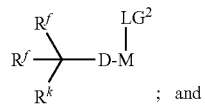
(E-2)

; and reacting (E-2) with

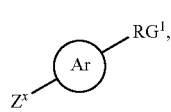
(D-2)

via said Z$^x$ moiety,
wherein
Z$^x$ is selected from the group consisting of H, —OH, —CH$_2$—OH, —SH, —N(R$^5$)H, —NH—CH$_3$ and —CH$_2$—N(R$^5$)H, wherein R$^5$ is selected from the group consisting of H, an optionally substituted (C$_1$-C$_5$)acyl and C$_1$-C$_6$ alkyl-O—C(O), wherein C$_1$-C$_6$ alkyl is optionally substituted.

In an example of the embodiment of the process and intermediates for preparing a compound having the Formula (E):

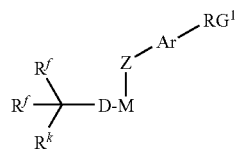
(E)

and N-oxides, hydrates, solvates, pharmaceutically acceptable salts, prodrugs and complexes thereof and racemic and scalemic mixtures, diastereomers, tautomers and enantiomers thereof, wherein
R$^k$ is selected from the group consisting of H, C$_1$-C$_4$alkyl, C$_3$-C$_6$cycloalkyl, C$_2$-C$_4$ alkenyl and C$_2$-C$_4$ alkynyl;
each R$^r$ is independently —O—C$_1$-C$_7$alkyl, or both R$^f$ taken together with the atom to which they are attached may form a cyclic acetal (a 5 to 8 member ring system), or a carbonyl group;
D is -(aryl), -(heterocyclyl) or -(heteroaryl), for example phenyl or pryidinyl (for example pyridinyl);
Z is —O—, —S—, —SO—, —SO$_2$—, —CH$_2$O—, —OCH$_2$—, —CH$_2$— or —N(R$^5$)—, for example —O—;
Ar is aryl or heteroaryl, for example selected from the group consisting of phenyl, pyrazine, pyridazine, pryimidine and pyridine, for example phenyl, each of which is optionally substituted with 0 to 4 R$^2$ groups, alternatively with between zero and four halo; and
RG$^1$ is nitro, —NH$_2$, —NH—C$_1$-C$_4$alkyl-, —NH—C$_2$-C$_4$alkenyl, —NH—C$_2$-C$_4$alkynyl, —NH—C$_3$-C$_6$cycloalkyl, —OH, —SH, —NH—NH$_2$, —NHOH, —N(Me)OH, —N(Me)NH$_2$, —N(Me)-NHMe, —CH$_2$NH$_2$ and —CH$_2$NHMe;

In another example of this embodiment of the process and intermediates for preparing a compound having the Formula (E)

D is -(aryl) or -(heteroaryl);
M is selected from the group consisting of

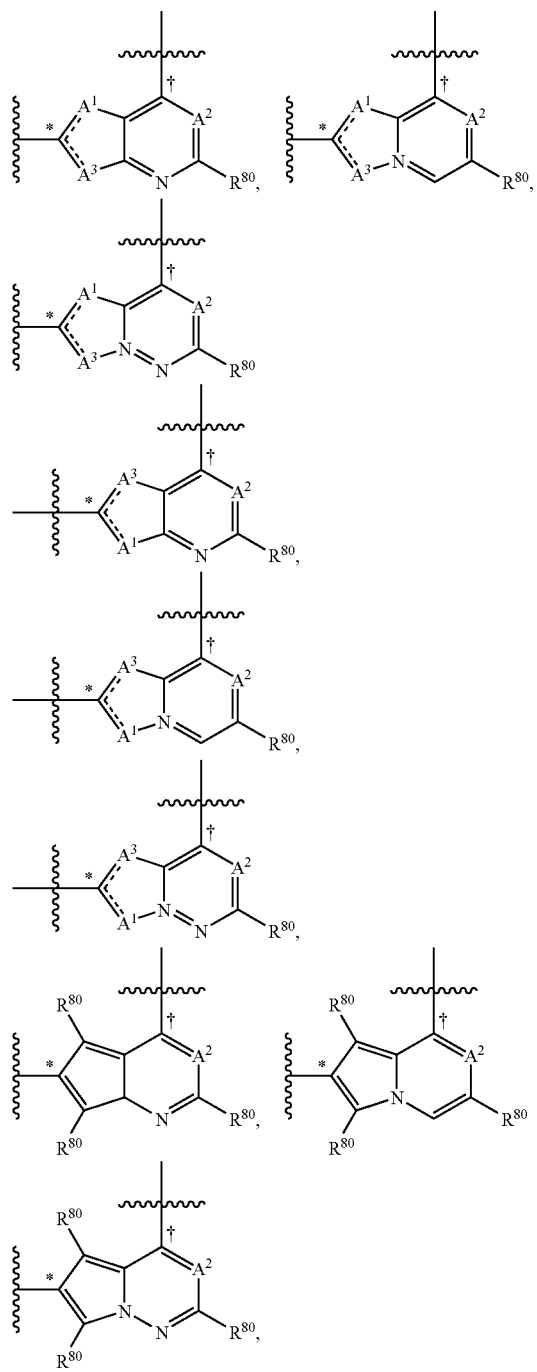

wherein * represents the point of attachment to group D and † represents the point of group Z;
Z is —O—;
Ar is aryl or heteroaryl, each of which is optionally substituted with 0 to 4 $R^2$ groups; and
$RG^1$ is nitro, —$NH_2$, —NH—$C_1$-$C_4$alkyl-, —NH—$C_2$-$C_4$alkenyl, —NH—$C_2$-$C_4$alkynyl, —NH—$C_3$-$C_6$cycloalkyl, —OH, —SH, —NH—$NIH_2$, —NHOH, —N(Me)OH, —N(Me)$NH_2$, —N(Me)-NHMe, —$CH_2NH_2$ or —$CH_2$NHMe.

In another example of this embodiment of the process and intermediates for preparing a compound having Formula (E), M is

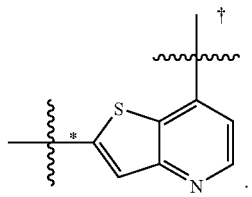

In another example of this embodiment of the process and intermediates for preparing a compound having Formula (E), $RG^1$ is nitro, wherein said nitro is subsequently reduced to —$NH_2$.

In another example of this embodiment of the process and intermediates for preparing a compound having Formula (E), compound (E-1) is prepared by protection of an aldehyde of Formula (E-3): OHC-D-$LG^1$ (E-3).

In another example of this embodiment of the process and intermediates for preparing a compound having Formula (E), D is phenyl or pyridinyl (for example pyridinyl).

In another embodiment the present invention provides a process and intermediates for preparing a compound having Formula (F):

(F)

and N-oxides, hydrates, solvates, pharmaceutically acceptable salts, prodrugs and complexes thereof and racemic and scalemic mixtures, diastereomers, tautomers and enantiomers thereof,
wherein
$R^{38}$, D, M, Z, Ar and G are as defined herein, the process comprising:
reacting a compound of Formula (E)

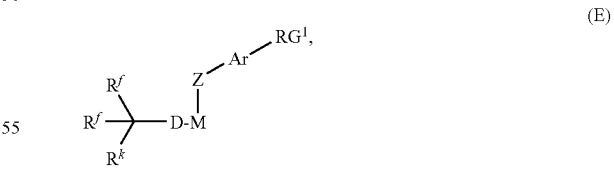

(E)

wherein
$R^k$ is selected from the group consisting of H, $C_1$-$C_4$alkyl, $C_3$-$C_6$cycloalkyl, $C_2$-$C_4$ alkenyl and $C_2$-$C_4$ alkynyl;
each $R^f$ is independently —O—$C_1$-$C_7$alkyl, or both $R^f$ taken together with the atom to which they are attached may form a cyclic acetal (a 5 to 8 member ring system), or a carbonyl group; and
$RG^1$ is nitro, —$NH_2$, —NH—$C_1$-$C_4$alkyl-, —NH—$C_2$-$C_4$alkenyl, —NH—$C_2$-$C_4$alkynyl, —NH—$C_3$-$C_6$cycloalkyl, —OH, —SH, —NH—NH$_2$, —NHOH, —N(Me)OH, —N(Me)NH$_2$, —N(Me)-NHMe, —CH$_2$NH$_2$, or —CH$_2$NHMe;

with a compound of Formula (A-2)

RG$^2$-G$^1$, (A-2)

wherein RG$^2$ is a functional group reacting with —RG$^1$, and RG$^2$-G$^1$ is a precursor of group G, such that the reaction of —RG$^1$ with RG$^2$-G$^1$ forms -G;

deprotecting

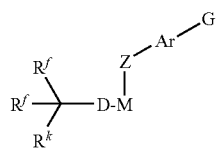

to yield

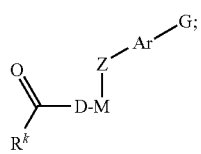

and
reacting the

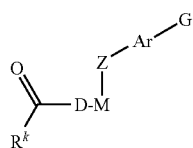

with a pre-R$^{38}$ group to provide the moiety R$^{38}$-D- to yield a compound having Formula (F).

In an example of this embodiment of the process and intermediates for preparing a compound having Formula (F), deprotecting

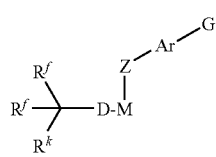

forms the aldehyde

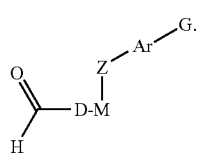

In another example of the embodiment of the process and intermediates for preparing a compound having Formula (F), D is aryl or heteroaryl, each of which is optionally substituted.

In another example of the embodiment of the process and intermediates for preparing a compound having Formula (F), D is phenyl or pyridinyl, each of which is optionally substituted.

In another example of the embodiment of the process and intermediates for preparing a compound having Formula (F), M is selected from the group consisting of

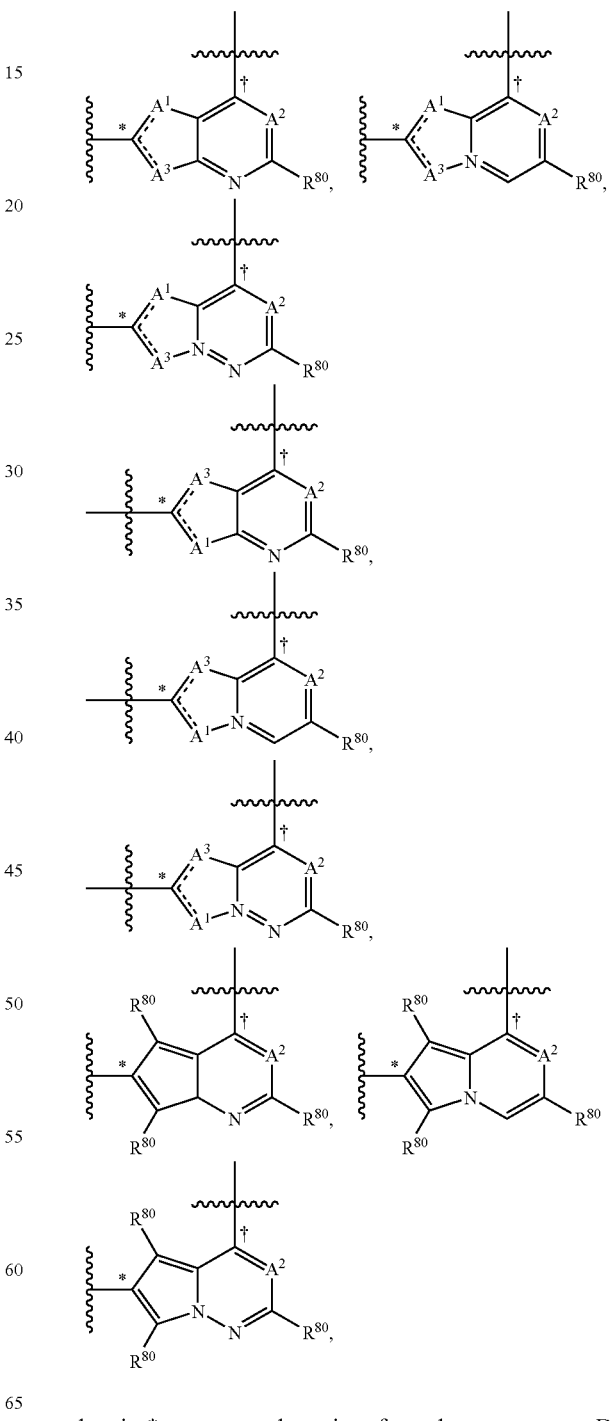

wherein * represents the point of attachment to group D and † represents the point of group Z.

In another example of the embodiment of the process and intermediates for preparing compounds having Formula (F), M is

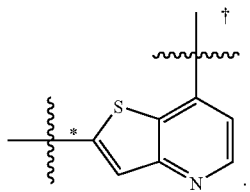 [SMILES: *c1cc2nccc(*)c2s1]

In another example of the embodiment of the process and intermediates for preparing a compound having Formula (F), Z is O.

In another example of the embodiment of the process and intermediates for preparing a compound having Formula (F), Ar is phenyl, optionally substituted with 0 to 4 $R^2$.

In another example of the embodiment of the process and intermediates for preparing a compound having Formula (F), G is a group B-L-T.

In another example of this embodiment of the process and intermediates for preparing a compound having Formula (F), G is a group

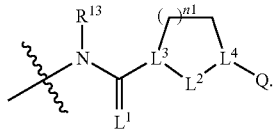

In another example of the embodiment of the process and intermediates for preparing a compound having Formula (F), G is selected from the group consisting of

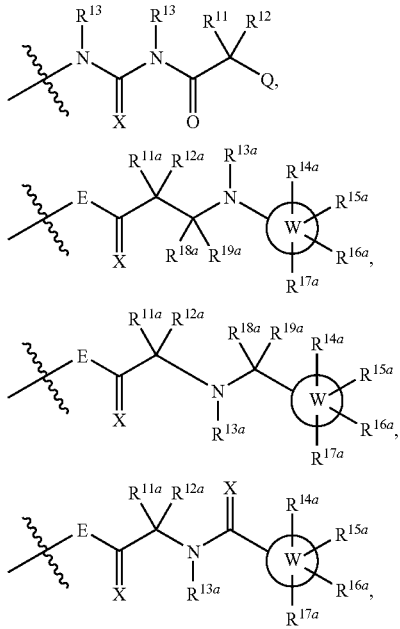

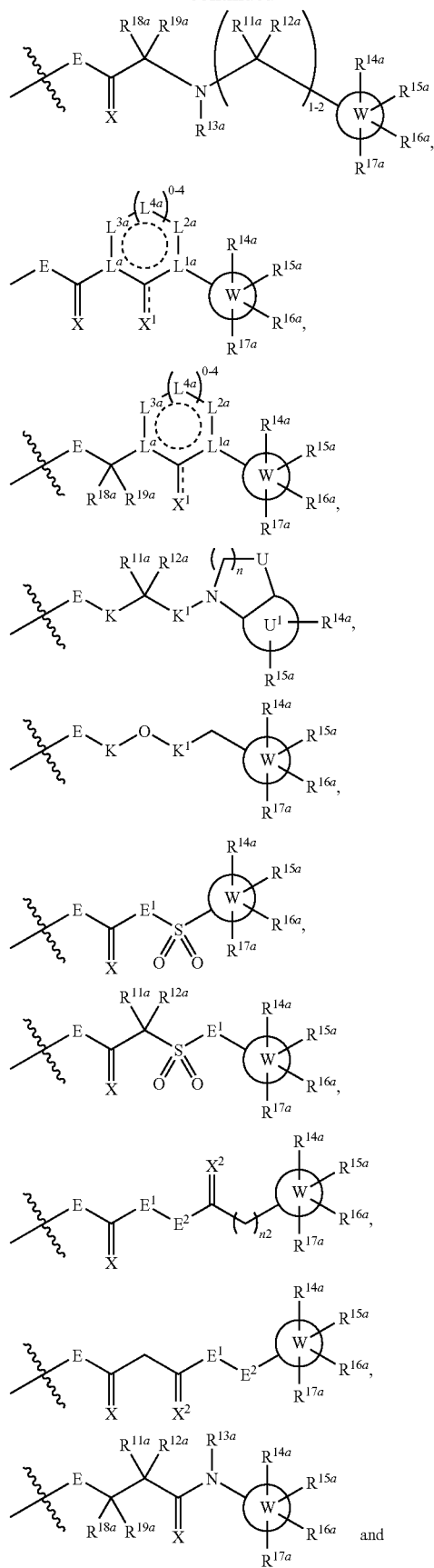

and

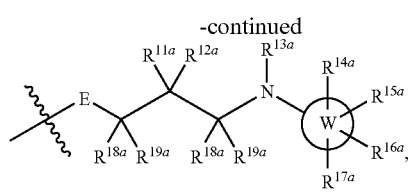
In another example of the embodiment of the process and intermediates for preparing a compound having Formula (F), G is selected from the group consisting of
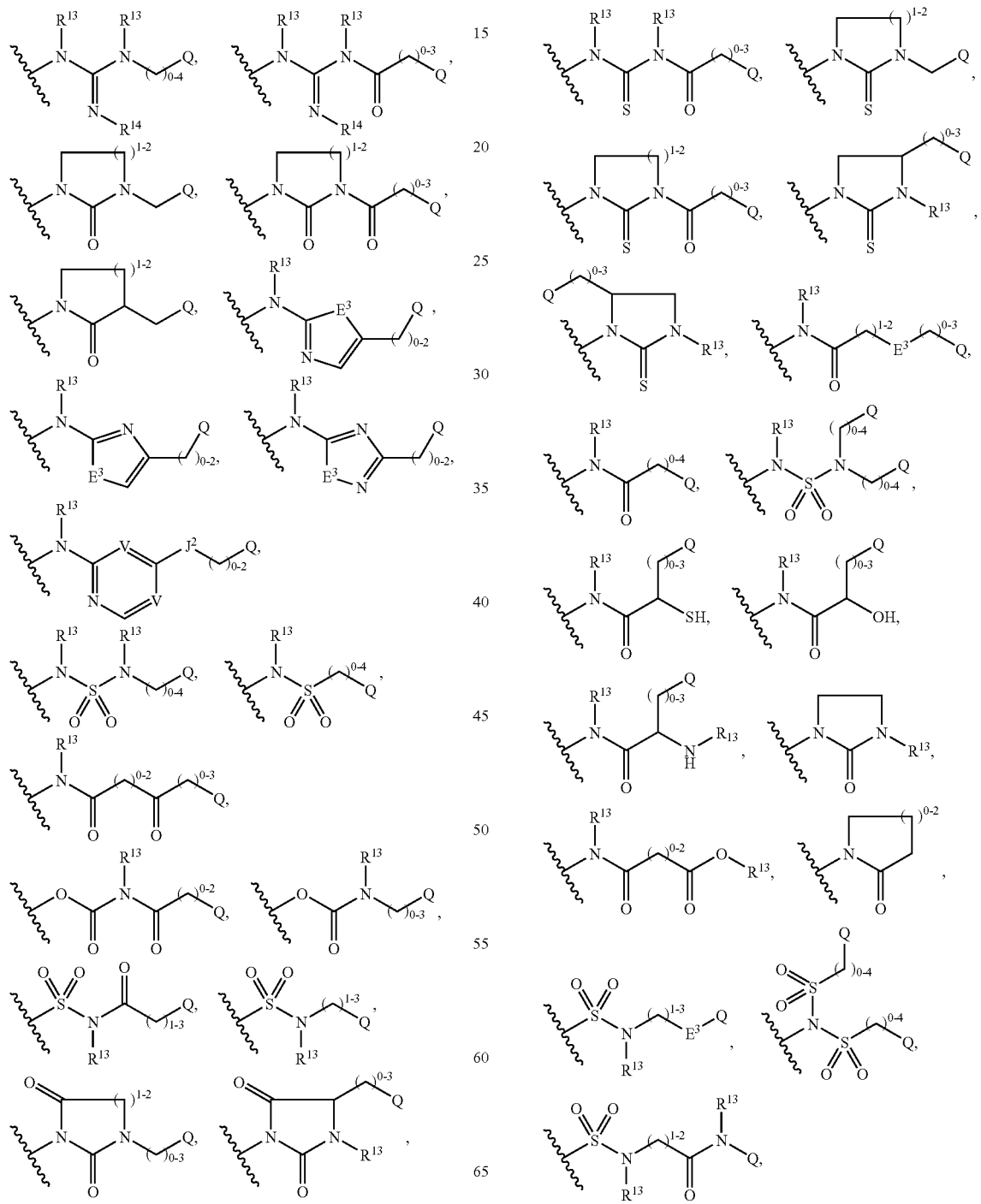

-continued

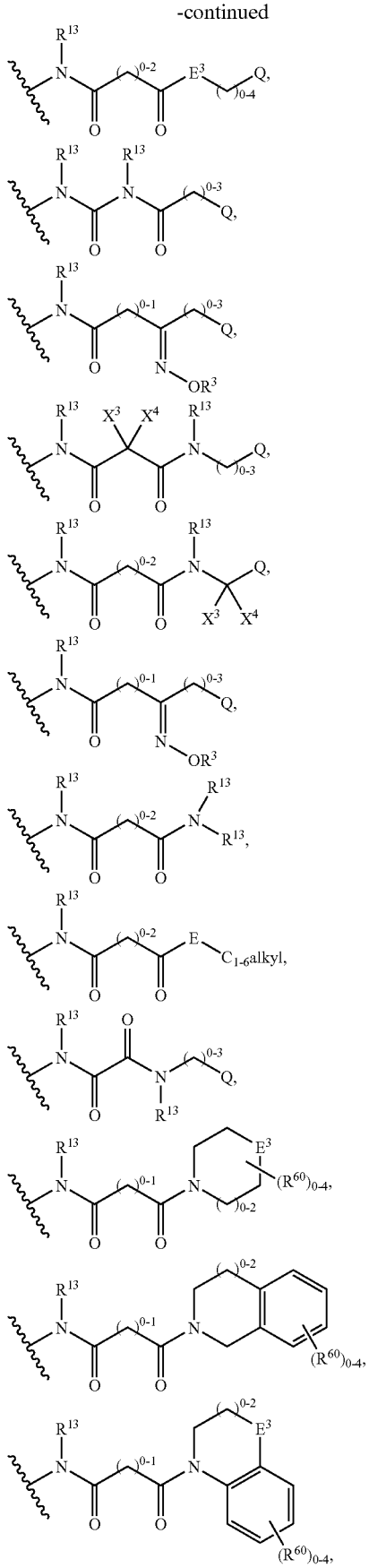

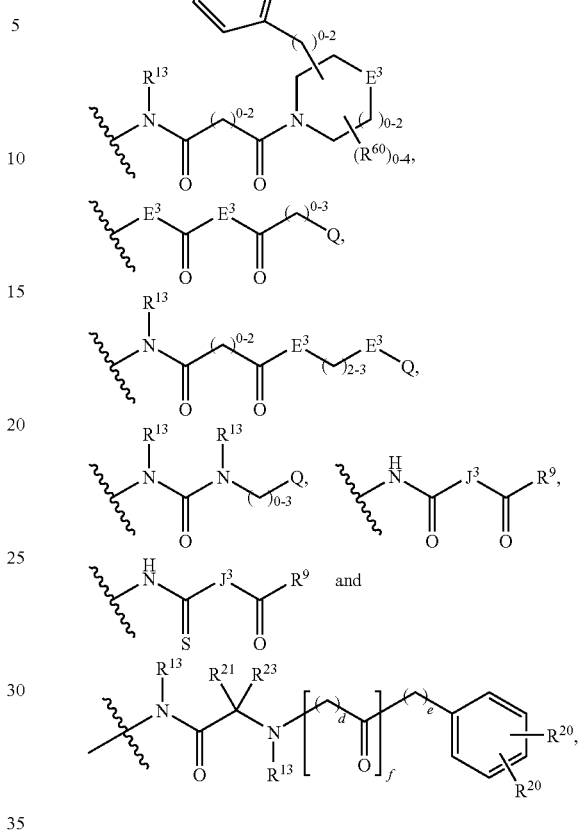

wherein
any methylene group is independently optionally substituted with $R^{25}$, wherein $R^{25}$ is selected from the group consisting of halogen, trihalomethyl, —CN, —NO$_2$, —NH$_2$, —OR$^3$, —NR$^3$, R$^4$, —S(O)$_{0-2}$R$^3$, —SO$_2$NR$^3$R$^3$, —CO$_2$R$^3$, —C(O)NR$^3$R$^3$, —N(R$^3$)SO$_2$R$^3$, —N(R$^3$)C(O)R$^3$, —N(R$^3$)CO$_2$R$^3$, —C(O)R$^3$, an optionally substituted aryl, an optionally substituted arylalkyl, an optionally substituted heteroarylalkyl, and an optionally substituted (C$_1$-C$_6$)alkyl, or two $R^{25}$, together with the carbon or carbons to which they are attached, can combine to form a three- to seven-membered alicyclic or heteroalicyclic, or two $R^{25}$, on a single carbon can be oxo;

$R^9$ is selected from the group consisting of a C$_{1-6}$ alkyl on which one or more hydrogen atoms are optionally substituted by —R$^{24}$, -T$^1$-R$^{15}$, or —NR$^{16}$R$^{17}$, a —N(R$^{18}$)(R$^{19}$) moiety and a saturated or unsaturated three- to eight-membered carbocyclic or heterocyclic group which is optionally substituted by a C$_{1-6}$ alkyl, a C$_{1-6}$ alkoxy, a halogen atom, nitro, a trifluoromethyl, a C$_{1-6}$ alkoxy carbonyl, cyano, a cyano C$_{1-6}$ alkyl, a C$_{1-6}$ alkylthio, a phenoxy, an acetyl, or a saturated or unsaturated five- or six-membered heterocyclyl ring wherein, when the three- to eight-membered carbocyclic or heterocyclic group is substituted by two C$_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, wherein $T^1$ is selected from the group consisting of —O—, —S— and —NH—;

R[24] represents a saturated or unsaturated three- to eight-membered carbocyclic or heterocyclic group;

R[15], R[16], and R[17], which may be the same or different, represent a $C_{1-6}$ alkyl or a saturated or unsaturated three- to eight-membered carbocyclic or heterocyclic group; wherein the three- to eight-membered carbocyclic or heterocyclic group represented by R[24], R[15], R[16], and R[17] is optionally substituted by a $C_{1-6}$ alkyl, a $C_{1-6}$ alkoxy, a halogen atom, nitro, a trifluoromethyl, a $C_{1-6}$ alkoxy carbonyl, a cyano, a cyano $C_{1-6}$ alkyl, a $C_{1-6}$ alkylthio, a phenoxy, an acetyl, or a saturated or unsaturated five- or six-membered heterocyclyl ring; and wherein when the three- to eight-membered carbocyclic or heterocyclic group is substituted by two $C_{1-6}$ alkyl groups, the two alkyl groups may combine together to form an alkylene chain; and wherein the three- to eight-membered carbocyclic or heterocyclic group may be a bicyclic group condensed with another saturated or unsaturated three- to eight-membered carbocyclic or heterocyclic group; and R[18] and R[19], which may be the same or different, represent (1) a hydrogen atom, (2) a $C_{1-6}$ alkyl which is optionally substituted by a $C_{1-6}$ alkoxy, a $C_{1-6}$ alkylthio, or a saturated or unsaturated three- to eight-membered carbocyclic or heterocyclic group in which the three- to eight-membered carbocyclic or heterocyclic group is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and wherein when the three- to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group, or (3) a saturated or unsaturated three- to eight-membered carbocyclic or heterocyclic group which is optionally substituted by a $C_{1-6}$ alkyl, a $C_{1-6}$ alkoxy, a halogen atom, nitro, a trifluoromethyl, a $C_{1-6}$ alkoxy carbonyl, cyano, a cyano $C_{1-6}$ alkyl, a $C_{1-6}$ alkylthio, a phenoxy, an acetyl, or a saturated or unsaturated five- or six-membered heterocyclyl ring and in which, when the three to eight-membered carbocyclic or heterocyclic group is substituted by two $C_{1-6}$ alkyl groups, the two alkyl groups may combine together to form an alkylene chain, or the three- to eight-membered carbocyclic or heterocyclic group may be a bicyclic group condensed with another saturated or unsaturated three- to eight-membered carbocyclic or heterocyclic group;

$X^3$ and $X^4$ are each independently selected from the group consisting of —H, halogen, cyano, nitro, $C_1$-$C_6$ alkyl, or $X^3$ and $X^4$ together with the atom to which they are attached form a $C_3$-$C_4$ cycloalkyl;

each $E^3$ is independently selected from the group consisting of —O—, —N(R[13])—, —CH$_2$— and —S(O)$_{0-2}$;

$J^2$ is selected from the group consisting of —O—, —N(R[13])—, —CH$_2$— and —C(=O)N(R[13]);

$J^3$ represents —C(R[26])(R[27])—, wherein

R[26] and R[27] are independently selected from the group consisting of a hydrogen atom, a $C_{1-4}$ alkyl, a $C_{1-4}$ alkoxy and —N(R[12b]), wherein R[12b] is a hydrogen atom or a $C_{1-4}$ alkyl;

each V is independently selected from the group consisting of =N— and =C(H)—;

R[21] and R[23] are independently selected from the group consisting of H, halogen, —OH, unsubstituted —O—($C_1$-$C_6$alkyl), substituted —O—($C_1$-$C_6$alkyl), unsubstituted —O-(cycloalkyl), substituted —O-(cycloalkyl), unsubstituted —NH($C_1$-$C_6$alkyl), substituted —NH($C_1$-$C_6$alkyl), —NH$_2$, —SH, unsubstituted —S—($C_1$-$C_6$alkyl), substituted —S—($C_1$-$C_6$alkyl), unsubstituted $C_1$-$C_6$alkyl and substituted $C_1$-$C_6$alkyl; or R[21] and R[23] taken together with the atom to which they are attached form a $C_3$-$C_7$ ring system, wherein said ring system is optionally substituted;

d is 0, 1, 2 or 3;

e is 0, 1, 2 or 3; and f is 0 or 1.

In another example of the embodiment of the process and intermediates for preparing a compound having Formula (F), G is selected from the group consisting of

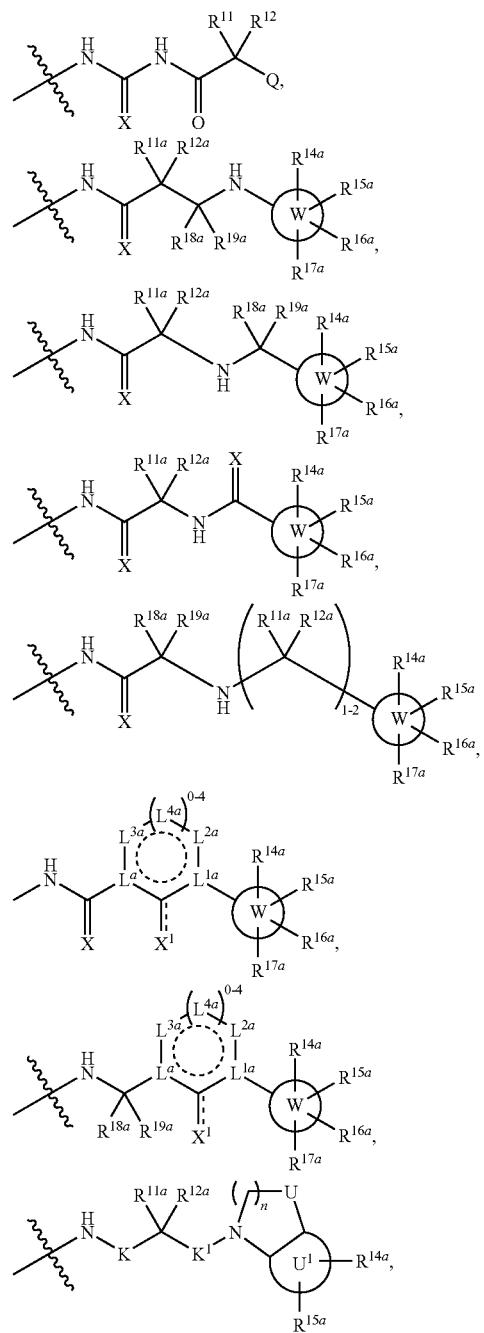

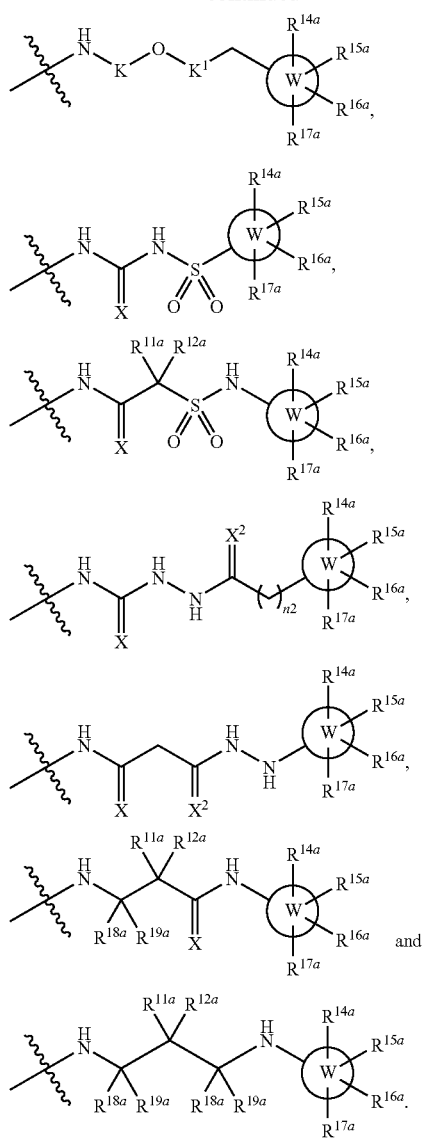
In another example of the embodiment of the process and intermediates for preparing a compound having Formula (F), G is selected from the group consisting of
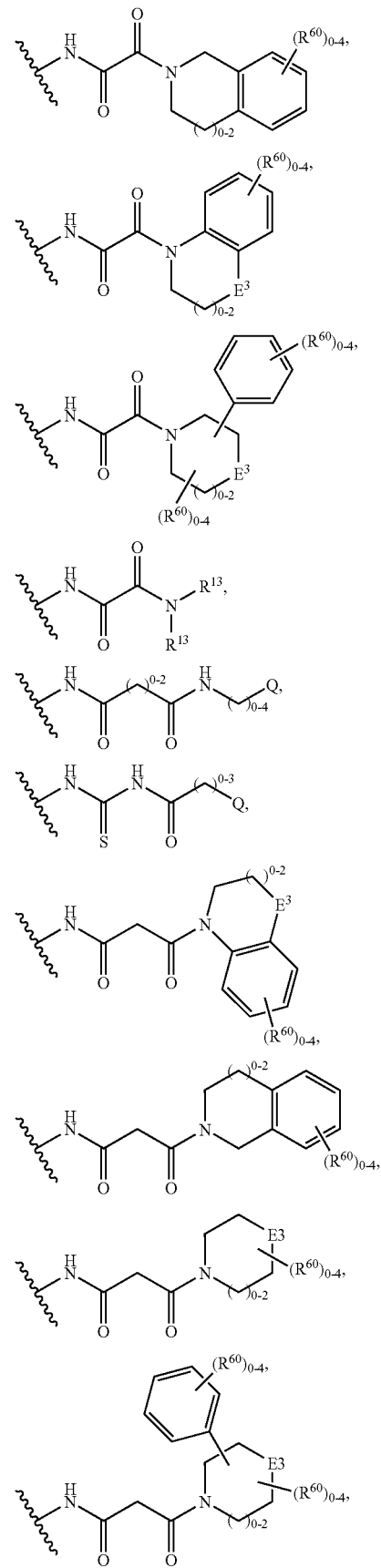

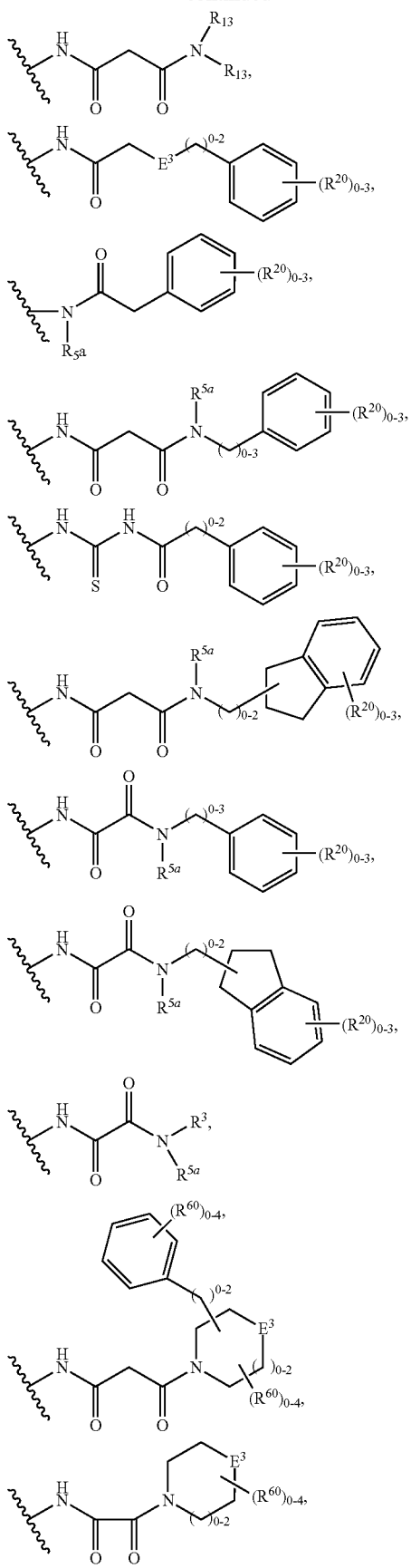

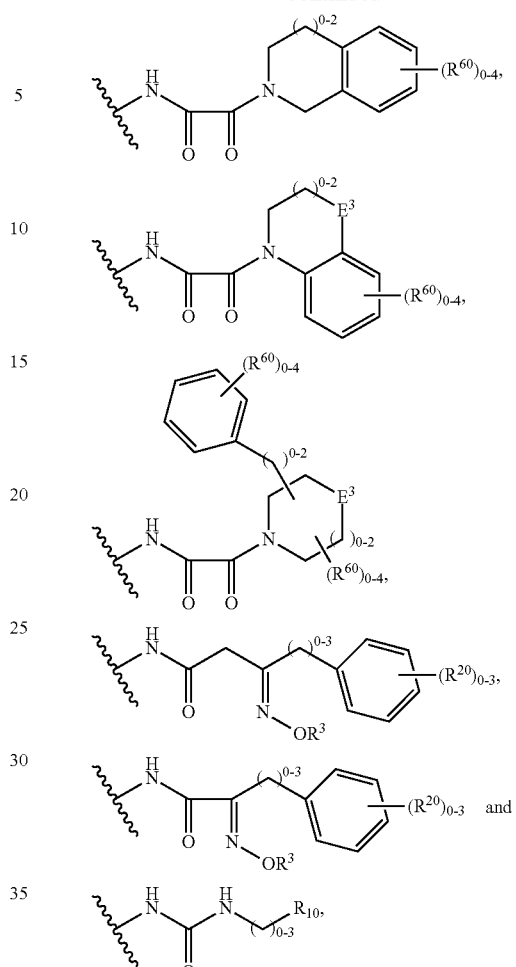

wherein each methylene in any of the above formulae, other than those in a depicted ring, is independently optionally substituted with $R^{25}$;

$R^{5a}$ is —H or an optionally substituted ($C_1$-$C_6$)alkyl;

$R^{10}$ is an azolyl, wherein one or more hydrogen atoms are optionally substituted by a moiety selected from the group consisting of a halogen, $C_{1-4}$ alkyl, $C_{1-4}$ alkoxy, $C_{1-4}$ alkylthio, trihalomethyl, nitro, amino optionally independently substituted by one or two of $C_{1-4}$ alkyl, a $C_{1-4}$ alkoxycarbonyl $C_{1-4}$ alkyl, a $C_{1-4}$ alkylcarbonyl and a $C_{3-5}$ cyclic alkyl.

In another example of the embodiment of the process and intermediates for preparing a compound having Formula (F), G is selected from the group consisting of

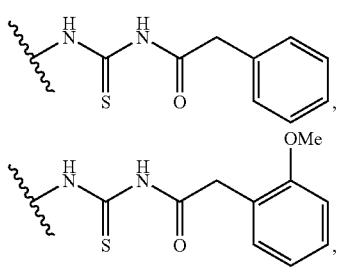

-continued
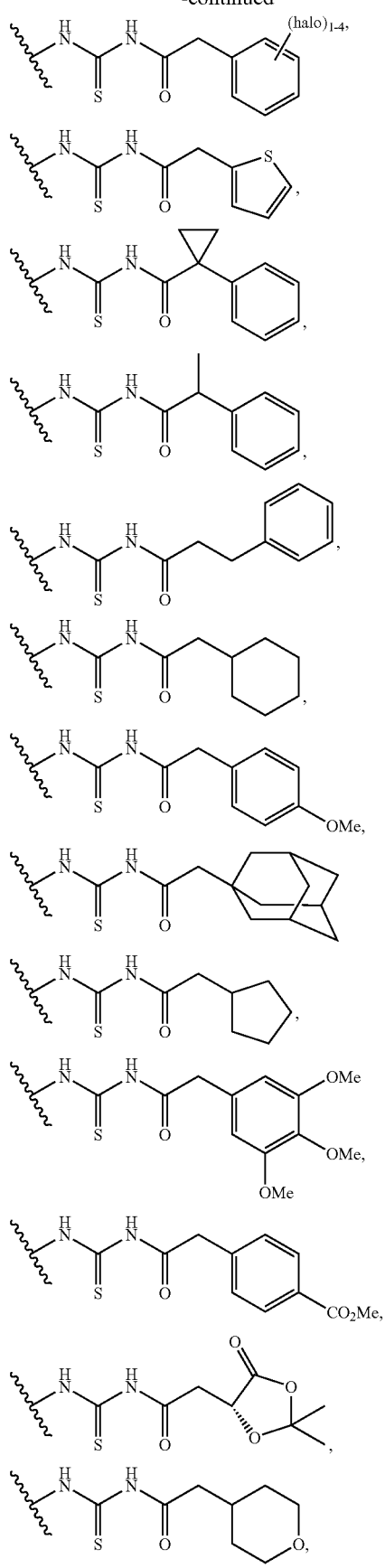
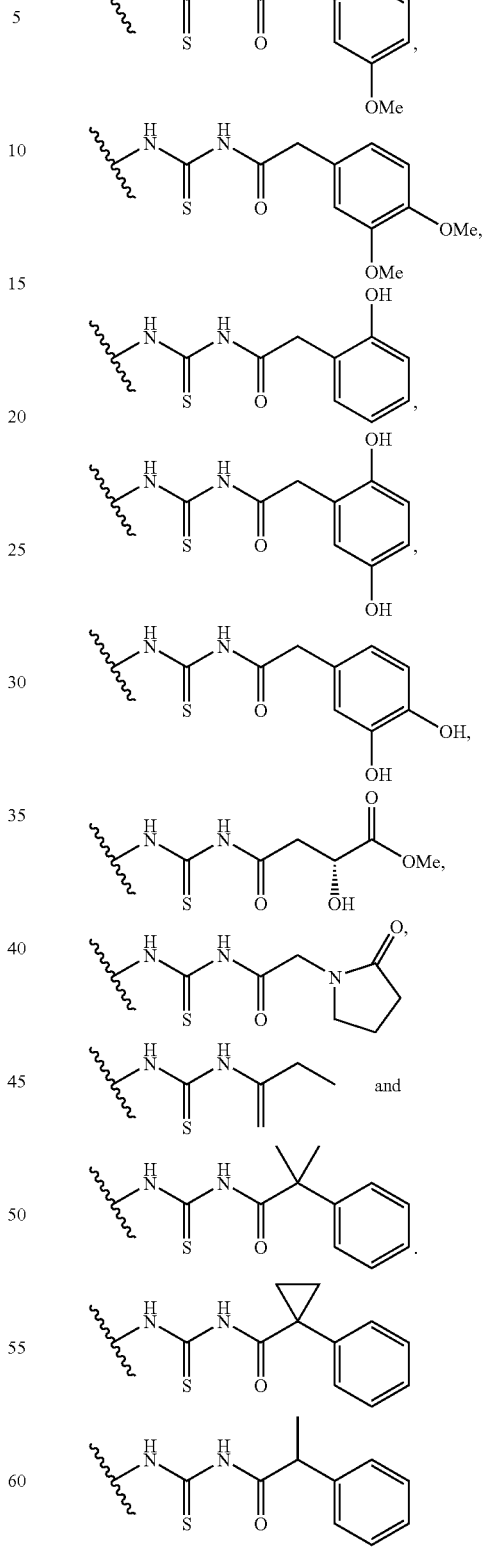
In another example of the embodiment of the process and intermediates for preparing a compound having Formula (F), G is selected from the group consisting of

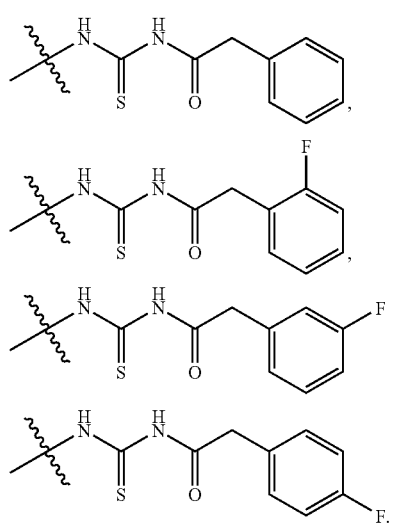
In another example of the embodiment of the process and intermediates for preparing a compound having Formula (F), G is selected from the group consisting of
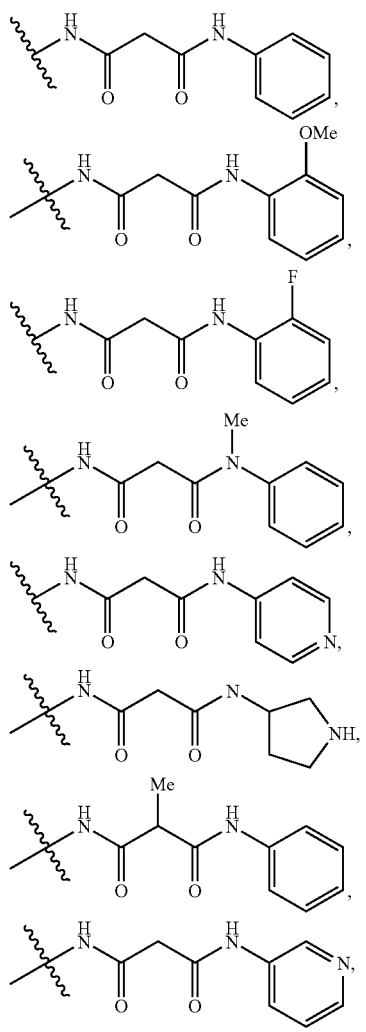
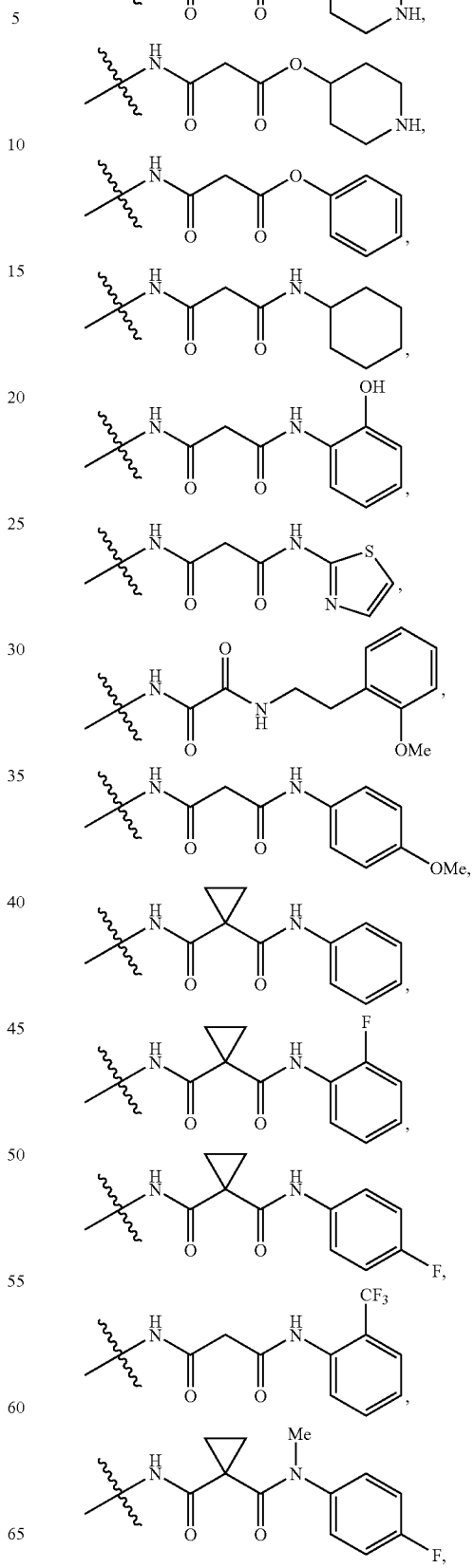

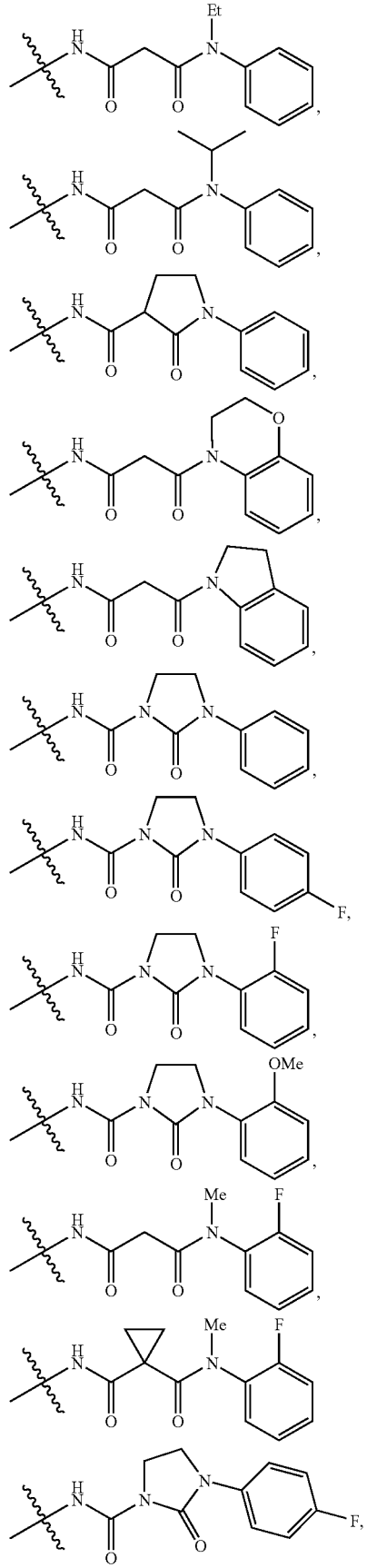
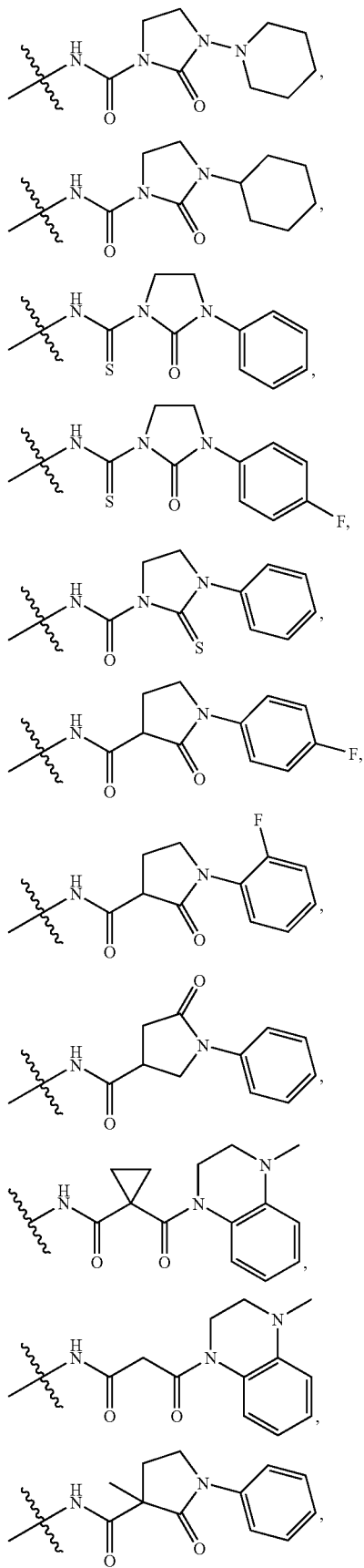

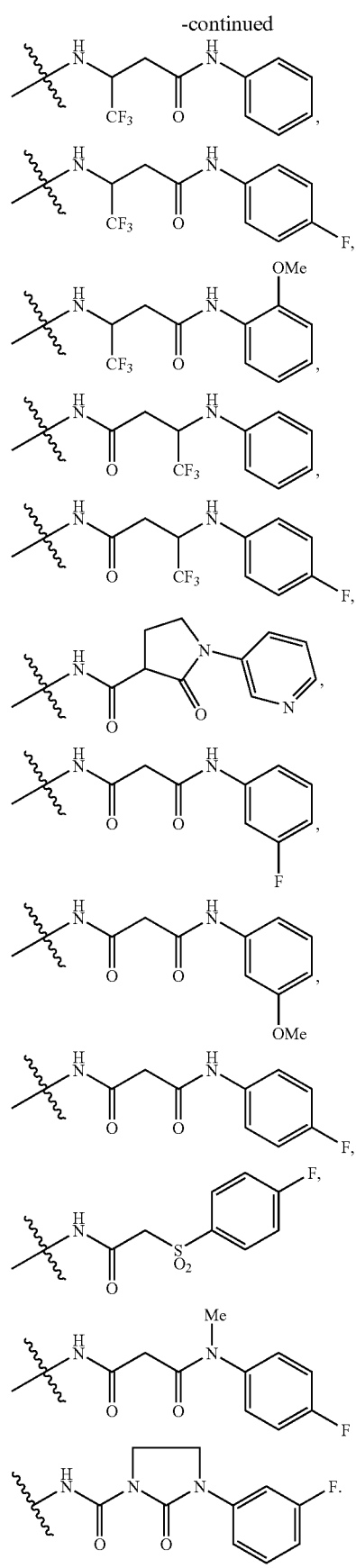
In another example of the embodiment of the process and intermediates for preparing a compound having Formula (F), G is selected from the group consisting of
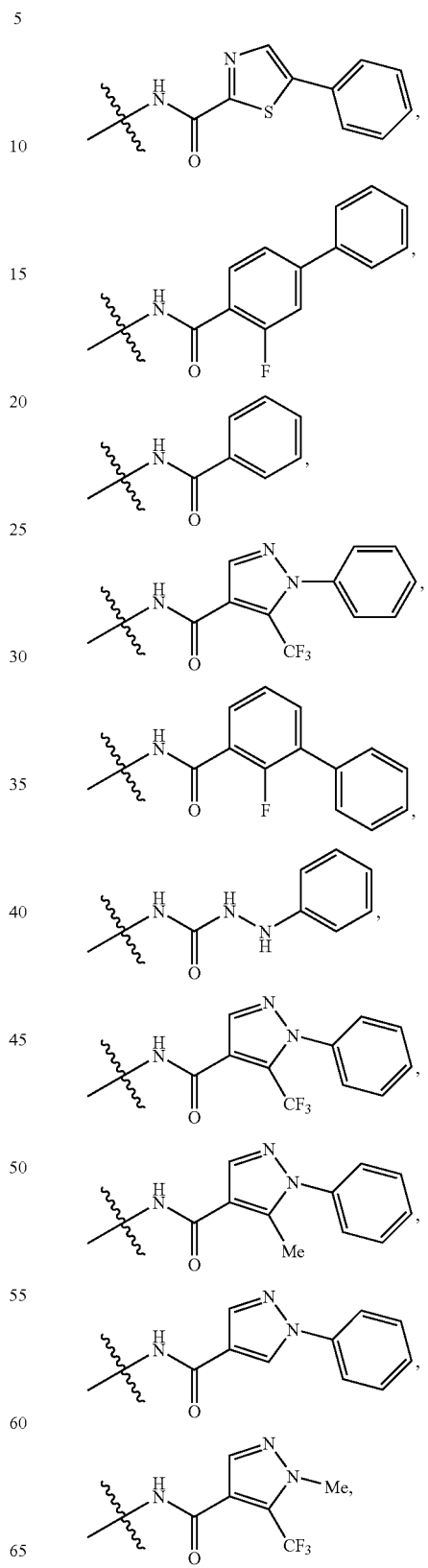

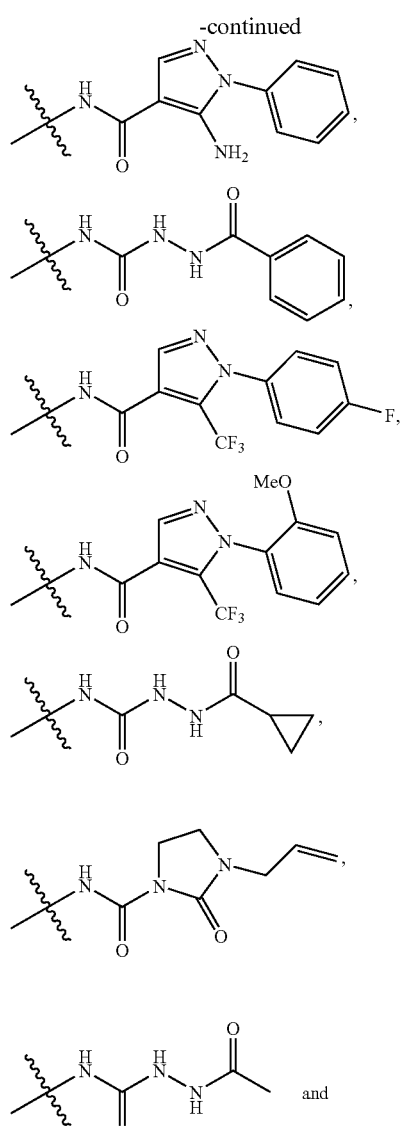

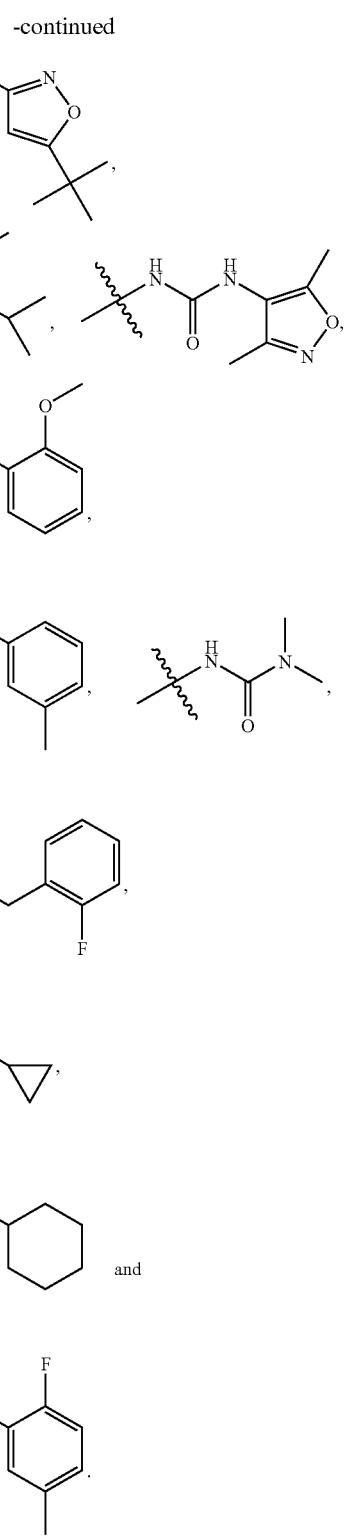

In another example of the embodiment of the process and intermediates for preparing a compound having Formula (F), G is selected from the group consisting of

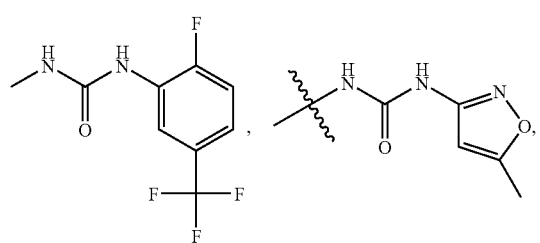

In another example of the embodiment of the process and intermediates for preparing a compound having Formula (F), $R^{38}$ is $-(CH_2)_n NH(CH_2)_m A^4 R^{37}$ or $-(CH_2)_n NR^{36}R^{39}$.

In another example of the embodiment of the process and intermediates for preparing a compound having Formula (F), $RG^1$, $RG^2-G^1$ and G are selected from the following combinations:

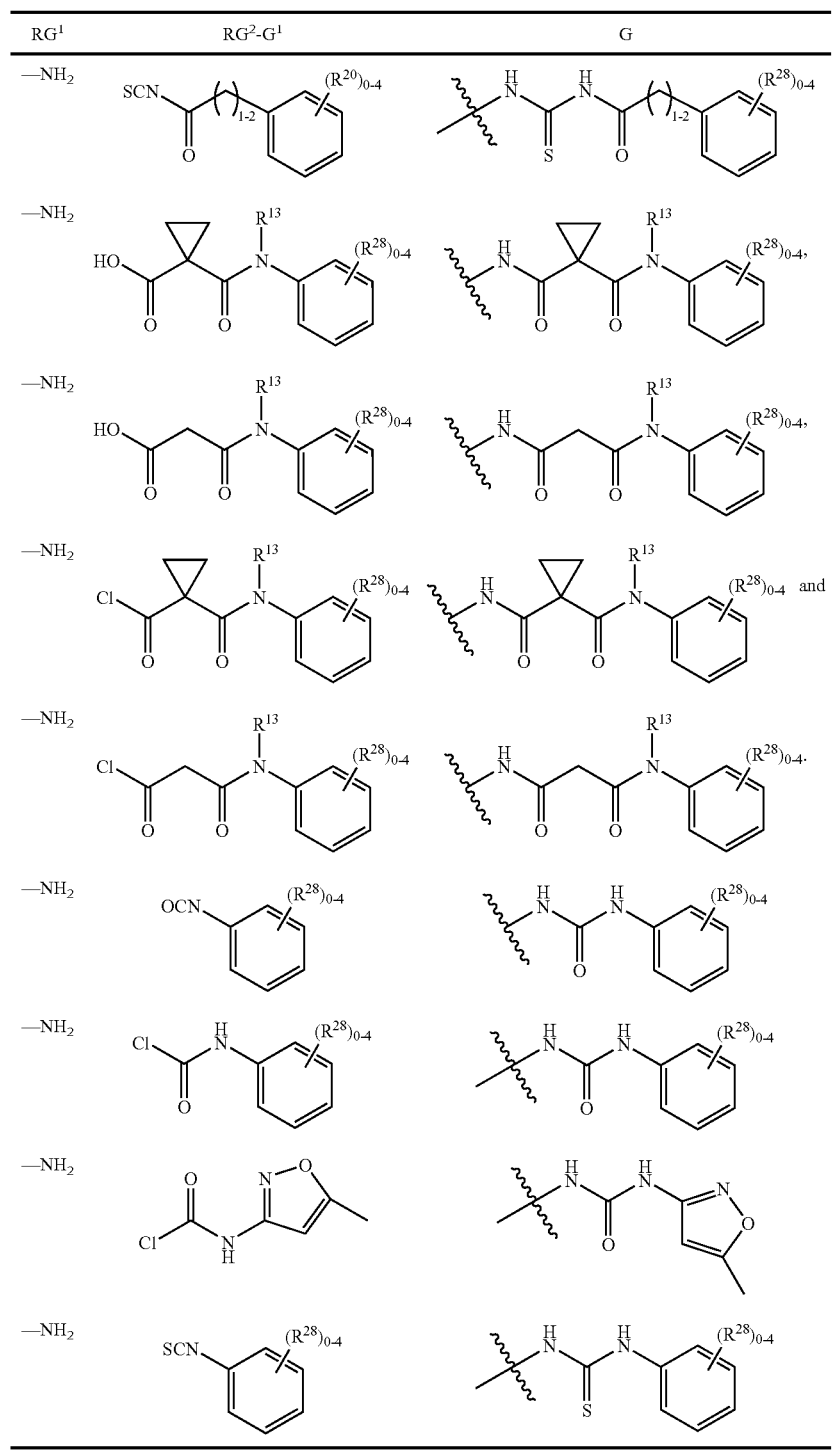

In another embodiment the present invention provides a process and intermediates for preparing a compound having Formula (D-1):

$$R^{38}\text{-D-M} \overset{LG^2}{|} \quad (D\text{-}1)$$

the process comprising providing an intermediate compound $R^{38}$-D-$LG^1$, wherein $R^{38}$ comprises zero or more protected reactive moities therein, and $LG^1$ is a leaving group; and reacting said intermediate compound $R^{38}$-D-$LG^1$ or protected intermediate group $R^{38}$-D-$LG^1$ with

wherein LG² is a leaving group, * represents the point of attachment of group R³⁸-D-, and † represents the point of attachment of group Z.

In an example of the embodiment of the process and intermediates for preparing a compound having Formula (D-1), D is optionally substituted -(aryl), optionally substituted -(heterocyclyl) or optionally substituted -(heteroaryl), for example optionally substituted phenyl or optionally substituted pryidinyl (for example optionally substituted pyridinyl).

In another example of the embodiment of the process and intermediates for preparing a compound having Formula (D-1), M is

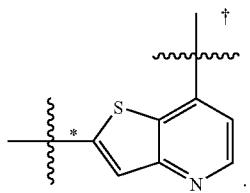 [SMILES: *c1cc2nccc(*)c2s1]

In another example of the embodiment of the process and intermediates for preparing a compound having Formula (D-1), $R^{38}$ is $C_1$-$C_6$alkyl, —$(CH_2)_j NR^{39}(CH_2)_n R^{36}$ or —$(CH_2)_n NR^{36}R^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, —OH, $C_1$-$C_6$alkyl, $C_3$-$C_{10}$cycloalkyl, —C(O)—$R^z$, —C(O)—O—$R^z$, —$SO_2$—$C_1$-$C_6$alkyl, and a protecting group used to protect secondary amino groups (for example tert-butoxycarbonyl (Boc), benzylocycarbonyl (Cbz), F-Moc, —$CH_2Ph$, —$COCF_3$, —C(O)—$R^z$ or —C(O)O—$R^z$) (alternatively $R^{39}$ is H or $C_1$-$C_6$alkyl, alternatively H), and $R^{36}$ is selected from the group consisting of H, —OH, $C_1$-$C_6$alkyl, —$(CH_2)_n O(CH_2)_i OR^{37}$, —$(CH_2)_n CN(CH_2)_n OR^{37}$, —$(CH_2)_n CN(CH_2)_n R^{37}$, and —$(CH_2)_n OR^{37}$, alternatively —$(CH_2)_n OR^{37}$, wherein each n is an independently selected integer ranging from 0 to 6 (alternatively 0 to 4, alternatively 0 to 2, alternatively 1 or 0, alternatively 0), $R^{37}$ is H, $C_1$-$C_6$alkyl or $C_3$-$C_{10}$cycloalkyl (alternatively H or $C_1$-$C_6$alkyl, alternatively $C_1$-$C_6$alkyl, alternatively $C_1$-$C_2$alkyl) and $R^z$ is selected from the group consisting of H, $C_1$-$C_6$alkyl, $C_1$-$C_6$cycloalkyl, $C_1$-$C_6$heterocyclyl and aryl (for example benzyl and $C_5$-$C_6$heterocyclyl).

In another example of the embodiment of the process and intermediates for preparing a compound having Formula (D-1), D is phenyl or pryidinyl (for example pyridinyl), $R^{38}$ is $C_1$-$C_6$alkyl, —$(CH_2)_j NR^9(CH_2)_n R^{36}$ or —$(CH_2)_n NR^{36}R^{39}$ wherein j is an integer from 0 to 4 (alternatively 1 to 4, alternatively 1 or 2, alternatively 1), n is an integer from 0 to 6 (alternatively 2 to 6, alternatively 2 to 4, alternatively, 1 or 2), $R^{39}$ is selected from the group consisting of H, —OH, $C_1$-$C_6$alkyl, $C_3$-$C_{10}$cycloalkyl, —C(O)—$R^z$, —C(O)—O—$R^z$, —$SO_2$—$C_1$-$C_6$alkyl (alternatively H or $C_1$-$C_6$alkyl, alternatively H), and a protecting group used to protect secondary amino groups (for example tert-butoxycarbonyl (Boc), benzylocycarbonyl (Cbz), F-Moc, —$CH_2Ph$, —$COCF_3$, —C(O)—$R^z$ or —C(O)O—$R^z$), (alternatively $R^{39}$ is H or $C_1$-$C_6$alkyl, alternatively H), and $R^{36}$ is selected from the group consisting of H, —OH, $C_1$-$C_6$ alkyl, —$(CH_2)_n O(CH_2)_i OR^{37}$, —$(CH_2)_n CN(CH_2)_n OR^{37}$, —$(CH_2)_n CN(CH_2)_n R^{37}$, and —$(CH_2)_n OR^{37}$, alternatively —$(CH_2)_n OR^{37}$, wherein each n is an independently selected integer ranging from 0 to 6 (alternatively 0 to 4, alternatively 0 to 2, alternatively 1 or 0, alternatively 0), $R^{37}$ is H, $C_1$-$C_6$alkyl or $C_3$-$C_{10}$cycloalkyl (alternatively H or $C_1$-$C_6$alkyl, alternatively $C_1$-$C_6$alkyl, alternatively $C_1$-$C_2$alkyl) and $R^z$ is selected from the group consisting of H, $C_1$-$C_6$alkyl, $C_1$-$C_6$cycloalkyl, $C_1$-$C_6$heterocyclyl and aryl (for example benzyl and $C_5$-$C_6$heterocyclyl).

In another example of the embodiment of the process and intermediates for preparing a compound having Formula (D-1), $R^{39}$ is selected from the group consisting of H, $C_1$-$C_6$alkyl, $C_1$-$C_6$cycloalkyl, —OMe, —C(O)—$C_1$-$C_6$alkyl, —C(O)—O—$C_1$-$C_6$alkyl, —$SO_2$—$C_1$-$C_6$alkyl, and a protecting group used to protect secondary amino groups.

In another example of the embodiment of the process and intermediates for preparing a compound having Formula (D-1), $R^{39}$ is a protecting group used to protect secondary amino groups, wherein said protecting group is selected from the group consisting of tert-butoxycarbonyl (Boc), benzyloxycarbonyl (Cbz), F-Moc, —$CH_2Ph$, —$COCF_3$, —C(O)—$R^z$ and —C(O)O—$R^z$.

In another embodiment the present invention provides a process and intermediates for preparing a compound having the Formula (E-2):

(E-2)

wherein $R^k$ is selected from the group consisting of H, $C_1$-$C_4$alkyl, $C_3$-$C_6$cycloalkyl, $C_2$-$C_4$ alkenyl and $C_2$-$C_4$ alkynyl;

each $R^f$ is independently —O—$C_1$-$C_7$alkyl, or both $R^f$ taken together with the atom to which there are attached may form a cyclic acetal (a 5 to 8 member ring system), or a carbonyl group;

LG² is a leaving group; and

D and M are as defined above, the process comprising reacting an intermediate compound of Formula (E-1):

(E-1)

wherein

LG¹ is a leaving group, with

wherein, * represents the point of attachment of group R³⁸-D-, and † represents the point of attachment of group Z.

In another example of the embodiment of the process and intermediates for preparing a compound having Formula (E-2), D is -(aryl), -(heterocyclyl) or -(heteroaryl), each of which is optionally substituted.

In another example of the embodiment of the process and intermediates for preparing a compound having Formula (E-2), M is

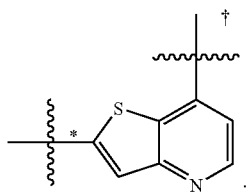 [SMILES: *c1cc2nccc(*)c2s1]

In another example of the embodiment of the process and intermediates for preparing a compound having Formula (E-2), $LG^1$ and $LG^2$ are independently selected from the group consisting of halo, alkoxy, triflate, mesylate, tosylate, acetate, trifluoroacetate, $SO_2Me$, nosylate and p-nitrophenolate and the like.

In another example of the embodiment of the process and intermediates for preparing a compound having Formula (E-2), D is phenyl or pryidinyl (for example pyridinyl).

In another example of the embodiment of the process and intermediates for preparing a compound having Formula (E-2), $R^{39}$ is selected from the group consisting of

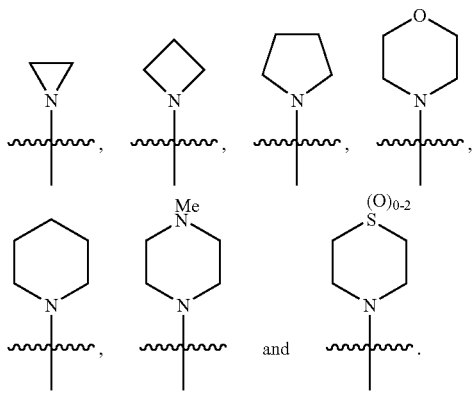

In another embodiment of the present invention, compounds having a Formula as described herein are provided.

In accordance with the present invention, compounds having a Formula (A), (A-1), (A-2), (A-3), (D), (D-1), (D-2), (D-3), (D-4), (D-5), (D-6), (D-7), (E), (E-1) or (E-2) are provided.

In accordance with the present invention, compounds prepared according to a process as described herein are provided.

Certain compounds of above formulas may generally be prepared according to the following Schemes. Tautomers and solvates (e.g., hydrates) of the compounds of above formulas are also within the scope of the present invention. Methods of solvation are generally known in the art. Accordingly, the compounds of the present invention may be in the free, hydrate or salt form, and may be obtained by methods exemplified by the following schemes below.

In certain embodiments of the processes provided for preparing compounds having a formula as described herein, steps involved in the processes optionally do not include chromatography, such as column chromatograph.

The following examples and preparations describe the manner and process of making and using the invention and are illustrative rather than limiting. It should be understood that there may be other embodiments which fall within the spirit and scope of the invention as defined by the claims appended hereto.

Examples of compounds according to the invention include those described in the examples below. Compounds were named using Chemdraw Ultra version 10.0 or version 8.0.3, which are available through Cambridgesoft.com, 100 Cambridge Park Drive, Cambridge, Mass. 02140, or were derived therefrom.

Synthetic Schemes and Experimental Procedures

Scheme A
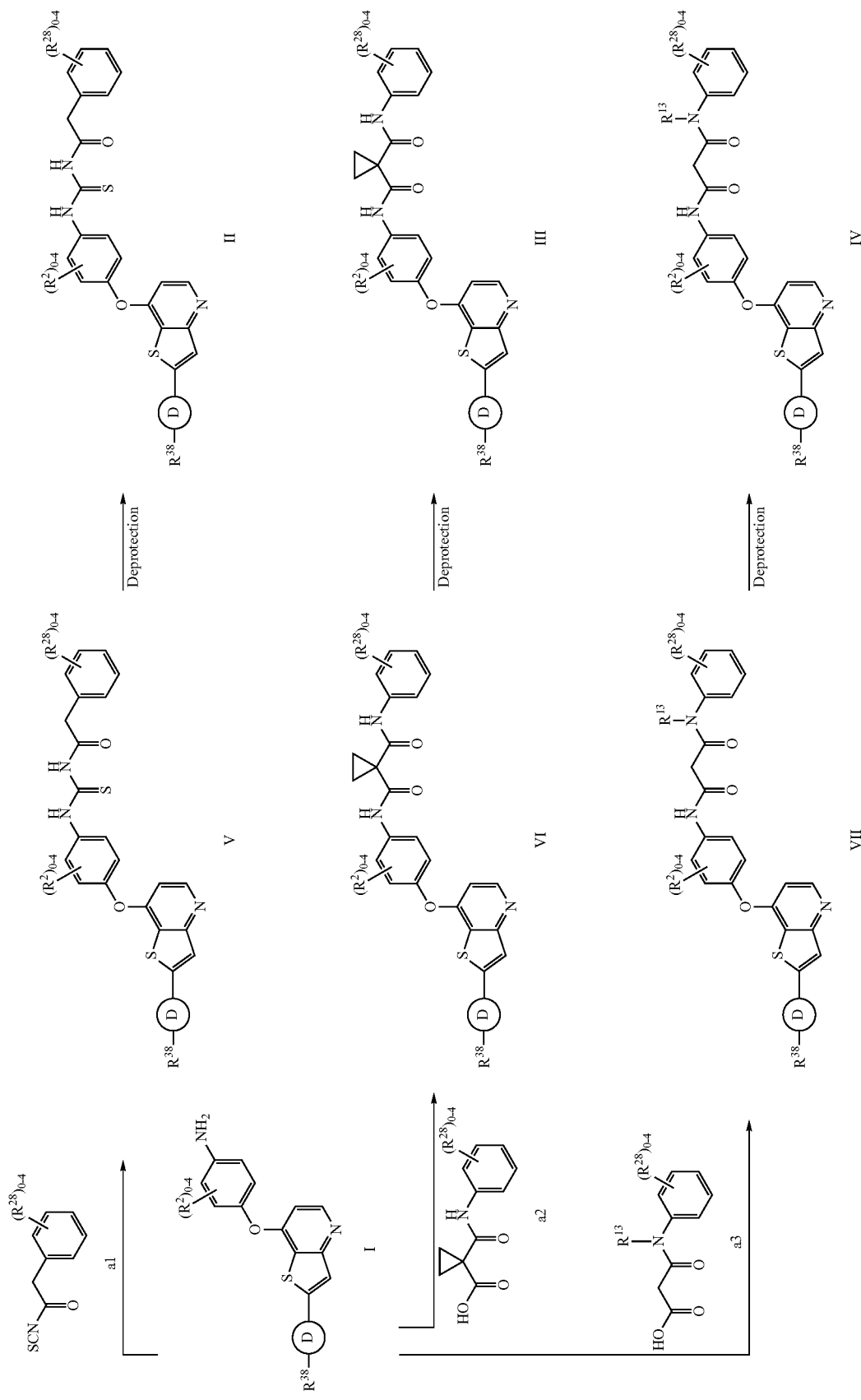

wherein each $R^2$ is independently selected from the group consisting of halo, cyano, $CF_3$, $C_1$-$C_4$alkyl, $C_2$-$C_4$alkenyl, $C_2$-$C_4$alkynyl and $C_3$-$C_6$cycloalkyl, $C_1$-$C_4$alkoxy, $C_3$-$C_6$cycloalkoxy;

each $R^{28}$ is independently selected from $R^{20}$, $R^{14a}$, $R^{15a}$, $R^{16a}$ and $R^{17a}$ (alternatively halo, cyano, $CF_3$, $C_1$-$C_4$alkoxy, $C_1$-$C_4$alkyl, $C_2$-$C_4$alkenyl, $C_2$-$C_4$alkynyl and $C_3$-$C_6$cycloalkyl)

$R^{38}$ is for example $C_1$-$C_6$alkyl, —$(CH_2)_j NR^{39}(CH_2)_n R^{36}$ or —$(CH_2)_n NR^{36} R^{39}$, wherein j is an integer from 0 to 4 (alternatively 1 to 4, alternatively 1 or 2, alternatively 1), n is an integer from 0 to 6 (alternatively 2 to 6, alternatively 2 to 4, alternatively still, 2), $R^{39}$ is selected from the group consisting of H, —OH, $C_1$-$C_6$alkyl, $C_3$-$C_{10}$cycloalkyl, —O—$C_1$-$C_4$alkyl, —$NMe_2$, —NHMe, $NEt_2$, —$SO_2$—$C_1$-$C_6$alkyl, tert-butoxycarbonyl (Boc), F-Moc, benzylocycarbonyl (Cbz), —$COCF_3$, —$CH_2Ph$, —C(O)—$R^z$, —C(O)O—$R^z$ or other protecting groups used to protect secondary amino groups (examples of such protective groups could be found e.g. in "Protective Groups in Organic Synthesis" T. W. Greene, Wiley, NY). Alternatively $R^{39}$ is selected from H, $C_1$-$C_6$alkyl, —C(O)—$R^z$ and —C(O)—O—$R^z$, alternatively H, and $R^{36}$ is selected from the group consisting of H, —OH, $C_1$-$C_6$ alkyl, —$(CH_2)_n O(CH_2)_i OR^{37}$, —$(CH_2)_i CN$ $(CH_2)_n OR^{37}$, —$(CH_2)_n CN(CH_2)_n R^{37}$, and —$(CH_2)_n A^4 R^{37}$, (alternatively —$(CH_2)_n A^4 R^{37}$), wherein n is an integer ranging from 0 to 6 (alternatively 0 to 4, alternatively 0 to 2, alternatively 1 or 0), i is an integer ranging from 2 to 6, $R^{37}$ is H, $C_1$-$C_6$alkyl or $C_3$-$C_{10}$cycloalkyl (alternatively H or $C_1$-$C_6$alkyl and $C_3$-$C_6$cycloalkyl), $A^4$ is O, S, SO, $SO_2$, NH or N (optionally substituted $C_1$-$C_4$alkyl) (alternatively O, S or N($C_1$-$C_4$alkyl)), and $R^z$ is selected from the group consisting of H, $C_1$-$C_6$alkyl, $C_1$-$C_6$cycloalkyl, $C_1$-$C_6$heterocyclyl and aryl (for example benzyl and $C_5$-$C_6$heterocyclyl); provided that if $R^{39}$ is H then no deprotection is required.

In an example, $R^{39}$ is a cyclic moiety selected from the structures below:

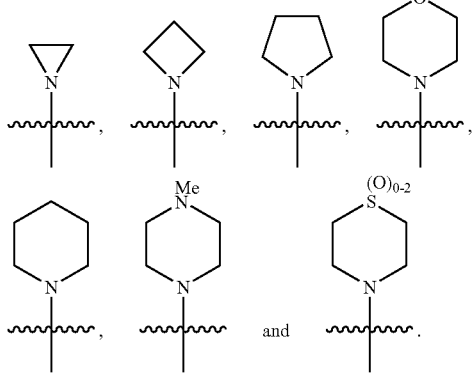

Compounds of the first embodiment (exemplified in the scheme A as chemical entities II, III and IV) prepared from the Boc-protected anilino derivatives I in two steps according to the scheme A. Thus, compounds I reacting with a substituted 2-arylacetyl isothiocyanates (a1) in a variety of solvents such as THF, acetone, toluene, DCM, $CHCl_3$, MeCN, DMF, DMSO, alcohols (MeOH, EtOH, iso-PrOH etc.) (for example in THF), or in a mixtures of the listed solvents (e.g. toluene-EtOH, THF-acetone, IPA-MeCN) (for example in toluene-EtOH or in IPA-MeCN) in the temperature range from −10° to +120° C. (for example 15-100° C.), followed by deprotection of the Boc-protecting group in the intermediate V, are converted into the kinase inhibitors II [WO 2006/019264 A1, US 2006/0287343 A1].

Boc-Deprotection is carried out in acidic media such as TFA, AcOH, TFA/DCM, HCl/DCM, HCl/dioxane, AcOH/HCl, AcOH/HCl/$H_2O$ and the like (for example in TFA, HCl/dioxane, AcOH/HCl or AcOH/HCl/$H_2O$).

Same compounds I reacting either with substituted 1-(phenylcarbamoyl)cyclopropanecarboxylic acids (a2) or with substituted 3-oxo-3-(phenylamino)propanoic acids (a3), followed by deprotection of the Boc-protecting groups of the intermediates VI and VII, are converted into the kinase inhibitors III and IV [US 2007/0004675 A1]. The reactions proceed in aprotic solvents such as DMF, THF, DMSO, pyridine (etc.) (for example in DMF), at ambient temperatures in the presence of amide coupling reagents known in the art (EDC, HATU, HBTU, BOP, DCC, DIC, CIP, PyBOP, HNTU, AOP, PPAA, PFTU, etc.) (for example EDC and HATU) and tertiary amines (e.g. $Et_3N$, DIPEA, N-methylmorpholine, N-methylpiperidine, DMAP, N,N-dimethylaniline, N,N-diethylaniline, DBU, DABCO, etc.) (for example DIPEA). Boc-Deprotection is carried out in the same way as in the case of compounds II—in acidic media such as TFA, AcOH, TFA/DCM, HCl/DCM, HCl/dioxane, AcOH/HCl, AcOH/HCl/$H_2O$ and the like To an ordinary person skilled in the art it should be understood that compounds III and IV may be prepared by a slightly different way from the compounds I using malonate derivatives such as aa2, aa3, aa4, and aa5, and anilines b as synthetic building blocks. It should also be understood that the alternative syntheses would involve hydrolysis of the alkyl ester functionalities as well as the Boc-deprotection steps.

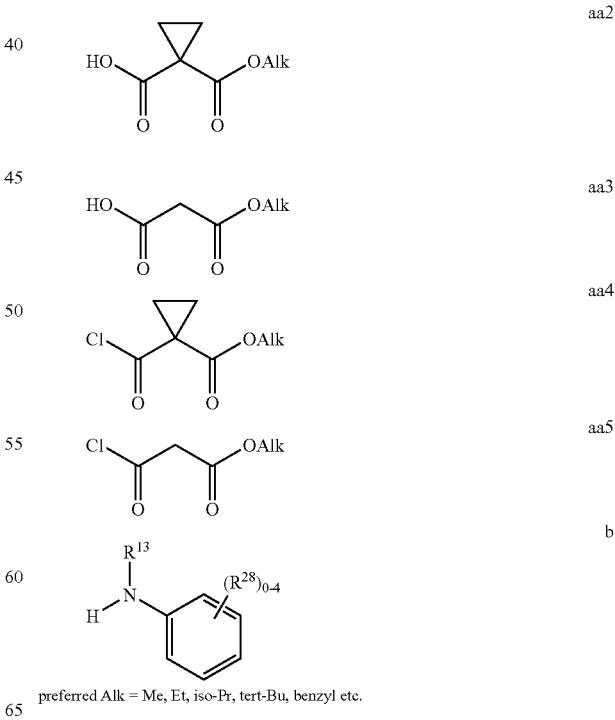

preferred Alk = Me, Et, iso-Pr, tert-Bu, benzyl etc.

Scheme B

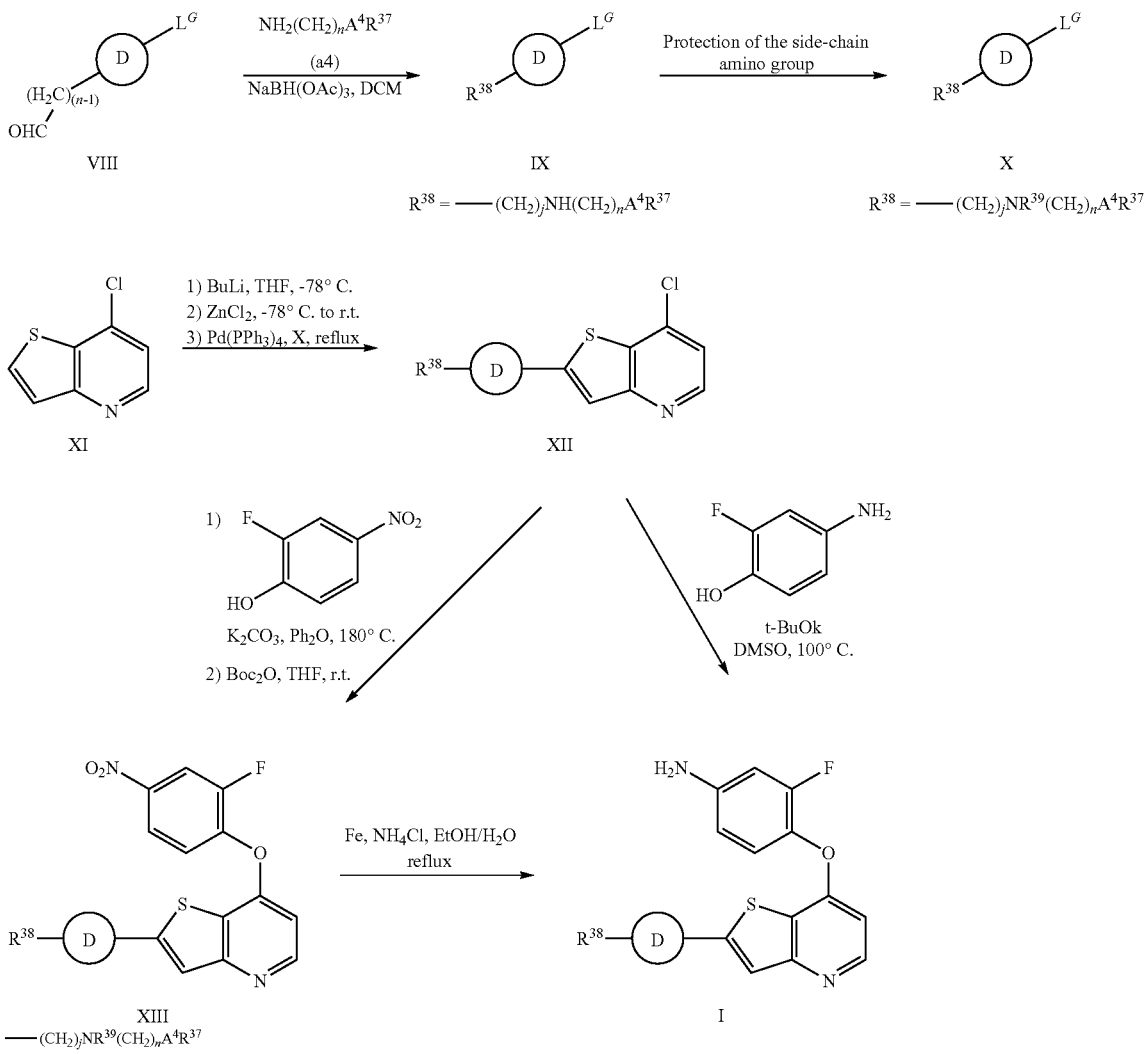

$L^G$ is a leaving group, preferably but not limited to, halo, triflate, mesylate, —SO₂Me;

$R^{39}$ is preferably —COCH₃, —COCF₃, —COCH₂Ph, —OC(O)OMe, —OC(O)O-tert-Bu or —OC(O)CH₂Ph;

$A^4$ is preferably O, S, SO, SO₂, or N(C₁-C₄-alkyl); and $R^{37}$ is preferably H, C₁-C₄-alkyl or C₃-C₆-cycloalkyl, wherein C₁-C₆-alkyl is optionally substituted;

Protected anilino derivatives I prepared according to the general Scheme B. A variety of aromatic or heteroaromatic aldehydes VIII undergo reductive amination by reacting with primary amines a4. The procedure is carried out under standard conditions (Abdel-Magid A. F. et al, J. Org. Chem., 1996, 61, 3849-3862), at temperatures between −20 and +60° C. in the presence of borohydride agents such as NaBH(OAc)₃, NaBH₃CN, NaBH₄, in solvents such as DCE, DCM, AcOH or THF (or mixtures thereof). The reductive amination products IX are then protected by a variety of protecting groups known in the art (e.g. "Protective Groups in Organic Synthesis" T. W. Greene, Wiley, NY); to form compounds X. Examples of protecting groups include but are not limited to acetyl-, trifluoroacetyl-, benzoyl-, tert-butoxycarbonyl (Boc), benzyloxycarbonyl, etc.

Attaching the building blocks X to the thienopyridine scaffold is achieved under Negishi reaction conditions (Scott R. W., et al, Org. process Research & Development, 2006, 10, 296-303; Ragan J. A., et al, Org. process Research & Development, 2003, 7, 676-683). Thus, metallation of 7-chlorothieno[3,2-b]pyridine (X¹) (Klemm, L. H. et al. J. Heterocyclic Chem., 22, 1985, 1249-1252) using reagents such as n-BuLi, sec-BuLi LDA and like in the temperature range from −78° C. to 15° C., for example from −15 to −5° C., followed by transmetallation with zinc chloride with a subsequent coupling to compounds X in the presence of a transition metal catalyst in the temperature range from 25 to 150° C., for example from 60 to 90° C. to form chlorides XII. The reactions are performed in aprotic solvents such as ether, THF, dioxane, benzene, toluene, xylenes, hexane, heptane. Alternative coupling reactions include but are not limited to Suzuki and Stille reactions. In these cases 7-chloro-2-iodothieno[3,2-b]pyridine (XIV, scheme C) (or its bromo-analogue 7-chloro-2-bromothieno[3,2-b]pyridine) could be used.

Compounds XII lead to the compounds I either directly by replacing the chlorine atom in XII by 4-amino-2-fluorophenol at elevated temperatures from 60 to 200° C., for example from 80 to 120° C.) in solvents such as DMF, DMA, DMSO, diphenyl ether, mono- and dichlorobenzenes, xylenes, etc. in the presence of bases such as NaH, NaHCO$_3$, NaHMDS, KH, K$_2$CO$_3$, tert-BuOK, etc., or via the intermediate nitro compounds XIII. Nitro compounds XIII are obtained, for example, by replacing the chlorine atom in XII with 2-fluoro-4-nitrophenol. The reaction proceeds at elevated temperatures (100-200° C.) in solvents such as DMF, DMA, DMSO, diphenyl ether, etc., in the presence of bases such as KH, K$_2$CO$_3$, NaH, Na$_2$CO$_3$, NaHCO$_3$, tert-BuOK, etc. Reduction of the nitro group in XIII is achieved using standard procedures known in art. Examples of such procedures include but are not limited to catalytic hydrogenation, iron—ammonium chloride, zinc-ammonium chloride, nickel chloride-sodium borohydride, etc. in organic solvents (alcohols, AcOEt, DMA, DMF) or aqueous solutions or mixtures MeOH/water, EtOH/water or like.

An alternative way of preparing nitro compounds XIII is shown in the Scheme C. Thus, 7-chloro-2-iodothieno[3,2-b]pyridine (XIV) (Ragan J. A. et al, Organic Process Research and Development 2003, 7, 676-683) is reacted with 2-fluoro-4-nitrophenol (120-200° C.) in solvents such as DMF, DMA, DMSO, diphenyl ether, etc. in the presence of bases such as KH, K$_2$CO$_3$, NaH, Na$_2$CO$_3$, NaHCO$_3$, tert-BuOK, etc., to form 7-(2-fluoro-4-nitrophenoxy)-2-iodothieno[3,2-b]pyridine (XV). This material undergoes Stille coupling reaction (e.g. Zhang N., et al; J. Org. Chem., 2001, 66, 1500-1502 or references therein) with a variety of aldehydes VIII, to form the nitro aldehydes XVI. The nitro aldehydes XVI undergo reductive amination by reacting with primary amines a4, to form the reductive amination products XVII. The procedure is carried out under standard conditions (Abdel-Magid A. F. et al, J. Org. Chem., 1996, 61, 3849-3862), at temperatures between −20 and +60° C. in the presence of borohydride agents such as NaBH(OAc)$_3$, NaBH$_3$CN, NaBH$_4$, in solvents such as DCE, DCM, AcOH or THF (or mixtures thereof). The reductive amination products XVII are then protected by a variety of protecting groups known in the art (e.g. "Protective Groups in Organic Synthesis" T. W. Greene, Wiley, NY) to form compounds XIII. Protecting groups include but are not limited to acetyl-, trifluoroacetyl-, benzoyl-, tert-butoxycarbonyl (Boc), benzyloxycarbonyl (Cbz), etc.

Scheme C

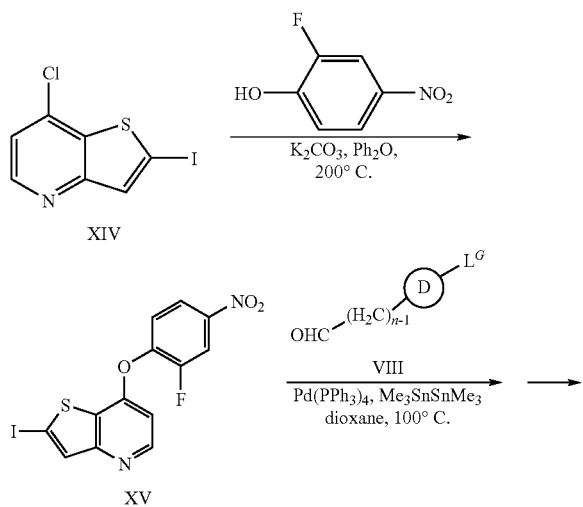

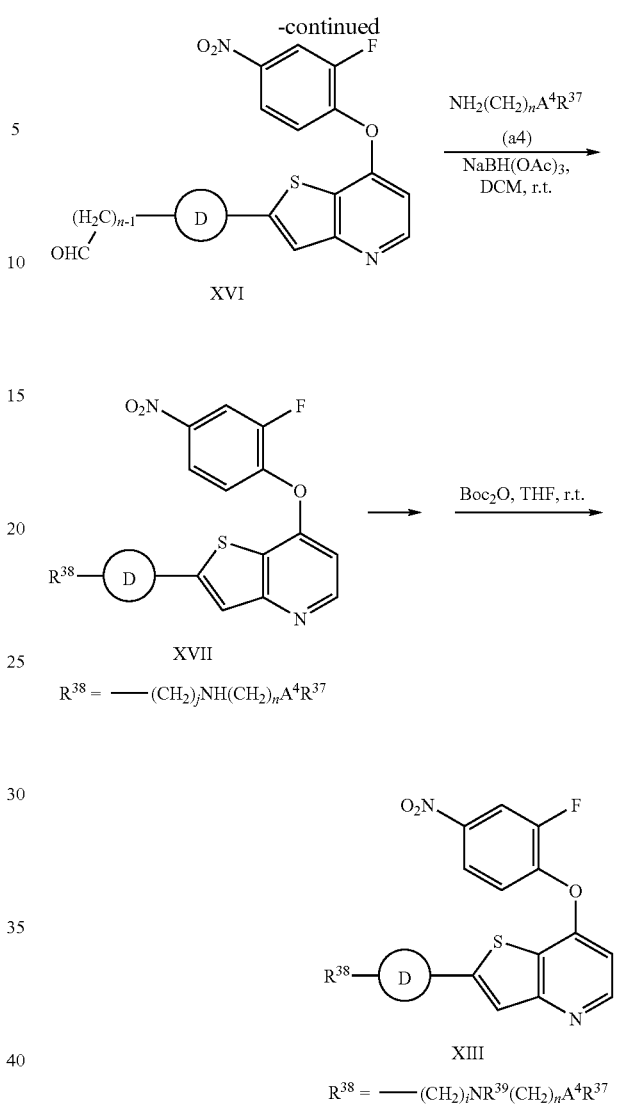

Heterocyclic kinase inhibitors II [WO 2006/019264 A1, US 2006/0287343 A1] can also be prepared from the anilino-compounds XVIII via a three-step reaction sequence shown in the scheme D.

Thus, compounds XVIII reacting with substituted 2-arylacetyl isothiocyanates (a1) in a variety of solvents such as THF, acetone, toluene, DCM, CHCl$_3$, MeCN, DMF, DMSO, alcohols (MeOH, EtOH, iso-PrOH etc.) (for example in THF), or in the mixtures of the listed solvents (e.g. toluene-EtOH, THF-acetone, IPA-MeCN) (for example in toluene-EtOH ot in IPA-MeCN) in the temperature range from −10° to +120° C. are converted into the compounds XIX. Deprotection of the protected carbonyl group in XIX yields compounds XX; it is for example carried out in aqueous acidic media such as AcOH/water, TFA/water, TFA/acetone/water, HCl/acetone/water, HCl/THF/water HCl/dioxane/water and like. Compounds XX undergo reductive amination by reacting with primary amines a4. The procedure is carried out under standard conditions (Abdel-Magid A. F. et al, J. Org. Chem., 1996, 61, 3849-3862), at temperatures between −20 and +60° C. in the presence of borohydride agents such as NaBH(OAc)$_3$, NaBH$_3$CN, NaBH$_4$, in solvents such as DCE, DCM, AcOH or THF (or mixtures thereof).

Scheme D

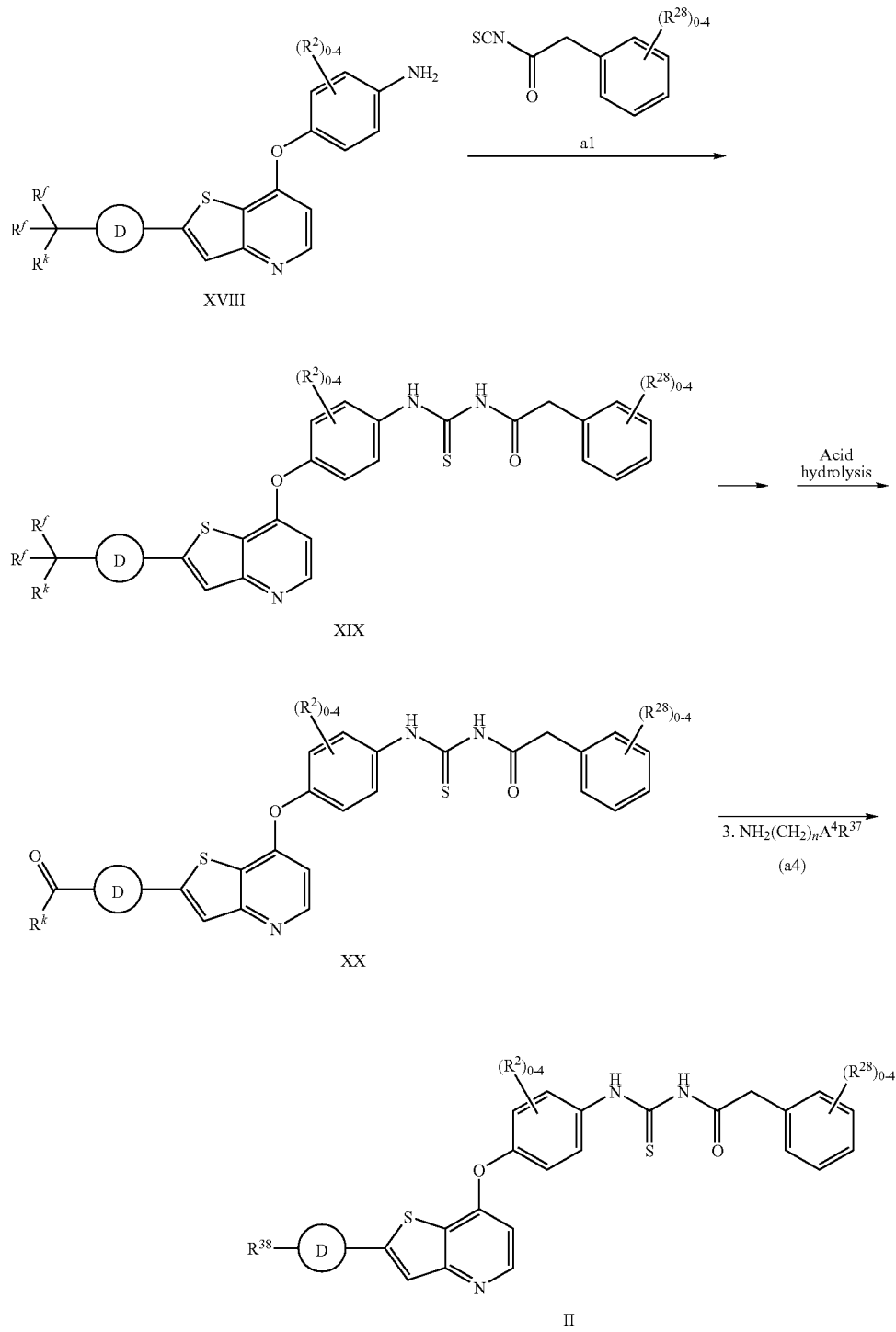

$R^k$ = H, $C_1$-$C_4$-alkyl, $C_1$-$C_6$-cyloalkyl, $C_1$-$C_4$-alkenyl, $C_1$-$C_4$-alkynyl;
$R^f$ = O-$C_1$-$C_7$ alkyl, or both substituents $R^f$ taken together may form a cylic acetal (a 5 to 8 member ring system) or a carbonyl group Similarly to the heterocyclic kinase inhibitors II the kinase inhibitors III and IV [US 2007/0004675 A1] can be prepared from the anilino-compounds XVIII. These transformations are shown in the schemes E and F. Thus, anilines XVIII reacting either with a variety of substituted 1-(arylcarbamoyl) cyclopropanecarboxylic acids (a2, scheme E) or with a variety of substituted 3-oxo-3-(arylamino)propanoic acids (a3 scheme F) form compounds XXI and XXIII, respectively.

Scheme E

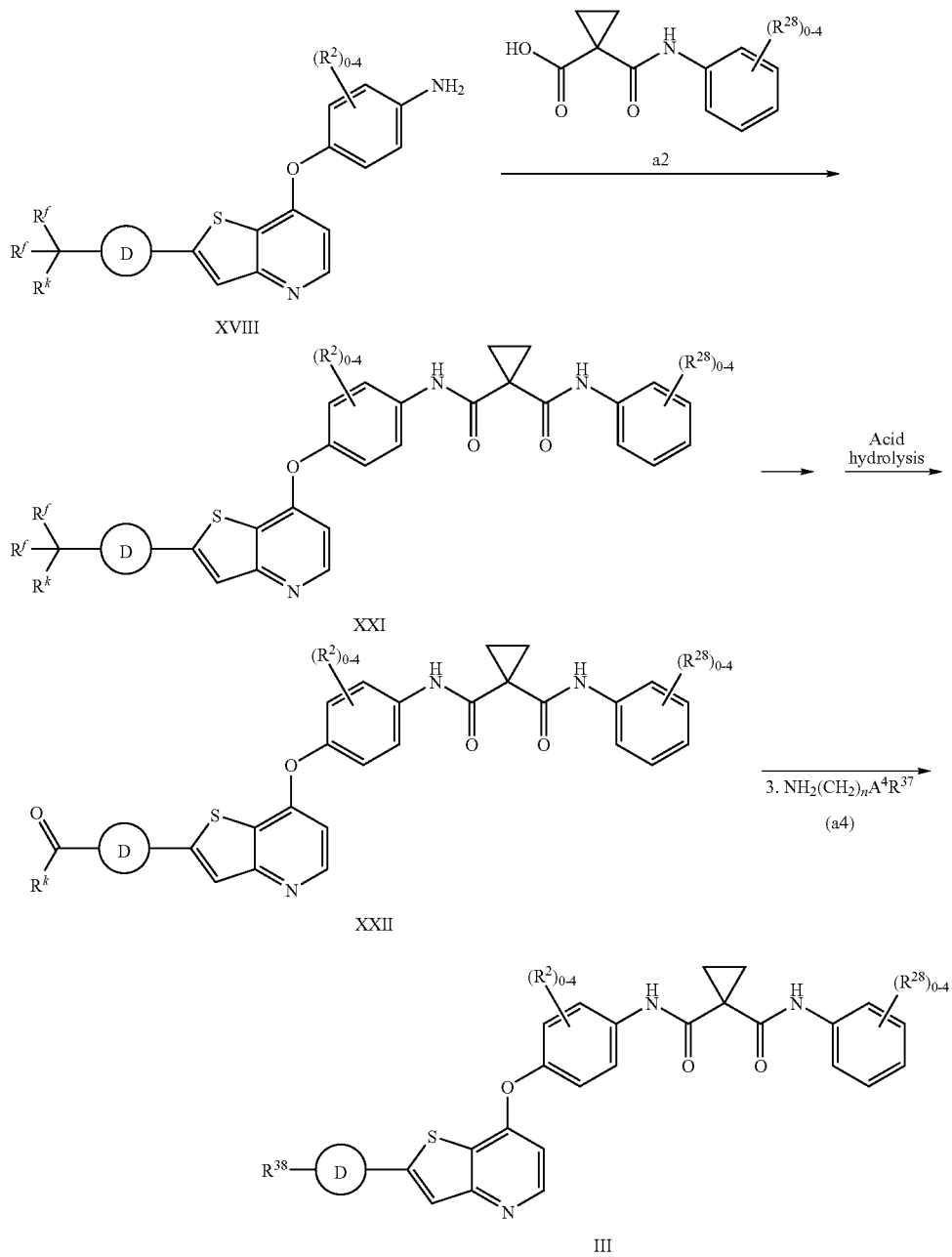

$R^{38} = \text{———}(CH_2)_j NH(CH_2)_n A^4 R^{37}$ $R^k$ = H, $C_1$-$C_4$-alkyl, $C_1$-$C_6$-cyloalkyl, $C_1$-$C_4$-alkenyl, $C_1$-$C_4$-alkynyl;
$R^f$ = O-$C_1$-$C_7$ alkyl, or both substituents $R^f$ taken together may form a cylic acetal (a 5 to 8 member ring system) or a carbonyl group The reactions for example proceed in aprotic solvents such as DMF, THF, DMSO, pyridine (etc.) at ambient temperatures in the presence of amide coupling reagents known in the art (EDC, HATU, HBTU, BOP, DCC, DIC, CIP, PyBOP, HNTU, AOP, PPAA, PFTU, etc.) and tertiary amines (e.g. Et$_3$N, DIPEA, N-methylmorpholine, N-methylpiperidine, DMAP, N,N-dimethylaniline, N,N-diethylaniline, etc.). Deprotection of the protected carbonyl groups in XXI and XXIII yields compounds XXII (scheme E) and XXIV (scheme F). Similarly to the deprotection of XIX (scheme D) it is for example carried out in aqueous acidic media: AcOH/water, TFA/water, TFA/acetone/water, HCl/acetone/water, HCl/THF/water HCl/dioxane/water and like.

Compounds XXII (scheme E) and XXIV (scheme F) undergo reductive amination by reacting with primary amines a4. The procedure is carried out under standard conditions (Abdel-Magid A. F. et al, J. Org. Chem., 1996, 61, 3849-3862), at temperatures between −20 and +60° C. in the presence of borohydride agents such as NaBH(OAc)$_3$, NaBH$_3$CN, NaBH$_4$, in solvents such as DCE, DCM, AcOH or THF (or mixtures thereof).

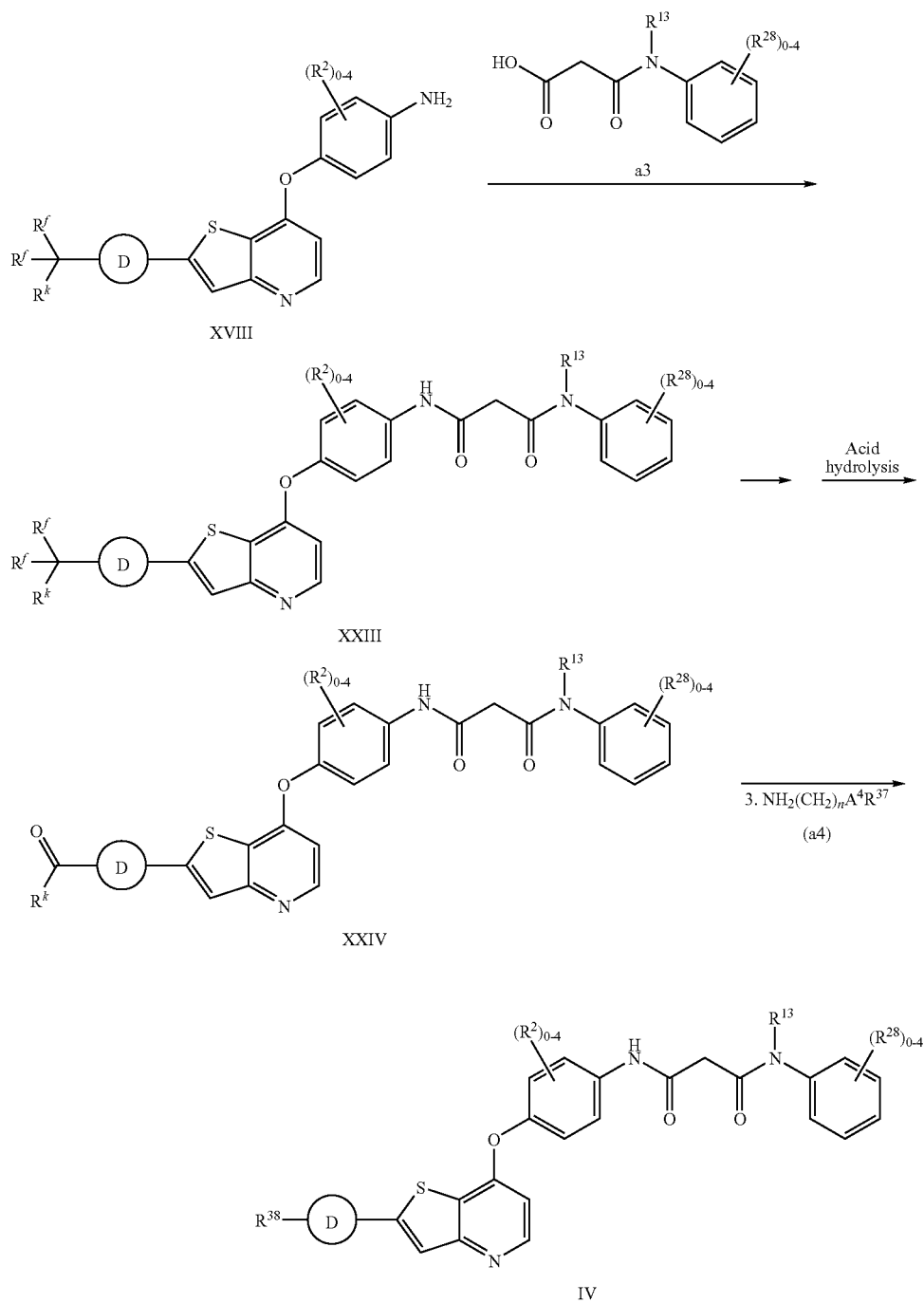

Scheme F $R^{38} = \text{—}(CH_2)_j NH(CH_2)_n A^4 R^{37}$ $R^k$ = H, $C_1$-$C_4$-alkyl, $C_1$-$C_6$-cyloalkyl, $C_1$-$C_4$-alkenyl, $C_1$-$C_4$-alkynyl;
$R^f$ = O-$C_1$-$C_7$ alkyl, or both substituents $R^f$ taken together may form a cylic acetal (a 5 to 8 member ring system) or a carbonyl group To an ordinary person skilled in the art it should be understood that compounds III and IV may also be prepared from the compounds XVIII using malonate derivatives such as aa2, aa3, aa4, and aa5, and anilines b as synthetic building blocks. It should also be understood that the alternative syntheses would involve hydrolysis of the alkyl ester functionalities and acetal protecting groups.

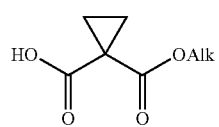

aa2

| | | |
|---|---|---|
| aa3 | 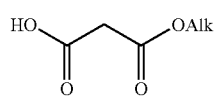 | b |
| | 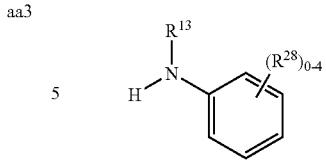 | |
| aa4 | preferred Alk = Me, Et, iso-Pr, tert-Bu, benzyl etc. | |
| aa5 | 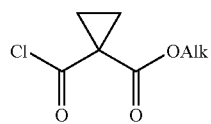 | |
| | 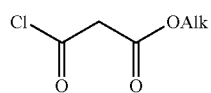 | |

Protected anilino derivatives XVIII can be prepared according to the general scheme G. A variety of aromatic or heteroaromatic aldehydes VIII undergo reactions with alcohols to form protected species XXV (e.g. "Protective Groups in Organic Synthesis" T. W. Greene, Wiley, NY). The reactions are carried out under anhydrous conditions in solvents such as toluene, benzene, $CHCl_3$ at reflux in the presence of acids such as PTSA, CSA and like. Amberlyst or Dowex 50 can be used for such a purpose as well. Azeotropic removal of water facilitates the reactions.

Scheme G

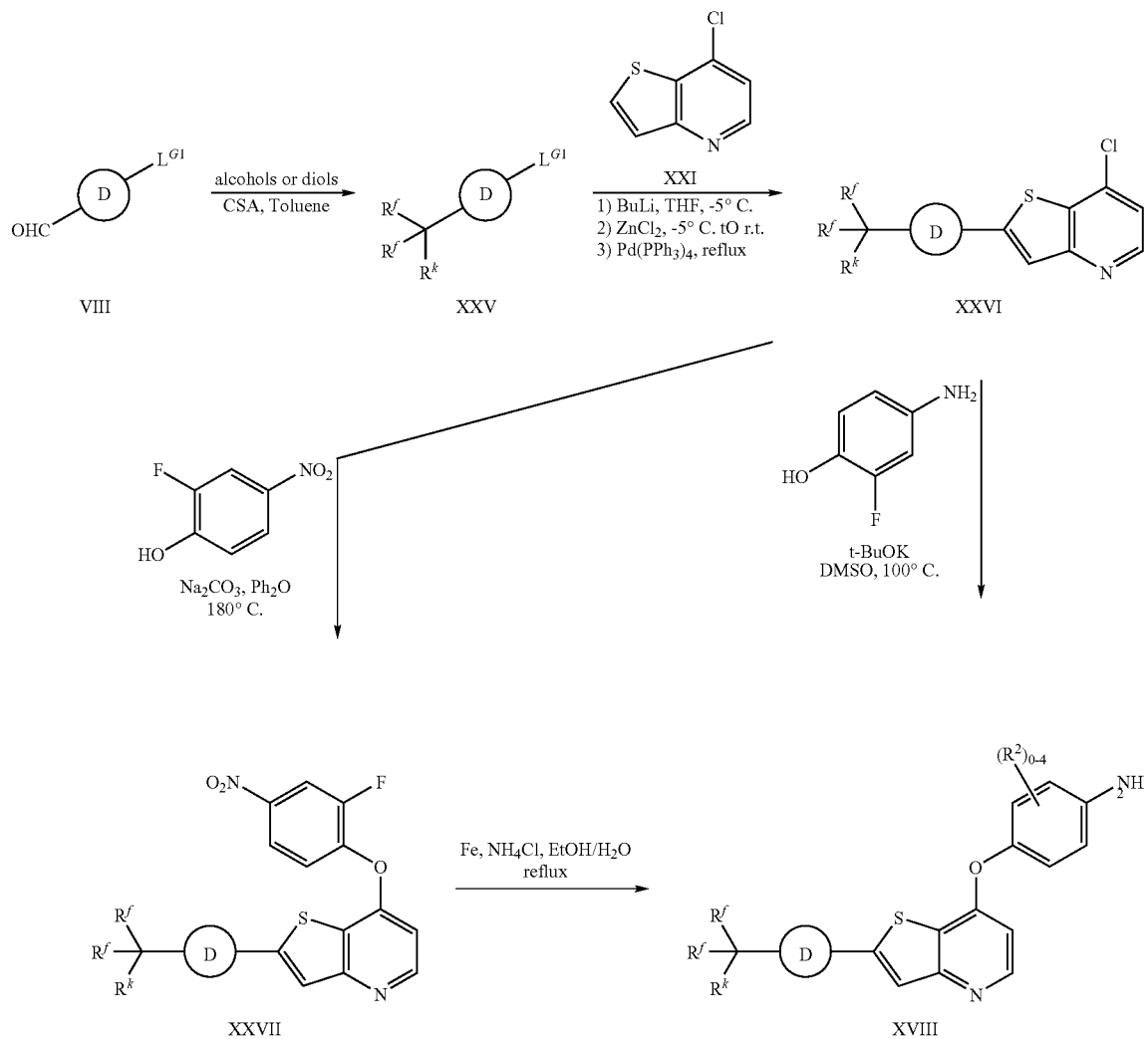

$R^k$ = H, $C_1$-$C_4$-alkyl, $C_1$-$C_6$-cyloalkyl, $C_1$-$C_4$-alkenyl, $C_1$-$C_4$-alkynyl;
$R^f$ = O-$C_1$-$C_7$ alkyl, or both substituents $R^f$ taken together may form a cylic acetal (a 5 to 8 member ring system) or a carbonyl group;

Attaching the building blocks XXV to the thienopyridine scaffold is achieved under Negishi reaction conditions (Scott R. W., et al, Org. process Research & Development, 2006, 10, 296-303; Ragan J. A., et al, Org. process Research & Development, 2003, 7, 676-683). Thus, metallation of 7-chlorothieno[3,2-b]pyridine (XI) (Klemm, L. H. et al. J. Heterocyclic Chem., 22, 1985, 1249-1252)) using reagents such as n-BuLi, sec-BuLi, LDA and like in the temperature range from −78° C. to 15° C., followed by transmetallation with zinc chloride with a subsequent coupling to compounds XXV in the presence of a transition metal catalyst in the temperature range from 25 to 150° C. (for example 60 to 90° C.), to form chlorides XXVI. The reactions are performed in aprotic solvents such as ether, THF, dioxane, benzene, toluene, xylenes, hexane, heptane. Alternative coupling reactions include Suzuki and Stille reactions. In these cases 7-chloro-2-iodothieno[3,2-b]pyridine (XIV, Scheme C) (or its bromo-analogue 7-chloro-2-bromothieno[3,2-b]pyridine) can be used.

Compounds XXVI can lead to the compounds XVIII either directly by replacing the chlorine atom in XXVI by 4-amino-2-fluorophenol at elevated temperatures (90-180° C.) (for example 80 to 110° C.) in solvents such as DMF, DMA, DMSO, diphenyl ether, etc. in the presence of bases such as KH, $K_2CO_3$, NaH, $Na_2CO_3$, $NaHCO_3$, NaHMDS, tert-BuOK, etc., or via the intermediate nitro compounds XXVII. Nitro compounds XXVII can be obtained by replacing the chlorine atom in XXVI with 2-fluoro-4-nitrophenol. The reaction proceeds at elevated temperatures (120-200° C.) in solvents such as DMF, DMA, DMSO, diphenyl ether, etc. in the presence of bases such as KH, $K_2CO_3$, NaH, $Na_2CO_3$, $NaHCO_3$, tert-BuOK etc. Reduction of the nitro group in XVIII can be achieved using standard procedures known in art. Examples of such procedures include iron-ammonium chloride, zinc-ammonium chloride, nickel chloride-sodium hydride, etc. in aqueous solutions or mixtures MeOH/water, EtOH/water or like, as well as the catalytic hydrogenation.

INTERMEDIATES AND EXAMPLES

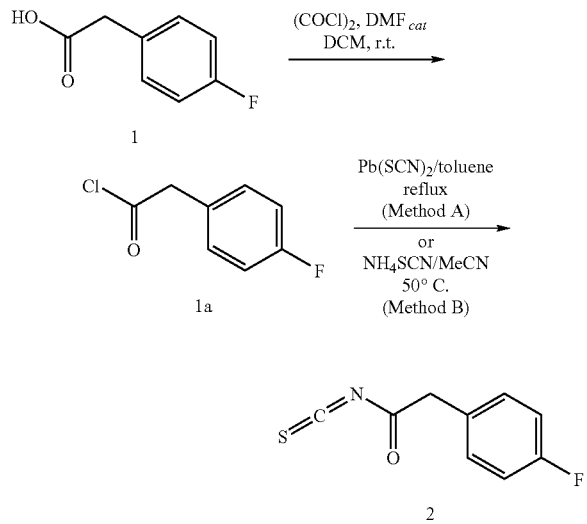

Scheme 1

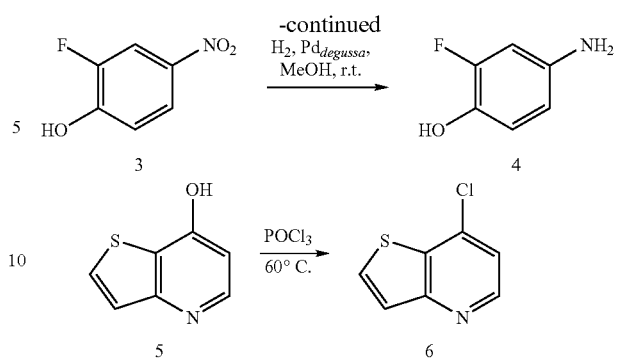

2-(4-Fluorophenyl)acetyl isothiocyanate (2)

Method A (for the Method B See Scheme 20)

To a solution of 4-fluorophenylacetic acid (1) (25 g, 162 mmol) in DCM (75 mL) was added oxalyl chloride (28.4 mL, 324 mmol) and 34 drops of DMF. The mixture was stirred at r.t. for 1 h-2 h and concentrated to produce 2-(4-fluorophenyl) acetyl chloride (1a) (yellow oil) that was re-dissolved in toluene (100 mL). To this solution was added lead(II) thiocyanate (55.0 g, 170 mmol). The mixture was heated to reflux for 1.5 h-2 h, cooled down, filtered and the filtrate was concentrated. The residue was applied onto a silica gel pad (20 cm) and eluted with EtOAc/hexanes (1/9), to afford after evaporation of the solvents title compound 2 (31 g, 98% yield) as a yellow oil. MS (m/z): 228.1 (M+H+ MeOH). $^1$H NMR (400 MHz, DMSO-$d_6$) δ (ppm): 7.26-7.22 (m, 2H), 7.09-7.07 (m, 2H), 3.84 (s, 2H).

4-Amino-2-fluorophenol (4)

To a degassed solution of 4-nitro-2-fluorophenol (3) (16 g, 102 mmol) in MeOH (150 mL) was added palladium on charcoal (10%) Degussa type (3.0 g, 2.82 mmol). The mixture was stirred at r.t. under hydrogen atmosphere for 3 h, filtered through a celite pad and evaporated under reduced pressure. The residue was triturated with $Et_2O$ (50 mL) to afford compound 4 (11.264 g, 87% yield) as a dark-brown solid. MS (m/z): 128.1 (M+H). $^1$H NMR (400 MHz, DMSO-$d_6$) δ (ppm): 8.57 (s, 1H), 6.62 (dd, J=10.0, 8.4 Hz, 1H), 6.34 (dd, J=13.4, 2.6 Hz, 1H), 6.20 (ddd, J=8.6, 2.6, 1.2 Hz, 1H), 4.67 (s, 2H).

7-Chlorothieno[3,2-b]pyridine (6)

To neat $POCl_3$ (200 mL, 2146 mmol) at 60° C. in a 500 mL round-bottom flask was added thieno[3,2-b]pyridin-7-ol (1 eq., 200 g, 1323 mmol) in small portions over 1.5 h. The reaction mixture was heated at 60° C. for 1 h and at 100° C. for an additional hour. After cooling down to 0° C., the reaction mixture was poured onto crushed ice (1 L) over a period of 30 min. After 15 min, $NH_4OH$ (1.5 L) was added to the mixture to form a grey precipitate that was collected by filtration, washed with water (50 mL) and air dried. The dry solid was suspended in EtOAc (1 L). The slurry was stirred at r.t. for 15 min, filtered and the filter was washed with EA (2×100 mL). The organic phase was collected, dried over $MgSO_4$ and concentrated. The residue was passed through a short silica gel pad (300 g, eluent—a gradient hexane/EtOAc, 8/2 to 5/5) and dried in the vacuum oven (35° C.) for 2 h to afford 6 as a off-white solid (214.8 g, 1266 mmol, 96% yield). MS (m/z): 170.0 (M+H). $^1$H NMR (400 MHz, DMSO-$d_6$) δ (ppm): 8.64 (d, J=5.1 Hz, 1H), 8.25 (d, J=5.5 Hz, 1H), 7.66 (d, J=5.5 Hz, 1H), 7.54 (d, J=5.1 Hz, 1H).

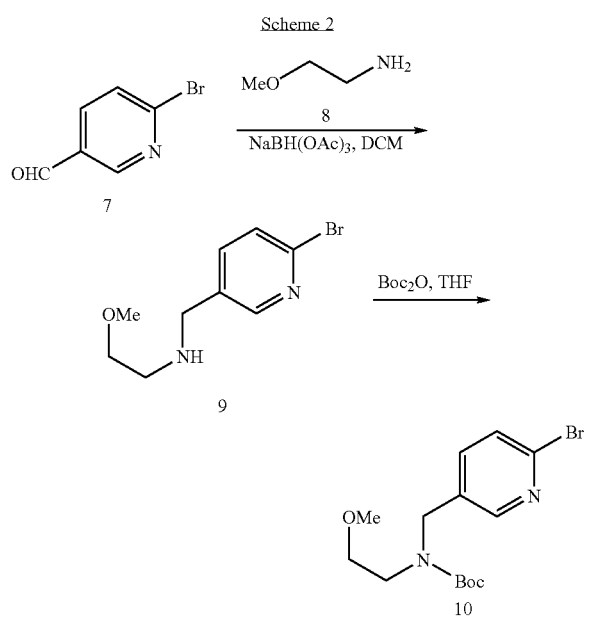

N-((6-Bromopyridin-3-yl)methyl)-2-methoxyethanamine (9)

To a solution of 6-bromonicotinaldehyde (7) (5 g, 26.9 mmol) in DCM (40 μL) was added 2-methoxyethylamine (8) (2.80 mL, 32.3 mmol). After 10 min, sodium triacetoxyborohydride (7.98 g, 37.6 mmol) was added to the mixture and the mixture was stirred at r.t. for 17 h. Additional amounts of DCM (100 mL), water (50 mL) and NH$_4$Cl (50 mL) were added to the reaction mixture, which turned into a biphasic system. The organic phase was collected and the aqueous layer was extracted with DCM (3×100 μL). The combined organic solution were washed with brine, dried over anhydrous MgSO$_4$ and concentrated under reduce pressure. The residue was purified by flash column chromatography (eluent a gradient DCM/MeOH from 98/2 to 95/5), to afford intermediate 9 (2.958 g, 45% yield) as a brown oil. MS (m/z): 245.1 (M+H).

$^1$H NMR (400 MHz, DMSO-d$_6$) δ (ppm): 8.31 (dd, J=2.6, 0.6 Hz, 1H), 7.70 (dd, J=8.2, 2.6 Hz, 1H), 7.58 (d, J=8.4 Hz, 1H), 3.69 (s, 2H), 3.37 (t, J=5.8 Hz, 2H), 3.22 (s, 3H), 2.60 (t, J=5.8 Hz, 2H).

tert-Butyl (6-bromopyridin-3-yl)methyl(2-methoxyethyl)carbamate (10)

To a solution of intermediate 9 (13.072 g, 53.3 mmol) in THF (40 mL) was added di-tert-butyl dicarbonate (14.86 mL, 64.0 mmol). The mixture was stirred at r.t. for 16 h and concentrated under reduce pressure. The residue was purified by flash column chromatography (eluent a gradient of hexane/EtOAc:7/3, 6/4, 5/5), to intermediate 10 (16.196 g, 88% yield) as a yellow oil. MS (m/z): 345.2 (M+H). $^1$H NMR (400 MHz, DMSO-d$_6$) δ (ppm): 8.26 (dd, J=2.4, 0.8 Hz, 1H), 7.64-7.58 (m, 2H), 4.39 (s, 2H), 3.40-3.33 (m, 4H), 3.20 (s, 3H), 1.41-1.31 (m, 9H).

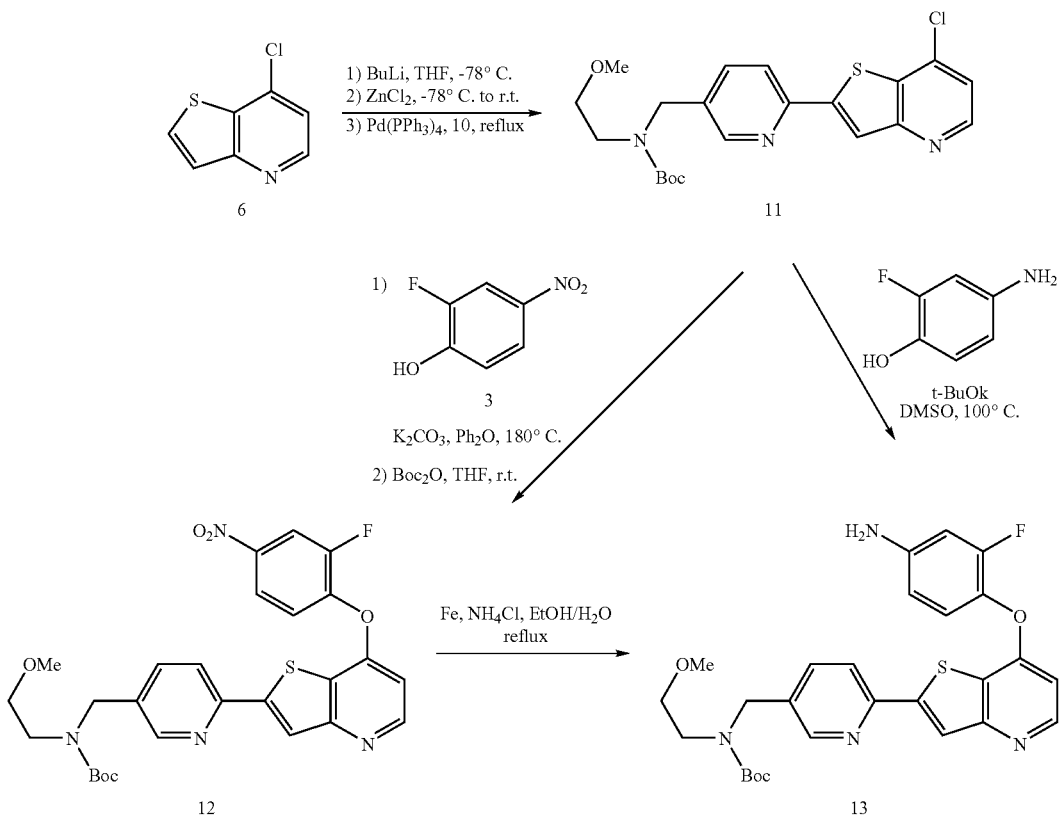

tert-Butyl (6-(7-chlorothieno[3,2-b]pyridin-2-yl) pyridin-3-yl)methyl(2-methoxyethyl)carbamate (11)

To a solution of 7-chlorothieno[3,2-b]pyridine (6) (8.84 g, 52.1 mmol) in THF (100 µL) at −78° C. was added n-butyl-lithium (20.86 mL, 52.1 mmol). After 30 min, zinc chloride (52.1 mL, 52.1 mmol) (1M in ether) was added at −78° C. and the reaction mixture was allowed to warm to r.t. After 1 h, palladium tetrakistriphenylphosphine (1.004 g, 0.869 mmol) and tert-butyl (6-bromopyridin-3-yl)methyl(2-methoxyethyl)carbamate (10) (6 g, 17.38 mmol) in THF (25.00 mL) were added and the mixture was heated to reflux for 1 h and cooled to room temperature. To the cooled reaction mixture were added NaHCO$_3$ (sat. aq.) (100 mL) and EtOAc (100 mL). The organic layer was collected and the aqueous layer was extracted with EtOAc (3×100 mL). The combined organic solutions were washed with brine, dried over anhydrous Na$_2$SO$_4$ and evaporated under reduce pressure. The residue was purified by flash column chromatography (eluent hexane/EtOAc:5/5, 3/7, 0/100), to afford intermediate 11 (5.41 g, 72% yield). MS (m/z): 434.2 (M+H). $^1$H NMR (400 MHz, DMSO-d$_6$) δ (ppm): 8.65 (d, J=5.1 Hz, 1H), 8.52 (d, J=1.6 Hz, 1H), 8.39 (s, 1H), 8.27 (d, J=8.0 Hz, 1H), 7.80 (dd, J=8.1, 2.1 Hz, 1H), 7.58 (d, J=5.1 Hz, 1H), 4.48 (s, 2H), 3.43-3.35 (m, 4H), 3.22 (s, 3H), 1.43-1.33 (m, 9H).

tert-Butyl (6-(7-(2-fluoro-4-nitrophenoxy)thieno[3,2-b]pyridin-2-yl)pyridin-3-yl)methyl(2-methoxyethyl)carbamate (12)

Method A (for the Method B See Scheme 7)

To a suspension of intermediate 11 (2 g, 4.61 mmol) in phenyl ether (5 mL) were added potassium carbonate (0.764 g, 5.53 mmol) and 2-fluoro-4-nitrophenol (3) (1.448 g, 9.22 mmol). The mixture was heated at 160° C. for 5 h, cooled to room temperature and partitioned between water and EtOAc. The organic phase was collected and the aqueous layer was extracted with EtOAc (3×100 mL). The combined organic solutions were washed with brine, dried over anhydrous Na$_2$SO$_4$, concentrated under reduce pressure and suspended in THF (20.00 mL). Di-tert-butyl dicarbonate (1.070 mL, 4.61 mmol) was added to this suspension and the mixture was stirred at r.t. for 30 min, and concentrated. The residue was purified by flash column chromatography (eluent hexane/EtOAc:5/5, 3/7, 0/100), to afford intermediate 12 (1.695 g, 66% yield) as a yellow gum. MS (m/z): 555.3 (M+H). $^1$H NMR (400 MHz, DMSO-d$_6$) δ (ppm): 8.61 (d, J=5.2 Hz, 1H), 8.49 (d, J=1.6 Hz, 1H), 8.46 (dd, J=10.4, 2.8 Hz, 1H), 8.37 (s, 1H), 8.26 (d, J=7.6 Hz, 1H), 8.20 (ddd, J=8.8, 2.8, 1.2 Hz, 1H), 7.79 (dd, J=8.4, 2.0 Hz, 1H), 7.70 (t, J=8.6 Hz, 1H), 6.96 (d, J=5.6 Hz, 1H), 4.47 (s, 2H), 3.43-3.33 (m, 4H), 3.22 (s, 3H), 1.42-1.33 (m, 9H).

tert-Butyl (6-(7-(4-amino-2-fluorophenoxy)thieno[3,2-b]pyridin-2-yl)pyridin-3-yl)methyl(2-methoxyethyl)carbamate (13)

Method A

To a suspension of intermediate 12 (5.853 g, 10.55 mmol) in EtOH (50 mL) and water (25 mL) were added ammonium chloride (0.480 g, 8.97 mmol) and iron powder (3 mL, 90 mmol). The mixture was heated to reflux for 1 h and filtered while hot. The filtrate was collected and concentrated to afford intermediate 13 (6.04 g, quantitative yield) as a yellow solid. MS (m/z): 525.3 (M+H). $^1$H NMR (400 MHz, DMSO-d$_6$) δ (ppm): 8.51 (d, J=2.0 Hz, 1H), 8.50 (d, J=5.6 Hz, 1H), 8.30 (s, 1H), 8.25 (d, J=7.6 Hz, 1H), 7.78 (d, J=8.2 Hz, 1H), 7.13 (t, J=9.2 Hz, 1H), 6.60 (dd, J=5.4, 0.6 Hz, 1H), 6.64 (dd, J=13.0, 2.6 Hz, 1H), 6.46 (ddd, J=8.8, 2.5, 0.7 Hz, 1H), 5.56 (s, 2H), 4.48 (s, 2H), 3.43-3.34 (m, 4H), 3.23 (s, 3H), 1.44-1.34 (m, 9H).

Method B

To a solution of 4-amino-2-fluorophenol (4) (1.933 g, 15.21 mmol) in DMSO (30 mL) was added potassium tert-butoxide (2.017 g, 17.97 mmol). After 30 min, intermediate 11 (6 g, 13.83 mmol) was added and the reaction mixture was heated at 100° C. for 45 min. The reaction mixture was then cooled down, poured in water (250 mL) at 40-45° C. and the resultant suspension was stirred for 30 min. The precipitate was collected by filtration, washed with water (2×30 mL) and dried overnight. The dry solid was triturated with Et$_2$O (50 mL), to afford intermediate 13 (4.18 g, 58% yield) as a brown solid. MS (m/z): 525.2 (M+H).

Scheme 4

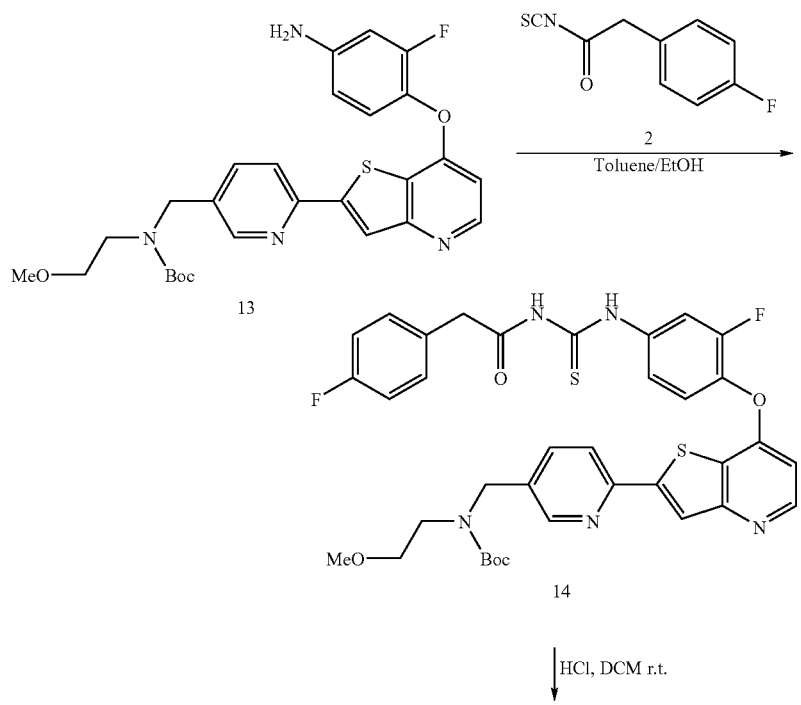

-continued

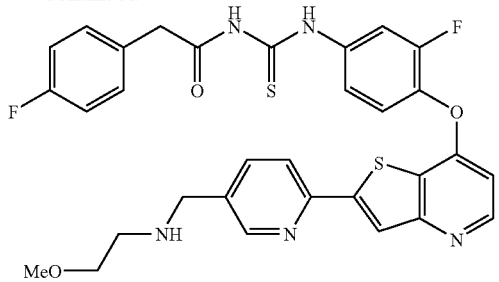

15: Example 1

Example 1

Version A tert-Butyl (6-(7-(2-fluoro-4-(3-(2-(4-fluorophenyl)acetyl)thioureido)phenoxy)thieno[3,2-b]pyridin-2-yl)pyridin-3-yl)methyl(2-methoxyethyl)carbamate (14)

To a suspension of intermediate 13 (5.53 g, 10.55 mmol) in toluene (80 mL) and EtOH (80 mL) was added 2-(4-fluorophenyl)acetyl isothiocyanate (2) (3.09 g, 15.83 mmol) in a minimum of toluene-EtOH mixture (1:1). The reaction mixture was stirred at r.t. for 45 min then concentrated. The residue was purified by flash column chromatography (eluent EtOAc), followed by two triturations: first one in a mixture Et$_2$O-EtOAc-hexanes and second one in Et$_2$O, to afford intermediate 14 (4.68 g, 62% yield) as a pink solid. $^1$H NMR (400 MHz, DMSO-d$_6$) δ (ppm): 12.49 (s, 1H), 11.84 (s, 1H), 8.55 (d, J=5.6 Hz, 1H), 8.51 (d, J=1.6 Hz, 1H), 8.34 (s, 1H), 8.27 (d, J=8.0 Hz, 1H), 8.04 (d, J=11.6 Hz, 1H), 7.79 (dd, J=8.2, 2.2 Hz, 1H), 7.55-7.54 (m, 2H), 7.38 (dd, J=8.6, 5.8 Hz, 2H), 7.18 (t, J=8.8 Hz, 2H), 6.69 (d, J=5.6 Hz, 1H), 4.48 (s, 2H), 3.84 (s, 2H), 3.43-3.34 (m, 4H), 3.23 (s, 3H), 1.44-1.34 (m, 9H). MS (m/z): 720.3 (M+H).

N-(3-Fluoro-4-(2-(5-((2-methoxyethoxy)methyl)pyridin-2-yl)thieno[3,2-b]pyridin-7-yloxy)phenylcarbamothioyl)-2-(4-fluorophenyl)acetamide (15, Example 1))

To a solution of intermediate 14 (8.41 g, 11.68 mmol) in DCM (100 mL) was added HCl in dioxane (5.84 mL, 23.37 mmol) (4M HCl in dioxane). After 10 min, a precipitate was formed and more HCl in dioxane (5.84 mL, 23.37 mmol) was added. The reaction mixture was stirred at r.t. for an additional 1 h, diluted with a mixture of 5% MeOH in DCM and neutralized to pH=7 with aqueous NaHCO$_3$. The layers were separated, the organic phase was collected and the aqueous layer was extracted with another portion of the mixture of 5% MeOH in DCM. The combined organic solutions were washed with brine, dried over anhydrous Na$_2$SO$_4$ and evaporated. The residue was triturated with MeOH, to afford compound 15 (4.96 g, 58% yield) as a beige solid. $^1$H NMR (400 MHz, DMSO-d$_6$) δ (ppm): 8.56 (d, J=1.2 Hz, 1H), 8.53 (d, J=5.2 Hz, 1H), 8.32 (s, 1H), 8.22 (d, J=8.0 Hz, 1H), 8.04 (dd, J=2.0 and 11.2 Hz, 1H), 7.89 (dd, J=2.0 and 8.0 Hz, 1H), 7.58-7.50 (m, 2H), 7.42-7.35 (m, 2H), 7.23-7.15 (m, 2H), 6.67 (d, J=5.2 Hz, 1H), 3.83 (s, 2H), 3.77 (s, 2H), 3.40 (t, J=6.0 Hz, 2H), 3.23 (s, 3H), 2.65 (t, J=6.0 Hz, 2H). MS (m/z): 620.1 (M+H).

Scheme 5

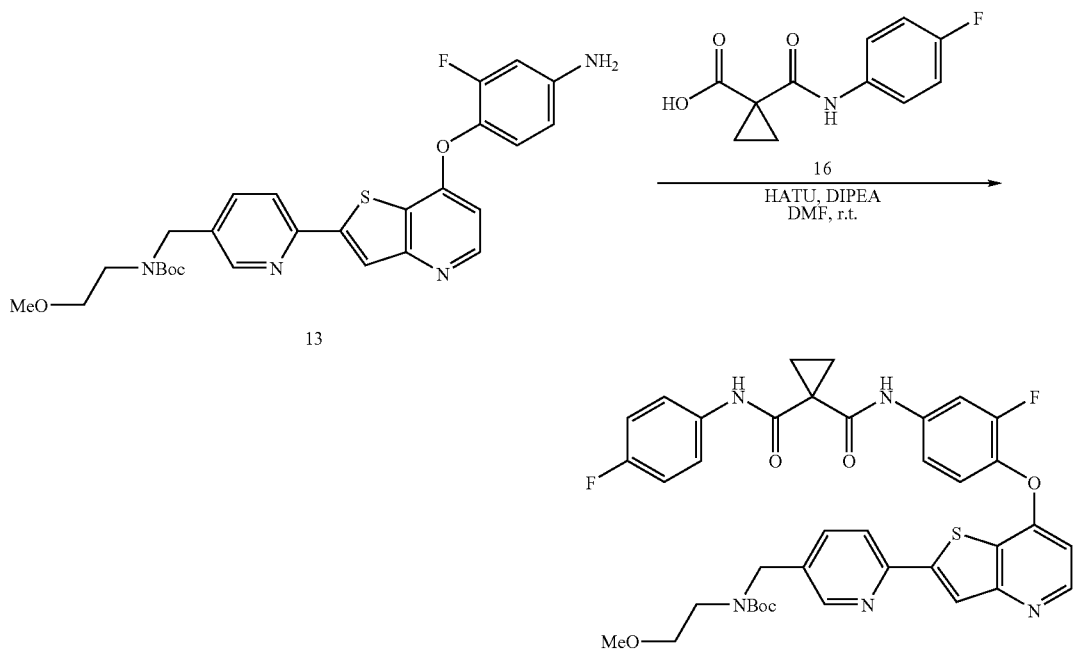

-continued

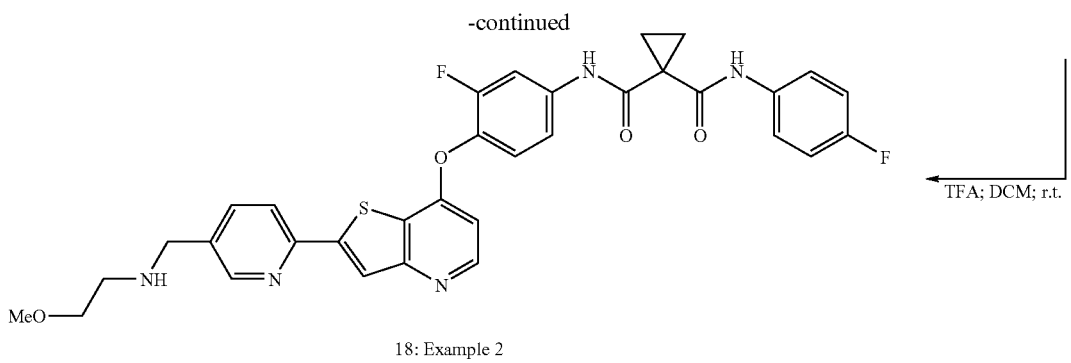

18: Example 2

Example 2 tert-Butyl (6-(7-(2-Fluoro-4-(1-(4-fluorophenylcarbamoyl)-cyclopropanecarboxamido)phenoxy)thieno[3,2-b]pyridin-2-yl)pyridin-3-yl)methyl(2-methoxyethyl)carbamate (17)

To intermediate 13 (0.58 g, 1.1 mmol) and DIPEA (0.58 mL, 0.43 g, 3.3 mmol) in dry DMF (20 mL) was added 1-(4-fluorophenylcarbamoyl)cyclopropanecarboxylic acid (16) [US 2007/0004675 A1] (0.35 g, 1.5 mmol) and HATU (0.72 g, 1.9 mmol). The mixture was stirred at r.t. for 18 h and partitioned between ethyl acetate and water. The organic phase was collected, washed with water, 1M NaOH, brine, dried (anhydrous MgSO₄), filtered, and concentrated. Silica gel chromatography (ethyl acetate) afforded intermediate 17 (0.60 g, 74% yield). $^1$H NMR (400 MHz, DMSO-d$_6$) δ (ppm): 10.40 (s, 1H), 10.01 (s, 1H), 8.52-8.49 (m, 2H), 8.33 (s, 1H), 8.27-8.24 (m, 1H), 7.92-7.88 (m, 1H), 7.78 (dd, J=8.2, 2.1 Hz, 1H) 7.65-7.60 (m, 2H), 7.52-7.42 (m, 2H), 7.14 (t, J=8.8 Hz, 2H), 6.65 (d, J=5.1 Hz 1H), 4.47 (s, 2H), 3.42-3.30 (m, 4H), 3.22 (s, 3H), 1.46-1.30 (m, 13H). MS (m/z): 730.1 (M+H).

N-(3-Fluoro-4-(2-(5-((2-methoxyethylamino)methyl)pyridin-2-yl)thieno[3,2-b]pyridin-7-yloxy)phenyl)-N-(4-fluorophenyl)cyclopropane-1,1-dicarboxamide (18, Example 2)

To the intermediate 17 (0.59 g, 0.81 mmol) in dichloromethane (50 mL) was added TFA (3 mL). The solution was stirred for 18 h, then concentrated. The residue was partitioned between dichloromethane and 1M NaOH, and filtered to remove insolubles. The organic phase was collected, washed with 1M NaOH, brine, dried (MgSO₄), filtered, and concentrated to afford compound 18 (0.35 g, 69% yield). $^1$H NMR (400 MHz, DMSO-d$_6$) δ (ppm): 10.40 (s, 1H), 10.01 (s, 1H), 8.55 (d, J=1.6 Hz, 1H), 8.51 (d, J=5.3 Hz, 1H), 8.31 (s, 1H), 8.22 (d, J=8.0 Hz, 1H), 7.92-7.87 (m, 2H), 7.65-7.61 (m, 2H), 7.52-7.43 (m, 2H), 7.17-7.12 (m, 2H), 6.64 (d, J=5.5 Hz, 1H), 3.77 (s, 2H), 3.40 (t, J=5.7 Hz, 2H), 3.23 (s, 3H), 2.64 (t, J=5.7 Hz, 2H), 1.46 (br s, 4H). MS (m/z): 630.1 (M+H).

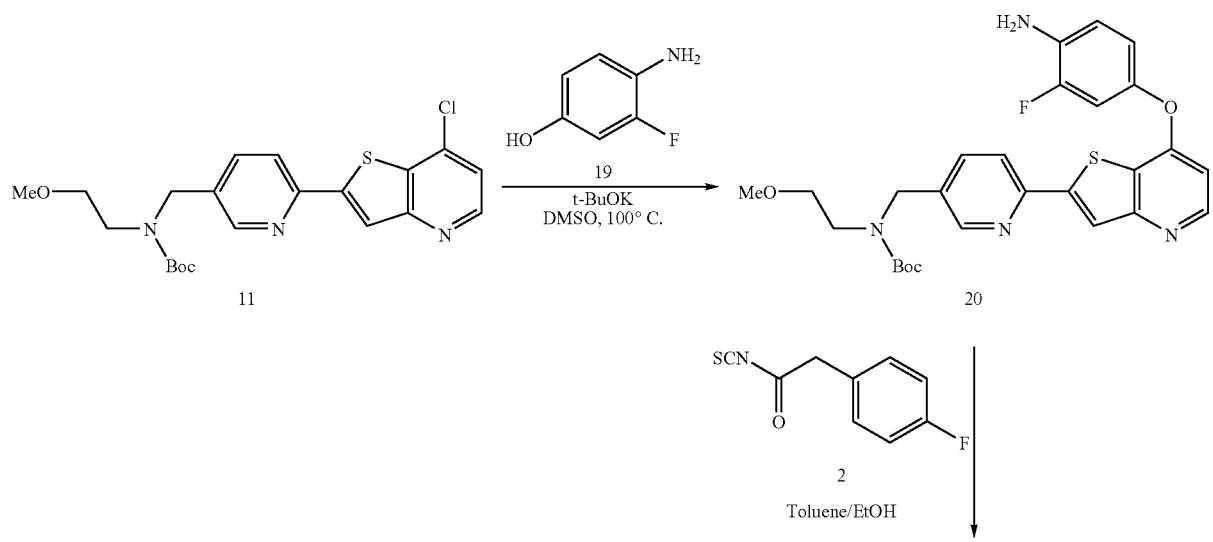

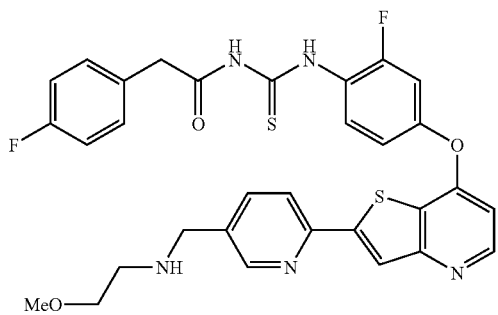

22: Example 3

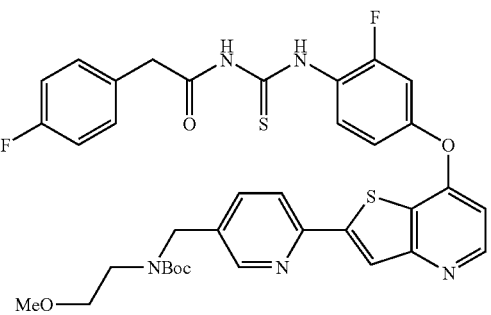

21

Example 3 tert-Butyl (6-(7-(4-amino-3-fluorophenoxy)thieno[3,2-b]pyridin-2-yl)pyridin-3-yl)methyl(2-methoxyethyl)carbamate (20)

To a solution of 4-amino-3-fluorophenol (19) in DMSO (12 mL) was added potassium tert-butoxide (0.824 g, 7.34 mmol). After 30 min, intermediate 11 (2.451 g, 5.65 mmol) was added and the reaction mixture was heated at 100° C. for 1.5 h, cooled to room temperature, poured in water (50 mL) at 40-45° C. and stirred for 30 min. EtOAc (40 mL), DCM (40 mL) and water (40 ml) were added and the pH was adjusted to 7 by addition of HCl. Solids were removed by filtration through a paper filter and the two phases were separated. The organic layer was collected, dried over anhydrous $Na_2SO_4$, filtered and concentrated. The residue was purified by flash column chromatography (eluent DCM/MeOH:99/1, 98/2, 95/5), to afford intermediate 20 (0.952 g, 32% yield). MS (m/z): 525.2 (M+H).

tert-Butyl (6-(7-(3-fluoro-4-(3-(2-(4-fluorophenyl)acetyl)thioureido)phenoxy)thieno[3,2-b]pyridin-2-yl)pyridin-3-yl)methyl(2-methoxyethyl)carbamate (21)

Following the procedure described above for the synthesis of compound 14 (scheme 4) but substituting compound 13 for compound 20 intermediate 21 was obtained (55% yield) MS (m/z): 720.3 (M+H).

N-(2-Fluoro-4-(2-(5-((2-methoxyethylamino)methyl)pyridin-2-yl)thieno[3,2-b]pyridin-7-yloxy)phenylcarbamothioyl)-2-(4-fluorophenyl)acetamide (22, Example 3)

HCl gas was bubbled into a solution of the intermediate 21 (150 mg, 0.209 mmol) in DCM (5 ml). The flask was capped and the mixture was stirred at r.t. for 2 hours, concentrated and the resultant yellow solid was triturated with $Et_2O$ to afford compound 22 (126 mg, 98% yield). $^1$H NMR (400 MHz, DMSO-$d_6$) δ (ppm): 12.27 (s, 1H), 11.94 (s, 1H), 9.50 (s, 1H), 8.78 (s, 1H), 8.47 (d, J=1.0 Hz, 1H), 8.42 (d, J=8.0 Hz, 1H), 8.21 (d, J=8.4 Hz, 1H), 8.12 (t, J=8.7 Hz, 1H), 7.53 (dd, J=11.9, 2.3 Hz, 1H), 7.38 (dd, J=8.5, 5.6 Hz, 2H), 7.26 (d, J=8.8 Hz, 1H), 7.18 (t, J=8.8 Hz, 2H), 6.95 (dd, J=5.7, 2.3 Hz, 1H), 4.26-4.24 (m, 2H), 3.84 (s, 2H), 3.64 (t, J=5.1 Hz, 2H), 3.30 (s, 3H), 3.13 (m, 2H) (presumably tri-hydrochloride salt). MS (m/z): 620.1 (M+H).

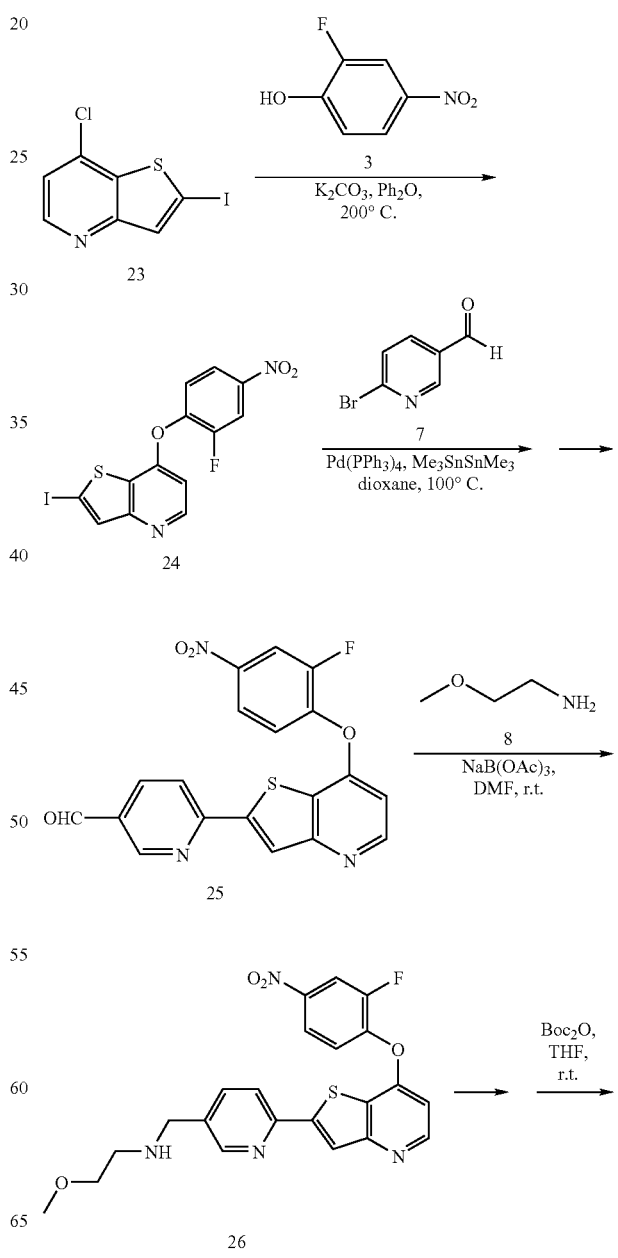

Scheme 7

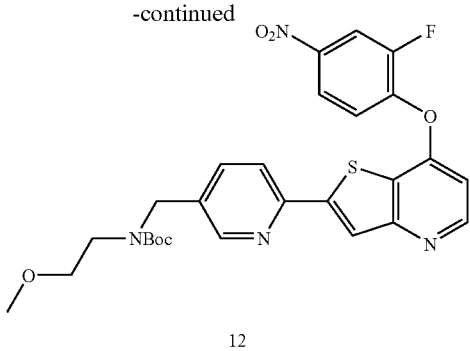

12

7-(2-Fluoro-4-nitrophenoxy)-2-iodothieno[3,2-b]pyridine (24)

A mixture of the 7-chloro-2-iodothieno[3,2-b]pyridine (23) (Ragan J. A. et al, Organic Process Research and Development 2003, 7, 676-683) (7.0 g, 23.7 mmol), 2-fluoro-4-nitrophenol (3) (11.15 g, 71.1 mmol), $K_2CO_3$ (13.08 g, 94.8 mmol) in $Ph_2O$ (30 ml) was heated at 200° C. for 3 h. The reaction mixture was cooled to room temperature, diluted with DCM and filtered; the filtrate was collected and then concentrated. The resultant solid was triturated with diethyl ether, to afford intermediate 24 (7.3 g, 74% yield), which was used directly in the next step with no additional purification. MS (m/z): 417.0 (M+H).

6-(7-(2-Fluoro-4-nitrophenoxy)thieno[3,2-b]pyridin-2-yl)nicotinaldehyde (25)

To a solution of intermediate 24 (6 g, 14.42 mmol) in dioxane (40 mL) were added 6-bromopyridine-3-carbaldehyde (7) (3.22 g, 17.30 mmol), palladium tetrakistriphenylphosphine (0.500 g, 0.433 mmol), and hexamethyldistannane (3.29 mL, 15.86 mmol). The mixture was heated at 100° C. for 20 h, concentrated, adsorbed on silica gel, placed onto a silica gel column and subjected to flash chromatography purification (eluent DCM/MeOH: 100/0, 99/1, 98/2, 97/3), to afford intermediate 25 (2.864 g, 50% yield). MS (m/z): 396.1 (M+H). N-((6-(7-(2-Fluoro-4-nitrophenoxy)thieno[3,2-b]pyridin-2-yl)pyridin-3-yl)methyl)-2-methoxyethanamine (26)

To a solution of 25 (2.864 g, 7.24 mmol) in DCM (30 mL) was added 2-methoxyethylamine (8) (0.756 mL, 8.69 mmol). After 45 min, sodium triacetoxyborohydride (2.149 g, 10.14 mmol) was added and the reaction mixture was stirred at r.t. for 18 h. More sodium triacetoxyborohydride (2.149 g, 10.14 mmol) was added and the mixture was stirred for an additional 2 h. The reaction mixture was quenched with saturated aqueous $NaHCO_3$ and the phases were separated. Organic phase was collected and the aqueous layer was extracted with DCM (3×100 mL). The combined organic solutions were concentrated and the residue was purified by flash column chromatography (eluent DCM/MeOH) to afford, intermediate 26 (1.742 g, 53% yield) as a yellow solid. $^1$H NMR (400 MHz, DMSO-$d_6$) δ (ppm): 8.62 (d, J=5.6 Hz, 1H), 8.55 (d, J=1.2 Hz, 1H), 8.48 (dd, J=10.2, 2.6 Hz, 1H), 8.37 (s, 1H), 8.26-8.23 (m, 1H), 8.21 (ddd, J=8.8, 2.8, 1.2 Hz, 1H), 7.90 (dd, J=8.4, 2.0 Hz, 1H), 7.71 (dd, J=9.0, 8.2 Hz, 1H), 6.97 (dd, J=5.6, 0.4 Hz, 1H), 3.78 (s, 2H), 3.40 (t, J=5.6 Hz, 2H), 3.24 (s, 3H), 2.65 (t, J=5.6 Hz, 2H). MS (m/z): 455.2 (M+H).

tert-Butyl (6-(7-(2-fluoro-4-nitrophenoxy)thieno[3,2-b]pyridin-2-yl)pyridin-3-yl)methyl(2-methoxyethyl)carbamate (12)

Method B

To a suspension of 26 (1.742 g, 3.83 mmol) in THF (30 mL) was added di-tert-butyl dicarbonate (1.335 mL, 5.75 mmol). The mixture was stirred at r.t. for 15 h and concentrated under reduce pressure. The residue was purified by flash column chromatography (eluent EtOAc), to afford intermediate 12 (1.657 g, 78% yield) as a yellow pale solid. MS (m/z): 555.3 (M+H).

Scheme 8

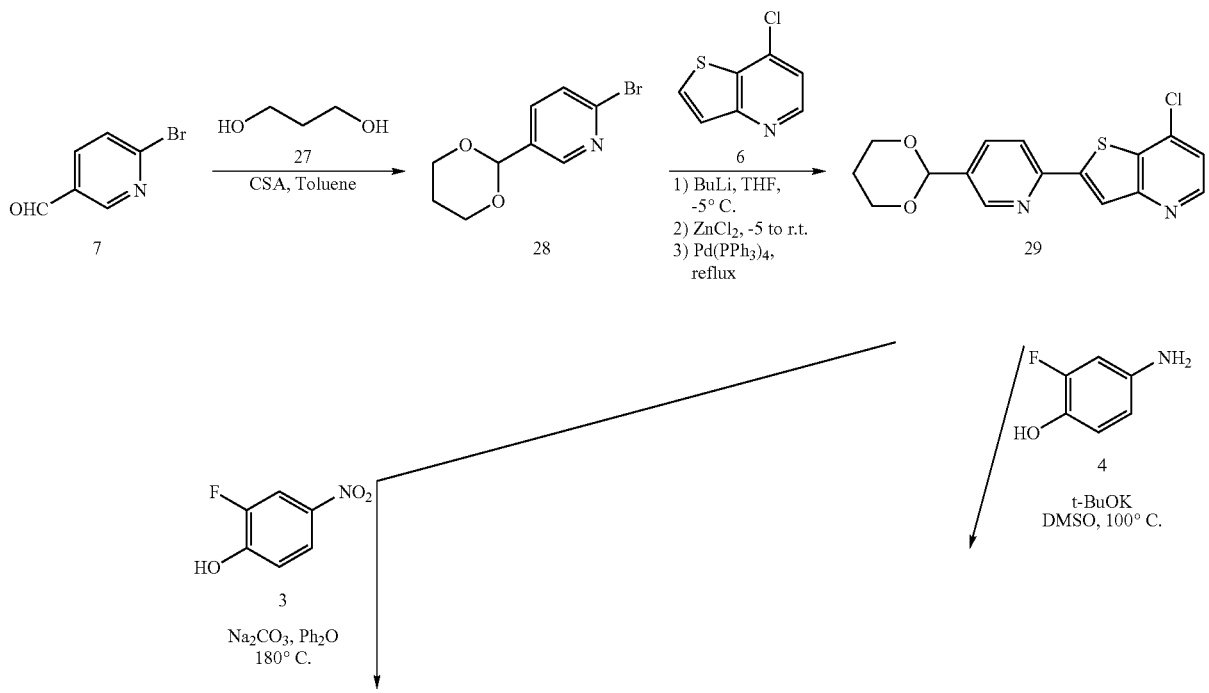

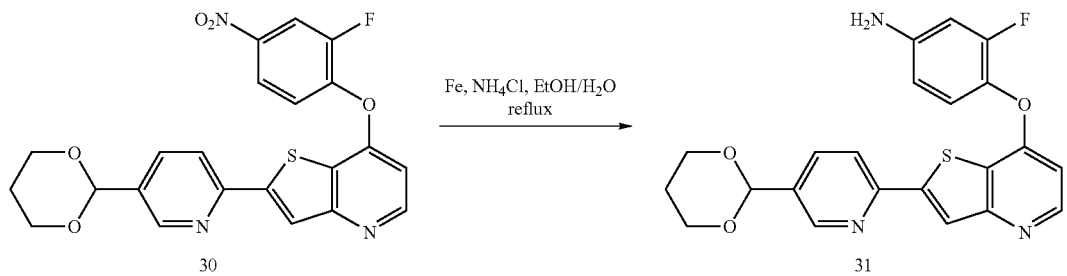

2-Bromo-5-(1,3-dioxan-2-yl)pyridine (28)

To a solution of 6-bromopyridine-3-carbaldehyde (7) (25 g, 134 mmol) in toluene (130 mL) were added 1,3-propanediol (27) (20.45 g, 269 mmol) and 10-camphorsulfonic acid (3.12 g, 13.44 mmol). The reaction mixture was heated to reflux, with azeotropic removal of the evolved water, for 50 minutes, cooled down to r.t. and concentrated. The residue was partitioned between EtOAc (150 mL) and saturated aqueous NaHCO$_3$ solution (100 mL). Organic phase was collected and the aqueous phase was extracted with EtOAc (2×150 mL). Combined organic fractions were washed with brine (100 mL), dried over Na$_2$SO$_4$, filtered and concentrated to yield a brown solid which was triturated with Et$_2$O and hexane (10/200 mL), to afford intermediate 28 (27.7 g, 84% yield) as a beige solid. MS (m/z): 244.1, 246.1 (M+H). $^1$H NMR (400 MHz, DMSO-d$_6$) δ (ppm): 8.40 (d, J=2.4 Hz, 1H), 7.35 (dd, J=8.0, 2.4 Hz, 1H), 7.66 (dd, J=8.0, 0.4 Hz, 1H), 5.61 (s, 1H), 4.15 (ddd, J=11.8, 5.0, 1.2 Hz, 2H), 3.98-3.91 (m, 2H), 2.028-1.95 (m, 1H), 1.46 (d quint, J=13.2, 1.2 Hz, 1H).

2-(5-(1,3-Dioxan-2-yl)pyridin-2-yl)-7-chlorothieno[3,2-b]pyridine (29)

To a solution of 7-chlorothieno[3,2-b]pyridine (6) (13.33 g, 79 mmol) in THF (204 mL) at −5° C./−10° C. was added n-BuLi (2.5 M in hexanes, 31.6 mL, 79 mmol) over 50 min. After 30 min, a solution of zinc chloride in ether (1M, 79 mL, 79 mmol) was added at −5° C./−10° C. over 50 min and the reaction mixture was allowed to warm-up to r.t. After 45 min, 2-bromo-5-(1,3-dioxan-2-yl)pyridine (28) (15.98 g, 65.5 mmol) and palladium tetrakistriphenylphosphine (2.27 g, 1.964 mmol) in THF (28 mL) were added and the mixture was heated to reflux for 2 h, cooled down to r.t., and concentrated. The residue was diluted with DCM (600 mL), H$_2$O (500 mL) and NH$_4$OH (100 mL), stirred at r.t. for 1 h and the phases were separated. The aqueous phase was extracted with DCM (2×100 mL); the combined organic phases were dried over anhydrous Na$_2$SO$_4$, filtered and concentrated. The residue was triturated with MTBE (150 mL), to afford intermediate 29 (12.796 g, 59% yield) as a beige solid. $^1$H NMR (400 MHz, DMSO-d$_6$) δ (ppm): 8.66-8.65 (m, 2H), 8.43 (d, J=0.8 Hz, 1H), 8.30 (d, J=8.4 Hz, 1H), 7.94 (d, J=8.4 Hz, 1H), 7.59 (dd, J=5.0, 0.6 Hz, 1H), 5.68 (s, 1H), 4.19 (dd, J=11.6, 4.8 Hz, 2H), 3.99 (t, J=11.4 Hz, 2H), 2.07-2.01 (m, 1H), 1.49 (d, J=13.2 Hz, 1H). MS (m/z): 333.1 (M+H).

2-(5-(1,3-Dioxan-2-yl)pyridin-2-yl)-7-(2-fluoro-4-nitrophenoxy)thieno[3,2-b]pyridine (30)

To a suspension of 29 (22.48 g, 67.5 mmol) in phenyl ether (65 mL) was added sodium carbonate (14.32 g, 135 mmol) and 2-fluoro-4-nitrophenol (3) (15.92 g, 101 mmol). The reaction mixture was heated at 180° C. for 2 h, cooled down to 40° C., diluted with DCM (300 mL), stirred at r.t. for 15 min and filtered. The filtrate was collected and concentrated to a minimal volume; Et$_2$O (200 mL) was added and the formed suspension was stirred for 30 min. The solid material was collected by filtration, to afford intermediate 30 (25.20 g, 55.6 mmol, 82% yield) as a beige solid. $^1$H NMR (400 MHz, DMSO-d) δ (ppm): 8.63-8.62 (m, 2H), 8.48 (dd, J=10.6, 2.6 Hz, 1H), 8.43 (s, 1H), 8.31 (d, J=8.0 Hz, 1H), 8.21 (dt, J=8.8, 1.2 Hz, 1H), 7.94 (dd, J=8.4, 2.0 Hz, 1H), 7.71 (t, J=8.6 Hz, 1H), 6.98 (d, J=5.2 Hz, 1H), 5.67 (s, 1H), 4.19 (dd, J=10.8, 5.2 Hz, 2H), 3.98 (td, J=12.0, 2.0 Hz, 2H), 2.08-1.99 (m, 1H), 1.46 (d, J=13.6 Hz, 1H). MS (m/z): 454.2 (M+H).

4-(2-(5-(1,3-dioxan-2-yl)pyridin-2-yl)thieno[3,2-b]pyridin-7-yloxy)-3-fluoroaniline (31)

Method A

To a suspension of 30 (10 g, 22.05 mmol) in EtOH (216 ml) and water (108 ml) was added iron powder (10.47 g, 187 mmol) and ammonium chloride (1.015 g, 18.97 mmol). The mixture was heated to reflux for 30 min, filtered while hot and the solids were washed with ether (200 mL). The filtrate and washings were combined and concentrated to afford intermediate 31 (9.62 g, 99% yield) as a beige solid. This material was used in the next step (Scheme 9) without additional purification. $^1$H NMR (400 MHz, DMSO-d$_6$) δ (ppm): 8.64 (d, J=2.0 Hz, 1H), 8.51 (dd, J=5.6, 2.0 Hz, 1H), 8.34 (s, 1H), 8.28 (dd, J=8.0, 0.8 Hz, 1H), 7.93 (dd, J=8.4, 2.0 Hz, 1H), 7.13 (t, J=9.0 Hz, 1H), 6.61 (dd, J=5.4, 0.6 Hz, 1H), 6.54 (dd, J=13.2, 2.4 Hz, 1H), 6.46 (ddd, J=8.8, 2.8, 0.6 Hz, 1H), 5.67 (s, 1H), 5.56 (s, 2H), 4.19 (dd, J=10.6, 5.0 Hz, 2H), 3.98 (td, J=12.0, 2.5 Hz, 2H), 2.09-1.99 (m, 1H), 1.49 (dt, J=13.2, 1.3 Hz, 1H). MS (m/z): 424.1 (M+H).

Method B

To a solution of 4-amino-2-fluorophenol (4) (7.42 g, 58.4 mmol) in DMSO (65 mL) was added potassium tert-butoxide (7.75 g, 69.0 mmol)). After 30 min, intermediate 29 (17.67 g, 53.1 mmol) was added and the reaction mixture was heated at 100° C. for 1.5 h, cooled down to room temperature, poured in water (300 mL) at 40-45° C. and stirred for 30 min. The solid was collected by filtration, washed with water (2×30 mL) and dried for 2 h. This material was triturated with ether (60 mL), to afford intermediate 31 (19.80 g, 88% yield) as a brown solid. MS (m/z): 424.1 (M+H).

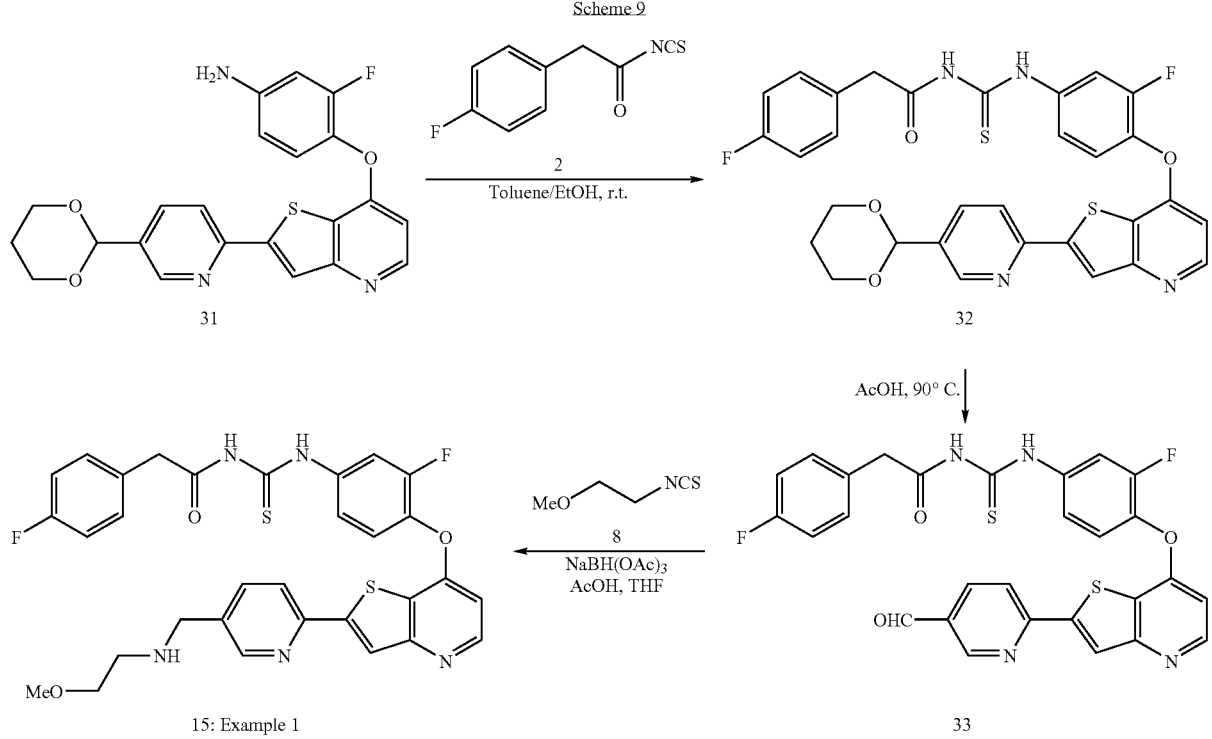

Example 1

Version B

N-(4-(2-(5-(1,3-Dioxan-2-yl)pyridin-2-yl)thieno[3,2-b]pyridin-7-yloxy)-3-fluorophenylcarbamothioyl)-2-(4-fluorophenyl)acetamide (32)

To a solution of 2 (2.69 g, 13.80 mmol) in toluene (16.5 mL) and ethanol (16.5 mL) was added a suspension of 31 (4.87 g, 11.50 mmol) in toluene (41 mL) and ethanol (41 mL). The mixture was stirred for 1 h at room temperature and concentrated under reduced pressure. The residue was purified by flash column chromatography (eluent EtOAc/MeOH, 98/2) to afford intermediate 32 (5.31 g, 8.58 mmol, 74% yield) as a beige solid. MS (m/z): 619.2 (M+H). $^1$H NMR (400 MHz, DMSO-$d_6$) δ (ppm): 12.47 (s, 1H), 11.83 (s, 1H), 8.63 (d, J=2.0 Hz, 1H), 8.54 (d, J=5.2 Hz, 1H), 8.38 (s, 1H), 8.28 (d, J=8.0 Hz, 1H), 8.02 (dd, J=12.4, 1.6 Hz, 1H), 7.92 (dd, J=8.2, 1.8 Hz, 1H), 7.54-7.52 (m, 2H), 7.37 (dd, J=8.6, 5.8 Hz, 2H), 7.17 (t, J=9.0 Hz, 2H), 6.68 (d, J=5.2 Hz, 1H), 5.66 (s, 1H), 4.18 (dd, J=10.6, 5.0 Hz, 2H), 3.97-3.94 (m, 2H), 3.82 (s, 2H), 2.10-1.98 (m, 1H), 1.47 (dd, J=14.0, 1.6 Hz, 1H).

N-(3-Fluoro-4-(2-(5-formylpyridin-2-yl)thieno[3,2-b]pyridin-7-yloxy)phenylcarbamothioyl)-2-(4-fluorophenyl)acetamide (33)

Method A:

To a solution of 80% acetic acid (104 mL AcOH/26 mL water) was added 32 (4.01 g, 6.48 mmol). The reaction mixture was heated at 90° C. overnight, cooled to r.t., to form a precipitate which was collected by filtration to afford intermediate 33 (2.4 g, 66% yield) as a beige solid. $^1$H NMR (400 MHz, DMSO-$d_6$) δ (ppm): 12.51 (s, 1H), 11.86 (s, 1H), 10.14 (s, 1H), 9.14 (s, 1H), 8.66 (d, J=5.6 Hz, 1H) 8.59 (s, 1H), 8.54 (d, J=8.0 Hz, 1H), 8.40 (d, J=8.4 Hz, 1H), 8.07 (d, J=12.8 Hz, 1H), 7.58 (s, 2H), 7.38 (t, J=7.2 Hz, 2H), 7.19 (t, J=8.6 Hz, 2H), 6.83 (d, J=5.6 Hz, 1H), 3.84 (s, 2H). MS (m/z): 560.9 (M+H).

Method B:

To a solution of 2 (5.27 g, 27.0 mmol) in toluene (50.0 mL) and ethanol (50.0 mL) was added a suspension of intermediate 31 (9.52 g, 22.5 mmol) in toluene (20 mL) and ethanol (20 mL) over 30 min. After few minutes, more of isothiocyanate (1 g) in ethanol/toluene (5 mL/5 mL) mixture was added over 1 min. The reaction mixture was stirred at r.t. for an additional 30 min and concentrated under reduced pressure. The residue was triturated with toluene (70 mL), filtered and washed with toluene (20 mL) to afford a beige solid material that was suspended in 80% acetic acid (204 mL) and heated at 90° C. overnight. The reaction mixture was cooled down to r.t., and the precipitate was collected by filtration, washed with 80% AcOH (2×30 mL) to afford compound 33 (8.24 g, 72% yield) as a yellow solid.

N-(3-Fluoro-4-(2-(5-((2-methoxyethoxy)methyl)pyridin-2-yl)thieno[3,2-b]pyridin-7-yloxy)phenylcarbamothioyl)-2-(4-fluorophenyl)acetamide (15, Example 1)

To a yellow suspension of 33 (5.05 g, 9.01 mmol) in THF (90 ml) was added 2-methoxyethylamine (3.93 ml, 45.0 mmol) and acetic acid (2.58 ml, 45.0 mmol). After 1 hour, sodium triacetoxyborohydride (9.55 g, 45.0 mmol) was added to the reaction mixture that was stirred at r.t. overnight. The reaction mixture was then quenched with 2N HCl (100 mL), stirred at r.t. for an additional 15 minutes and basified to pH 9 with 2N NaOH. Most of the THF was removed under reduced pressure and a solid material precipitated. The material was collected by filtration, washed with water (3×100 mL), dried in the vacuum oven at 40° C. for 60 h, to afford compound 15 (3.52 g, 63% yield) as a light beige solid. $^1$H NMR (400 MHz, DMSO-d$_6$) δ (ppm): 12.49 (s, 1H), 11.85 (s, 1H), 9.35 (bs, 1H), 8.75 (d, J=1.6 Hz, 1H), 8.59 (d, J=5.2 Hz, 1H), 8.45 (s, 1H), 8.37 (d, J=8.0 Hz, 1H), 8.16 (dd, J=2.0 and 8.0 Hz, 1H), 8.04 (dd, J=1.6 and 11.6 Hz, 1H), 7.60-7.52 (m, 2H), 7.42-7.35 (m, 2H), 7.23-7.15 (m, 2H), 6.74 (d, J=5.2 Hz, 1H), 4.29-4.23 (m, 2H), 3.83 (s, 2H), 3.63 (t, J=4.8 Hz, 2H), 3.31 (s, 3H), 3.18-3.12 (m, 2H). MS (m/z): 620.1 (M+H).

2-Bromo-5-(1,3-dioxolan-2-yl)pyridine (35)

Following the procedure described above for the synthesis of compound 28 (Scheme 8) but substituting 1,3-propanediol (27) for 1,2-ethanediol (34), title compound 35 was obtained in 61% yield [Romero-Salguero, F. J.; Lehn, J-M; Tetrahedron Letters, 40, 1999, 859-862]. $^1$H NMR (400 MHz, DMSO-d$_6$) δ (ppm): 8.45 (d, J=2.3 Hz, 1H), 7.79 (ddd, J=8.2, 2.5, 0.4 Hz, 1H), 7.69 (dd, J=8.2, 0.8 Hz, 1H), 5.83 (s, 1H), 4.10-3.93 (m, 4H). MS (m/z): 230.0 (M+H).

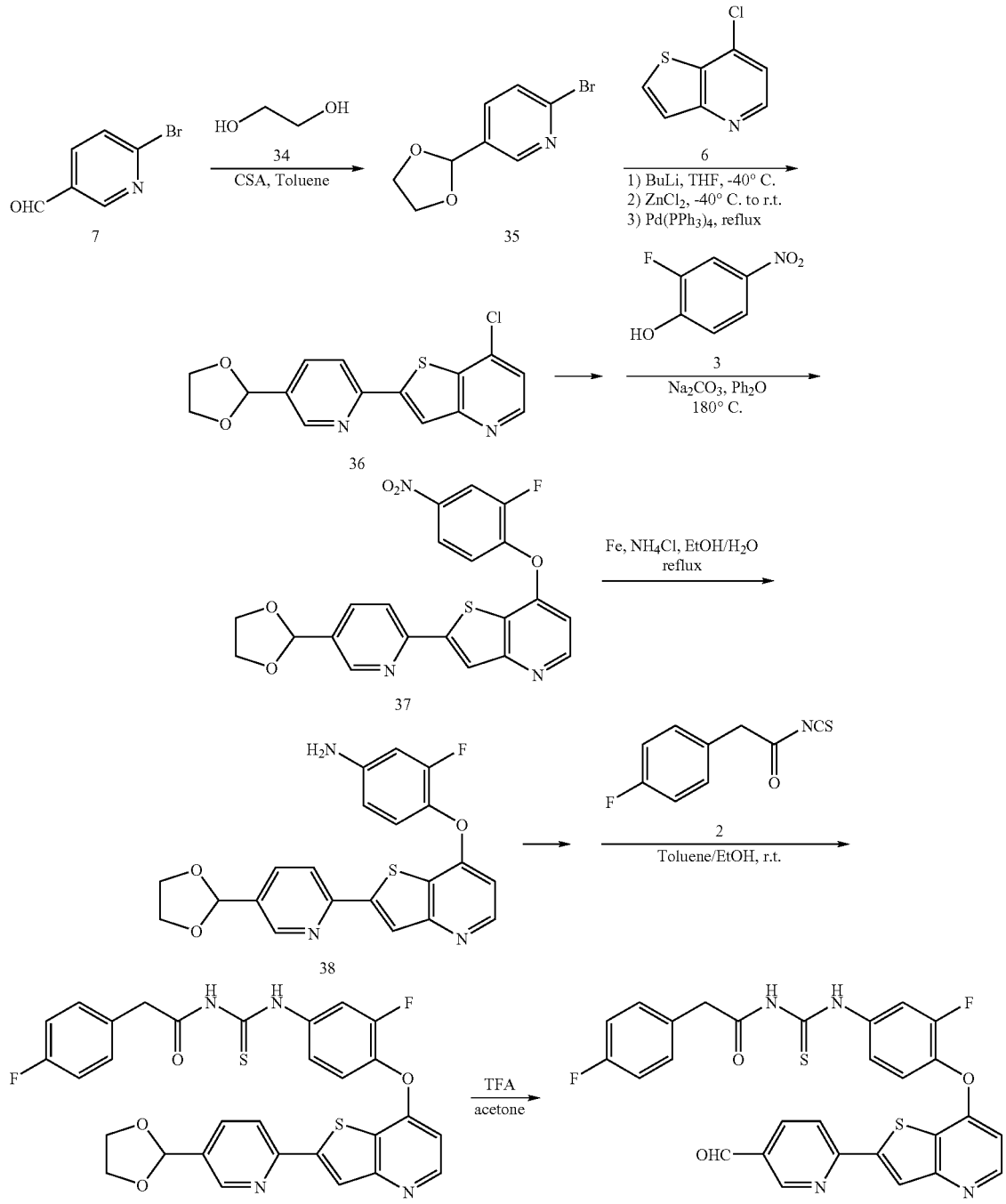

2-(5-(1,3-Dioxolan-2-yl)pyridin-2-yl)-7-chlorothieno[3,2-b]pyridine (36)

Following the procedure described above for the synthesis of compound 29 (Scheme 8) but substituting compound 28 for compound 35, title compound 36 was obtained in 79% yield. $^1$H NMR (400 MHz, DMSO-$d_6$) δ (ppm): 8.70 (d, J=1.8 Hz, 1H), 8.67 (d, J=5.1 Hz, 1H), 8.48 (s, 1H), 8.35 (d, J=8.4 Hz, 1H), 8.00 (dd, J=8.2, 2.1 Hz, 1H), 7.61 (d, J=5.1 Hz, 1H), 5.90 (s, 1H), 4.13-4.07 (m, 2H), 4.05-3.99 (m, 2H). MS (m/z): 319.2 (M+H).

2-(5-(1,3-Dioxolan-2-yl)pyridin-2-yl)-7-(2-fluoro-4-nitrophenoxy)thieno[3,2-b]pyridine (37)

Following the procedure described above for the synthesis of compound 30 (Scheme 8) but substituting compound 29 for compound 36, title compound 37 was obtained in 72% yield. $^1$H NMR (400 MHz, DMSO-$d_6$) δ (ppm): 8.68 (d, J=1.8 Hz, 1H), 8.64 (d, J=5.5 Hz, 1H), 8.49 (dd, J=10.4, 2.5 Hz, 1H), 8.47 (s, 1H), 8.35 (d, J=8.4 Hz, 1H), 8.23-8.21 (m, 1H), 8.00 (dd, J=8.2, 2.0 Hz, 1H), 7.73 (t, J=8.5 Hz, 1H), 6.99 (d, J=5.5 Hz, 1H), 5.89 (s, 1H), 4.12-4.06 (m, 2H), 4.04-3.98 (m, 2H). MS (m/z): 440.1 (M+H).

4-(2-(5-(1,3-Dioxolan-2-yl)pyridin-2-yl)thieno[3,2-b]pyridin-7-yloxy)-3-fluoroaniline (38)

Following the procedure described above for the synthesis of compound 31 (Scheme 8) but substituting compound 30 for compound 37, title compound 38 was obtained in 95% yield. $^1$H NMR (400 MHz, DMSO-$d_6$) δ (ppm): 8.68 (d, J=1.8 Hz, 1H), 8.50 (d, J=5.5 Hz, 1H), 8.36 (s, 1H), 8.29 (d, J=8.2 Hz, 1H), 7.96 (dd, J=8.2, 2.0 Hz, 1H), 7.11 (t, J=9.0 Hz, 1H), 6.60 (d, J=5.3 Hz, 1H), 6.53 (dd, J=13.1, 2.5 Hz, 1H), 6.44 (dd, J=8.7, 1.9 Hz, 1H), 5.87 (s, 1H), 5.55 (s, 2H), 4.11-4.07 (m, 2H), 4.00-3.97 (m, 2H). MS (m/z): 410.2 (M+H).

N-(4-(2-(5-(1,3-Dioxolan-2-yl)pyridin-2-yl)thieno[3,2-b]pyridin-7-yloxy)-3-fluorophenylcarbamothioyl)-2-(4-fluorophenyl)acetamide (39)

Following the procedure described above for the synthesis of compound 32 (Scheme 9) but substituting compound 31 for compound 38, title compound 39 was obtained in 60% yield. $^1$H NMR (400 MHz, DMSO-$d_6$) δ (ppm): 12.49 (s, 1H), 12.48 (s, 1H), 8.69 (d, J=2.0 Hz, 1H), 8.56 (d, J=5.5 Hz, 1H), 8.42 (s, 1H), 8.33 (dd, J=8.2, 0.8 Hz, 1H), 8.07-8.03 (m, 1H), 7.99 (dd, J=8.2, 2.2 Hz, 1H), 7.56-7.55 (m, 2H), 7.38 (dd, J=8.7, 5.6 Hz, 2H), 7.19 (t, J=9.0 Hz, 2H), 6.70 (d, J=5.5 Hz, 1H), 5.90 (s, 1H), 4.12-4.06 (m, 2H), 4.04-3.98 (m, 2H), 3.84 (s, 2H). MS (m/z): 605.1 (M+H).

N-(3-Fluoro-4-(2-(5-formylpyridin-2-yl)thieno[3,2-b]pyridin-7-yloxy)phenylcarbamothioyl)-2-(4-fluorophenyl)acetamide (33)

Method C (Methods A and B Described within the Scheme 9):
To a solution of 39 (0.32 g, 0.529 mmol) in acetone (50 mL) was added water (20 mL) and TFA (2 mL). The mixture was then heated to reflux for 3 h, cooled to r.t. and left stirred overnight. Finally the mixture was cooled on ice and the white solid precipitate was isolated by suction filtration then dried in vacuum to afford compound 33 (0.32 g, quantitative yield, presumably as di-trifluoroacetate salt) as a colorless solid that could be used directly for the synthesis of compound 15, Example 1 (scheme 9). MS (m/z): 561.2 (M+H).

Scheme 11

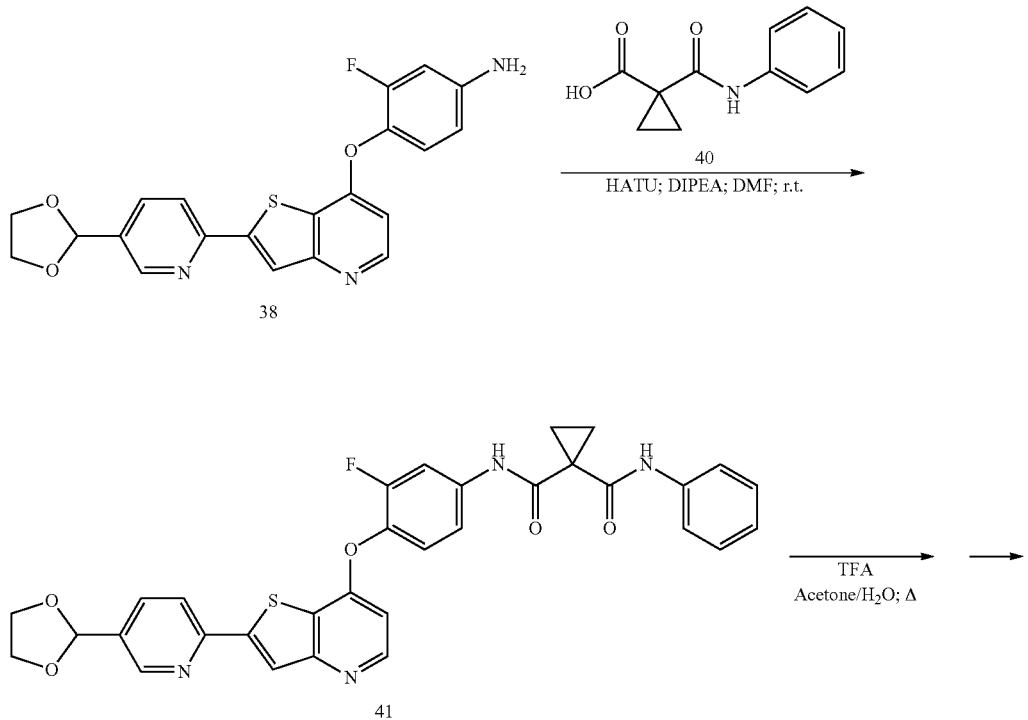

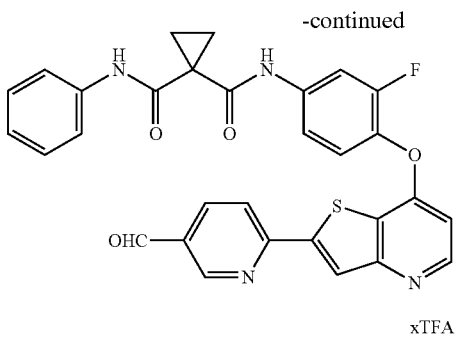
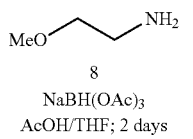

42

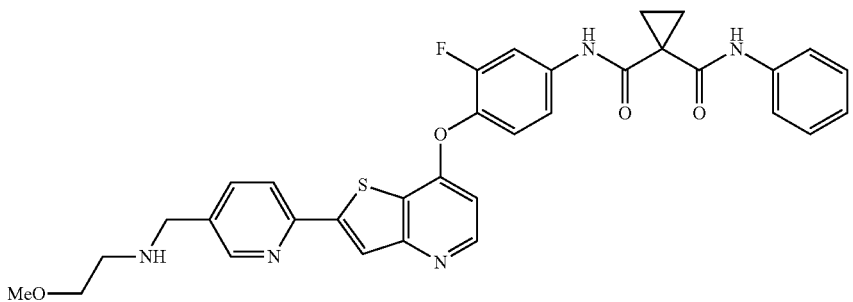

43: Example 4

Example 4

N-(4-(2-(5-(1,3-Dioxolan-2-yl)pyridin-2-yl)thieno[3,2-b]pyridin-7-yloxy)-3-fluorophenyl)-N-phenylcyclopropane-1,1-dicarboxamide (41)

To intermediate 38 (0.46 g, 1.1 mmol) in dry DMF (20 mL) was added 1-(phenylcarbamoyl)cyclopropanecarboxylic acid (40) (0.46 g, 2.2 mmol) [US 2007/0004675 A1], DIPEA (0.98 mL, 5.6 mmol) and HATU (1.07 g, 2.81 mmol) and the mixture was stirred at r.t. for 18 h. The mixture was then partitioned between ethyl acetate and water; the organic phase was collected, washed with water, 1M NaOH, saturated NH$_4$Cl, and brine, dried (anhydrous MgSO$_4$), filtered and concentrated. Silica gel chromatography (2% methanol in ethyl acetate) afforded intermediate 41 (0.23 g, 34% yield). $^1$H NMR (400 MHz, DMSO-d$_6$) δ (Ppm): 10.37 (s, 1H), 9.98 (s, 1H), 8.68 (s, 1H), 8.53 (d, J=5.3 Hz, 1H), 8.40 (s, 1H), 8.31 (d, J=8.2 Hz, 1H), 7.97 (dd, J=8.2, 2.0 Hz, 1H), 7.90 (dd, J=13.1, 2.0 Hz, 1H), 7.62 (d, J=7.6 Hz, 2H), 7.53-7.46 (m, 2H), 7.30 (t, J=7.4 Hz, 2H), 7.06 (t, J=7.4 Hz, 1H), 6.66 (d, J=5.3 Hz, 1H), 5.88 (s, 1H), 4.11-3.97 (m, 4H), 1.47 (br s, 4H). MS (m/z): 597.2 (M+H).

N-(3-Fluoro-4-(2-(5-formylpyridin-2-yl)thieno[3,2-b]pyridin-7-yloxy)phenyl)-N-phenylcyclopropane-1,1-dicarboxamide (42)

Intermediate 41 (0.22 g, 0.37 mmol) was dissolved in acetone (50 mL) to give a colorless solution. The reaction mixture was diluted with water (20 mL) and TFA (2 mL), heated to reflux for 2 h, then cooled and concentrated. The precipitated product was isolated by suction filtration. A small amount of toluene (5 mL) was added to the wet solid, the mixture was concentrated to remove water azeotropically, and dried in vacuum to afford intermediate 42 (0.21 g, 103% yield, presumably as tri-fluoroacetate salt). MS (m/z): 553.2 (M+H).

N-(3-Fluoro-4-(2-(5-((2-methoxyethylamino)methyl)pyridin-2-yl)thieno[3,2-b]pyridin-7-yloxy)phenyl)-N-phenylcyclopropane-1,1-dicarboxamide, (43, Example 4)

Intermediate 42 (0.20 g, 0.362 mmol) and 2-methoxyethylamine (8) (0.158 mL, 1.810 mmol) were dissolved in THF (50 mL) to give a colorless solution. Sodium triacetoxyborohydride (0.384 g, 1.810 mmol) was added and the mixture was stirred at r.t. for 20 h. Additional 2-methoxyethylamine (8) (0.158 mL, 1.810 mmol) and sodium triacetoxyborohydride (0.384 g, 1.810 mmol) were added, and the mixture was stirred for a further 20 h. The mixture was then concentrated, partitioned between water and dichloromethane; organic phase was collected, washed with H$_2$O, 1M NaOH, and brine, dried (anhydrous MgSO$_4$), filtered and concentrated. The residue was purified by Gilson Reverse Phase HPLC (Aquasil C$_{18}$, 40-90% MeOH/water, 30 min, elutes ~20 min), and the product was lyophilized. Starting material 42 (50 mg) was also isolated.

The recovered starting material was re-subjected to the reaction conditions except in acetic acid (5 ml), with 2-methoxyethylamine (8) (1 mL) and sodium trisacetoxyborohydride (0.030 g). After stirring for 5 min the mixture was concentrated. The residue was purified by Gilson Reverse Phase HPLC as before. The isolated product was combined with that above to produce compound 43 (0.13 g, 59% yield) as a colorless solid. $^1$H NMR (400 MHz, DMSO-d$_6$) δ (ppm): 10.37 (s, 1H), 9.98 (s, 1H), 8.68 (s, 1H), 8.53 (d, J=5.3 Hz, 1H), 8.40 (s, 1H), 8.31 (d, J=8.2 Hz, 1H), 7.97 (dd, J=8.2, 2.0 Hz, 1H), 7.90 (dd, J=13.1, 2.0 Hz, 1H), 7.62 (d, J=7.6 Hz, 2H), 7.53-7.46 (m, 2H), 7.30 (t, J=7.4 Hz, 2H), 7.06 (t, J=7.4 Hz, 1H), 6.66 (d, J=5.3 Hz, 1H), 5.88 (s, 1H), 4.11-3.97 (m, 4H), 1.47 (br s, 4H). MS (m/z): 597.2 (M+H).

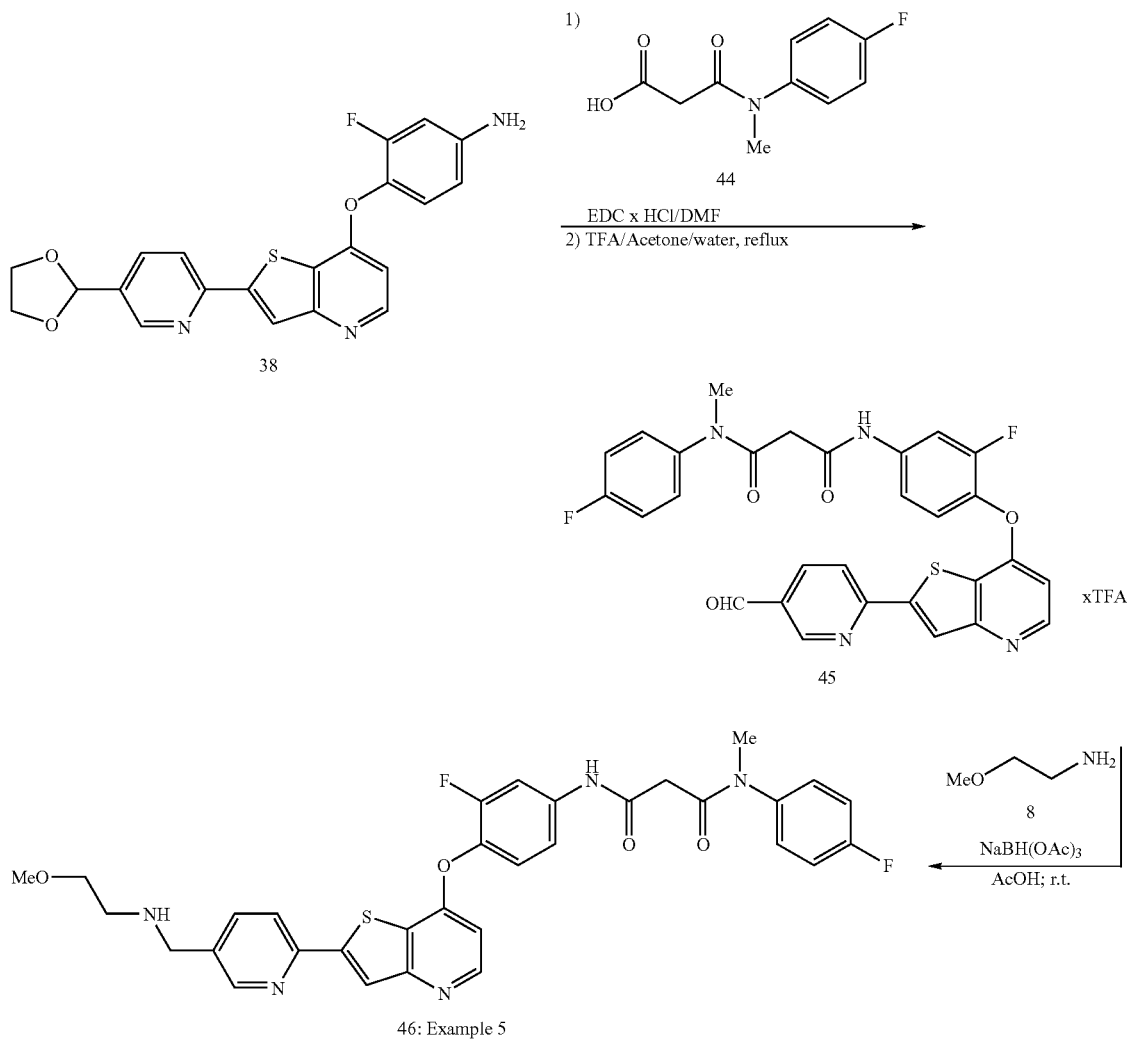

Scheme 12

Example 5

N¹-(3-Fluoro-4-(2-(5-formylpyridin-2-yl)thieno[3,2-b]pyridin-7-yloxy)phenyl)-N3-(4-fluorophenyl)-N3-methylmalonamide (45)

To intermediate 38 (0.35 g, 0.86 mmol) in dry DMF (25 mL) was added 3-((4-fluorophenyl)(methyl)amino)-3-oxo-propanoic acid (44) [US 2007/0004675 A1] (0.36 g, 1.7 mmol) [Met-036], and EDC.HCl (0.33 g, 1.7 mmol) and the mixture was stirred at r.t. for 2 h. The mixture was then partitioned between ethyl acetate and water; the organic phase was collected, washed with water, saturated NaHCO$_3$, and brine, dried (anhydrous MgSO$_4$), filtered and concentrated. The crude product was dissolved in acetone (50 mL) to give a colorless solution. The solution was diluted with water (20 mL) and TFA (2 mL), and heated to reflux for 3 h. It was then cooled and concentrated. The residue was then partitioned between ethyl acetate and water, the organic phase was collected, washed with water, saturated NaHCO$_3$, and brine, dried (anhydrous MgSO$_4$), filtered and concentrated to produce intermediate 45 (0.27 g, 57% yield). MS (m/z): 559.2 (M+H).

N¹-(3-Fluoro-4-(2-(5-((2-methoxyethylamino)methyl)pyridin-2-yl)thieno[3,2-b]pyridin-7-yloxy)phenyl)-N3-(4-fluorophenyl)-N³-methylmalonamide (46, Example 5)

Intermediate 45 (0.25 g, 0.45 mmol) and 2-methoxyethylamine (8) (0.67 g, 9.0 mmol) were dissolved in AcOH (10 mL) to give a colorless solution, which was allowed to stir for 30 min. Sodium trisacetoxyborohydride (0.29 g, 1.3 mmol) was added and the mixture was stirred at r.t. for 1 h, poured into conc. NH$_4$OH and dichloromethane. The organic phase was washed with water, saturated NaHCO$_3$, and brine, dried (anhydrous MgSO$_4$), filtered and concentrated. The residue was purified by Gilson Reverse Phase HPLC (Aquasil C$_{1-8}$, 25-80% MeOH/water, 30 min) and lyophilized providing compound 46 (132 mg, 48% yield). $^1$H NMR (400 MHz, DMSO-d$_6$) δ (ppm): 10.28 (s, 1H), 8.58 (s, 1H), 8.52 (d, J=5.3 Hz, 1H), 8.33 (s, 1H), 8.24 (d, J=8.0 Hz, 1H), 8.15 (s, 1H), 7.91 (dd, J=8.0, 2.0 Hz, 1H), 7.79 (dd, J=12.9, 2.0 Hz, 1H), 7.49-7.43 (m, 3H), 7.33-7.27 (m, 3H), 6.66 (d, J=5.3 Hz, 1H), 3.92 (s, 2H), 3.42 (t, J=5.7 Hz, 2H), 3.25 (s, 3H), 3.23 (s, 2H), 3.19 (s, 3H), 2.69 (t, J=5.5 Hz, 2H). MS (m/z): 618.3 (M+H).

Scheme 13

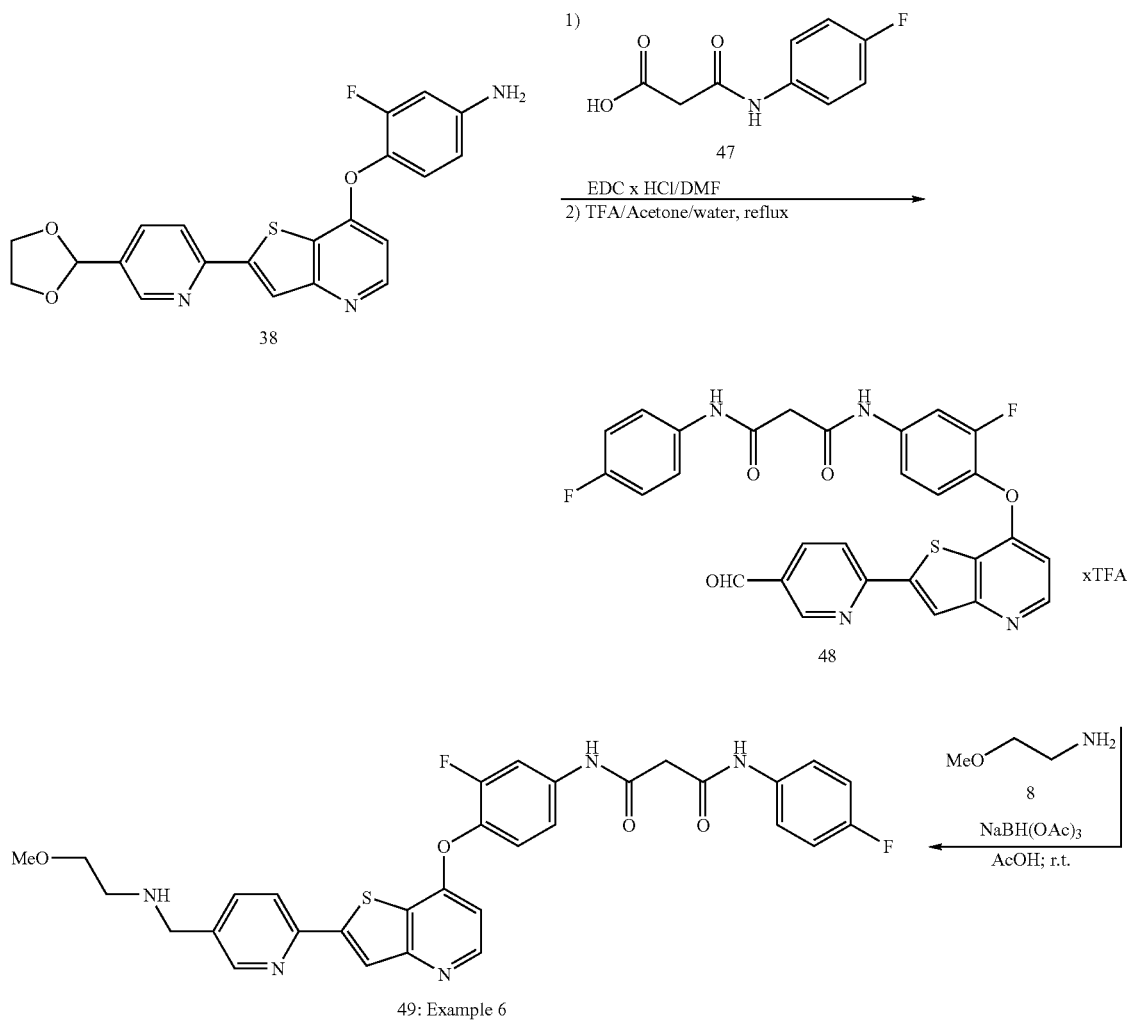

Example 6

$N^1$-(3-fluoro-4-(2-(5-formylpyridin-2-yl)thieno[3,2-b]pyridin-7-yloxy)phenyl)-$N^3$-(4-fluorophenyl)malonamide (48)

To intermediate 38 (0.40 g, 0.98 mmol) in dry DMF (20 mL) was added 3-(4-fluorophenylamino)-3-oxopropanoic acid (47) (0.39 g, 2.0 mmol) [US 2007/0004675 A1], and EDC.HCl (0.38 g, 2.0 mmol) and the mixture was stirred at r.t. for 2 h. The mixture was then partitioned between ethyl acetate and water resulting in precipitate. The precipitate was isolated by suction filtration and combined with the organic phase from the filtrate, concentrated, and dried in vacuum. The residue was dissolved in acetone (50 mL) to give a colorless solution. The solution was diluted with water (20 mL) and TFA (2 mL), heated to reflux for 3 h, then cooled and concentrated. The precipitated product was isolated by suction filtration, and dried in vacuum to afford intermediate 48 (0.35 g, 66%, presumably as the trifluoroacetate salt). $^1$H NMR (400 MHz, DMSO-$d_6$) δ (ppm): 10.59 (s, 1H), 10.29 (s, 1H), 10.14 (s, 1H), 9.15 (s, 1H), 8.59 (s, 1H), 8.58 (m, 1H), 8.52 (d, J=8.2 Hz, 1H), 8.39 (dd, J=8.2, 2.0 Hz, 1H), 7.90 (dd, J=13.1, 2.2 Hz, 1H), 7.65-7.60 (m, 2H), 7.54-7.44 (m, 2H), 7.17 (t, J=8.8 Hz, 2H), 6.75 (d, J=5.5 Hz, 1H), ~3.50 (s, 2H, obscured by water peak). MS (m/z): 545.2 (M+H).

$N^1$-(3-fluoro-4-(2-(5-((2-methoxyethylamino)methyl)pyridin-2-yl)thieno[3,2-b]pyridin-7-yloxy)phenyl)-$N^3$-(4-fluorophenyl)malonamide (49, Example 6)

Intermediate 48 (0.35 g, 0.64 mmol) and 2-methoxyethylamine (8) (1.2 g, 16 mmol) were dissolved in AcOH (10 mL) to give a yellow suspension, and stirred for 30 min. Sodium triacetoxyborohydride (0.27 g, 1.3 mmol) was added and the mixture was stirred at r.t. for 18 h. The reaction mixture was poured into conc. $NH_4OH$ and dichloromethane. The resulting suspension was collected by filtration and rinsed with water to provide a solid material. The material was triturated with diethyl ether and ethyl acetate, and dried in vacuum to afford compound 49 (166 mg, 43%). $^1$H NMR (400 MHz, DMSO-$d_6$) δ (ppm): 10.61 (s, 1H), 10.32 (s, 1H), 8.57 (s, J=1.4 Hz, 1H), 8.52 (d, J=5.5 Hz, 1H), 8.33 (s, 1H), 8.23 (d, J=8.0 Hz, 1H), 7.91 (d, J=2.2 Hz, 1H), 7.89-7.86 (m, 1H), 7.66-7.60 (m, 2H), 7.51 (t, J=8.8 Hz, 1H), 7.44 (dd, J=9.0, 2.0 Hz, 1H), 7.20-7.14 (m, 2H), 6.68 (d, J=5.5 Hz, 1H), 3.78 (s, 2H), 3.51 (s, 2H), 3.41 (t, J=5.7 Hz, 2H), 3.24 (s, 3H), 2.65 (t, J=5.7 Hz, 2H). MS (m/z): 604.2 (M+H).

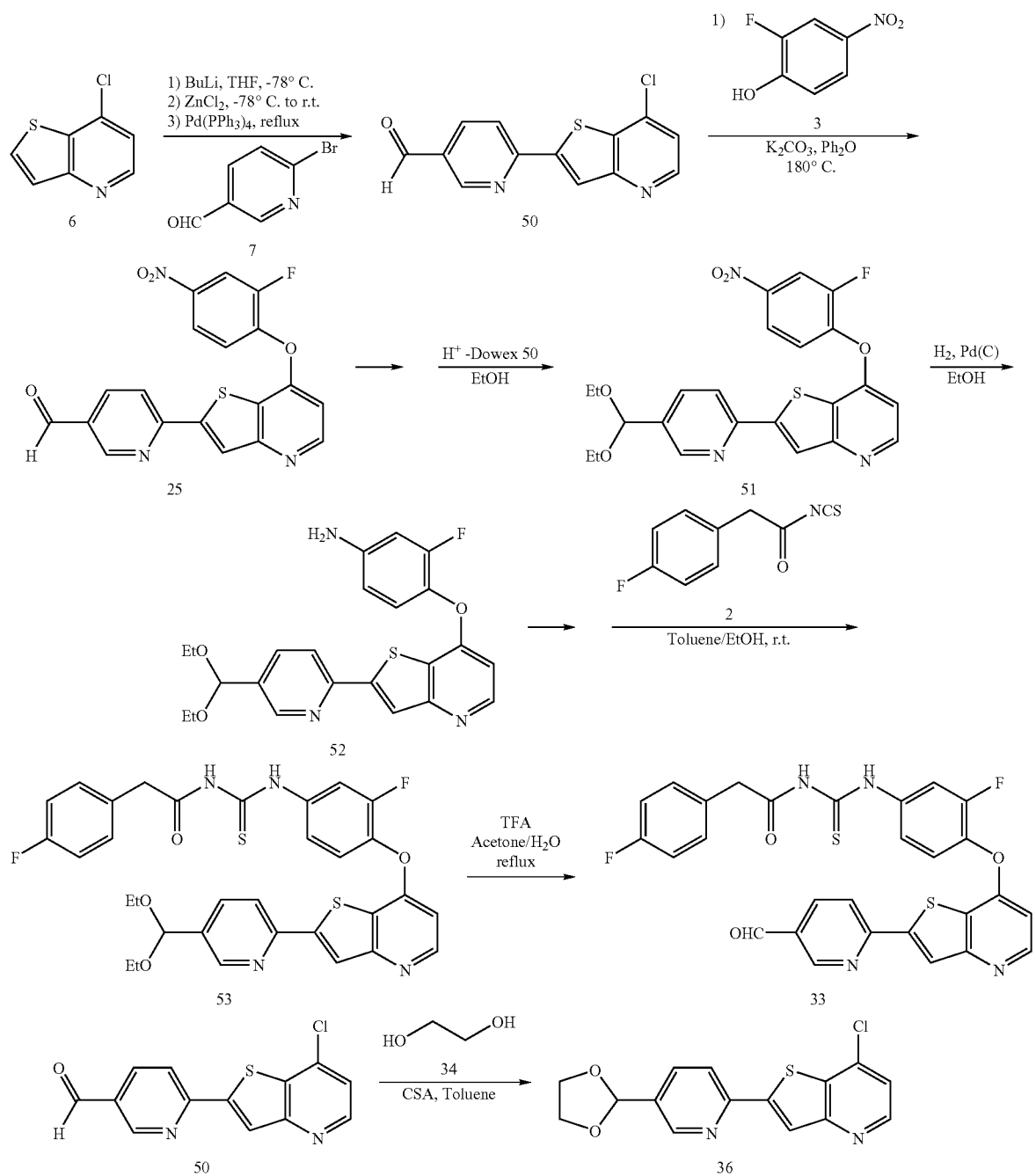

Scheme 14

6-(7-Chlorothieno[3,2-b]pyridin-2-yl)nicotinaldehyde (50)

7-Chlorothieno[3,2-b]pyridine (6) (4.02 g, 23.70 mmol) was dissolved in THF (150 mL) to give a colorless solution. The solution was cooled to −40° C. in an acetonitrile/dry ice bath. n-BuLi (9.95 mL, 24.88 mmol, 2.5M in hexanes) was added dropwise. The dark mixture was then stirred for 15 min followed by an addition of zinc chloride (24.88 mL, 24.88 mmol, 1M in ether). The mixture was warmed to 0° C., then tetrakistriphenylphosphine palladium (1.095 g, 0.948 mmol) was added. The mixture was then stirred for 10 min and 6-bromonicotinaldehyde (7) (4.41 g, 23.70 mmol) was added. The mixture was heated to reflux and a precipitate formed rapidly. After 3 h, the reaction mixture was cooled down to r.t., quenched with 2 mL NH$_4$Cl and left overnight. The solid was isolated by suction filtration, rinsed with small amount of THF and triturated with a mixture of water (200 mL) and EtOAc (100 mL) followed by an additional trituration with acetic acid (1×100 mL), to afford intermediate 50 (4.95 g, 76% yield). $^1$H NMR (400 MHz, DMSO-d$_6$) δ (ppm): 10.13 (s, 1H), 9.14 (d, J=1.4 Hz, 1H), 8.70 (d, J=5.1 Hz, 1H), 8.65 (s, 1H), 8.53 (d, J=8.4 Hz, 1H), 8.39 (dd, J=2.1, 8.4 Hz, 1H), 7.65 (d, J=4.9 Hz, 1H). MS (m/z): 275.1 (M+H).

Step 2: 6-(7-(2-Fluoro-4-nitrophenoxy)thieno[3,2-b]pyridin-2-yl)nicotinaldehyde (25)

Method B (Method A is provided within the scheme 7)

Following the procedure described above for the synthesis of compound 30 (Scheme 8) but substituting compound 29 for compound 50 and sodium carbonate for potassium carbonate, title compound 25 was obtained in 55% yield. $^1$H NMR (400 MHz, DMSO-$d_6$) δ (ppm): 10.13 (s, 1H), 9.13 (dd, J=2.2, 0.8 Hz, 1H), 8.67 (d, J=5.5 Hz, 1H), 8.65 (s, 1H), 8.54 (d, J=8.6 Hz, 1H), 8.50 (dd, J=10.5, 2.6 Hz, 1H), 8.40 (dd, J=8.3, 2.1 Hz, 1H), 8.23 (ddd, J=9.1, 2.7, 1.5 Hz, 1H), 7.75 (dd, J=8.9, 8.1 Hz, 1H), 7.03 (dd, J=5.3, 0.6 Hz, 1H). MS (m/z): 396.1 (M+H).

2-(5-(Diethoxymethyl)pyridin-2-yl)-7-(2-fluoro-4-nitrophenoxy)thieno[3,2-b]pyridine (51)

The Dowex-50 resin (0.75 g) and intermediate 25 (0.95 g, 2.4 mmol) were suspended in EtOH (100 mL). The reaction mixture was heated to reflux for 2 hours. More Dowex-50 resin (0.30 g) was then added and the mixture was heated to reflux for another 3 hours. It was then cooled down to r.t. and filtered through a celite pad. The filtrate was concentrated under reduce pressure. The residue was purified by flash column chromatography eluting with 50-75% EtOAc in hexanes, to afford intermediate 54 (0.35 g, 31% yield) as a colorless crystalline solid. $^1$H NMR (400 MHz, DMSO-$d_6$) δ (ppm): 8.63-8.61 (m, 2H), 8.48 (dd, J=10.5, 2.6 Hz, 1H), 8.42 (s, 1H), 8.30 (dd, J=8.2, 0.8 Hz, 1H), 8.20 (ddd, J=9.0, 2.7, 1.4 Hz, 1H), 7.92 (ddd, J=8.2, 2.2, 0.4 Hz, 1H), 7.71 (dd, J=9.0, 8.0 Hz, 1H), 6.97 (dd, J=5.4, 0.5 Hz, 1H), 5.62 (s, 1H), 3.64-3.50 (m, 4H), 1.17 (t, J=7.0 Hz, 6H). MS (m/z): 470.1 (M+H).

4-(2-(5-(Diethoxymethyl)pyridin-2-yl)thieno[3,2-b]pyridin-7-yloxy)-3-fluoroaniline (52)

The intermediate 51 (0.29 g, 0.62 mmol) was solubilized in EtOH (100 mL) and palladium on charcoal 10% (0.075 g) was added. The reaction mixture was stirred overnight under hydrogen atmosphere, filtered through a celite pad and the filtrate was concentrated under reduce pressure. The residue was purified by column chromatography with 60-80% EtOAc in hexanes to afford intermediate 52 (0.14 g, 52% yield) as a colorless solid. MS (m/z): 440.1 (M+H).

N-(4-(2-(5-(Diethoxymethyl)pyridin-2-yl)thieno[3,2-b]pyridin-7-yloxy)-3-fluorophenylcarbamothioyl)-2-(4-fluorophenyl)acetamide (53)

Following the procedure described above for the synthesis of compound 32 (Scheme 9) but substituting compound 31 for compound 52, title compound 53 was obtained in 31% yield. $^1$H NMR (400 MHz, DMSO-$d_6$) δ (ppm): 12.46 (s, 1H), 11.82 (s, 1H), 8.63 (d, J=2.2 Hz, 1H), 8.54 (d, J=5.5 Hz, 1H), 8.37 (s, 1H), 8.29 (dd, J=8.2, 0.8 Hz, 1H), 8.02 (d, J=11.9 Hz, 1H), 7.91 (dd, J=8.1, 1.7 Hz, 1H), 7.53-7.52 (m, 2H), 7.37 (dd, J=8.8, 5.7 Hz, 2H), 7.17 (t, J=9.0 Hz, 2H), 6.68 (dd, J=5.4, 0.9 Hz, 1H), 5.63 (s, 1H), 3.82 (s, 2H), 3.64-3.50 (m, 4H), 1.17 (t, J=7.0 Hz, 6H). MS (m/z): 635.1 (M+H).

N-(3-Fluoro-4-(2-(5-formylpyridin-2-yl)thieno[3,2-b]pyridin-7-yloxy)phenylcarbamothioyl)-2-(4-fluorophenyl)acetamide (33)

Method D (Methods B and C described within the Scheme 9):

Intermediate 53 (0.050 g, 0.078 mmol) was dissolved in a mixture of acetone and water 4:1 (20 mL). Trifluoroacetic acid (2.1 mL) was added and the mixture was heated to reflux for 2 hours, cooled down to r.t.; and the solid was isolated by suction filtration. The material was rinsed with a mixture of acetone and water (1:1) then dried in vacuum to afford compound 33 (0.030 g, 68% yield), which could be used in the synthesis of compound 15 (Example 1). MS (m/z): 561.1 (M+H).

2-(5-(1,3-Dioxolan-2-yl)pyridin-2-yl)-7-chlorothieno[3,2-b]pyridine (36)

Method B (Method A was described within the Scheme 10):

A suspension of intermediate 50 (2.69 g, 9.79 mmol), ethylene glycol (34) (2.184 mL, 39.2 mmol), and (1R)-(−)-10-camphorsulfonic acid (0.227 g, 0.979 mmol) in toluene (150 mL) was heated to reflux with a Dean-Stark trap. After 3 h, the mixture was cooled down and filtered through a celite pad (while warm). The filtrate was washed with water, saturated aqueous NaHCO$_3$, NaOH (aq) and brine. It was then dried over MgSO$_4$ and concentrated to afford intermediate 36 (2.77 g, 89% yield) as an off-white solid. MS (m/z): 319.1 (M+H).

Scheme 15

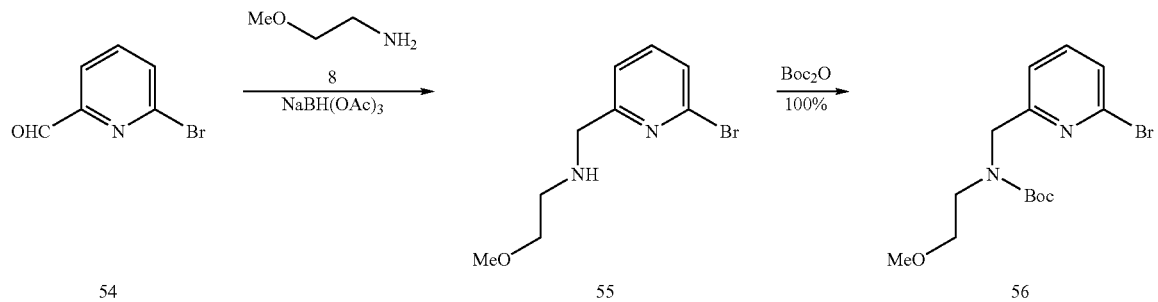

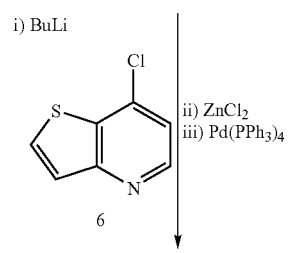

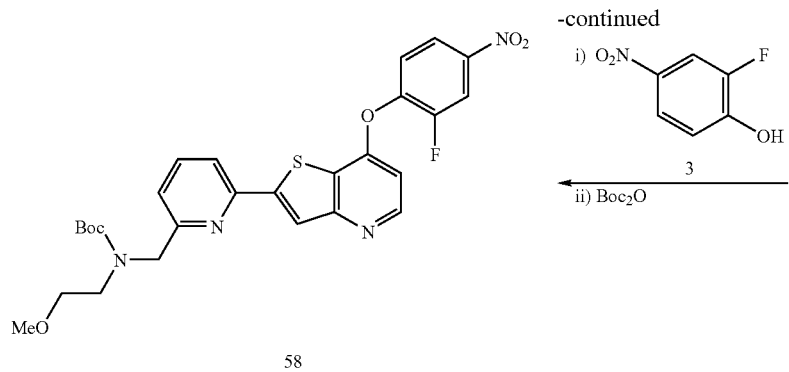

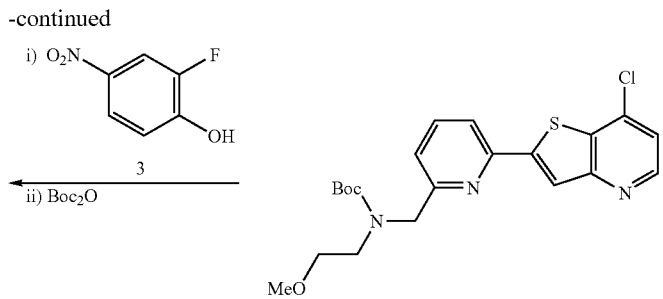

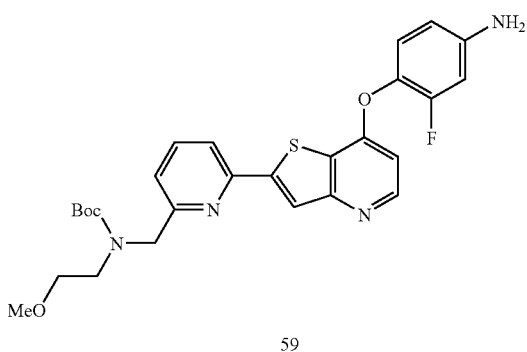

N-((6-Bromopyridin-2-yl)methyl)-2-methoxyethanamine (55)

A mixture of 6-bromo-2-pyridinecarboxaldehyde (54) (20 g, 108 mmol) and 2-methoxy ethanamine (10.3 mL, 8.88 g, 118 mmol) in DCM (1.3 L) was stirred at room temperature for 10 min. It was then treated with NaBH(OAc)$_3$ (25 g, 118 mmol) and stirred at room temperature overnight. The reaction mixture was quenched with water (400 mL) and acidified to pH=4 with 1M HCl (~140 mL). The two phases were separated and the organic layer was extracted with 0.25M HCl (2×500 mL). The aqueous layers were combined, basified to pH=9 with 4N NaOH, extracted with DCM (1×500 mL), dried over Na$_2$SO$_4$, filtered and concentrated yielding 25.2 g of 55 (96%). MS (m/z): 245.1 (M+1).

tert-Butyl (6-bromopyridin-2-yl)methyl(2-methoxyethyl)carbamate (56)

To a solution of 55 (25.19 g, 103 mmol) in THF (32.1 ml) Boc$_2$O (23.86 ml, 103 mmol) was added in small portions (solid). The reaction mixture was stirred for 2 hours. It was then concentrated yielding 56 (37.6 g, 100% yield) which was used without further purification. MS (m/z): 345.1 (M+1).

tert-Butyl (6-(7-chlorobenzo[b]thiophen-2-yl)pyridin-2-yl)methyl(2-methoxyethyl)carbamate (57)

A solution of 7-chlorothieno[3,2-b]pyridine (6) (4.49 g, 26.6 mmol) in THF (20 ml) was treated with 2.5 M hexane solution of n-BuLi (11.1 mL, 27.9 mmol) at −78° C. and allowed to stir at the same temperature for 45 min. The reaction mixture was then treated with 1M ether solution of ZnCl$_2$ (28 mL, 28 mmol) and stirred at room temperature for an additional 1 h. The reaction mixture was then treated with 56 (2.3 g, 6.7 mmol) and Pd(PPh$_3$)$_4$ and was heated to reflux for 2 hrs. It was quenched with saturated NaHCO$_3$ (50 mL) and extracted with EtOAc (2×50 mL). The extract was dried over anhydrous Na$_2$SO$_4$, filtered and evaporated. Obtained crude product was purified by flash chromatography (using the gradient 60-80% EtOAc/hexanes as an eluent), yielding 57 (1.43 g, 50% yield). MS (m/z): 434.2 (M+1).

tert-Butyl (6-(7-(2-fluoro-4-nitrophenoxy)benzo[b]thiophen-2-yl)pyridin-2-yl)methyl(2-methoxyethyl)carbamate (58)

A solution of 57 (1.43 g, 3.3 mmol) and 2-fluoro-4-nitrophenol (3) (1.03 g, 6.61 mmol) in diphenyl ether (30 mL) were stirred overnight at 160° C. The reaction mixture was cooled down to room temperature, diluted with THF (30 mL), treated with Et$_3$N (1.38 mL, 9.9 mmol) and Boc-anhydride (1.08 g, 4.95 mmol) and stirred at room temperature for 2 h. It was then diluted with EtOAc (100 mL) and washed with saturated NaHCO$_3$ (100 mL). The organic phase was collected, dried over Na$_2$SO$_4$, filtered and concentrated. Obtained crude product was purified by flash chromatography (using the gradient 70-100% EtOAc in hexanes as an eluent), yielding 58 (850 mg, 47% yield). MS (m/z): 555.2 (M+1).

tert-butyl (6-(7-(4-amino-2-fluorophenoxy)thieno[3,2-b]pyridin-2-yl)pyridin-2-yl)methyl(2-methoxyethyl)carbamate (59)

A solution of 58 (1 g, 1.81 mmol) and NH$_4$Cl (97 mg, 1.8 mmol) in a 2:1 mixture of EtOH and water (30 mL) was treated with iron powder (605 mg, 10.8 mmol) and stirred at reflux for 1 hour. The reaction mixture was then filtered through a celite pad and concentrated yielding title compound 59 (980 mg, 100% yield) that was used in the next step (scheme 18) without further purification. MS (m/z): 525.2 (M+1).

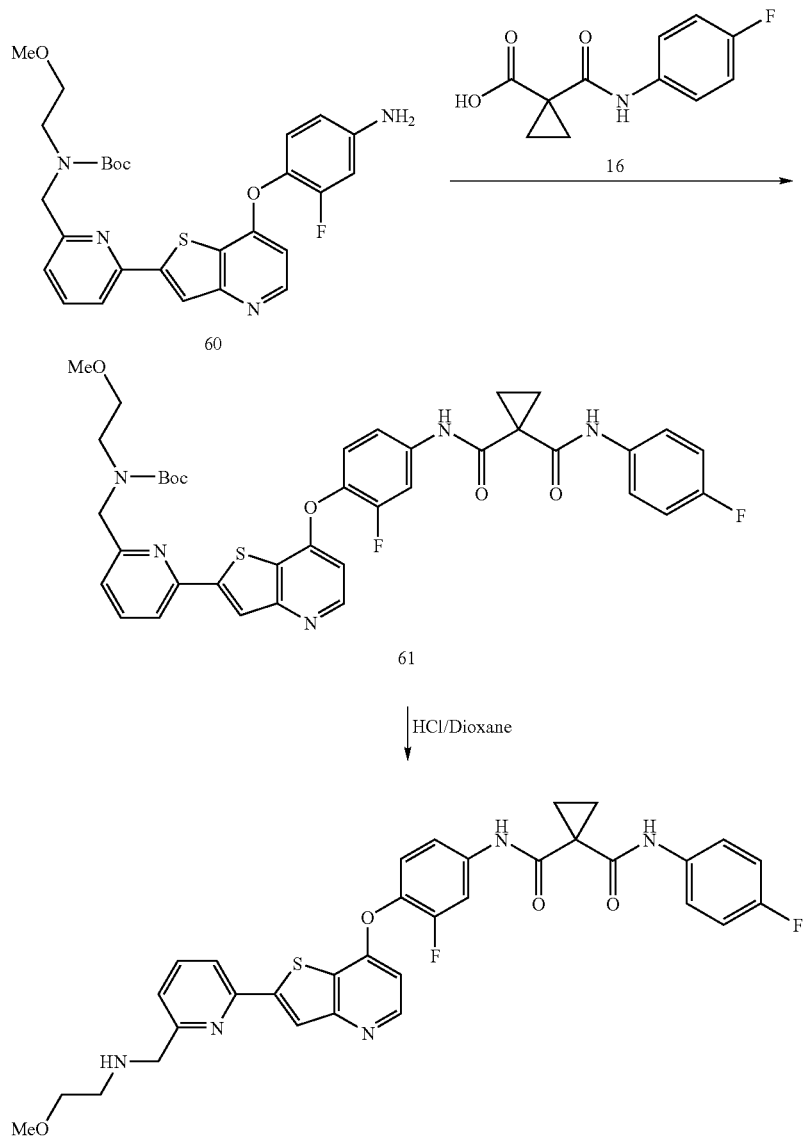

62: Example 7

Example 7

Step 1. tert-Butyl (6-(7-(2-fluoro-4-(1-(4-fluorophenylcarbamoyl)cyclopropane carboxamido)phenoxy)thieno[3,2-b]pyridin-2-yl)pyridin-2-yl)methyl(2-methoxyethyl) carbamate (61)

A solution of 60 (800 mg, 1.53 mmol), 1-(4-fluorophenylcarbamoyl)cyclopropanecarboxylic acid (16) [US 2007/0004675 A1] (512 mg, 2.3 mmol) and DIPEA (1.1 mL, 6.1 mmol) in DMF (10 mL) was treated with HATU (1162 mg, 3.06 mmol) at 0° C. The mixture was then stirred at room temperature overnight, diluted with EtOAc, washed sequentially with H$_2$O, 1M NaOH and saturated NaCl, dried over Na$_2$SO$_4$, filtered and concentrated. The obtained crude product was purified by flash chromatography (using 75-85-100% EtOAc/hexanes as an eluent) yielding 61 (495 mg, 45%). MS (m/z): 730.3 (M+1).

Step 2: N-(3-Fluoro-4-(2-(6-((2-methoxyethylamino)methyl)pyridin-2-yl)thieno[3,2-b]pyridin-7-yloxy)phenyl)-N-(4-fluorophenyl)cyclopropane-1,1-dicarboxamide (62)

HCl gas was bubbled into a solution of 61 (280 mg, 0.38 mmol) in DCM (150 mL). The flask was capped and the mixture was stirred at room temperature for 30 min. The reaction mixture was then washed with 1M NaOH (2×100 mL) and saturated NaCl (100 mL), dried over Na$_2$SO$_4$, filtered and concentrated yielding title compound 62 (215 mg 89% yield). $^1$H NMR (400 MHz, DMSO-d$_6$) δ (ppm): 8.51 (d, J=5.5 Hz, 1H), 8.32 (s, 1H), 8.11 (d, J=7.7 Hz, 1H), 7.90 (m, 2H), 7.62 (m, 2H), 7.45 (m, 3H), 7.13 (t, J=8.8 Hz, 2H), 6.61 (d, J=5.1 Hz, 1H), 3.86 (s, 2H), 3.40 (m, 2H), 3.22 (s, 3H), 2.72 (m, 2H), 1.41 (br.s, 4H). MS (m/z): 630.3 (M+1).

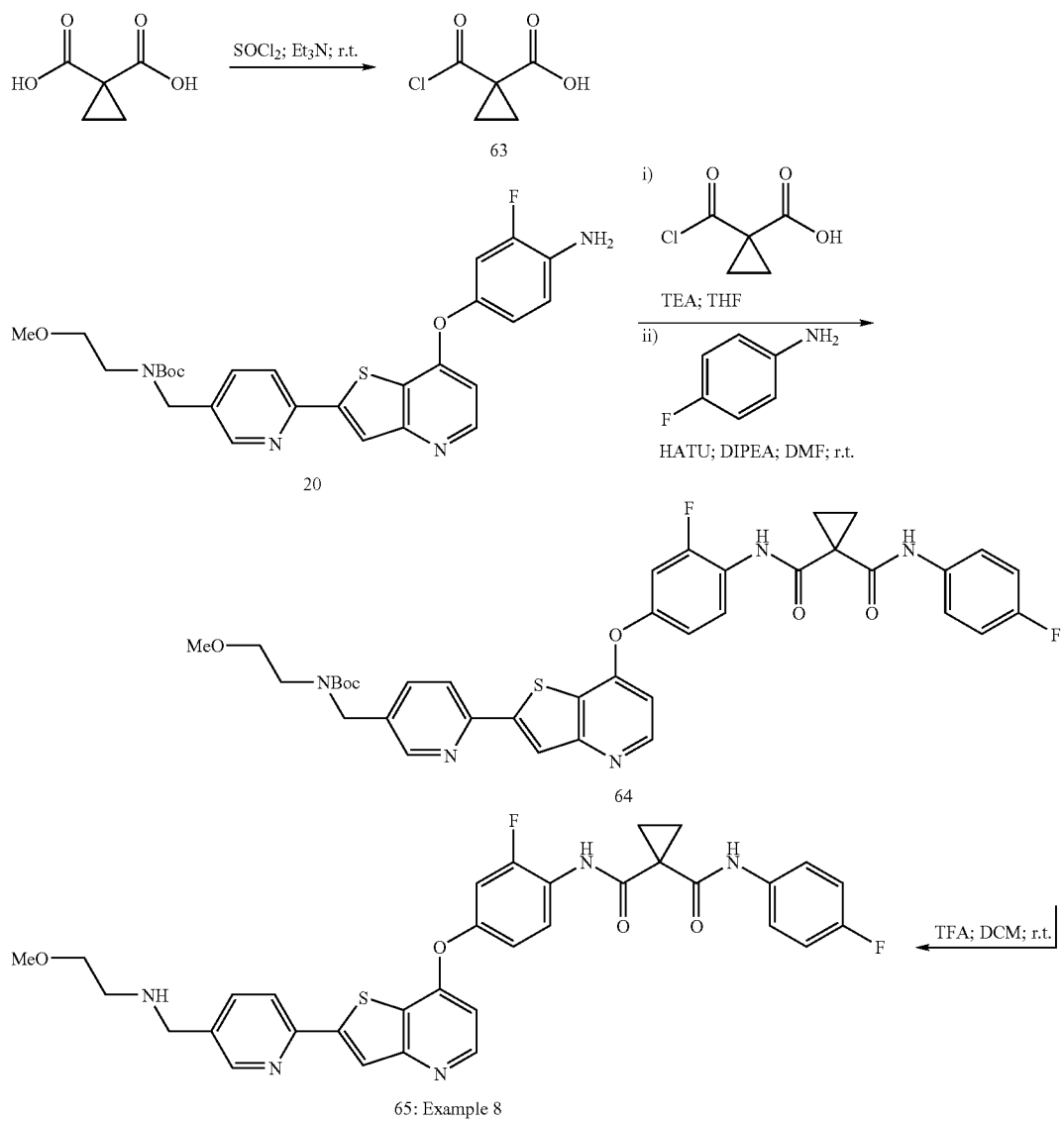

Example 8

1-(Chlorocarbonyl)cyclopropanecarboxylic acid (63)

To 1,1-cyclopropanedicarboxylic acid (1.70 g, 13.1 mmol) in dry THF (50 mL) was added triethylamine (1.9 mL, 1.4 g, 13.7 mmol) and the mixture was cooled to 0° C. Thionyl chloride (0.95 mL, 1.6 g, 13.1 mmol) was added and the resulting suspension was allowed to warm to room temperature and stirred for 2 h. This suspension of 63 (~0.26 M) was used without further purification in the following reaction.

tert-Butyl (6-(7-(3-fluoro-4-(1-(4-fluorophenylcarbamoyl)cyclopropanecarboxamido)phenoxy)thieno[3,2-b]pyridin-2-yl)pyridin-3-yl)methyl(2-methoxyethyl)carbamate, (64)

To aniline 20 (40 mg, 0.076 mmol, Scheme 6) and triethylamine (0.20 mL, 1.4 mmol) in THF (10 mL) at r.t. was added a solution of 63 (1.0 mL, 0.26 mmol) in THF and the resulting mixture was stirred for 3 h. The reaction mixture was then quenched with water (1.0 mL) and concentrated. The residue was partitioned between ethyl acetate and water, and the organic phase was washed with water and brine, dried (MgSO$_4$), filtered and concentrated. The residue was dissolved in DMF (10 mL) and diisopropylethylamine (0.2 mL, 0.14 g, 1.1 mmol), 4-fluoroaniline (50 mg, 0.45 mmol), and HATU (75 mg, 0.20 mmol) were sequentially added. The mixture was stirred for 4 h at r.t. and partitioned between ethyl acetate and water. The organic phase was separated, washed with water, sat. NaHCO$_3$, and brine, dried (MgSO$_4$), filtered and concentrated. Silica gel chromatography of the residue (eluent ethyl acetate) provided 64 (34 mg, 61%). MS (m/z)=730.5 (M+H).

N-(2-Fluoro-4-(2-(5-((2-methoxyethylamino)methyl)pyridin-2-yl)thieno[3,2-b]pyridin-7-yloxy)phenyl)-N-(4-fluorophenyl)cyclopropane-1,1-dicarboxamide (65)

To 64 (52 mg g, 0.071 mmol) in dichloromethane (25 mL) was added TFA (3 mL). The solution was stirred for 24 h, then concentrated. The residue was purified by reverse phase HPLC (Aquasil C-18 column, 45-90% MeOH/H$_2$O+ HCO$_2$H, 30 min. linear gradient elution). The eluate was evaporated and lyophilized. The obtained solid was triturated with diethyl ether to afford the title compound 65 (27 mg, 60% yield). $^1$H NMR (400 MHz, DMSO-d$_6$) δ (ppm): 10.66 (s, 1H); 9.95 (s, 1H); 8.55-8.53 (m, 2H); 8.32 (s, 1H); 8.23-8.21 (m, 1H); 7.99 (t, J=8.8, 1H); 7.88 (dd, J=8.0, 2.2, 1H); 7.61-7.58 (m, 2H); 7.43-7.40 (m, 1H); 7.19-7.13 (m, 3H); 6.75 (d, J=5.3, 1H); 3.77 (s, 2H); 3.40 (t, J=5.7, 2H); 3.23 (s, 3H); 2.64 (t, J=5.3, 2H); 1.60-1.55 (m, 4H). MS (m/z)=630.3 (M+H).

Example 1

Version C

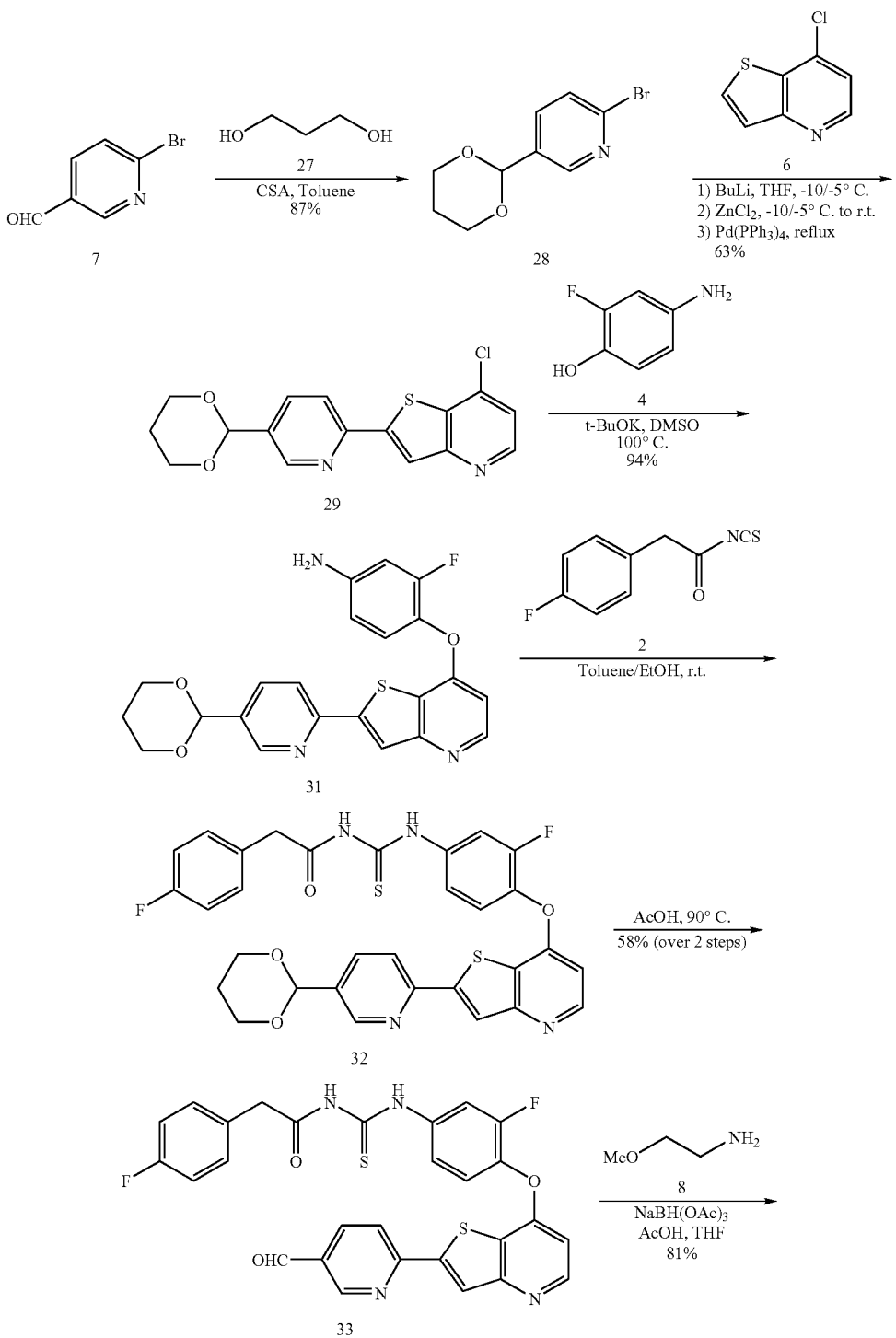

Scheme 18

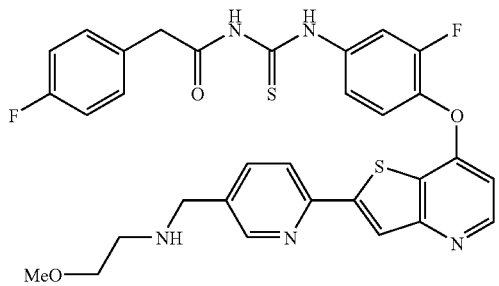

15: Example 1

Step 1: 2-Bromo-5-(1,3-dioxan-2-yl)pyridine (28)

To a solution of 6-bromopyridine-3-carbaldehyde 7 (47.2 g, 254 mmol) in toluene (130 mL) in a 250 mL round-bottom flask was added 1,3-propanediol (38.6 g, 508 mmol) and 10-camphorsulfonic acid (2.95 g, 12.69 mmol). The reaction mixture was heated to reflux, with azeotropic removal of the evolved water, for 1 h, cooled down to r.t. and concentrated. The residue was partitioned between EtOAc (150 mL) and NaHCO$_3$ soln (100mL). Organic phase was collected and the aqueous phase was extracted with EA (2×150 mL). Combined organic fractions were washed with brine (100 mL), dried over Na$_2$SO$_4$, filtered and concentrated to yield a brown solid which was triturated with Et$_2$O/Hex (10/150 mL) for 1 h, filtered to give 28 (53.98 g, 221 mmol, 87% yield) as a beige solid. MS (m/z): 243.1 (M+1)

Step 2: 2-(5-(1,3-Dioxan-2-yl)pyridin-2-yl)-7-chlorothieno[3,2-b]pyridine (29)

To a solution of chlorothienopyridine 6 (22.93 g, 135 mmol) in THF (325 mL) at −5° C./−10° C. in a 1 L round-bottom flask was added n-BuLi (2.5 M in hexanes, 54.1 mL, 135 mmol) over 20 min. After 30 min, a solution of zinc chloride in ether (1M, 135 mL, 135 mmol) was added at −5° C./−10° C. over 20 min and the reaction mixture was allowed to warm-up to r.t. After 1 h, the bromide 28 (27.5 g, 113 mmol) and Pd(PPh$_3$)$_4$ (1.953 g, 1.169 mmol) in THF (48.8 mL) were added and the mixture was heated to reflux for 2 h, cooled down to r.t. and concentrated. The residue was diluted with DCM (1000 mL)/H$_2$O (800 mL)/NH$_4$OH (200 mL), stirred at r.t. for 1 h and the phases were separated. The aqueous phase was extracted with DCM (2×100 mL), the organic phase and the extracts were combined, dried over anhydrous Na$_2$SO$_4$, filtered and concentrated. The residue was triturated with MTBE (100 mL) and collected by filtration (washed with MTBE, 2×20 mL) to give 29 (23.73 g, 71.3 mmol, 63.3% yield) as a beige solid. MS (m/z): 333.1 (M+1)

Step 3: 2-(5-(1,3-Dioxan-2-yl)pyridin-2-yl)-7-yloxy)-3-fluoroaniline (31)

To a solution of aminophenol 4 (8.40 g, 66.1 mmol) in DMSO (75 ml) in a 250 mL round-bottom flask was added potassium tert-butoxide (8.77 g, 78 mmol). After 30 min, chloride 29 (20 g, 60.1 mmol) was added and the mixture was heated at 100° C. for 1.5 h. After cooling to r.t., the mixture was poured into water (300 mL) at 40° C. and the formed suspension was stirred for 30 min. The solid was collected by filtration, washed with water (2×30 mL) and dried under vacuum for 2 h. It was then triturated with Et$_2$O (60 mL) for 2 h and collected by filtration to give a brown solid of 31 (23.8 g, 56.2 mmol, 94% yield). MS (m/z): 424.1 (M+1)

Step 4: N-(4-(2-(5-(1,3-Dioxan-2-yl)pyridin-2-yl)thieno[3,2-b]pyridin-7-yloxy)-3-fluorophenylcarbamothioyl)-2-(4-fluorophenyl)acetamide (32)

To a solution of isothiocyanate 2 (13.17 g, 67.4 mmol) in a mixture of toluene (100 ml)/EtOH (100 ml) in a 500 mL round-bottom flask was added aniline 31 (23.8 g, 56.2 mmol). The mixture was stirred for 1 h at room temperature and concentrated. The solid was triturated with toluene (100 mL) for 1 h, collected by filtration, washed with toluene (20 ml). The solid was dried under vacuum for 2 h to give crude 32 (35.10 g) which was used in the next step without any further purification. MS (m/z): 619.1 (M+1)

Step 5: N-(3-Fluoro-4-(2-(5-formylpyridin-2-yl)thieno[3,2-b]pyridin-7-yloxy)phenylcarbamothioyl)-2-(4-fluorophenyl)acetamide (33)

A suspension of crude 32 (35.10 g) in AcOH 80% (576 mL) in a 1 L round-bottom flask was heated at 90° C. for 18 h, cooled to r.t. to form a precipitate which was collected by filtration to give 33 (18.41 g, 32.8 mmol, 58% yield over two steps) as a beige solid. MS (m/z): 561.1 (M+1)

Step 6: N-(3-Fluoro-4-(2-(5-((2-methoxyethoxy)methyl)pyridin-2-yl)thieno[3,2-b]pyridin-7-yloxy)phenylcarbamothioyl)-2-(4-fluorophenyl)acetamide (15)

To a suspension of aldehyde 33 (17.06 g, 30.04 mmol) and 2-methoxyethylamine (13.25 ml, 152 mmol) in THF (300 ml) in a 1 L round-bottom flask was added AcOH (8.71 ml, 152 mmol)). After 1 h, NaBH(OAc)$_3$ (32.2 g, 152 mmol) was added and the reaction mixture was stirred for 20 h at r.t. and was then quenched with HCl 2M (300 mL) After 1 h, NaOH 2N (350 mL) was added until pH 11 and the mixture was concentrated. The solid was subjected to chromatographic purification through a pad of silica gel, eluent 2%-10% MeOH/DCM, to give 15 (8.59 g, 13.86 mmol, 81% yield) as a white solid. MS (m/z): 620.2 (M+1)

Example 1
Version D
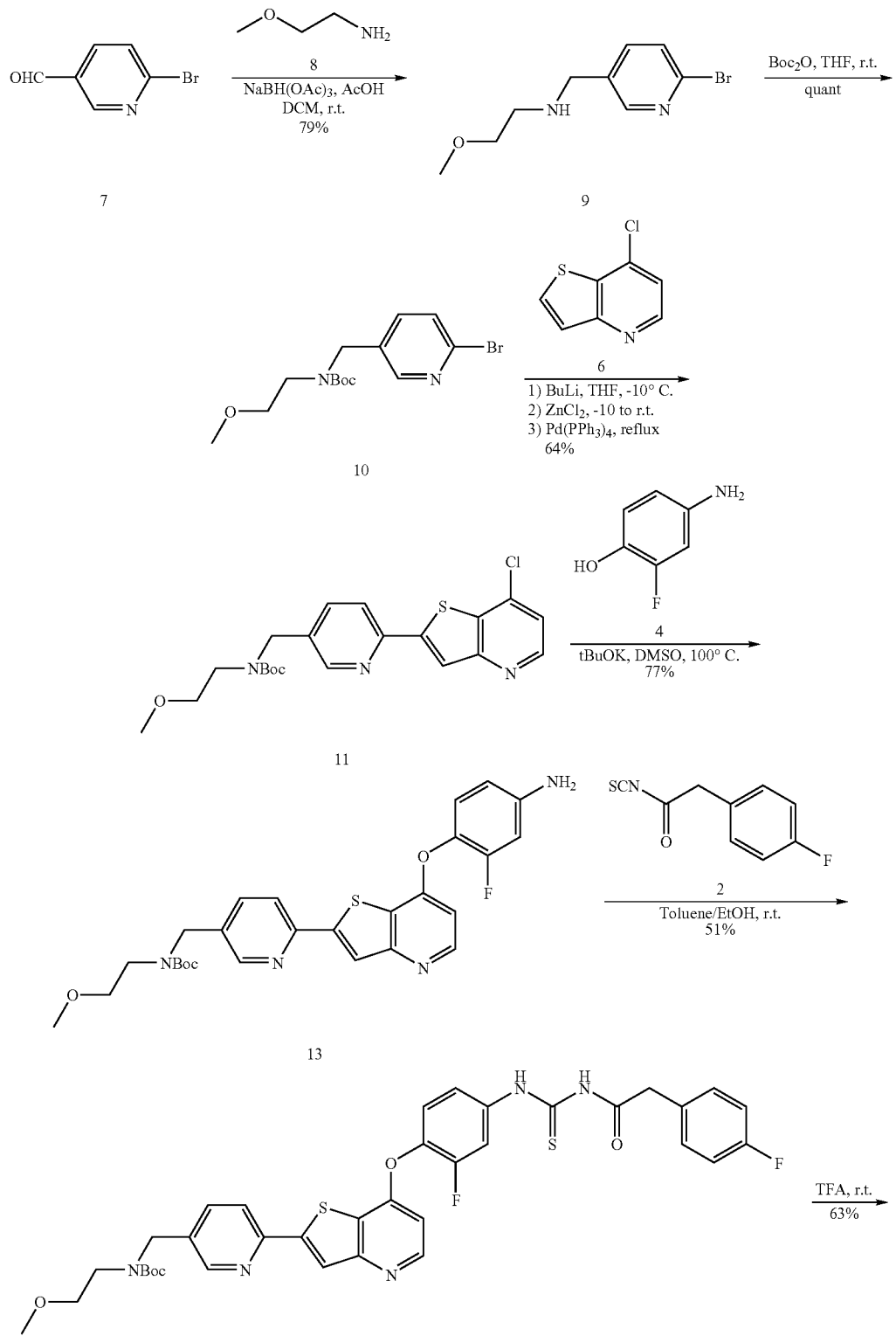
Scheme 19

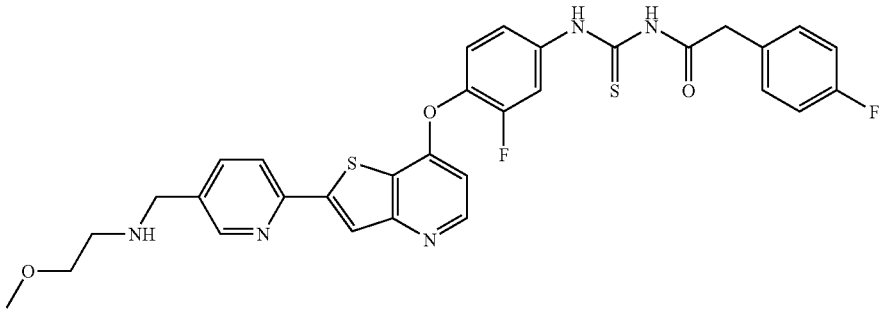

15: Example 1

Step 1: N-((6-bromopyridin-3-yl)methyl)-2-methoxyethanamine (9)

To a dark-yellow solution of 6-bromopyridine-3-carbaldehyde 7 (30 g, 161 mmol) in DCM (300 ml) and 2-methoxyethylamine 8 (1.05 eq, 14.72 ml, 169 mmol) in a 1 L round-bottom flask was added acetic acid (1 eq, 9.23 mL, 161 mmol). After 15 min, sodium triacetoxyborohydride (1.05 eq, 35.9 g, 169 mmol) was added over 10 min and the reaction mixture was stirred at r.t. for 30 min. The reaction mixture was then quenched with 10% HCl (200 mL). The two layers were separated and the organic layer was extracted with 10% HCl (2×100 mL). The aqueous layers were combined, basified to pH=9 with 4M NaOH (450 mL), extracted with EA (3×150 mL) and combined organic extracts were washed with brine (150 mL), dried over $Na_2SO_4$, filtered and evaporated to afford 9 as brown oil that could be used crude for next step (31.1 g, 127 mmol, 79% yield). MS (m/z): 245.1 (M+1)

Step 2: tert-butyl (6-bromopyridin-3-yl)methyl(2-methoxyethyl)carbamate (10)

Amine 9 (36.64 g, 149 mmol) was dissolved in THF (60 mL) in a 250 mL round-bottom flask, to give a brown solution. To this solution, solid Boc-anhydride (1.03 eq, 33.6 g, 154 mmol) was added in small portions. The reaction mixture was stirred at r.t. for 1.5 hours, evaporated to dryness and the residue was dried on the vacuum pump for a few minutes to afford 10 (as brown oil) that was used crude for next step (55.12 g, 160 mmol, quant). MS (m/z): 345.1 (M+1)

Step 3: N-((6-(7-chlorobenzo[b]thiophen-2-yl)pyridin-3-yl)methyl)-2-methoxy ethanamine (11)

To a solution of 7-chlorothieno[3,2-b]pyridine 6 (7.37 g, 43.4 mmol, 1.5 eq) in THF (70 mL) at −10° C. in a 250 mL round-bottom flask was added n-BuLi (17.38 mL, 43.4 mmol, 1.5 eq). After 1 h, $ZnCl_2$ (1M in ether) (43.4 mL, 43.4 mmol, 1.5 eq) was added at −10° C. and the reaction mixture was allowed to warm up to r.t. After 1 h, Pd(PPh₃)₄ (0.669 g, 0.579 mmol, 0.02 eq) and bromide 10 (10 g, 29 mmol, 1 eq) in THF (10.5 mL) were added and the mixture was heated to reflux for 1 h. After cooling to room temperature the reaction mixture was concentrated to dryness. DCM (200 mL)/water (160 mL)/NH₄OH (40 mL) were added to the solid and the resultant mixture (an emulsion) was stirred for 1 h. Brine (50 ml) was added to the emulsion and the stirring was continued for an additional 10 min. The mixture was then filtered through a paper filter and phases were separated. The aqueous phase was extracted with DCM (2×50 mL). The organic phases were combined, dried over $Na_2SO_4$ and concentrated to dryness. MTBE (30 mL) was added to the solid and the suspension was stirred for 30 min. The solid was collected by filtration, washed with MTBE (2×5 mL) and dried to afford of 11 as a beige solid (8.02 g, 64% yield). MS (m/z): 434.2 (M+1).

Step 4: tert-butyl (6-(7-(4-amino-2-fluorophenoxy)thieno[3,2-b]pyridin-2-yl)pyridin-3-yl)methyl(2-methoxyethyl)carbamate (13)

To a solution of 4-amino-2-fluorophenol (10.55 g, 83 mmol, 1.2 eq) in DMSO (150 mL) in a 100 mL round-bottom flask was added potassium tert-butoxide 95% (10.08 g, 90 mmol, 1.3 eq). After 30 min, 11 (30 g, 69.1 mmol) was added and the reaction mixture and was heated at 100° C. for 2 h, cooled to room temperature, poured into water (400 mL) at 40-45° C. and stirred for 30 min. The precipitate was collected by filtration, washed with water (2×50 mL) and dried under vacuum overnight. The solid was triturated with MTBE (200 mL) for 3 h and filtered to give 13 as beige solid (28.00 g, 77% yield). MS (m/z): 525.3 (M+1).

Step 5: tert-butyl (6-(7-(2-fluoro-4-(3-(2-(4-fluorophenyl)acetyl)thioureido)phenoxy)thieno[3,2-b]pyridin-2-yl)pyridin-3-yl)methyl(2-methoxyethyl)carbamate (14)

To a suspension of isothiocyanate 2 (5.50 g, 28.2 mmol) in a mixture of toluene (20 mL)/EtOH (20 mL) in a 500 mL round-bottom flask was added aniline 13 (10 g, 19.06 mmol) in a mixture of toluene (50 mL)/EtOH (50 mL). After 30 min, additional amount of isothiocyanate 2 (1 g, 5.12 mmol) in a mixture toluene (5 mL)/EtOH (5 mL) was added to the reaction mixture which was stirred at r.t. for an additional 45 min. The reaction mixture was concentrated under reduced pressure and the residue was co-evaporated with MeOH (40 mL) to dryness. Finally MeOH (80 mL) was added to the dry residue to produce a precipitate that was stirred at room temperature for 14 h, collected by filtration, dried for 2 h under vacuum to afford 14 as beige solid (7 g, 51% yield). MS (m/z): 720.3 (M+1)

Step 7: N-(3-fluoro-4-(2-(5-((2-methoxyethylamino)methyl)pyridin-2-yl)thieno[3,2-b]pyridin-7-yloxy)phenylcarbamothioyl)-2-(4-fluorophenyl)acetamide (15)

To solid 14 (7.00 g, 9.72 mmol) in a 250 mL round-bottom flask was added TFA (20 mL). The addition was a little bit exothermic. The mixture was stirred at r.t. for 2 h then concentrated and co-evaporated with MTBE (2×100 mL) to obtain a solid that was triturated with MTBE (80 mL) for 2 h. The solid was collected by filtration, washed with MTBE (2×10 mL) and dried in vacuum for 1 h. The dry solid was partitioned between the mixture of DCM/MeOH: (9/1, 300 mL) and NaHCO$_3$ (200 mL). The phases were separated. The organic phase was collected and the aqueous phase was extracted with DCM/MeOH: 9/1 (2×150 mL). Organic phases were combined, washed with brine (100 mL), dried over Na$_2$SO$_4$ and concentrated. The solid residue was triturated with EA (40 mL) for 1 h, collected by filtration, washed with EA (2×5 mL), dried in vacuum for 1 h to afford 15 as beige solid (3.77 g, 63% yield). MS (m/z): 620.6 (M+1).

Example 1

Version E

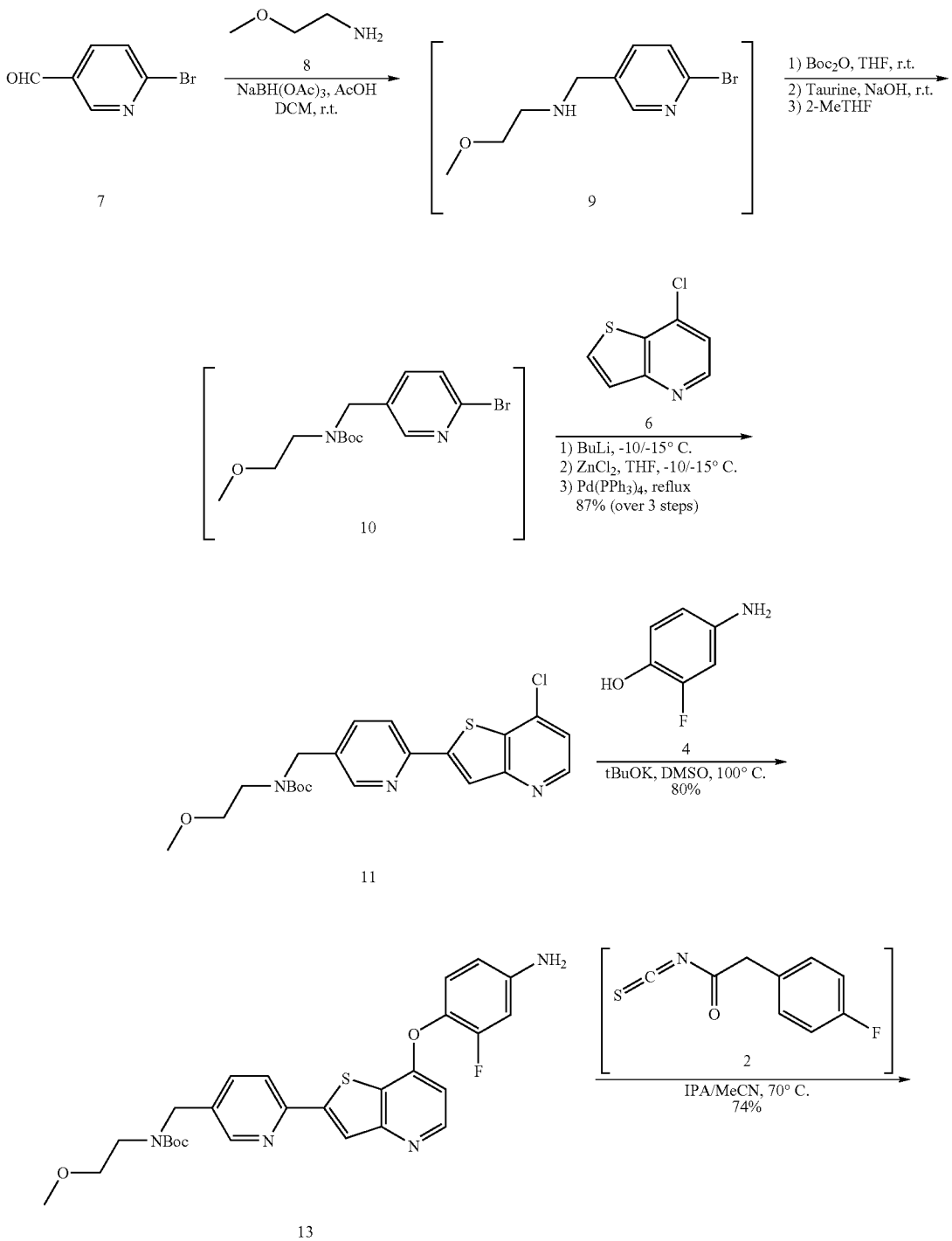

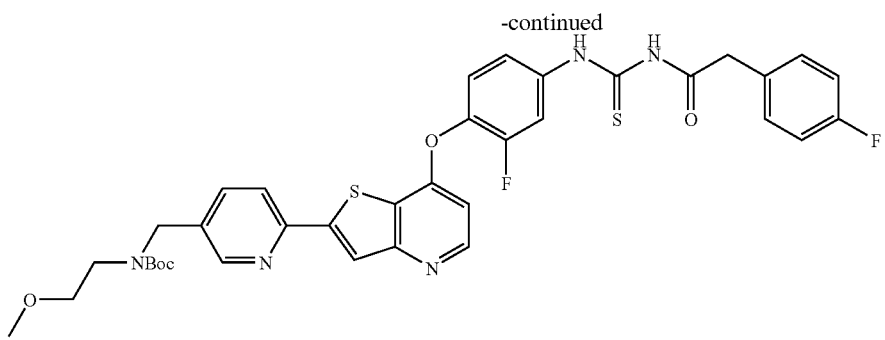

14

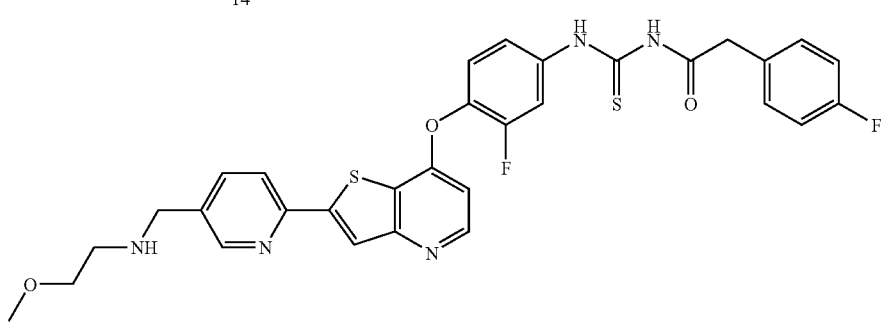

15: Example 1

Steps 1-3 (combined): tert-Butyl (6-(7-chlorothieno [3,2-b]pyridin-2-yl)pyridin-3-yl)methyl(2-methoxyethyl)carbamate (11)

To a solution of 6-bromopyridine-3-carboxaldehyde (7) (20 g, 113 mmol) in DCM (240 mL) cooled to 0-5° C. was added 2-methoxyethylamine (8) (24.23 g, 323 mmol, 3 eq.) over 5 min followed by AcOH (1.05 eq., 6.46 mL, 113 mmol) over 10 min. The reaction mixture was stirred for 15 min at 0-5° C. then for 30 min at r.t. NaBH(OAc)$_3$ was added portion wise and the reaction mixture was stirred at room temperature for an additional 2 h. The reaction mixture was quenched by addition of 10% aqueous HCl (160 mL). The layers were separated. The organic phase was collected and extracted with 10% aqueous HCl (2×100 mL). The original aqueous phase (also acidic) and the acidic extracts were combined and basified to pH 9 with NaOH 4M (500 mL). The basic solution was extracted with DCM (3×200 mL). The organic phase was collected, washed with water (3×250 mL) and brine (400 mL) then concentrated to a volume of 100-120 mL. THF (250 mL) was added and the resultant solution was concentrated to a volume of 100-120 mL. A second portion of THF (250 mL) was added and the resultant solution containing crude N-((6-bromopyridin-3-yl)methyl)-2-methoxyethanamine (9) was concentrated again to a volume of 215 to 230 mL.

To this solution was added Boc$_2$O (30 mL, 129 mmol, 1.2 eq.) over 15 min and the reaction mixture was stirred at r.t. for 1 h. A solution of taurine (1.5 q., 20.22 g, 162 mmol) in NaOH 2M (1.5 eq., 81 ml) was added slowly and the resultant mixture was stirred at r.t. for 16 h. Finally, 1N NaOH solution (100 mL) and 2-MeTHF (251 mL) were added and the mixture was stirred for 15 minutes. The layers were separated. The organic phase was collected, washed with 1N NaOH solution (100 mL), water (100 mL) and brine (100 mL) then dried over MgSO$_4$ and concentrated to a volume of 50-60 mL containing tert-butyl (6-bromopyridin-3-yl)methyl(2-methoxyethyl)carbamate (10). The solution of 10 was used in the next step.

To a solution of 7-chlorothieno[3,2-b]pyridine (6, scheme 1) (27.4 g 162 mmol, 1.5 eq.) in THF (260 mL at −10 to −15° C.) was added n-BuLi (65.2 mL, 2.5 M in hexane, 1.5 eq., 162 mmol) over 10 min. The reaction mixture was stirred at −10 to −15° C. for 30 minutes then added via canula to a suspension of zinc chloride (1.5 eq., 22.03 g, 162 mmol) in THF (100 mL) at −10 to −15° C. over a period of 15 min. The combined reaction mixture was stirred for 15 min at −10 to −15° C., then at r.t. for another 45 min.

Pd(PPh$_3$)$_4$ (2.49 g, 2.15 mmol, 0.02 eq.) was dissolved in the solution of tert-butyl (6-bromopyridin-3-yl)methyl(2-methoxyethyl)carbamate (10) (made during the step 2). This pooled solution was added to the reaction mixture which was heated at reflux for 1.5 h. After cooling down to r.t., 2-MeTHF (400 mL), water (400 mL) and NH$_4$OH (270 mL) were added. The mixture was stirred at r.t. for 30 min and the layers were separated. The aqueous phase was extracted with 2-MeTHF (2×200 mL). The organic phase and the extracts were combined, washed with water (250 mL) and brine (250 mL), and concentrated to dryness. The brown solid residue was triturated with MTBE (135 mL) for 1 h, collected by filtration and washed with MTBE (2×30 mL). The product was dried in a vacuum oven (45° C.) to afford title compound 11 as a beige solid (40.65 g, 94 mmol, 87% yield over three steps).

$^1$H NMR (400 MHz, DMSO-d$_6$): 8.64 (d, J=5.2 Hz, 1H), 8.52 (d, J=1.6 Hz, 1H), 8.39 (s, 1H), 8.27 (d, J=8.0 Hz, 1H), 7.80 (dd, J=2.0 and 8.0 Hz, 1H), 7.57 (d, J=5.2 Hz, 1H), 4.48 (s, 2H), 3.46-3.20 (m, 4H), 3.22 (s, 3H), 1.48-1.30 (m, 9H). M+H, 434.2

Step 4: tert-butyl (6-(7-(4-amino-2-fluorophenoxy) thieno[3,2-b]pyridin-2-yl)pyridin-3-yl)methyl(2-methoxyethyl)carbamate (13)

To a solution of 4-amino-2-fluorophenol (4, scheme 1) (14.29 g, 112 mmol 1.2 eq.,) in DMSO (117 mL) was added potassium tert-butoxide (13.66 g, 122 mmol, 1.3 eq.,) over 5 min. The reaction mixture was stirred at r.t. for 30 minutes. tert-Butyl (6-(7-chlorothieno[3,2-b]pyridin-2-yl)pyridin-3-yl)methyl(2-methoxyethyl)carbamate (11) (40.65 g, 94 mmol, 1 eq) was added and the reaction mixture was heated at 100° C. for 1.5 h. Additional amounts of the phenol 4 (0.83 g, 6.53 mmol, 0.07 eq.) in DMSO (5 mL) and potassium tert-butoxide (1.05 g, 9.38 mmol, 0.1 eq.) were added to the reaction mixture which was heated at 100° C. for an additional 30 min. After cooling down to r.t., the reaction mixture was poured into water (900 mL) at 40° C. over 15 min. After stirring for 15 min at 40° C., the mixture was cooled to r.t. over 1 h. The solid was collected by filtration and the cake was washed with water (2×115 mL). The product was dried in vacuum for 16 h then triturated with MTBE (115 mL) for 1 h, collected by filtration and the cake was washed with MTBE (2×20 mL). The product was dried in a vacuum oven (45° C.) to afford title compound 13 as a beige solid (44.02 g, 84 mmol, 90% yield).

$^1$H NMR (400 MHz, DMSO-d$_6$): 8.51 (d, J=2.0 Hz, 1H), 8.50 (d, J=5.6 Hz, 1H), 8.30 (s, 1H), 8.24 (d, J=8.0 Hz, 1H), 7.78 (dd, J=2.4 and 8.0 Hz, 1H), 7.12 (dd, J=9.2 Hz, 1H), 6.60 (dd, J=0.4 and 5.6 Hz, 1H), 6.54 (dd, J=2.4 and 13.0 Hz, 1H), 6.45 (ddd, J=0.4, 2.4 and 9.2 Hz, 1H), 5.55 (s, 2H), 4.47 (s, 2H), 3.48-3.32 (m, 4H), 3.22 (s, 3H), 1.48-1.30 (m, 9H). M+H, 525.3

Step 5: tert-butyl (6-(7-(2-fluoro-4-(3-(2-(4-fluorophenyl)acetyl)thioureido)phenoxy)thieno[3,2-b]pyridin-2-yl)pyridin-3-yl)methyl(2-methoxyethyl)carbamate (14)

To a solution of 4-fluorophenylacetic acid (1, scheme 1) (26.5 g, 172 mmol) in DCM (93 mL) was added oxalyl chloride (2 eq., 30.1 mL, 344 mmol) over 5 min and DMF (0.005 eq., 0.067 mL, 0.86 mmol) over 1 min. The reaction mixture was stirred at r.t for 2 h then concentrated. The residual DCM was removed as an azeotrope with toluene (2×20 mL) to afford intermediate 2-(4-fluorophenyl)acetyl chloride (1a) (30.85 g, 179 mmol, assumed quantitative yield) as yellow oil. Part of that material was used as is in the next step.

To a solution of crude 1a (27.4 g, 159 mmol) from the previous step in MeCN (159 mL) was added ammonium thiocyanate (12.69 g, 167 mmol, 1.05 eq.). The fine yellow slurry was heated at 50° C. for 1 h. After cooling down to 0° C., the reaction mixture was filtered through a Celite pad and the cake was washed with MeCN (10 mL). The filtrate and washings were combined and concentrated to a volume of 30-40 mL, cooled again to 0° C. and filtered through a Celite pad. The cake was washed with MeCN (10 mL). The filtrate and washings were combined and concentrated to the same volume of 30-40 mL. The resultant solution contained 2-(4-fluorophenyl)acetyl isothiocyanate (2, assumed quantitative yield, Method B). Half of this solution was used in the next step.

To a solution of 13 (39.02 g, 74.4 mmol, 1 eq.,) in IPA (780 mL,) at 70° C. was added a solution of crude 2 in MeCN (19.5 mL) from the previous step, over 15 min. The reaction mixture was heated at 70° C. for 20 min. After cooling down to r.t. over 2 h, the reaction mixture turned into a suspension and was stirred at r.t. for an additional 14 h. After cooling down to 0° C., the solid was collected by filtration and the product cake was washed with cold IPA (50 mL) then dried in vacuum to produce the title compound 14 as a beige solid (47.62 g, 66.2 mmol, 89% yield).

$^1$H NMR (400 MHz, DMSO-d$_6$): 12.48 (s, 1H), 11.84 (s, 1H), 8.55 (d, J=5.6 Hz, 1H), 8.51 (d, J=1.6 Hz, 1H), 8.34 (s, 1H), 8.26 (d, J=8.4 Hz, 1H), 8.4 (dd, J=2.0 and 13.2 Hz, 1H), 7.79 (dd, J=2.0 and 8.0 Hz, 1H), 7.58-7.50 (m, 2H), 7.42-7.35 (m, 2H), 7.23-7.15 (m, 2H), 6.68 (d, J=5.6 Hz, 1H), 4.47 (s, 2H), 3.83 (s, 2H), 3.48-3.32 (m, 4H), 3.22 (s, 3H), 1.50-1.30 (m, 9H). M+H, 720.2

Step 6: N-(3-fluoro-4-(2-(5-((2-methoxyethylamino) methyl)pyridin-2-yl)thieno[3,2-b]pyridine-7-yloxy) phenylcarbamothioyl)-2-(4-fluorophenyl)acetamide (15)

To a suspension of 14 (45.06 g, 62.6 mmol, 1 eq.,) in AcOH (338 mL) was added 1N HCl (188 mL) over 1 min. The reaction mixture was heated at 40° C. for 2 h. After cooling down to r.t., water (676 mL) was added. The reaction mixture turned into a suspension and was stirred at r.t. for 15 min. The solid was collected by filtration and the product cake was washed with water (2×100 mL) then dried in vacuum for 30 min to afford a crude hydrochloride salt of 15 as a white solid.

To a suspension of crude hydrochloride salt of 15 in THF (300 mL) was added a saturated solution of NaHCO$_3$ (1 L). After 2 h, EtOAc was added (1.2 L) and the mixture was stirred at r.t. for 10 min. The layers were separated. The aqueous phase was collected, extracted with a mixture of EtOAc (400 mL) and THF (100 mL). The organic layer and the extract were combined and washed with brine (600 mL), dried over Na$_2$SO$_4$, filtered and concentrated to a volume of 120-140 mL. EtOAc (120 mL) was added to that solution which once again was concentrated to a volume of 120-140 mL. EtOAc (120 mL) was added for the third time and the solution was concentrated again to a volume of 120-140 mL to form a suspension. The solid was collected by filtration and washed with EtOAc (2×40 mL) then dried in vacuum over 17 h to afford the title compound 15 as a beige solid (29.14 g, 47 mmol, 75% yield).

$^1$H NMR (400 MHz, DMSO-d$_6$): 8.58 (d, J=1.6 Hz, 1H), 8.55 (d, J=5.2 Hz, 1H), 8.34 (s, 1H), 8.25 (d, J=7.6 Hz, 1H), 8.04 (dd, J=1.6 and 13.2 Hz, 1H), 7.92 (dd, J=2.0 and 8.4 Hz, 1H), 7.58-7.52 (m, 2H), 7.42-7.35 (m, 2H), 7.22-7.16 (m, 2H), 6.68 (dd, J=0.8 and 5.2 Hz, 1H), 3.83 (s, 4H), 3.42 (t, J=5.6 Hz, 2H), 3.24 (s, 3H), 2.70 (t, J=5.6 Hz, 2H). M+H, 620.2

Analytical Methods.

Purity of both target compounds and synthetic intermediates were determined by a standard HPLC method using H$_2$O (0.1% formic acid)/MeOH (0.05% formic acid) gradient as a mobile phase on an Agilent Zorbax XDB-C8 50×4.6 mm (3.5 μm) column and/or Thermo Aquasil C18 100×4.6 mm (5 μm) column.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A process for preparing a compound of Formula (A):

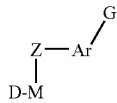

(A)

and pharmaceutically acceptable salts thereof,
wherein
D is pyridine optionally substituted with 1 to 5 independently selected $R^{38}$;
M is

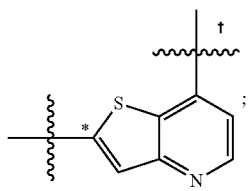 [SMILES: *c1cc2nccc(*)c2s1]

Z is —O—;
Ar is phenyl; and
G is

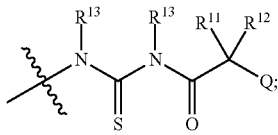

wherein
each $R^{38}$ is independently selected from —$(CH_2)_j NR^{39}(CH_2)_n R^{36}$ and —$(CH_2)_n NR^{36}R^{39}$, wherein each j is an integer independently ranging from 0 to 4 and n is an integer ranging from 0 to 6;
$R^{36}$ is selected from the group consisting of H, —OH, $C_1$-$C_6$ alkyl, —$(CH_2)_n O(CH_2)_i OR^{37}$, —$(CH_2)_n CN(CH_2)_n OR^{37}$, —$(CH_2)_n CN(CH_2)_n R^{37}$, and —$(CH_2)_n OR^{37}$, wherein each n is an integer independently ranging from 0 to 6 and i is an integer ranging from 2 to 6;
$R^{37}$ is selected from H, —O—$C_1$-$C_6$alkyl, and optionally substituted $C_1$-$C_6$alkyl;
$R^{39}$ is selected from the group consisting of H and $C_1$-$C_6$ alkyl;
$R^{13}$ is —H,
Q is phenyl optionally substituted with between zero and four halogens;
$R^{11}$ and $R^{12}$ are H
the process comprising
reacting a compound represented by the Formula (A-1)

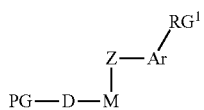

(A-1)

wherein
PG is a $R^{38}$ substituent protected with a protecting group; and $RG^1$ is —$NH_2$; with a compound represented by the Formula (A-2):

$RG^2$-$G^1$ (A-2), wherein $RG^2 G^1$ is

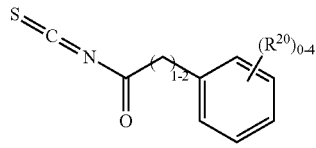

wherein the reaction is performed at 70° C. in a mixture of isopropanol and acetonitrile, such that the reaction of —$RG^1$ with $RG^2$-$G^1$ forms

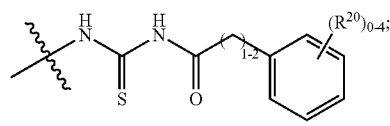

and removing the protecting group.

2. The process according to claim 1, wherein G is selected from the group consisting of

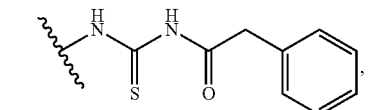

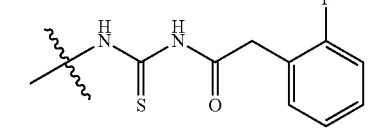

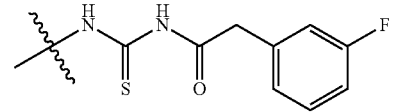

and

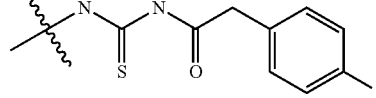

3. The process according to claim 1, wherein D is substituted with one $R^{38}$, wherein $R^{38}$ is —$(CH_2)_j NR^{39}(CH_2)_n R^{36}$, wherein j is an integer from 0 to 4, n is an integer from 0 to 6, $R^{39}$ is H or $C_1$-$C_6$alkyl, and $R^{36}$ is —$(CH_2)_n OR^{37}$, wherein n is an integer ranging from 0 to 6, and $R^{37}$ is H or $C_1$-$C_6$alkyl.

4. The process according to claim 1 wherein $RG^2$-$G^1$ is

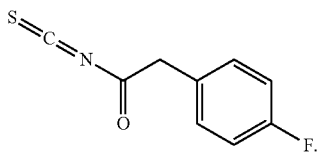 [SMILES: O=C(Cc1ccc(F)cc1)N=C=S]

UNITED STATES PATENT AND TRADEMARK OFFICE
CERTIFICATE OF CORRECTION

PATENT NO. : 8,907,091 B2
APPLICATION NO. : 12/231297
DATED : December 9, 2014
INVENTOR(S) : Franck Raeppel et al.

Page 1 of 1

It is certified that error appears in the above-identified patent and that said Letters Patent is hereby corrected as shown below:

In the Claims

Column 163, line 52, Claim 1, "halogens" should be --$R^{20}$ wherein $R^{20}$ is a halogen--

Signed and Sealed this
Twenty-first Day of April, 2015

Michelle K. Lee
*Director of the United States Patent and Trademark Office*